United States Patent
Guerin et al.

(10) Patent No.: US 9,522,106 B2
(45) Date of Patent: *Dec. 20, 2016

(54) COMPOSITION FOR DYEING KERATINOUS FIBRES COMPRISING A DIRECT DYE HAVING A DISULPHIDE/THIOL FUNCTIONAL GROUP, A THICKENING POLYMER, AN ETHOXYLATED FATTY ALCOHOL AND/OR A NONIONIC SURFACTANT, AN ALKALINE AGENT AND A REDUCING AGENT

(75) Inventors: Frédéric Guerin, Paris (FR); Chrystel Pourille, Sannois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/001,321

(22) PCT Filed: Feb. 17, 2012

(86) PCT No.: PCT/EP2012/052746
§ 371 (c)(1),
(2), (4) Date: Oct. 31, 2013

(87) PCT Pub. No.: WO2012/113720
PCT Pub. Date: Aug. 30, 2012

(65) Prior Publication Data
US 2014/0075687 A1    Mar. 20, 2014

Related U.S. Application Data

(60) Provisional application No. 61/448,755, filed on Mar. 3, 2011, provisional application No. 61/448,759, filed on Mar. 3, 2011.

(30) Foreign Application Priority Data

Feb. 25, 2011   (FR) ..................................... 11 51553
Feb. 25, 2011   (FR) ..................................... 11 51554

(51) Int. Cl.
| | | |
|---|---|---|
| *A61Q 5/10* | (2006.01) | |
| *A61K 8/49* | (2006.01) | |
| *A61K 8/41* | (2006.01) | |
| *A61K 8/46* | (2006.01) | |
| *A61K 8/60* | (2006.01) | |
| *A61K 8/73* | (2006.01) | |
| *A61Q 5/06* | (2006.01) | |

(52) U.S. Cl.
CPC .............. *A61K 8/4933* (2013.01); *A61K 8/41* (2013.01); *A61K 8/46* (2013.01); *A61K 8/49* (2013.01); *A61K 8/4926* (2013.01); *A61K 8/4946* (2013.01); *A61K 8/604* (2013.01); *A61K 8/731* (2013.01); *A61Q 5/065* (2013.01); *A61Q 5/10* (2013.01)

(58) Field of Classification Search
CPC ........ A61Q 5/056; A61Q 5/10; A61K 8/4926; A61K 8/41; A61K 8/731; A61K 8/4933; A61K 8/46; A61K 8/49; A61K 8/4946; A61K 8/604
USPC .............................. 8/405, 407, 437, 465, 648
See application file for complete search history.

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 3,100,739 A | 8/1963 | Kaiser et al. |
| 3,148,125 A | 9/1964 | Strianse et al. |
| 3,524,842 A | 8/1970 | Grossmann et al. |
| 3,578,386 A | 5/1971 | Kalopissis et al. |
| 3,617,163 A | 11/1971 | Kalopissis et al. |
| 3,645,705 A | 2/1972 | Miller et al. |
| 3,665,036 A | 5/1972 | Kalopissis et al. |
| 3,817,698 A | 6/1974 | Kalopissis et al. |
| 3,867,456 A | 2/1975 | Kalopissis et al. |
| 3,869,454 A | 3/1975 | Lang et al. |
| 3,915,921 A | 10/1975 | Schlatzer, Jr. |

(Continued)

FOREIGN PATENT DOCUMENTS

| | | |
|---|---|---|
| DE | 2527638 A1 | 5/1976 |
| DE | 2538363 A1 | 5/1976 |

(Continued)

OTHER PUBLICATIONS

STIC Search Report dated Aug. 27, 2014.*

(Continued)

*Primary Examiner* — Eisa Elhilo
(74) *Attorney, Agent, or Firm* — The Marbury Law Group, PLLC

(57) ABSTRACT

A subject-matter of the invention is a method for dyeing and/or lightening keratinous fibres, such as the hair, employing i) at least one direct dye having a disulphide, thiol or protected thiol functional group and ii) at least one thickening organic polymer, iii) at least one (poly)ethoxylated fatty alcohol and/or one nonionic surfactant, iv) at least one alkaline agent and v) at least one reducing agent. Another subject-matter of the invention is a composition comprising the ingredients i) to v), the use of the combination of i), ii), iii), iv) and v) for dyeing and/or lightening keratinous fibres and a multicompartment kit comprising the ingredients i) to v). The dyeing method and the composition according to the invention make it possible in particular to obtain a lasting coloration on keratinous fibres which is intense, chromatic and/or homogeneous, with or without the use of an oxidizing agent.

27 Claims, No Drawings

(56) References Cited

U.S. PATENT DOCUMENTS

| | | | |
|---|---|---|---|
| 3,955,918 A | 5/1976 | Lang | |
| 3,969,087 A | 7/1976 | Saito et al. | |
| 3,985,499 A | 10/1976 | Lang et al. | |
| 4,025,301 A | 5/1977 | Lang | |
| 4,131,576 A | 12/1978 | Iovine et al. | |
| 4,137,180 A | 1/1979 | Naik et al. | |
| 4,151,162 A | 4/1979 | Lang et al. | |
| 4,226,784 A | 10/1980 | Kalopissis et al. | |
| 4,237,243 A | 12/1980 | Quack et al. | |
| 4,509,949 A | 4/1985 | Huang et al. | |
| 4,823,985 A | 4/1989 | Grollier et al. | |
| 4,874,554 A | 10/1989 | Lange et al. | |
| 4,886,517 A | 12/1989 | Bugaut et al. | |
| 4,956,175 A | 9/1990 | Maignan et al. | |
| 5,015,767 A | 5/1991 | Maignan et al. | |
| 5,085,860 A | 2/1992 | Junino et al. | |
| 5,089,578 A | 2/1992 | Valint et al. | |
| 5,106,612 A | 4/1992 | Maignan et al. | |
| 5,154,918 A | 10/1992 | Maignan et al. | |
| 5,156,911 A | 10/1992 | Stewart | |
| 5,334,377 A | 8/1994 | Junino et al. | |
| 5,449,805 A | 9/1995 | Junino et al. | |
| 5,466,878 A | 11/1995 | Junino et al. | |
| 5,468,477 A | 11/1995 | Kumar et al. | |
| 5,500,209 A | 3/1996 | Ross et al. | |
| 5,519,063 A | 5/1996 | Mondet et al. | |
| 5,583,257 A | 12/1996 | Junino et al. | |
| 5,700,454 A | 12/1997 | Malle | |
| 5,708,151 A | 1/1998 | Möckli | |
| 5,725,882 A | 3/1998 | Kumar et al. | |
| 5,736,125 A | 4/1998 | Morawsky et al. | |
| 5,783,657 A | 7/1998 | Pavlin et al. | |
| 5,843,416 A | 12/1998 | Malle | |
| 5,879,413 A | 3/1999 | Pengilly et al. | |
| 5,888,252 A | 3/1999 | Möckli | |
| 5,919,273 A | 7/1999 | Rondeau et al. | |
| 5,935,558 A | 8/1999 | Malle | |
| 5,985,257 A | 11/1999 | Malle | |
| 5,993,490 A | 11/1999 | Rondeau et al. | |
| 6,045,591 A | 4/2000 | Deneulenaere | |
| 6,136,042 A | 10/2000 | Maubru | |
| 6,174,968 B1 | 1/2001 | Hoxmeier | |
| 6,179,881 B1 | 1/2001 | Henrion et al. | |
| 6,225,390 B1 | 5/2001 | Hoxmeier | |
| 6,458,167 B1 | 10/2002 | Genet et al. | |
| 6,492,502 B2 | 12/2002 | Henrion et al. | |
| 6,797,013 B1 | 9/2004 | Lang et al. | |
| 6,822,039 B1 | 11/2004 | Monfreux-Gaillard et al. | |
| 6,863,883 B1 | 3/2005 | Tsujino et al. | |
| 7,717,964 B2 * | 5/2010 | Daubresse et al. | 8/405 |
| 7,744,657 B2 | 6/2010 | Greaves et al. | |
| 7,780,743 B2 | 8/2010 | Greaves et al. | |
| 8,038,731 B2 | 10/2011 | Daubresse et al. | |
| 8,328,880 B2 | 12/2012 | Daubresse et al. | |
| 2001/0001332 A1 | 5/2001 | Henrion et al. | |
| 2002/0165368 A1 | 11/2002 | Henrion et al. | |
| 2005/0188478 A1* | 9/2005 | Plos | 8/405 |
| 2006/0080791 A1 | 4/2006 | Daubresse et al. | |
| 2006/0195990 A1 | 9/2006 | Lagrange | |
| 2006/0248662 A1* | 11/2006 | Legrand | 8/405 |
| 2009/0126125 A1 | 5/2009 | Greaves et al. | |
| 2009/0172897 A1 | 7/2009 | Daubresse et al. | |
| 2009/0313769 A1 | 12/2009 | Daubresse et al. | |
| 2009/0320216 A1 | 12/2009 | Greaves et al. | |
| 2010/0287714 A1 | 11/2010 | Greaves et al. | |
| 2011/0011417 A1 | 1/2011 | Greaves et al. | |
| 2012/0177587 A1 | 7/2012 | Daubresse et al. | |
| 2013/0074276 A1 | 3/2013 | Daubresse et al. | |
| 2014/0082855 A1* | 3/2014 | Rapold et al. | 8/406 |

FOREIGN PATENT DOCUMENTS

| | | | |
|---|---|---|---|
| DE | 4137005 A1 | 5/1993 | |
| DE | 4220388 A1 | 12/1993 | |
| EP | 0173109 A2 | 3/1986 | |
| EP | 0354835 A1 | 2/1990 | |
| EP | 0368763 A1 | 5/1990 | |
| EP | 0432000 A1 | 6/1991 | |
| EP | 0465342 A1 | 1/1992 | |
| EP | 0503853 A2 | 9/1992 | |
| EP | 0514282 A1 | 11/1992 | |
| EP | 0497144 A1 | 8/1993 | |
| EP | 0577473 A1 | 1/1994 | |
| EP | 0653202 A1 | 5/1995 | |
| EP | 0714954 A2 | 6/1996 | |
| EP | 0750899 A2 | 1/1997 | |
| EP | 0850636 A1 | 7/1998 | |
| EP | 0850637 A1 | 7/1998 | |
| EP | 0918053 A1 | 5/1999 | |
| EP | 0920856 A1 | 6/1999 | |
| EP | 1062940 A1 | 12/2000 | |
| EP | 1133975 A2 | 9/2001 | |
| EP | 1133976 A2 | 9/2001 | |
| EP | 1647580 A1 | 4/2006 | |
| EP | 1652554 A1 | 5/2006 | |
| EP | 2070988 A2 | 6/2009 | |
| EP | 2075289 A1 | 7/2009 | |
| FR | 1221122 A | 5/1960 | |
| FR | 1516943 A | 2/1968 | |
| FR | 1540423 A | 8/1968 | |
| FR | 1560664 A | 3/1969 | |
| FR | 1567219 A | 5/1969 | |
| FR | 2189006 A1 | 1/1974 | |
| FR | 2275462 A1 | 1/1976 | |
| FR | 2281162 A1 | 3/1976 | |
| FR | 2285851 A1 | 4/1976 | |
| FR | 2416723 A1 | 9/1979 | |
| FR | 2570946 A1 | 4/1986 | |
| FR | 2586913 A1 | 3/1987 | |
| FR | 2679448 A1 | 1/1993 | |
| FR | 2692481 A1 | 12/1993 | |
| FR | 2757385 A1 | 6/1998 | |
| FR | 2788433 A1 | 7/2000 | |
| FR | 2910278 A1 | 6/2008 | |
| FR | 2921256 A1 | 3/2009 | |
| FR | 2921380 A1 | 3/2009 | |
| FR | 2933297 A1 | 1/2010 | |
| GB | 738585 A | 10/1955 | |
| GB | 1163385 A | 9/1969 | |
| GB | 1195386 A | 6/1970 | |
| GB | 1514466 A | 6/1978 | |
| WO | 9301797 A1 | 2/1993 | |
| WO | 9501772 A1 | 1/1995 | |
| WO | 9515144 A1 | 6/1995 | |
| WO | 9744004 A1 | 11/1997 | |
| WO | 9842298 A1 | 10/1998 | |
| WO | 9844012 A1 | 10/1998 | |
| WO | 9948465 A1 | 9/1999 | |
| WO | 0031154 A1 | 6/2000 | |
| WO | 0068282 A1 | 11/2000 | |
| WO | 0119333 A1 | 3/2001 | |
| WO | 0166646 A1 | 9/2001 | |
| WO | 03029359 A1 | 4/2003 | |
| WO | 2005097051 A2 | 10/2005 | |
| WO | 2007110531 A2 | 10/2007 | |
| WO | 2007110532 A2 | 10/2007 | |
| WO | 2007110533 A2 | 10/2007 | |
| WO | 2007110534 A2 | 10/2007 | |
| WO | 2007110535 A2 | 10/2007 | |
| WO | 2007110536 A2 | 10/2007 | |
| WO | 2007110537 A2 | 10/2007 | |
| WO | 2007110538 A2 | 10/2007 | |
| WO | 2007110539 A2 | 10/2007 | |
| WO | 2007110540 A2 | 10/2007 | |
| WO | 2007110541 A2 | 10/2007 | |
| WO | 2007110542 A2 | 10/2007 | |
| WO | 2009034059 A2 | 3/2009 | |
| WO | 2009040354 A1 | 4/2009 | |
| WO | 2009109457 A2 | 9/2009 | |
| WO | WO 2009/109457 A2 * | 9/2009 | |
| WO | 2012113722 A2 | 8/2012 | |
| WO | 2012113723 A2 | 8/2012 | |
| WO | 2012113724 A2 | 8/2012 | |

(56) References Cited

FOREIGN PATENT DOCUMENTS

OTHER PUBLICATIONS

Antioxidant (Wikipedia, the free encyclopedia (No date).*
International Search Report and Written Opinion for PCT/EP2012/052746.
Morishima, Yotaro, "Self-Assembling Amphiphilic Polyelectrolytes and their Nanostructures," Chinese Journal of Polymer Science, vol. 18, No. 40, 2000, pp. 323-336.
Morishima, Yotaro, "Micelle Formation of Random Copolymers of Sodium 2-(acrylamido)-2-methylpropanesulfonate and a Nonionic Surfactant Macromonomer in Water as Studied by Fluorescence and Dynamic Light Scattering," Macromolecules, vol. 33, No. 10, 2000, pp. 3694-3704.
Morishima, Yotaro, "Solution Properties of Micelle Networks Formed by Nonionic Moieties Covalently Bound to a Polyelectrolyte: Salt Effects on Rheological Behavior," Langmuir, vol. 16, No. 12, 2000, pp. 5324-5332.
Morishima, Yotaro, "Stimuli Responsive Amphiphilic Copolymers of Sodium 2-(acrylamido)-2-methylpropanesulfonate and Associative Macromonomers," Polym. Preprint, Div. Polym. Chem., 40(2), 1999, pp. 220-221.
English language abstract for DE 4137005 (May 13, 1993).
English language abstract for DE 4220388 (Dec. 23, 1993).
English language abstract for EP 0368763 (May 16, 1990).
English language abstract for EP 0577473 (Jan. 5, 1994).
English language abstract for FR 2679448 (Jan. 29, 1993).
English language abstract for FR 2692481 (Dec. 24, 1993).
English language abstract for FR 2910278 (Jun. 27, 2008).
English language abstract for FR 2921256 (Mar. 27, 2009).
English language abstract for FR 2921380 (Mar. 27, 2009).
English language abstract for FR 2933297 (Jan. 8, 2010).
International Search Report and Written Opinion for related application PCT/EP2012/052748.
Co-pending U.S. Appl. No. 14/001,324; National Stage of International Application No. PCT/EP2012/052748; Frédéric Guerin et al., "Composition for Dyeing Keratin Fibres Comprising a Direct Dye Bearing a Disulfide/Thiol Function, a Nonionic Surfactant, an Amphoteric Surfactant, an Ethoxylated Fatty Alcohol, an Alkaline Agent and a Reducing Agent," filed Aug. 23, 2013.
International Search Report and Written Opinion for related application PCT/EP2012/052751.
Co-pending U.S. Appl. No. 14/001,326; National Stage of International Application No. PCT/EP2012/052751; Frédéric Guerin et al., "Composition for Dyeing Keratin Fibres Comprising a Direct Dye Bearing a Disulfide/Thiol Function, a Non-Cellulose-Based Thickening Polymer, an Alkaline Agent and a Reducing Agent," filed Aug. 23, 2013.
International Search Report and Written Opinion for related application PCT/EP2012/052752.
Co-pending U.S. Appl. No. 14/001,318; National Stage of International Application No. PCT/EP2012/052752; Chrystel Pourille, "Composition for Dyeing Keratin Fibres Comprising a Direct Dye Bearing a Disulphide/Thiol Function, a Sparingly or Non-Ethoxylated Fatty Alcohol, a Cationic Surfactant, an Alkaline Agent and a Reducing Agent," filed Aug. 23, 2013.
Griffin, William C., "Calculation of HLB Values of Non-Ionic Surfactants," Journal of the Society of Cosmetic Chemists, May 1954, pp. 249-256.
Hamley, I.W., "Crystallization in Block Copolymers," Advances in Polymer Science, vol. 148, (1999), pp. 113-137.
Hunger, Klaus et al., "Pigments, Organic," Ullmann's Encyclopedia of Industrial Chemistry, vol. 27, (2012), pp. 380-423.
"Microbial Polysaccharides," Kirk-Othmer Encyclopedia of Chemical Technology, Third Edition, vol. 15, pp. 439-458.
McGregor, E.A., et al., "Polymers in Nature," published by John Wiley & Sons, Chapter 6, (1980), pp. 240-328.
Nojima, Shuichi et al., Melting Behavior of Poly(•-caprolactone)-block-Polybutadiene Copolymers, American Chemical Society, Macromolecules 1999, 32, pp. 3727-3734.
Rangarajan, Pratima et al., Morphology of Semicrystalline Block Copolymere of Ethylene-(Ethylene-alt-propylene), American Chemical Society, Macromolecules 1993, 26, pp. 4640-4645.
Richter, D., et al., "Polymer Aggregates with Crystalline Cores: The System Polyethylene-Poly (ethylenepropylene)," American Chemical Society, Macromolecules 1997, 30, pp. 1053-1068.
Viscardi, Guido et al., "Disperse and Cationic Azo Dyes from Heterocyclic Intermediates," Dyes and Pigments, 19 (1992), pp. 69-79.
Volz, Hans G., "Pigments, Inorganic, 1. General," Ullmann's Encyclopedia of Industrial Chemistry, vol. 27, pp. 225-256.
Final Office Action for co-pending U.S. Appl. No. 14/001,324 (Sep. 5, 2014).
Final Office Action for co-pending U.S. Appl. No. 14/001,324 (Dec. 29, 2014).
Non-Final Office Action for co-pending U.S. Appl. No. 14/001,326 (Sep. 4, 2014).
Final Office Action for co-pending U.S. Appl. No. 14/001,326 (Dec. 18, 2014).
Non-Final Office Action for co-pending U.S. Appl. No. 14/001,318 (Sep. 11, 2014).
Final Office Action for co-pending U.S. Appl. No. 14/001,318 (Dec. 29, 2014).
Non-Final Office Action for co-pending U.S. Appl. No. 14/001,326 (Jun. 1, 2015).

* cited by examiner

COMPOSITION FOR DYEING KERATINOUS FIBRES COMPRISING A DIRECT DYE HAVING A DISULPHIDE/THIOL FUNCTIONAL GROUP, A THICKENING POLYMER, AN ETHOXYLATED FATTY ALCOHOL AND/OR A NONIONIC SURFACTANT, AN ALKALINE AGENT AND A REDUCING AGENT

CROSS REFERENCE TO RELATED APPLICATIONS

This is a national stage application of PCT/EP2012/052746, filed internationally on Feb. 17, 2012, which claims priority to U.S. Provisional Application Nos. 61/448,755 and 61/448,759, filed on Mar. 3, 2011, as well as French Application Nos. 1151553 and 1151554, filed on Feb. 25, 2011, all of which are incorporated herein by reference in their entireties.

A subject-matter of the invention is a method for dyeing and/or lightening keratinous fibres starting from direct dyes.

It is known practice to dye keratinous fibres by direct dyeing or semi-permanent dyeing. Direct dyeing or semi-permanent dyeing consists in introducing colour via a coloured molecule that becomes adsorbed onto the surface of the hair or that penetrates into the hair. Thus, the method conventionally used in direct dyeing consists in applying, to the keratinous fibres, direct dyes which are coloured and colouring molecules having affinity for the fibres, in leaving the fibres in contact with the colouring molecules and in then optionally rinsing the fibres. Generally, this technique leads to chromatic colorations.

Scientific research has been conducted for several years to modify the colour of keratinous substances, especially keratinous fibres, and in particular to mask white fibres, to modify the colour of the fibres permanently or temporarily, and to satisfy new desires and needs in terms of colours and durability.

A description is given, in Applications EP 1 647 580, WO 2005/097051, EP 2 004 759, EP 2 075 289, WO 2007/110541, WO 2007/110540, WO 2007/110539, WO 2007/110538, WO 2007/110537, WO 2007/110536, WO 2007/110535, WO 2007/110534, WO 2007/110533, WO 2007/110532, WO 2007/110531, EP 2 070 988, WO 2009/040354 and WO 2009/034059, of direct dyes having a disulphide, thiol or protected thiol functional group which make it possible to colour the hair. The colours obtained are not sufficiently satisfactory, in particular in terms of intensity of colouration, of selectivity of the colour between the root and the tip, and of chromaticity of the colour.

The aim of the present invention is to provide novel systems for hair dyeing, this being the case even without the use of a chemical oxidizing agent, which make it possible to obtain improved colourations, in particular in terms of persistence with regard to external agents, homogeneity in the colouring (low selectivity between the root and the tip of the keratinous fibres), intensity, and/or which do not detrimentally affect the cosmetic properties of the keratinous fibres.

This aim is achieved with the present invention, a first subject-matter of which is a cosmetic composition comprising:
i) at least one direct dye having a disulphide, thiol or protected thiol functional group, in particular of formula (I):

$$A\text{-}(X)_p\text{—}C_{sat}\text{—}S\text{—}U \qquad (I)$$

the salts thereof with an organic or inorganic acid, the optical or geometric isomers thereof, the tautomers thereof, and the solvates thereof, such as the hydrates, in which formula (I):
U represents a radical chosen from:
  a) —S—$C'_{sat}$—$(X')_{p'}$-A'; and
  b) —Y;
A and A', which are identical or different, represent a radical comprising at least one quaternized cationic chromophore or at least one chromophore carrying a quaternized or quaternizable cationic group;
Y represents i) a hydrogen atom or ii) a protective group for the thiol functional group;
X and X', which are identical or different, represent a saturated or unsaturated and linear or branched divalent $C_1$-$C_{30}$ hydrocarbon chain which is optionally interrupted and/or optionally terminated at one or both of its ends by one or more divalent groups or their combinations chosen from:
  —N(R)—, —N$^+$(R)(R)—, —O—, —S—, —CO— or —SO$_2$— with R, which are identical or different, chosen from a hydrogen, a $C_1$-$C_4$ alkyl radical, a hydroxyalkyl radical or an aminoalkyl radical;
a fused or nonfused, saturated or unsaturated and aromatic or non-aromatic (hetero)cyclic radical which optionally comprises one or more identical or different heteroatoms and which is optionally substituted;
p and p', which are identical or different, have the value 0 or 1;
$C_{sat}$ and $C'_{sat}$, which are identical or different, represent a linear or branched, or cyclic, $C_1$-$C_{18}$ alkylene chain which is optionally substituted;
ii) at least one thickening organic polymer;
iii) at least one (poly)ethoxylated fatty alcohol and/or at least one nonionic surfactant preferably other than the (poly)ethoxylated fatty alcohol or alcohols;
iv) at least one alkaline agent, preferably comprising at least one amino group; and
v) at least one reducing agent.

Another subject-matter of the invention is a method for dyeing and/or lightening keratinous fibres, in particular dark keratinous fibres, by applying, to the said fibres, the ingredients i) to v) as defined above, the said ingredients being applied together or separately.

Another subject-matter of the invention is the use of the composition comprising i), ii), iii), iv) and v) as defined above in the dyeing and/or lightening of keratinous fibres.

Another subject-matter of the invention is a multicompartment kit comprising i), ii), iii), iv) and v) as defined above.

The colorations obtained are attractive, aesthetic, intense, strong, chromatic and very fast or persistent with respect to common attacking factors or everyday assaults such as sun, sebum and especially with respect to perspiration, and other hair treatments such as successive shampooing, while at the same time respecting the keratin fibres. The intensity obtained is particularly noteworthy. The same is true for the colour homogeneity or selectivity of the colour.

Within the meaning of the present invention and unless otherwise indicated:
a "direct dye having a disulphide functional group" is a direct dye comprising one or more cationic chromophores which absorb(s) light in the visible spectrum and comprising a disulphide bond: —S—S— between two carbon atoms which is preferably indirectly connected to the chromophore(s) of the dye, i.e. at least one methylene group occurs between the chromophores and the —S—S— functional group;

a "direct dye having a protected thiol functional group" is a direct dye comprising a chromophore and comprising a protected thiol functional group —SY, where Y is a protective group known to a person skilled in the art, such as, for example, those described in the works *"Protective Groups in Organic Synthesis"*, T. W. Greene, published by John Wiley & Sons, NY, 1981, pp. 193-217; "Protecting Groups", P. Kocienski, Thieme, 3rd ed., 2005, chap. 5; and Ullmann's Encyclopedia, *"Peptide Synthesis"*, pp. 4-5, 2005, Wiley-VCH Verlag GmbH & Co. KGaA, Weinheim 10.1002/14356007.a19 157; it being understood that the said protected thiol functional group is preferably indirectly connected to the chromophore of the dye, i.e. at least one methylene group occurs between the chromophore and the —SY functional group;

a "direct dye having a thiol functional group" is a direct dye comprising a chromophore and comprising a thiol functional group —SY', where Y' is i) a hydrogen atom; ii) an alkali metal; iii) an alkaline earth metal; iv) an ammonium group $N^+R^\alpha R^\beta R^\gamma R^\delta$ or a phosphonium group $P^+R^\alpha R^\beta R^\gamma R^\delta$ with $R^\alpha$, $R^\beta$, $R^\gamma$ and $R^\delta$, which are identical or different, representing a hydrogen atom or a ($C_1$-$C_4$)alkyl group preferably comprising a thiol functional group —SH, it being understood that the said thiol functional group is preferably indirectly connected to the chromophore of the dye, i.e. at least one methylene group occurs between the chromophore and the —SY' functional group;

a "chromophore" is a radical resulting from a dye, that is to say a radical resulting from a molecule which absorbs light in the visible region of the radiation visibly perceptible by man, i.e. having an absorption wavelength $\lambda_{abs}$ of between 400 and 800 nm inclusive; the chromophore can be fluorescent, i.e. is capable of absorbing in the UV and visible region at a wavelength $\lambda_{abs}$ of between 250 and 800 nm inclusive and is capable of re-emitting in the visible region at an emission wavelength $\lambda_{em}$ of between 400 and 800 nm inclusive;

a "chromophore" is said to be "quaternized cationic" or "carrying a quaternized cationic group" if it comprises, in its structure, at least one permanent cationic charge composed of at least one atom of quaternized nitrogen (ammonium) or of quaternized phosphorus (phosphonium), preferably of nitrogen;

a group is said to be "carrying a quaternizable cationic group" when it comprises, in its structure, at least one tertiary amine or one tertiary phosphine at the end of a hydrocarbon chain, preferably a $C_1$-$C_{10}$ alkyl chain, and in particular such as —(CR'R")$_p$—N(R$_a$)—R$_b$ with R' and R", which are identical or different, representing a hydrogen atom or a ($C_1$-$C_6$)alkyl group; R$_a$ and R$_b$, which are identical or different, representing a ($C_1$-$C_6$) alkyl group, a monohydroxy($C_1$-$C_6$)alkyl group or a polyhydroxy($C_1$-$C_6$)alkyl group or else R$_a$ and R$_b$ form, together with the nitrogen atom which carries them, a heterocycloalkyl group, such as morpholino, which, once quaternized, will become morpholinium, piperidino, which, once quaternized, will become piperidinium, imidazolyl, which, once quaternized, will become imidazolium or piperazino, which, once quaternized, will become piperazinium; and p representing an integer between 1 and 10 inclusive; preferably, R' and R" representing a hydrogen atom, R$_a$ and R$_b$ represent a ($C_1$-$C_4$)alkyl group and p is between 2 and 5;

the dyes according to the invention comprise one or more chromophores and these dyes are capable of absorbing light at a wavelength $\lambda_{abs}$ of in particular between 400 and 700 nm inclusive;

the "fluorescent" dyes according to the invention are dyes comprising at least one fluorescent chromophore, and these dyes are capable of absorbing in the visible region at a wavelength $\lambda_{abs}$ of in particular between 400 and 800 nm inclusive and of re-emitting in the visible region at a greater wavelength $\lambda_{em}$ than that absorbed of between 400 and 800 nm inclusive. The difference in the absorption and emission wavelength, also known as Stoke's shift, is between 1 nm and 100 nm inclusive. More preferably, the fluorescent dyes are dyes capable of absorbing at a wavelength $\lambda_{abs}$ of between 420 nm and 550 nm inclusive and of re-emitting in the visible region at a wavelength $\lambda_{em}$ of between 470 and 600 nm inclusive;

the chromophores are said to be "different" when they differ in their chemical structure and can be chromophores resulting from different families or from the same family provided that different chemical structures are exhibited: for example, the chromophores can be chosen from the family of the azo dyes but can differ in the chemical structure of the radicals constituting them or in the respective positions of these radicals;

an "alkylene chain" represents an acyclic $C_1$-$C_{20}$ divalent hydrocarbon chain; particularly a $C_1$-$C_6$ chain and more particularly a $C_1$-$C_2$ chain when the chain is linear; optionally substituted by one or more identical or different groups chosen from i) hydroxyl, ii) ($C_1$-$C_2$)alkoxy, iii) (poly)hydroxy($C_2$-$C_4$)alkoxy(di)($C_1$-$C_2$)(alkyl)amino, iv) $R^a$—$Z^a$—$C(Z^b)$—$Z^c$— and v) $R^a$—$Z^a$—$S(O)_t$—$Z^c$—, with $Z^a$ and $Z^b$, which are identical or different, representing an oxygen or sulphur atom or an NR$^{a1}$ group, $Z^c$ representing a bond, an oxygen or sulphur atom or an NR$^a$ group, $R^a$ representing an alkali metal, a hydrogen atom or an alkyl group or else is absent if another part of the molecule is cationic, R$^{a1}$ representing a hydrogen atom or an alkyl group and t having the value 1 or 2; more particularly, the iv) groups are chosen from carboxylate —C(O)O$^-$ or —C(O)OMetal (Metal=alkali metal), carboxyl —C(O)—OH, guanidino H$_2$N—C(NH)—NH—, amidino H$_2$N—C(NH)—, (thio)urea H$_2$N—C(O)—NH— and H$_2$N—C(S)—NH—, aminocarbonyl —C(O)—NR$^{a1}$$_2$ or aminothiocarbonyl —C(S)—NR$^{a1}$$_2$, carbamoyl R$^{a1}$—C(O)—NR$^{a1}$— or thiocarbamoyl R$^{a1}$—C(S)—NR$^{a1}$—, with R$^{a1}$, which are identical or different, representing a hydrogen atom or a ($C_1$-$C_4$) alkyl group;

a "saturated or unsaturated divalent $C_1$-$C_{30}$ hydrocarbon chain which is optionally substituted" represents hydrocarbon chain, in particular a $C_1$-$C_8$ hydrocarbon chain, optionally comprising one or more conjugated or nonconjugated π double bonds; in particular, the hydrocarbon chain is saturated; the said chain is optionally substituted by one or more identical or different groups chosen from i) hydroxyl, ii) ($C_1$-$C_2$)alkoxy, iii) (poly)hydroxy($C_2$-$C_4$)alkoxy(di)($C_1$-$C_2$)(alkyl)amino, iv) $R^a$—$Z^a$—$C(Z^b)$—$Z^c$— and v) $R^a$—$Z^a$—$S(O)_t$—$Z^c$—, with $Z^a$ and $Z^b$, which are identical or different, representing an oxygen or sulphur atom or an NR$^{a1}$ group, $Z^c$ representing a bond, an oxygen or sulphur atom or an NR$^a$ group, R$^a$ representing an alkali metal, a hydrogen atom or an alkyl group or else is absent if another part of the molecule is cationic, R$^{a\prime}$ representing a hydrogen atom or an alkyl group and t having the value 1 or 2; more particularly, the iv) groups are chosen from carboxylate —C(O)O$^-$ or —C(O)OMetal (Metal=alkali metal), carboxyl —C(O)—OH, guanidino H$_2$N—C(NH)—NH—, amidino H$_2$N—C(NH)—, (thio)urea H$_2$N—C(O)—NH— and H$_2$N—C(S)—NH—, aminocarbonyl —C(O)—NR$^{a\prime}_2$ or aminothiocarbonyl —C(S)—NR$^{a\prime}_2$, carbamoyl R$^{a\prime}$—C(O)—NR$^{a\prime}$— or thiocarbamoyl R$^{a\prime}$—C(S)—NR$^{a\prime}$—, with R$^{a\prime}$, which are identical or different, representing a hydrogen atom or a (C$_1$-C$_4$)alkyl group;

the "aryl" or "heteroaryl" radicals or the aryl or heteroaryl part of a radical can be substituted by at least one substituent carried by a carbon atom, chosen from:

- a C$_1$-C$_{16}$, preferably C$_1$-C$_8$, alkyl radical optionally substituted by one or more radicals chosen from the following radicals: hydroxyl, C$_1$-C$_2$ alkoxy, (poly)hydroxy(C$_2$-C$_4$)alkoxy, acylamino or amino substituted by two identical or different C$_1$-C$_4$ alkyl radicals which optionally carry at least one hydroxyl group or it being possible for the two radicals to form, with the nitrogen atom to which they are attached, a saturated or unsaturated 5- to 7-membered, preferably 5- or 6-membered, heterocycle which is optionally substituted and which optionally comprises another heteroatom identical to or different from nitrogen;
- a halogen atom;
- a hydroxyl group;
- a C$_1$-C$_2$ alkoxy radical;
- a (poly)hydroxy(C$_2$-C$_4$)alkoxy radical;
- an amino radical;
- a 5- or 6-membered heterocycloalkyl radical;
- a 5- or 6-membered heteroaryl radical which is optionally cationic, preferably imidazolium, and which is optionally substituted by a (C$_1$-C$_4$)alkyl radical, preferably a methyl radical;
- an amino radical substituted by one or two identical or different C$_1$-C$_6$ alkyl radicals which optionally carry at least:
  i) one hydroxyl group,
  ii) one amino group optionally substituted with one or two optionally substituted C$_1$-C$_3$ alkyl radicals, the said alkyl radicals possibly forming with the nitrogen atom to which they are attached a saturated or unsaturated, optionally substituted 5- to 7-membered heterocycle, optionally comprising at least one other heteroatom identical to or different from nitrogen,
  iii) one quaternary ammonium group —N$^+$R'R''R'''M$^-$, for which R', R'' and R''', which are identical or different, represent a hydrogen atom or a C$_1$-C$_4$ alkyl group and M$^-$ represents the counterion of the corresponding organic or inorganic acid or of the corresponding halide,
  iv) or one 5- or 6-membered heteroaryl radical which is optionally cationic, preferably imidazolium, and which is optionally substituted by a (C$_1$-C$_4$)alkyl radical, preferably a methyl radical;
- an acylamino (—NR—C(O)—R') radical in which the R radical is a hydrogen atom or a C$_1$-C$_4$ alkyl radical optionally carrying at least one hydroxyl group and the R' radical is a C$_1$-C$_2$ alkyl radical;
- a carbamoyl ((R)$_2$N—C(O)—) radical in which the R radicals, which are identical or different, represent a hydrogen atom or a C$_1$-C$_4$ alkyl radical optionally carrying at least one hydroxyl group;
- an alkylsulfonylamino (R'—S(O)$_2$—N(R)—) radical in which the R radical represents a hydrogen atom or a C$_1$-C$_4$ alkyl radical optionally carrying at least one hydroxyl group and the R' radical represents a C$_1$-C$_4$ alkyl radical or a phenyl radical;
- an aminosulphonyl ((R)$_2$N—S(O)$_2$—) radical in which the R radicals, which are identical or different, represent a hydrogen atom or a C$_1$-C$_4$ alkyl radical optionally carrying at least one hydroxyl group,
- a carboxyl radical in the acid or the salified form (preferably with an alkali metal or a substituted or unsubstituted ammonium);
- a cyano group;
- a nitro or nitroso group;
- a polyhaloalkyl group, preferentially trifluoromethyl;

the cyclic or heterocyclic part of a non-aromatic radical may be substituted with at least one substituent chosen from the following groups:

- hydroxyl;
- C$_1$-C$_4$ alkoxy or (poly)hydroxy(C$_2$-C$_4$)alkoxy;
- C$_1$-C$_4$ alkyl;
- alkylcarbonylamino (R—C(O)—N(R')—), in which the R' radical is a hydrogen atom or a C$_1$-C$_4$ alkyl radical optionally carrying at least one hydroxyl group and the R radical is a C$_1$-C$_2$ alkyl radical or an amino radical optionally substituted by one or two identical or different C$_1$-C$_4$-alkyl groups themselves optionally carrying at least one hydroxyl group, it being possible for the said alkyl radicals to form, with the nitrogen atom to which they are attached, a saturated or unsaturated 5- to 7-membered heterocycle which is optionally substituted and which optionally comprises at least one other heteroatom identical to or different from nitrogen;
- alkylcarbonyloxy (R—C(O)—O—), in which the R radical is a C$_1$-C$_4$ alkyl radical or an amino group optionally substituted by one or two identical or different C$_1$-C$_4$ alkyl groups themselves optionally carrying at least one hydroxyl group, it being possible for the said alkyl radicals to form, with the nitrogen atom to which they are attached, a saturated or unsaturated 5- to 7-membered heterocycle which is optionally substituted and which optionally comprises at least one other heteroatom identical to or different from nitrogen;
- alkoxycarbonyl (R-G-C(O)—), in which the R radical is a C$_1$-C$_4$ alkoxyl radical and G is an oxygen atom or an amino group optionally substituted by a C$_1$-C$_4$ alkyl group itself optionally carrying at least one hydroxyl group, it being possible for the said alkyl radical to form, with the nitrogen atom to which they are attached, a saturated or unsaturated 5- to 7-membered heterocycle which is optionally substituted and which optionally comprises at least one other heteroatom identical to or different from nitrogen;
- a cyclic or heterocyclic radical or a nonaromatic part of an aryl or heteroaryl radical can also be substituted by one or more oxo groups;
- a hydrocarbon chain is unsaturated when it comprise one or more double bonds and/or one or more triple bonds;
- an "aryl" radical represents a monocyclic or fused or nonfused polycyclic carbon-based group comprising from 6 to 22 carbon atoms, at least one ring of which is aromatic; preferably, the aryl radical is a phenyl, biphenyl, naphthyl, indenyl, anthracenyl or tetrahydronaphthyl;

a "heteroaryl radical" represents a monocyclic or fused or nonfused polycyclic 5- to 22-membered group which is optionally cationic and which has from 1 to 6 heteroatoms chosen from nitrogen, oxygen, sulphur and selenium atoms, at least one ring of which is aromatic; preferably a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrylyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and its ammonium salt;

a "heterocyclic radical" is a monocyclic or fused or nonfused polycyclic 5- to 22-membered radical which can comprise one or two nonaromatic unsaturations and which comprises from 1 to 6 heteroatoms chosen from nitrogen, oxygen, sulphur and selenium atoms;

a "heterocycloalkyl radical" is a heterocyclic radical comprising at least one saturated ring;

a "cationic heteroaryl radical" is a heteroaryl group as defined above which comprises an endocyclic or exocyclic quaternized cationic group, when the cationic charge is endocyclic, it is included in the electron delocalization by resonance; it concerns, for example, a pyridinium, imidazolium or indolinium group:

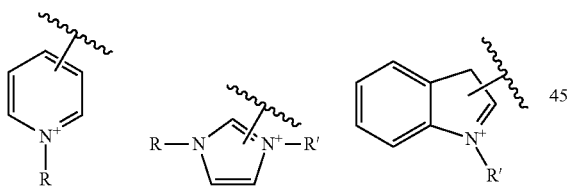

with R and R' being a substituent of heteroaryl as defined above and in particular a (hydroxy)($C_1$-$C_8$) alkyl group, such as methyl;

when the cationic charge is exocyclic, it concerns, for example, an ammonium or phosphonium substituent $R^+$, such as trimethylammonium, occurring outside the heteroaryl, such as pyridinyl, indolyl, imidazolyl, or naphthalimidyl, in question:

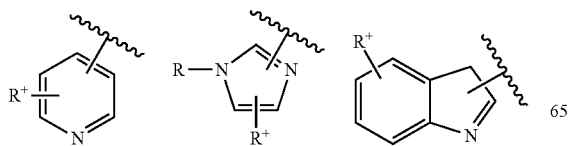

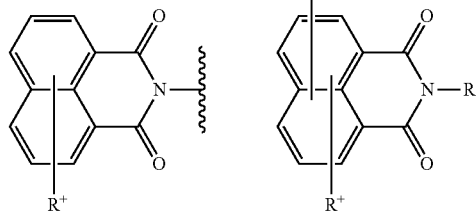

with R a substituent of heteroaryl as defined above and $R^+$ an ammonium $R_aR_bR_cN^+$—, phosphonium $R_aR_bR_cP^+$— or ammonium $R_aR_bR_cN^+$—($C_1$-$C_6$) alkylamino group with $R_a$, $R_b$ and $R_c$, which are identical or different, representing a hydrogen atom or a ($C_1$-$C_8$) alkyl group, such as methyl;

an "cationic aryl having an exocyclic charge" is understood to mean an aryl ring, the quaternized cationic group of which occurs outside the said ring; it concerns in particular an ammonium or phosphonium substituent $R^+$, such as trimethylammonium, occurring outside the aryl, such as phenyl or naphthyl:

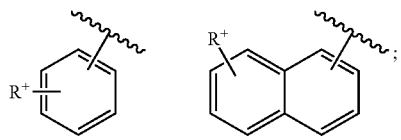

an "alkyl radical" is a linear or branched $C_1$-$C_{20}$, preferably $C_1$-$C_8$, hydrocarbon radical;

an "alkenylene radical" is an unsaturated divalent hydrocarbon radical as defined above which can comprise from 1 to 4 conjugated or nonconjugated —C=C— double bonds; in particular, the alkenylene group comprises 1 or 2 unsaturation(s);

the expression "optionally substituted" assigned to the alkyl radical implies that the said alkyl radical can be substituted by one or more radicals chosen from the following radicals: i) hydroxyl, ii) $C_1$-$C_4$ alkoxy, iii) acylamino, iv) amino optionally substituted by one or two identical or different $C_1$-$C_4$ alkyl radicals, it being possible for the said alkyl radicals to form, with the nitrogen atom which carries them, a 5- to 7-membered heterocycle optionally comprising another heteroatom identical to or different from nitrogen; or v) a quaternary ammonium group —N$^+$R'R"R'"M$^-$ for which R', R" and R'", which are identical or different, represent a hydrogen atom or a $C_1$-$C_4$ alkyl group or else —N$^+$R'R"R'" form a heteroaryl, such as imidazolium, optionally substituted by a ($C_1$-$C_4$)alkyl group, and M$^-$ represents the counterion of the corresponding organic or inorganic acid or of the corresponding halide;

an "alkoxy radical" is an alkyl-oxy radical for which the alkyl radical is a linear or branched $C_1$-$C_6$, preferably $C_1$-$C_8$, hydrocarbon radical;

when the alkoxy group is optionally substituted, this implies that the alkyl group is optionally substituted as defined above;

the "height of tone" is the unit known to hairstyling professionals and published in the work "Science des traitements capillaires" [Science of Hair Treatments] by Charles Zviak, 1988, published by Masson, pp. 215 and 278, the heights of tone range from 1 (black) to 10

(light light blond), one unit corresponding to one tone; the higher the figure, the lighter the shade;

the "dark" keratinous fibre is a keratinous fibre which exhibits a lightness L*, calculated in the C.I.E.L*a*b* system, of less than or equal to 45 and preferably of less than or equal to 40, it furthermore being known that L*=0 is equivalent to black and L*=100 is equivalent to white;

"naturally dark or artificially darkened" hair is hair, the height of tone of which is less than or equal to 6 (dark blond) and preferably less than or equal to 4 (chestnut). Artificially coloured hair is hair, the colour of which has been modified by a colouring treatment, for example a colouring with direct dyes or oxidation dyes;

"thickening polymer" is understood to mean a polymer which, introduced at 1% by weight into an aqueous solution or an aqueous/alcoholic solution comprising 30% of ethanol and at pH=7 or into an oil chosen from liquid petrolatum, isopropyl myristate or cyclopentadimethylsiloxane, makes it possible to achieve a viscosity of at least 100 cPs, preferably 500 cPs, at 25° C. and at a shear rate of 1 s$^{-1}$. This viscosity may be measured using a cone/plate viscometer (Haake R600 rheometer or the like). The thickening polymers can be thickeners of the aqueous phase and/or of the fatty phase, preferably of the aqueous phase;

"organic" thickening polymer is understood to mean a thickening polymer as defined above which is composed of carbon, hydrogen and optionally nitrogen, oxygen, sulphur, halogens, such as fluorine, chlorine or bromine, and phosphorus, alkali metals, such as sodium or potassium, or alkaline earth metals, such as magnesium or calcium. The organic polymers according to the invention do not comprise silicon;

"(poly)ethoxylated" fatty alcohol is understood to mean a fatty alcohol which comprises one or more hydroxyl groups and which carries, in its molecule, one or more ethylene oxide —CH$_2$—CH$_2$—O— groups; fatty alcohol is understood to mean the fatty alcohols comprising between 10 and 200 carbon atoms, preferably C$_8$-C$_{30}$ fatty alcohols;

"organic or inorganic acid salt" is understood to mean more particularly the salts chosen from a salt derived i) from hydrochloric acid HCl, ii) from hydrobromic acid HBr, iii) from sulphuric acid H$_2$SO$_4$, iv) from alkylsulphonic acids Alk-S(O)$_2$OH, such as methylsulphonic acid and ethylsulphonic acid; v) from arylsulphonic acids Ar—S(O)$_2$OH, such as benzenesulphonic acid and toluenesulphonic acid; yl) from citric acid; vii) from succinic acid; viii) from tartaric acid; ix) from lactic acid; x) from alkoxysulphinic acids Alk-O—S(O)OH, such as methoxysulphinic acid and ethoxysulphinic acid; xi) from aryloxysulphinic acids, such as tolueneoxysulphinic acid and phenoxysulphinic acid; xii) from phosphoric acid H$_3$PO$_4$; xiii) from acetic acid CH$_3$C(O)OH; xiv) from triflic acid CF$_3$SO$_3$H and xv) from tetrafluoroboric acid HBF$_4$;

"anionic counterion" is understood to mean an anion or an anionic group resulting from an organic or inorganic acid which counterbalances the cationic charge of the dye; more particularly, the anionic counterion is chosen from i) halides, such as chloride or bromide; ii) nitrates; iii) sulphonates, including (C$_1$-C$_6$)alkylsulphonates Alk-S(O)$_2$O$^-$, such as methylsulphonate or mesylate and ethylsulphonate; iv) arylsulphonates Ar—S(O)$_2$O$^-$, such as benzenesulphonate and toluenesulphonate or tosylate; v) citrate; vi) succinate; vii) tartrate; viii) lactate; ix) alkylsulphates Alk-O—S(O)O$^-$, such as methylsulphate and ethylsulphate; x) arylsulphates Ar—O—S(O)O$^-$, such as benzenesulphate and toluenesulphate; xi) alkoxysulphates Alk-O—S(O)$_2$O$^-$, such as methoxysulphate and ethoxysulphate; xii) aryloxysulphates Ar—O—S(O)$_2$O$^-$; xiii) phosphates O=P(OH)$_2$—O$^-$, O=P(O$^-$)$_2$—OHO=P(O$^-$)$_3$ and HO—[P(O)(O$^-$)]$_w$—P(O)(O$^-$)$_2$, with w being an integer; xiv) acetate; xv) triflate; xvi) borates, such as tetrafluoroborate, xvii) sulphate (O=)$_2$S(O$^-$)$_2$ or SO$_4^{2-}$ and hydrogen sulphate HSO$_4^-$;

the anionic counterion resulting from an organic or inorganic acid provides for the electrical neutrality of the molecule; thus, it is understood that, when the anion comprises several anionic charges, then the same anion can be used for the electrical neutrality of several cationic groups in the same molecule or else can be used for the electrical neutrality of several molecules; for example, a disulphide dye of formula (I), which comprises two cationic chromophores, can comprise either two "singly charged" anionic counterions or one "doubly charged" anionic counterion, such as (O=)$_2$S(O$^-$)$_2$ or O=P(O$^-$)$_2$—OH;

furthermore, the addition salts which can be used in the context of the invention are chosen in particular from the addition salts with a cosmetically acceptable base, such as the basifying agents as defined below, for example alkali metal hydroxides, such as sodium hydroxide or potassium hydroxide, aqueous ammonia, amines or alkanolamines;

the expression "at least one" is equivalent to "one or more"; and the expression "inclusive" for a range of concentrations means that the limits of the range come within the defined interval.

1). The Composition of the Invention

The composition according to the invention is cosmetic, i.e. it occurs in a cosmetic medium and comprises:
i) at least one cationic direct dye having a disulphide functional group or a thiol or protected thiol functional group;
ii) at least one thickening organic polymer;
iii) at least one (poly)ethoxylated alcohol and/or at least one nonionic surfactant;
iv) at least one alkaline agent; and
v) at least one reducing agent.

The Cosmetic Medium:

"Cosmetic medium" is understood to mean a medium appropriate for the dyeing of keratinous fibres, also known as dyeing vehicle, which is a cosmetic medium generally composed of water or of a mixture of water and one or more organic solvents or of a mixture or organic solvents. Preferably, the composition comprises water and in a content of in particular between 5% and 95% inclusive, with respect to the total weight of the composition.

"Organic solvent" is understood to mean an organic substance capable of dissolving another substance without modifying it chemically.

The Organic Solvents:

Mention may be made, as organic solvent, for example, of lower C$_1$-C$_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, aromatic alcohols, such as benzyl alcohol or phenoxyethanol, and their mixtures.

The organic solvents are preferably present in proportions preferably of between approximately 0.1 and 40% by weight inclusive, with respect to the total weight of the dyeing composition, and more preferably between 1 and 30% by weight approximately and more particularly still of between 5 and 25% by weight inclusive, with respect to the total weight of the composition.

i) Direct Dyes Having a Disulphide or Thiol Functional Group of the Invention:

The direct dye or dyes having a disulphide, thiol or protected thiol functional group employed in the invention is/are of formula (I) as defined above.

According to a specific form of the invention, the dyes (I) are disulphide dyes, i.e. dyes for which U represents the following radical a) —S—C'$_{sat}$—(X')$_p$-A', and more particularly the dyes of formula (I) are symmetrical, i.e. are such that A=A', C$_{sat}$=C'$_{sat}$, X=X' and p=p'.

According to another specific form of the invention, the dyes of formula (I) having the thiol functional group are as defined above, i.e. U representing the radical b) Y.

Another specific embodiment of the invention is concerned with fluorescent dyes having a disulphide, thiol or protected thiol functional group.

i). 1) Y:

According to a specific embodiment of the invention, the direct dye of formula (I) is a thiol dye, i.e. Y represents i) a hydrogen atom.

In accordance with another specific embodiment of the invention, in the abovementioned formula (I), Y is a protective group known to a person skilled in the art, such as, for example, those described in the works "*Protective Groups in Organic Synthesis*", T. W. Greene, published by John Wiley & Sons, NY, 1981, pp. 193-217; "*Protecting Groups*", P. Kocienski, Thieme, 3rd ed., 2005, chap. 5, and Ullmann's Encyclopedia, "*Peptide Synthesis*", pp. 4-5, 2005, Wiley-VCH Verlag GmbH & Co. KGaA, Weinheim, 10.1002/14356007.a19 157.

In particular, Y represents a protective group for the thiol functional group chosen from the following radicals:
- ($C_1$-$C_4$)alkylcarbonyl;
- ($C_1$-$C_4$)alkylthiocarbonyl;
- ($C_1$-$C_4$)alkoxycarbonyl;
- ($C_1$-$C_4$)alkoxythiocarbonyl;
- ($C_1$-$C_4$)alkylthio-thiocarbonyl;
- (di)($C_1$-$C_4$)(alkyl)aminocarbonyl;
- (di)($C_1$-$C_4$)(alkyl)aminothiocarbonyl;
- arylcarbonyl, such as phenylcarbonyl;
- aryloxycarbonyl;
- aryl($C_1$-$C_4$)alkoxycarbonyl;
- (di)($C_1$-$C_4$)(alkyl)aminocarbonyl, such as dimethylaminocarbonyl;
- ($C_1$-$C_4$)(alkyl)arylaminocarbonyl;
- carboxyl;
- $SO_3^-M^+$, with $M^+$ representing an alkali metal, such as sodium or potassium, or else a counterion of the cationic chromophore A and $M^+$ are absent;
- optionally substituted aryl, such as phenyl, dibenzosuberyl or 1,3,5-cyclo-heptatrienyl;
- optionally substituted heteroaryl; including in particular the following, cationic or noncationic, heteroaryls comprising from 1 to 4 heteroatoms:
  i) 5-, 6- or 7-membered monocyclic, such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepinyl, azepinium, oxazepinyl, oxazepinium, thiepinyl, thiepinium, imidazolyl or imidazolium;
  ii) 8- to 11-membered bicyclic, such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium or thienocycloheptadienyl, these mono- or bicyclic groups optionally being substituted by one or more groups, such as ($C_1$-$C_4$) alkyl groups, for example the methyl group, or polyhalo($C_1$-$C_4$)alkyl groups, such as the trifluoromethyl group;
  iii) or the following tricyclic ABC group:

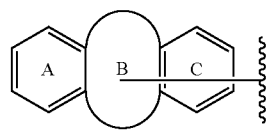

in which the two rings A and C optionally comprise a heteroatom and the ring B is a 5-, 6- or 7-membered ring, particularly a 6-membered ring, and comprises at least one heteroatom, such as piperidyl or pyranyl;
- optionally substituted and optionally cationic heterocycloalkyl, the heterocycloalkyl group representing in particular a saturated or partially saturated 5-, 6- or 7-membered monocyclic group comprising from 1 to 4 heteroatoms chosen from oxygen, sulphur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl or di/tetrahydropyrimidinyl, these groups optionally being substituted by one or more groups, such as ($C_1$-$C_4$) alkyl, oxo or thioxo; or the heterocycle representing the following group:

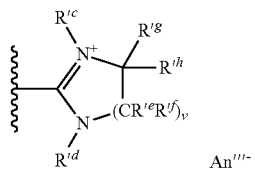

in which $R'^C$, $R'^d$, $R'^e$, $R'^f$, $R'^g$ and $R'^h$, which are identical or different, represent a hydrogen atom or a ($C_1$-$C_4$)alkyl group, or else two groups, $R'^g$ with $R'^h$ and/or $R'^e$ with $R'^f$, form an oxo or thioxo group, or else $R'^g$ with $R'^e$ together form a cycloalkyl; and v represents an integer between 1 and 3 inclusive; preferably, $R'^c$ to $R'^h$ represent a hydrogen atom; and An'''$^-$ represents a counterion; —C(NR'$^c$R'$^d$)=N$^+$R'$^e$R'$^f$An'''$^-$, with $R'^C$, $R'^d$, $R'^e$ and $R'^f$, which are identical or different, representing a hydrogen atom or a ($C_1$-$C_4$)alkyl group; preferably, $R^{lc}$ to $R^{lf}$ represent a hydrogen atom; and $An'''^-$ represents a counterion;

—C($NR^{lc}R^{ld}$)=$NR^{le}$, with $R^{lc}$, $R^{ld}$ and $R^{le}$ as defined above;

optionally substituted (di)aryl($C_1$-$C_4$)alkyl, such as 9-anthracenylmethyl, phenylmethyl or diphenylmethyl optionally substituted by one or more groups chosen in particular from ($C_1$-$C_4$)alkyl, ($C_1$-$C_4$)alkoxy, such as methoxy, hydroxyl, alkylcarbonyl or (di)($C_1$-$C_4$)(alkyl)amino, such as dimethylamino;

optionally substituted (di)heteroaryl($C_1$-$C_4$)alkyl; the heteroaryl group is in particular cationic or nonactionic, is monocyclic and comprises 5 or 6 ring members and from 1 to 4 heteroatoms chosen from nitrogen, oxygen and sulphur, such as the pyrrolyl, furanyl, thiophenyl, pyridyl, pyridyl N-oxide, such as 4-pyridyl or 2-pyridyl N-oxide, pyrylium, pyridinium or triazinyl groups, optionally substituted by one or more groups, such as alkyl, particularly methyl; advantageously, the (di)heteroaryl($C_1$-$C_4$) alkyl is (di)heteroarylmethyl or (di)heteroarylethyl;

$CR^1R^2R^3$, with $R^1$, $R^2$ and $R^3$, which are identical or different, representing a halogen atom or a group chosen from:
($C_1$-$C_4$)alkyl;
—($C_1$-$C_4$)alkoxy;
optionally substituted aryl, such as phenyl optionally substituted by one or more groups, such as ($C_1$-$C_4$)alkyl, ($C_1$-$C_4$)alkoxy or hydroxyl;
optionally substituted heteroaryl, such as thiophenyl, furanyl, pyrrolyl, pyranyl, pyridyl, optionally substituted by a ($C_1$-$C_4$)alkyl group;
P($Z^1$)$R^{l1}R^{l2}R^{l3}$, with $R^{l1}$ and $R^{l2}$, which are identical or different, representing a hydroxyl, ($C_1$-$C_4$)alkoxy or alkyl group, $R^{l3}$ representing a hydroxyl or ($C_1$-$C_4$)alkoxy group and $Z^1$ representing an oxygen or sulphur atom;
a sterically hindered ring; and
optionally substituted alkoxyalkyl, such as methoxymethyl (MOM), ethoxyethyl (EOM) and isobutoxymethyl.

According to a specific embodiment, the protected thiol dyes of formula (I) comprise a Y group chosen from i) cationic, aromatic, 5- or 6-membered monocyclic heteroaryl comprising from 1 to 4 heteroatoms chosen from oxygen, sulphur and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium or imidazolium; ii) cationic 8- to 11-membered bicyclic heteroaryl, such as indolinium, benzimidazolium, benzoxazolium or benzothiazolium, these mono- or bicyclic heteroaryl groups optionally being substituted by one or more groups, such as alkyl, for example methyl, or polyhalo($C_1$-$C_4$)alkyl, for example trifluoromethyl; iii) or the following heterocyclic group:

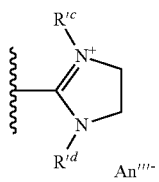

in which $R^{lc}$ and $R^{ld}$, which are identical or different, represent a hydrogen atom or a ($C_1$-$C_4$)alkyl group; preferably, $R^{lc}$ to $R^{ld}$ represent a ($C_1$-$C_4$)alkyl group, such as methyl; and $An'''^-$ represents a counterion.

In particular, Y represents a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium, imidazolium, benzimidazolium, benzoxazolium or benzothiazolium, these groups optionally being substituted by one or more ($C_1$-$C_4$)alkyl groups, in particular methyl.

In particular, Y represents a protective group, such as:
($C_1$-$C_4$)alkylcarbonyl, such as methylcarbonyl or ethylcarbonyl;
arylcarbonyl, such as phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl, such as dimethylaminocarbonyl;
($C_1$-$C_4$)(alkyl)arylaminocarbonyl; optionally substituted aryl, such as phenyl;
5- or 6-membered monocyclic heteroaryl, such as imidazolyl or pyridyl;
cationic 5- or 6-membered monocyclic heteroaryl, such as pyrylium, pyridinium, pyrimidinium, pyrazinium, pyridazinium, triazinium or imidazolium; these groups optionally being substituted by one or more identical or different ($C_1$-$C_4$)alkyl groups, such as methyl;
cationic 8- to 11-membered bicyclic heteroaryl, such as benzimidazolium or benzoxazolium; these groups optionally being substituted by one or more identical or different ($C_1$-$C_4$)alkyl groups, such as methyl;
cationic heterocycle of following formula:

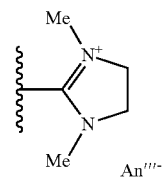 [SMILES: *C1=[N+](C)CCN1C]

—C($NH_2$)=$N^+H_2An'''^-$; with $An'''^-$ being an anionic counterion as defined above;
—C($NH_2$)=NH;
$SO_3^-M^+$, with $M^+$ representing an alkali metal, such as sodium or potassium.

i). 2) $C_{sat}$ and $C'_{sat}$:

As indicated above, in the formula (I), $C_{sat}$ and $C'_{sat}$, represent, independently of one another, a linear or branched or cyclic $C_1$-$C_{18}$ alkylene chain which is optionally substituted.

Mention may be made, as substituent, of the following groups: i) amino, ii) ($C_1$-$C_4$)alkylamino, iii) di($C_1$-$C_4$)alkylamino or iv) $R^a$—$Z^a$—C($Z^b$)—$Z^c$—, in which $Z^a$ and $Z^b$, which are identical or different, represent an oxygen or sulphur atom or an $NR^{a'}$ group, $Z^c$ represents a bond, an oxygen or sulphur atom or an $NR^a$ group, $R^a$ represents an alkali metal, a hydrogen atom or a $C_1$-$C_4$ alkyl group and $R^{a'}$ represents a hydrogen atom or a $C_1$-$C_4$ alkyl group; more particularly, the groups iv) are chosen from carboxylate —C(O)$O^-$ or —C(O)OMetal (Metal=alkali metal), carboxyl —C(O)—OH, guanidino $H_2N$—C(NH)—NH—, amidino H₂N—C(NH)—, (thio)urea H₂N—C(O)—NH— and H₂N—C(S)—NH—, aminocarbonyl —C(O)—NR$^{a'}_2$ or aminothiocarbonyl —C(S)—NR$^{a'}_2$, carbamoyl R$^{a'}$—C(O)—NR$^{a'}$— or thiocarbamoyl R$^{a'}$—C(S)—NR$^{a'}$—, with R$^{a'}$, which are identical or different, representing a hydrogen atom or a (C₁-C₄)alkyl group; the said substituent or substituents are preferably present on the carbon in the β or γ position with respect to the sulphur atoms of the disulphide, thiol or protected thiol group.

Preferably, in the case of formula (I), $C_{sat}$ and $C'_{sat}$ represent a —(CH₂)$_k$— chain with k being an integer between 1 and 8 inclusive.

i). 3) X and X':

In accordance with a specific embodiment of the invention, in the abovementioned formula (I), when p and p' are equal to 1, X and X', which are identical or different, represent the following sequence:

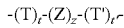

the said sequence being symmetrically connected in the formula (I) as follows:

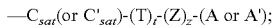

in which:

T and T', which are identical or different, represent one or more radicals or their combinations chosen from: —O—; —S—; —N(R)—; —N⁺(R)(R°)—; —S(O)—; —S(O)₂—; —C(O)—; with R and R°, which are identical or different, representing a hydrogen atom or a C₁-C₄ alkyl, C₁-C₄ hydroxyalkyl or aryl(C₁-C₄)alkyl radical; and a cationic or noncationic heterocycloalkyl or heteroaryl radical which is preferably monocyclic, which preferably comprises two heteroatoms (more preferably two nitrogen atoms) and which preferably comprises from 5 to 7 ring members, more preferably imidazolium;

the indices t and t', which may be identical or different, are equal to 0 or 1;

Z represents:
—(CH₂)$_m$—, with m an integer between 1 and 8;
—(CH₂CH₂O)$_q$— or —(OCH₂CH₂)$_q$—, in which q is an integer between 1 and 5 inclusive;
an aryl, alkylaryl or arylalkyl radical, the alkyl radical of which is a C₁-C₄ alkyl radical and the aryl radical of which is preferably a C₆ aryl radical, optionally being substituted by at least one SO₃M group with M representing a hydrogen atom, an alkali metal or an ammonium group substituted by one or more identical or different and linear or branched C₁-C₁₈ alkyl radicals optionally carrying at lest one hydroxyl;

z is 0 or 1.

Moreover, according to one particular embodiment of the invention, Z represents:

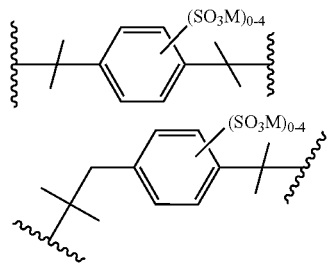

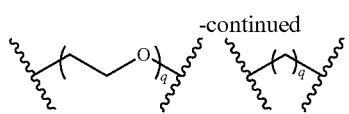

where M represents a hydrogen atom, an alkali metal or an ammonium group or an ammonium group substituted by one or more identical or different and linear or branched C₁-C₁₀ alkyl radicals optionally carrying at least one hydroxyl; 0-4 represents an integer between 0 and 4 inclusive and q represents an integer between 1 and 6 inclusive.

i). 4). A and A':

The A and/or A' radicals of the formula (I) comprise at least one quaternized cationic chromophore or at least one chromophore carrying a quaternized or quaternizable cationic group.

According to a preferred embodiment of the invention, the dye (I) according to the invention is a disulphide and comprises identical quaternized cationic chromophores A and A'.

More particularly, the dye of formula (I) according to the invention is a disulphide and is symmetrical, i.e. comprises a C₂ axis of symmetry, i.e. the formula (I) is such that:

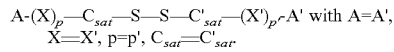

Mention may be made, as chromophores of use in the present invention, of those resulting from the following dyes: acridines; acridones; anthranthrones; anthrapyrimidines; anthraquinones; azines; (poly)azos; hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bisisoindolines; carboxanilides; coumarins; cyanines, such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids, such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, in particular nitro (hetero)aromatics; oxadiazoles; oxazines; perylones; perynones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaraines; tetrazoliums; thiazines; thioindigos; thiopyronines; triarylmethanes or xanthenes.

Mention may in particular be made, for cationic azo chromophores, of those resulting from the cationic dyes described in the *Kirk Othmer Encyclopedia of Chemical Technology*, "Dyes, Azo", J. Wiley & Sons, updated on 19 Apr. 2010.

Mention may be made, among the azo chromophores A and/or A' which can be used according to the invention, of the radicals resulting from the cationic azo dyes described in Patent Applications WO 95/15144, WO 95/01772 and EP-714 954.

According to a preferred embodiment of the invention, the coloured chromophore A and/or A' is chosen from cationic chromophores, preferably those resulting from the dyes known as "basic dyes".

Mention may be made, among azo chromophores, of those described in the Colour Index International, 3rd edition, in particular the following compounds:

Basic Red 22
Basic Red 76
Basic Yellow 57
Basic Brown 16
Basic Brown 17

Among the cationic quinone chromophores A and/or A', those mentioned in the abovementioned Colour Index International are suitable and mention may be made, among these, inter alia, of the radicals resulting from the following dyes:

Basic Blue 22
Basic Blue 99

Among the cationic azine chromophores A and/or A', those listed in the Colour Index International are suitable, for example the radicals resulting from the following dyes:

Basic Blue 17
Basic Red 2.

Mention may be made, among the cationic triarylmethane chromophores A and/or A' which can be used according to the invention, in addition to those listed in the Colour Index, of the radicals resulting from the following dyes:

Basic Green 1
Basic Violet 3
Basic Violet 14
Basic Blue 7
Basic Blue 26.

Mention may also be made of the cationic chromophores resulting from the dyes described in the documents U.S. Pat. No. 5,888,252, EP 1 133 975, WO 03/029359, EP 860 636, WO 95/01772, WO 95/15144 and EP 714 954. Mention may also be made of those listed in the encyclopaedia, "The chemistry of synthetic dyes", by K. Venkataraman, 1952, Academic Press, Vol. 1 to 7, in "Kirk Othmer's Encyclopaedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons.

Preferably, the chromophores A and/or A' are chosen from those resulting from dyes of azo and hydroazono type.

According to a specific embodiment, the A and/or A' radicals in the formula (I) comprise at least one cationic azo chromophore resulting from dyes described in EP 850 636, FR 2 788 433, EP 920 856, WO 9948465, FR 2 757 385, EP 850 637, EP 918 053, WO 9744004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 0166646, U.S. Pat. No. 5,708,151, WO 9501772, WO 515144, GB 1 195 386, U.S. Pat. Nos. 3,524,842, 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

According to one alternative form, A and/or A' of the formula (I) comprise at least one cationic radical carried by or included in at least one of the chromophores.

Preferably, the cationic radical is a quaternary ammonium; more preferentially, the cationic charge is endocyclic.

These cationic radicals are, for example, a cationic radical:
having an exocyclic (di/tri)($C_1$-$C_8$)alkylammonium charge, or
having an endocyclic charge, such as the following cationic heteroaryl groups: acridinium, benzimidazolium, benzobistriazolium, benzopyrazolium, benzopyridazinium, benzoquinolium, benzothiazolium, benzotriazolium, benzoxazolium, bipyridinium, bistetrazolium, dihydrothiazolium, imidazopyridinium, imidazolium, indolium, isoquinolium, naphthoimidazolium, naphthooxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the following cationic hydrazono chromophores of formulae (II) to (III') and of the following cationic azo chromophores (IV), (IV'), (V) and (V'):

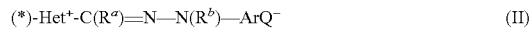 (II)

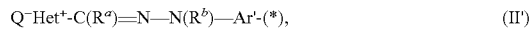 (II')

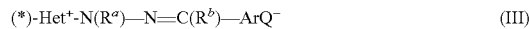 (III)

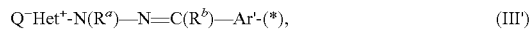 (III')

 (IV)

 (IV')

 (V)

 (V')

formulae (II) to (V') with:
Het$^+$ representing a cationic heteroaryl radical, preferably having an endocyclic cationic charge, such as imidazolium, indolium, or pyridinium, optionally substituted preferably by at least one ($C_1$-$C_8$)alkyl group, such as methyl;
Ar$^+$ representing an aryl radical, such as phenyl or naphthyl, having an exocyclic cationic charge, preferably ammonium, particularly tri($C_1$-$C_8$)alkylammonium, such as trimethylammonium;
Ar representing an aryl group, especially phenyl, optionally substituted, preferentially by one or more electron-donating groups, such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) by a hydroxyl group, iv) aryl($C_1$-$C_8$) alkylamino, v) optionally substituted N—($C_1$-$C_8$)alkyl-N-aryl($C_1$-$C_8$)alkylamino or alternatively Ar represents a julolidine group;
Ar' being an optionally substituted divalent (hetero) arylene group, such as phenylene, particularly paraphenylene or naphthalene, which are optionally substituted, preferably by one or more ($C_1$-$C_8$)alkyl, hydroxyl or ($C_1$-$C_8$)alkoxy groups;
Ar'' being an optionally substituted (hetero)aryl group, such as phenyl or pyrazolyl, which are optionally substituted, preferably by one or more $(C_1-C_8)$alkyl, hydroxyl, $(di)(C_1-C_8)(alkyl)$amino, $(C_1-C_8)$alkoxy or phenyl groups;

$R^a$ and $R^b$, which are identical or different, representing a hydrogen atom or a $(C_1-C_8)$alkyl group which is optionally substituted, preferably by a hydroxyl group; or alternatively the substituent $R^a$ with a substituent of Het$^+$ and/or $R^b$ with a substituent of Ar forming, together with the atoms which carry them, a (hetero) cycloalkyl;

$R^a$ and $R^b$ particularly representing a hydrogen atom or a $(C_1-C_4)$alkyl group optionally substituted by a hydroxyl group;

$Q^-$ representing an organic or inorganic anionic counterion, such as a halide or an alkyl sulphate;

(*) representing the part of the chromophore connected to the remainder of the molecule of formula (I).

Mention may in particular be made of the chromophores having an endocyclic azo or hydrazono cationic charge of formulae (II) to (IV'), as defined above, more particularly those of formula (II) to (IV') resulting from the dyes described in Patent Applications WO 95/15144, WO 95/01772 and EP-714954. Preferably the following chromophores:

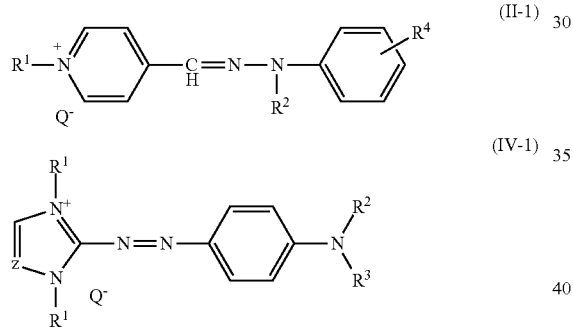

formulae (II-1) and (IV-1) with:
$R^1$ representing a $(C_1-C_4)$alkyl group, such as methyl;
$R^2$ and $R^3$, which are identical or different, representing a hydrogen atom or a $(C_1-C_4)$alkyl group, such as methyl; and
$R^4$ representing a hydrogen atom or an electron-donating group, such as $(C_1-C_8)$alkyl, optionally substituted, $(C_1-C_8)$alkoxy, optionally substituted, and $(di)(C_1-C_8)(alkyl)$amino, optionally substituted on the alkyl group or groups by a hydroxyl group; in particular $R^4$ is a hydrogen atom;
Z representing a CH group or a nitrogen atom, preferentially CH,
$Q^-$ being as defined above;
it being understood that the chromophore (II-1) or (IV-1) is connected to the remainder of the molecule of formula (I) via $R^2$, $R^1$ or $R^4$, in which case one of the hydrogen atoms of $R^2$, $R^1$ or $R^4$ is replaced with X or X', if p=1 or p'=1, or else with $C_{sat}$ or $C_{sat'}$ if p=0 or p'=0.

In particular, the chromophores (II-1) and (IV-1) result from Basic Red 51, Basic Yellow 87 and Basic Orange 31, or their derivatives:

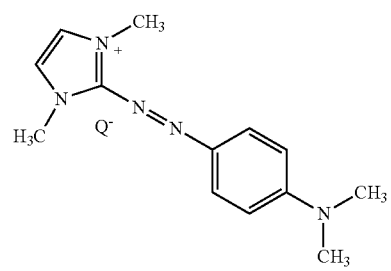

Basic Red 51

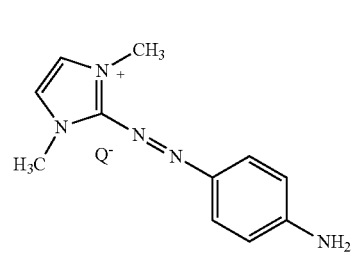

Basic Orange 31

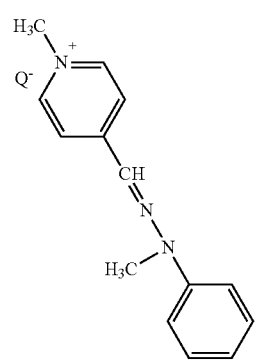

Basic Yellow 87 with $Q^-$ a an anionic counterion as defined above, particularly a halide, such as chloride, or an alkyl sulphate, such as methyl sulphate or mesylate.

According to a specific embodiment of the invention, the dye of formula (I) is fluorescent, i.e. it comprises at least one fluorescent chromophore as defined above.

Mention may be made, as fluorescent chromophores A and/or A' of use in the present invention, of the radicals resulting from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), diketopyrrolopyrroles, fluorindines, (poly)methines (in particular cyanines and styryls/hemicyanines), naphthalimides, naphthanilides, naphthylamine (such as dansyls), oxadiazoles, oxazines, perylones, perynones, perylenes, polyenes/carotenoids, squaraines, stilbenes or xanthenes.

Mention may also be made of the fluorescent dyes A and/or A' described in the documents EP 1 133 975, WO 03/029359, EP 860 636, WO 95/01772, WO 95/15144 and EP 714 954 and those listed in the encyclopaedia "*The chemistry of synthetic dyes*", by K. Venkataraman, 1952, Academic Press, Vol 1 to 7, in "*Kirk Othmer's Encyclopaedia of Chemical Technology*", in the chapter "Dyes and Dye Intermediates", 1993, Wiley and Sons, in various chapters of "*Ullmann's Encyclopedia of Industrial Chemistry*", 7th edition, Wiley and Sons, and in *The Handbook—A Guide to Fluorescent Probes and Labeling Technologies*, 10th Ed., Molecular Probes/Invitrogen—Oregon 2005, distributed on the Internet or in the preceding printed editions.

According to a preferred alternative form of the invention, the fluorescent chromophore A and/or A' is cationic and comprises at least one quaternary ammonium radical, such as those resulting from the polymethine dyes of following formulae (VI) and (VI'):

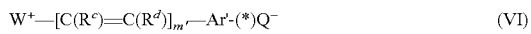  (VI)

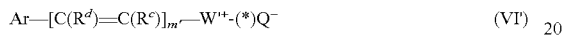  (VI')

formulae (VI) and (VI') with:

$W^+$ representing a cationic heterocyclic or heteroaryl group, particularly comprising a quaternary ammonium optionally substituted by one or more $(C_1-C_8)$alkyl groups optionally substituted in particular by one or more hydroxyl groups;

$Q'^+$ representing a divalent heterocyclic or heteroaryl radical as defined for $W^+$;

Ar representing an aryl group, such as phenyl or naphthyl, optionally substituted preferably by i) one or more halogen atoms, such as fluorine or chlorine; ii) one or more $(C_1-C_8)$alkyl groups, preferably $(C_1-C_4)$alkyl groups, such as methyl; iii) one or more hydroxyl groups; iv) one or more $(C_1-C_8)$alkoxy groups, such as methoxy; v) one or more hydroxy$(C_1-C_8)$alkyl groups, such as hydroxyethyl; vi) one or more amino or (di)$(C_1-C_8)$alkylamino groups, preferably with the alkyl part a $(C_1-C_4)$alkyl group, optionally substituted by one or more hydroxyls, such as (di)hydroxyethylamino; vii) one or more acylamino groups; viii) one or more heterocycloalkyl groups, such as piperazinyl or piperidinyl, or 5- or 6-membered heteroaryl groups, such as pyrrolidinyl, pyridinyl and imidazolinyl;

Ar' being a divalent aryl radical as defined for Ar;

m' representing an integer between 1 and 4 inclusive; in particular, m has the value 1 or 2, more preferably 1;

$R^c$ and $R^d$, which are identical or different, representing a hydrogen atom or an optionally substituted $(C_1-C_8)$ alkyl, preferably $(C_1-C_4)$alkyl, group or else $R^c$, contiguous with $W^+$ or $W'^+$, and/or $R^d$, contiguous with Ar or Ar', forming, with the atoms which carry them, a (hetero)cycloalkyl; in particular, $R^c$ is contiguous with $W^+$ or $W'^+$ and forms a (hetero)cycloalkyl, such as cyclohexyl;

$Q^-$ being an organic or inorganic anionic counterion as defined above;

(*) representing the part of the chromophore connected to the remainder of the formula (I).

According to another alternative form, the disulphide, thiol or protected thiol dye is a quaternized or quaternizable fluorescent dye such as in the formula (I) with p and p' equal to 1 and A and/or A' representing a naphthalimidyl radical optionally carrying an exocyclic cationic charge of formula (VII) or (VII'):

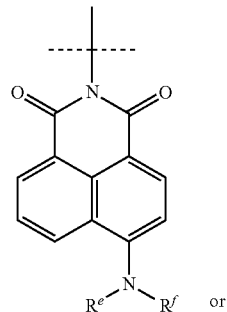  (VII)

or

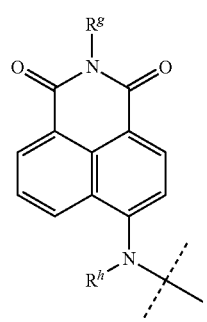  (VII')

in which formulae (VII) and (VII'):

$R^e$, $R^f$, $R^g$, and $R^h$, which are identical or different, represent a hydrogen atom or a $C_1-C_6$ alkyl group which is optionally substituted, preferably by a di$(C_1-C_6)$alkylamino or tri$(C_1-C_6)$alkylammonium group, such as trimethylammonium;

† represents the bond which connects the naphthalimidyl radical to the remainder of the molecule via X or X', if p=1 or p'=1, or else via $C_{sat}$ or $C_{sat'}$, if p=0 or p'=0.

According to one embodiment of the invention, p=1, z=t'=0, t=1 and T represents —N(R)—, preferably in the para position on Ar with respect to the olefin functional group —C($R^c$)=C($R^d$)—.

In one alternative form in particular, p=1, z=t'=0, t=1 and T represents —N(R)—, preferably in the para position on Ar with respect to the styryl functional group —C($R^c$)=C($R^d$)—, and T' represents an —N(R)—, —N$^+$(R)($R^o$)— or imidazolium group.

Preferably, $W^+$ or $W'^+$ is an imidazolium, pyridinium, benzimidazolium, pyrazolium, benzothiazolium and quinolinium optionally substituted by one or more identical or different $C_1-C_4$ alkyl radicals.

According to a particularly preferred embodiment of the invention, A and/or A' represent the chromophore (VI') as defined above with m'=1, Ar representing a phenyl group substituted in the para position with respect to the styryl group —C($R^d$)=C($R^c$)— by a (di)(hydroxy)($C_1-C_6$)(alkyl) amino group, such as dihydroxy($C_1-C_4$)alkylamino, and representing an imidazolium or pyridinium group, preferably an ortho- or para-pyridinium group.

Mention may be made, as examples of dyes of the invention, of the disulphide dyes chosen from the formulae (VIII) to (XIV) and the thiol or protected thiol dyes chosen from the following formulae (VIII') to (XIV'):

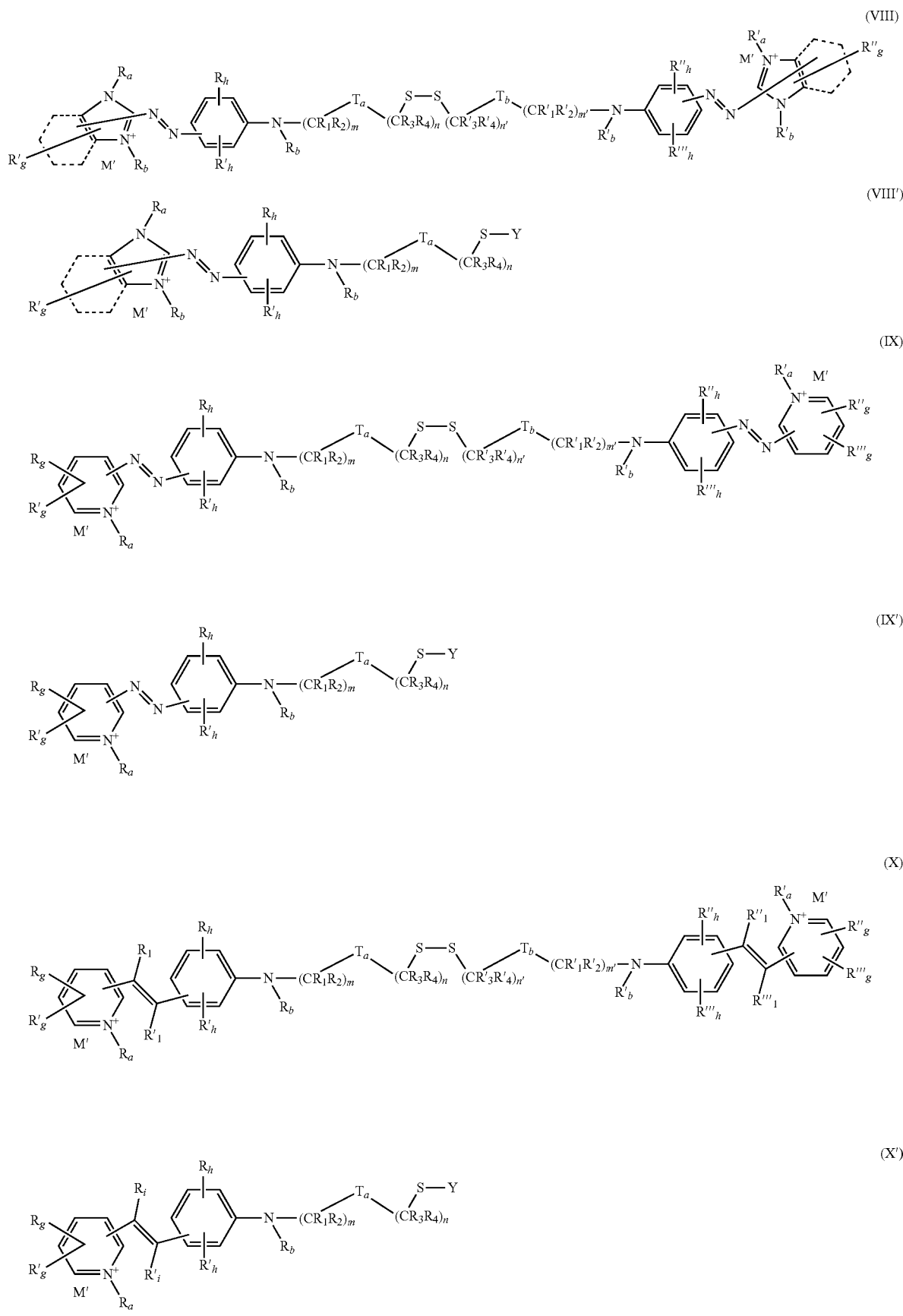

-continued
(XI)
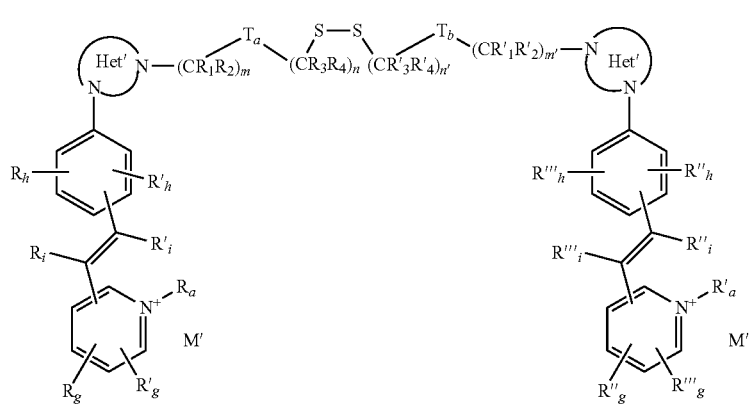
(XI')
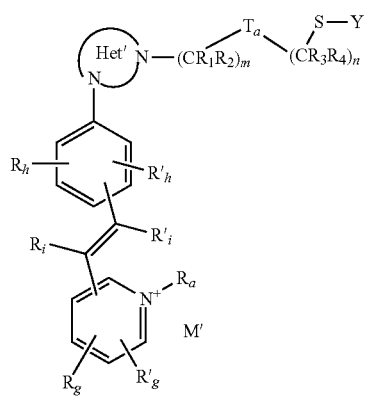
(XII)
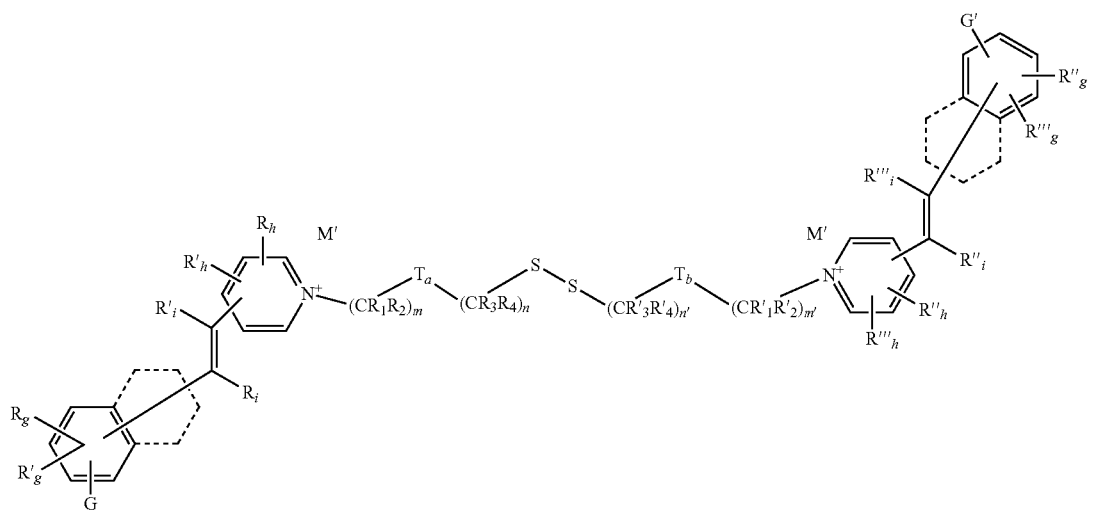
(XII')
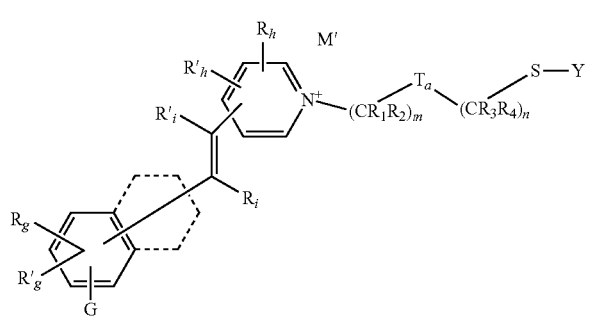

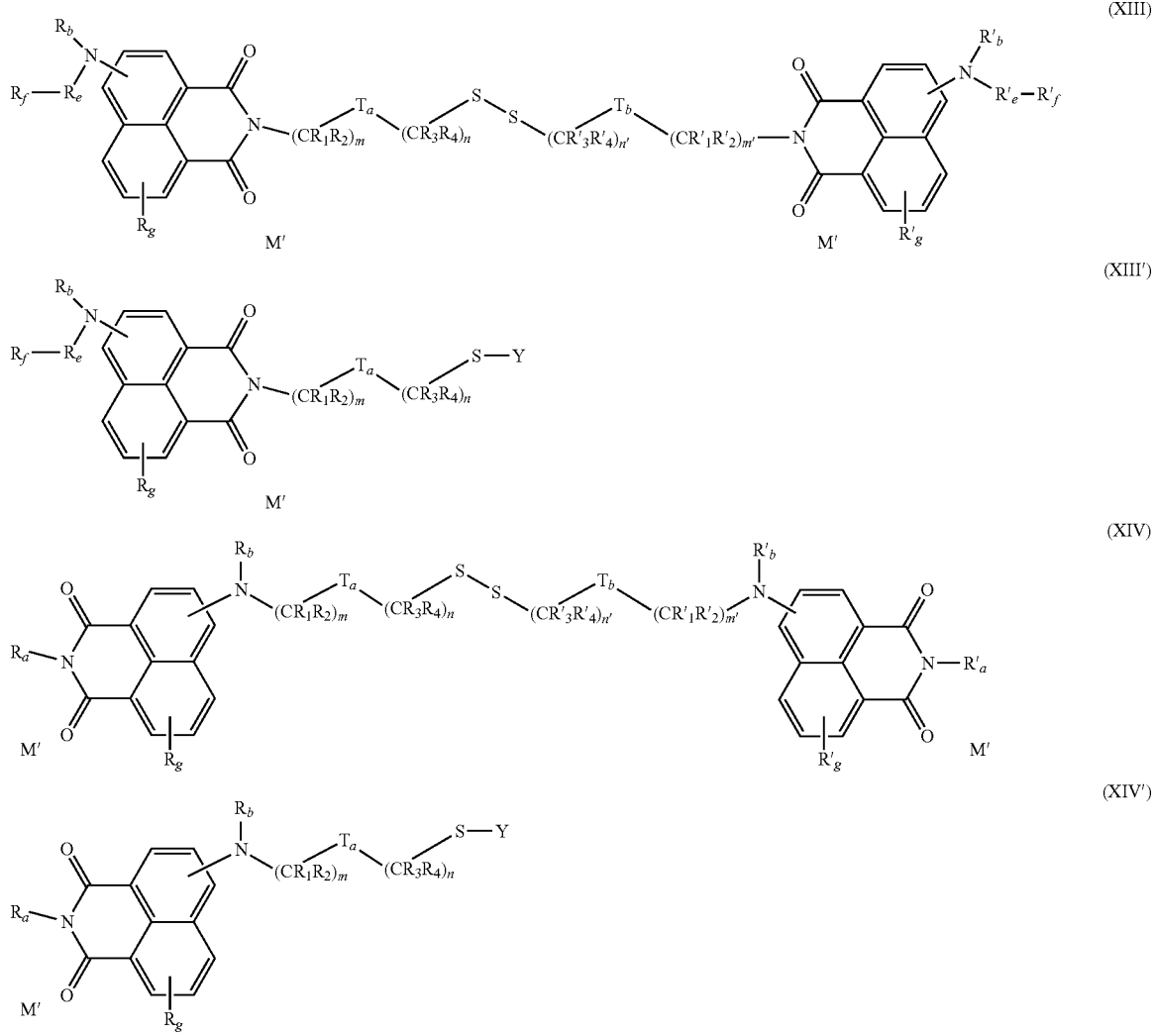

in which formulae (VIII) to (XIV) and (VIII') to (XIV'):
- G and G', which are identical or different, represent an $-NR_cR_d$, $-NR'_cR'_d$ or $C_1$-$C_6$ alkoxy group which is optionally substituted but is preferably unsubstituted; preferably, G and G' represent an $-NR_cR_d$ and $-NR'_cR'_d$ group respectively;
- $R^1$, $R^2$, $R^3$ and $R^4$, which are identical or different, represent a hydrogen atom or a $C_1$-$C_6$ alkyl group, preferably a hydrogen atom;
- $R_a$ and $R'_a$, which are identical or different, represent an aryl($C_1$-$C_4$)alkyl group or a $C_1$-$C_6$ alkyl group optionally substituted by a hydroxyl or amino, $C_1$-$C_4$ alkylamino or di($C_1$-$C_4$)alkylamino group, it being possible for the said alkyl radicals to form, with the nitrogen atom which carries them, a 5- to 7-membered heterocycle optionally comprising another heteroatom different from or identical to nitrogen; preferably, $R_a$ and $R'_a$ represent a $C_1$-$C_3$ alkyl group optionally substituted by a hydroxyl group, or a benzyl group;
- $R_b$ and $R'_b$, which are identical or different, represent a hydrogen atom, an aryl($C_1$-$C_4$)alkyl group or a $C_1$-$C_6$ alkyl group which is optionally substituted; preferably $R_b$ and $R'_b$ represent a hydrogen atom or a $C_1$-$C_3$ alkyl or benzyl group;
- $R_c$, $R'_c$, $R_d$ and $R'_d$, which are identical or different, represent a hydrogen atom, an aryl($C_1$-$C_4$)alkyl or $C_1$-$C_6$ alkoxy group or a $C_1$-$C_6$ alkyl group which is optionally substituted; $R_c$, $R'_c$, $R_d$ and $R'_d$ preferably represent a hydrogen atom, a hydroxyl, $C_1$-$C_3$ alkoxy, amino or (di)($C_1$-$C_3$)alkylamino group, or a $C_1$-$C_3$ alkyl group optionally substituted by i) a hydroxyl group, ii) an amino group, iii) a (di)($C_1$-$C_3$)alkylamino group or iv) a quaternary ammonium group $(R'')(R''')(R'''')N^+$—; or else two adjacent radicals, $R_c$ and $R_d$ or $R'_c$ and $R'_d$, carried by the same nitrogen atom together form a heterocyclic or heteroaryl group; preferably, the heterocycle or the heteroaryl is monocyclic and comprises between 5 and 7 ring members; more preferably, the groups are chosen from imidazolyl and pyrrolidinyl;
- $R_e$ and $R'_e$, which are identical or different, represent a linear or branched $C_1$-$C_6$ alkylene or $C_2$-$C_6$ alkenylene hydrocarbon chain which is optionally unsaturated;
- $R_f$ and $R'_f$, which are identical or different, represent a di($C_1$-$C_4$)alkylamino, $(R'')(R''')N$— or quaternary ammonium $(R'')(R''')(R'''')N^+$— group where R", R'" and R"", which are identical or different, represent a hydrogen atom or a $C_1$-$C_4$ alkyl group or else (R")(R'")

(R'''')N$^+$— represents an optionally substituted cationic heteroaryl group, preferably an imidazolinium group optionally substituted by a $C_1$-$C_3$ alkyl group;

$R_g$, $R'_g$, $R''_g$, $R'''_g$, $R_h$, $R'_h$, $R''_h$ and $R'''_h$, which are identical or different, represent a hydrogen atom, a halogen atom, an amino, $C_1$-$C_4$ alkylamino, di($C_1$-$C_4$)alkylamino, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulphonylamino radical, an aminosulphonyl radical or a $C_1$-$C_{16}$ alkyl radical optionally substituted by a group chosen from $C_1$-$C_{12}$ alkoxy, hydroxyl, cyano, carboxyl, amino, $C_1$-$C_4$ alkylamino and di($C_1$-$C_4$)alkylamino, or else the two alkyl radicals carried by the nitrogen atom of the amino group form a 5- to 7-membered heterocycle optionally comprising another heteroatom identical to or different from the nitrogen atom; preferably, $R_g$, $R'_g$, $R''_g$, $R'''_g$, $R_h$, $R'_h$, $R''_h$ and $R'''_h$ represent a hydrogen or halogen atom or a $C_1$-$C_3$ alkyl group;

or else two groups $R_g$ and $R'_g$, $R''_g$ and $R'''_g$, $R_h$ and $R'_h$ and $R''_h$ and $R'''_h$, carried by two adjacent carbon atoms, together form a benzo or indeno ring or a fused heterocycloalkyl or fused heteroaryl group; the benzo, indeno, heterocycloalkyl or heteroaryl ring optionally being substituted by a halogen atom, an amino, $C_1$-$C_4$ alkylamino, di($C_1$-$C_4$)alkylamino, nitro, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy alkoxycarbonyl or alkylcarbonylamino radical, an acylamino, carbamoyl or alkylsulphonylamino radical, an aminosulphonyl radical or a $C_1$-$C_{16}$ alkyl radical optionally substituted by a group chosen from $C_1$-$C_{12}$ alkoxy, hydroxyl, cyano, carboxyl, amino, $C_1$-$C_4$ alkylamino and di($C_1$-$C_4$)alkylamino, or else the two alkyl radicals carried by the nitrogen atom of the amino group form a 5- to 7-membered heterocycle optionally comprising another heteroatom identical to or different from the nitrogen atom; preferably, $R_g$ and $R'_g$ and $R''_g$ and $R'''_g$ together form a benzo group;

or else two groups $R_i$ and $R_g$, $R'''_i$ and $R'''_g$, $R'_i$ and $R'_h$ and/or $R''_i$ and $R''_h$ together form a fused (hetero)cycloalkyl, preferably cycloalkyl, such as cyclohexyl;

or else, when G represents —$NR_cR_d$ and G' represents —$NR'_cR'_d$, two groups $R_c$ and $R'_g$, $R'_c$ and $R''_g$, $R_d$ and $R_g$ and $R'_d$ and $R'''_g$ together form a heteroaryl or saturated heterocycle optionally substituted by one or more $C_1$-$C_6$ alkyl groups, preferably a heterocycle comprising one or two heteroatoms chosen from nitrogen and oxygen and comprising between 5 and 7 ring members; more preferably, the heterocycle is chosen from the morpholinyl, piperazinyl, piperidinyl and pyrrolidinyl groups;

$R_i$, $R'_i$, $R''_i$ and $R'''_i$, which are identical or different, represent a hydrogen atom or a $C_1$-$C_4$ alkyl group;

$R_1$, $R_2$, $R_3$, $R_4$, $R'_1$, $R'_2$, $R'_3$ and $R'_4$, which are identical or different, represent a hydrogen atom or a $C_1$-$C_4$ alkyl, $C_1$-$C_{12}$ alkoxy, hydroxyl, cyano, carboxyl, amino, $C_1$-$C_4$ alkylamino or di($C_1$-$C_4$)alkylamino group, it being possible for the said alkyl radicals to form, with the nitrogen atom which carries them, a 5- to 7-membered heterocycle optionally comprising another heteroatom different from or identical to nitrogen; preferably $R_1$, $R_2$, $R_3$, $R_4$, $R'_1$, $R'_2$, $R'_3$ and $R'_4$ are hydrogen atoms or an amino group; more preferably, $R_1$, $R_2$, $R_3$, $R_4$, $R'_1$, $R'_2$, $R'_3$ and $R'_4$ represent a hydrogen atom;

$T_a$ and $T_b$, which are identical or different, represent i) either a σ covalent bond, ii) or one or more radicals or their combinations chosen from —$SO_2$—, —O—, —S—, —N(R)—, —N$^+$(R)(R°)— or —CO—, with R and R°, which are identical or different, representing a hydrogen atom, a $C_1$-$C_4$ alkyl or $C_1$-$C_4$ hydroxyalkyl radical or an aryl($C_1$-$C_4$)alkyl; preferably, $T_a$ is identical to $T_b$ and represents a σ covalent bond or a group chosen from —N(R)—, —C(O)—N(R)—, —N(R)—C(O)—, —O—C(O)—, —C(O)—O— and —N$^+$(R)(R°)—, with R and R°, which are identical or different, representing a hydrogen atom or a $C_1$-$C_4$ alkyl group; more preferably, $T_a$ and $T_b$ represent a σ bond; iii) or a cationic or noncationic heterocycloalkyl or heteroaryl radical which are preferably monocyclic, which are preferably identical, which preferably comprise two heteroatoms (more preferably two nitrogen atoms) and which preferably comprise from 5 to 7 ring members, such as imidazolium;

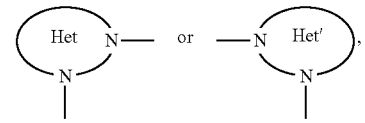

which are identical or different, represent an optionally substituted heterocyclic group; preferably, the heterocycles are identical, monocyclic and saturated and comprise, in total, two nitrogen atoms and from 5 to 8 ring members;

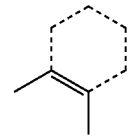

represents an aryl or heteroaryl group fused to the imidazolium or phenyl ring; or else is absent from the imidazolium or phenyl ring; preferably, when the ring is present, the ring is a benzo;

m, m', n and n', which are identical or different, represent an integer between 0 and 6 inclusive with m+n and m'+n', which are identical or different, representing an integer between 1 and 10 inclusive; preferably, m+n=m'+n'=an integer between 2 and 4 inclusive; more preferably, m+n=m'+n'=an integer equal to 2;

Y is as defined above; in particular, Y represents a hydrogen atom or a protective group, such as:
($C_1$-$C_4$)alkylcarbonyl, such as methylcarbonyl or ethylcarbonyl;
arylcarbonyl, such as phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl, such as dimethylaminocarbonyl;
($C_1$-$C_4$)(alkyl)arylaminocarbonyl;
optionally substituted aryl, such as phenyl;

5- or 6-membered monocyclic heteroaryl, such as imidazolyl or pyridyl;

cationic 5- or 6-membered monocyclic heteroaryl, such as pyrylium, pyridinium, pyrimidinium, pyrazinium, pyridazinium, triazinium or imidazolium; these groups optionally being substituted by one or more identical or different $(C_1-C_4)$alkyl groups, such as methyl;

cationic 8- to 11-membered bicyclic heteroaryl, such as benzimidazolium or benzoxazolium; these groups optionally being substituted by one or more identical or different $(C_1-C_4)$alkyl groups, such as methyl;

cationic heterocycle of following formula:

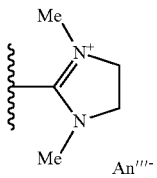

—$C(NH_2)$=$N^+H_2An'''^-$; with $An'''^-$ being an anionic counterion as defined above;
—$C(NH_2)$=$NH$;
$SO_3^-M^+$, with $M^+$ representing an alkali metal, such as sodium or potassium; and M' representing an anionic counterion, derived from an organic or inorganic acid salt or from an organic or inorganic base, that ensures the electrical neutrality of the molecule.

In particular, the dyes of formula (I) are chosen from disulphide, thiol or protected thiol dyes having a naphthalimidyl chromophore chosen from the formulae (XIII), (XIII'), (XIV) and (XIV') as defined above.

According to a preferred form of the invention, the dyes of formula (I) are chosen from the disulphide, thiol or protected thiol dyes chosen from the following formulae (XV) to (XV'):

with $R_a$, $R_b$ and $R_c$, which are identical or different, representing a hydrogen atom or a $(C_1-C_4)$alkyl group; or else two alkyl groups $R_a$ and $R_b$ of the amino or ammonium group form a 5- to 7-membered heterocycle optionally comprising another heteroatom identical to or different from the nitrogen atom, such as morpholinyl, piperazinyl, piperidinyl, pyrrolyl, morpholinium, piperazinium, piperidinium or pyrrolinium, and $An^-$ representing an anionic counterion;

R' and R'', which are identical or different, represent a hydrogen atom or a group as defined for R for R''' respectively;

$R_g$, $R'_g$, $R''_g$, $R'''_g$, $R_h$, $R'_h$, $R''_h$ and $R'''_h$, which are identical or different, represent a hydrogen or halogen atom, an amino, (di)$(C_1-C_4)$alkylamino, cyano, carboxyl, hydroxyl, trifluoromethyl, acylamino, $C_1-C_4$ alkoxy, (poly)hydroxy$(C_2-C_4)$alkoxy, $(C_1-C_4)$alkylcarbonyloxy, $(C_1-C_4)$alkoxycarbonyl, $(C_1-C_4)$alkylcarbonylamino, acylamino, carbamoyl or $(C_1-C_4)$alkylsulphonylamino group, an aminosulphonyl radical or a $(C_1-C_{16})$alkyl radical optionally substituted by a group chosen from $(C_1-C_{12})$alkoxy, hydroxyl, cyano, carboxyl, amino or (di)$(C_1-C_4)$alkylamino, or else the two alkyl radicals carried by the nitrogen atom of the amino group form a 5- to 7-membered heterocycle optionally comprising another heteroatom which is identical to or different from the nitrogen atom; in particular, $R_g$, $R'_g$, $R''_g$, $R'''_g$, $R_h$, $R'_h$, $R''_h$ and $R'''_h$ represent a hydrogen atom or a $(C_1-C_4)$alkyl group;

$R'_i$, $R''_i$, $R'''_i$ and $R''''_i$, which are identical or different, represent a hydrogen atom or a $(C_1-C_4)$alkyl group; in particular, $R'_i$, $R''_i$, $R'''_i$ and $R''''_i$ represent a hydrogen atom;

m, m', which are identical or different, represent an integer between 1 and 10 inclusive, in particular an integer between 2 and 4 inclusive; preferably m and m' have the value 2;

p, p', q and q', which are identical or different, represent an integer between 1 and 6 inclusive;

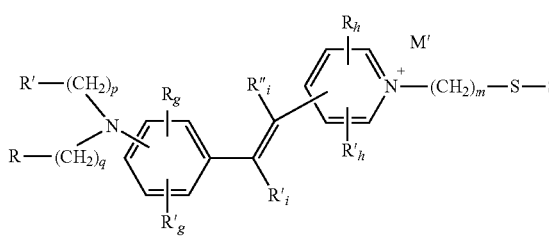

(XV)

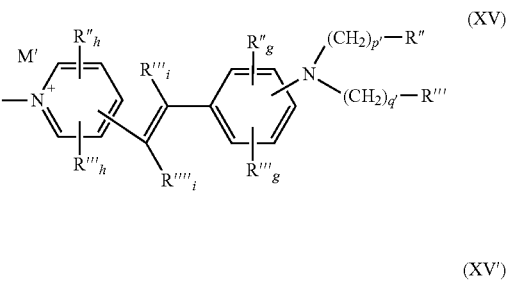

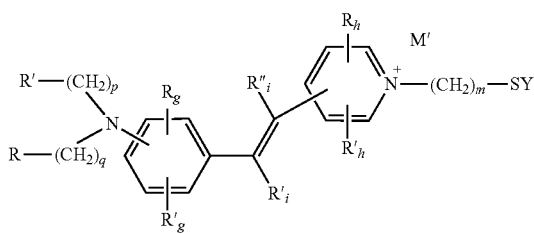

(XV')

their organic or inorganic acid salts, optical isomers, geometrical isomers and solvates, such as hydrates;

in which formulae (XV) and (XV'):

R and R''', which are identical or different, represent a hydroxyl group or an amino ($NR_aR_b$) or ammonium ($N^+R_aR_bR_c$) $An^-$ group, preferably a hydroxyl group, M' represents an anionic counterion; and Y is as defined above;

it being understood that, when the compound of formula (XV) or (XV') comprises other cationic parts, it is combined with one or more anionic counterions which make it possible to achieve the electrical neutrality of the formula (XV) or (XV').

According to a specific form of the invention, the dyes of the invention belong to the formula (XVa) or (XV'a), which has an ethenylene group connecting the pyridinium part to the phenyl in the ortho or para position of the pyridinium, i.e. as 2,4'-, 4,2'- or 4,4'-:

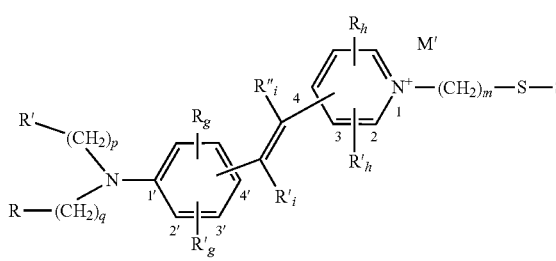

(XVa)

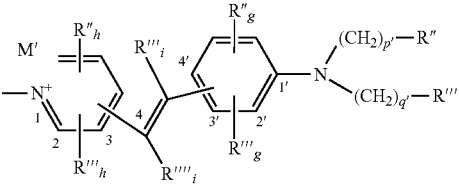

(XV'a)

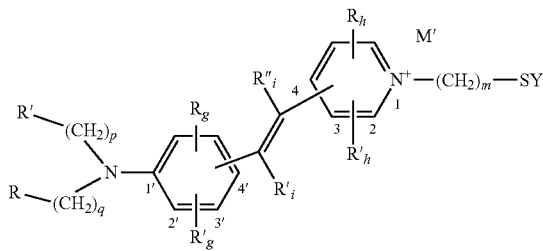

with R, R', R", R''', $R_g$, $R'_g$, $R''_g$, $R'''_g$, $R_h$, $R'_h$, $R''_h$, $R'''_h$, $R'_i$, $R''_i$, $R'''_i$, $R''''_i$, m, m', p, p', q, q', Y and M' as defined above in the formulae (XV) and (XV'). In particular, $R_h$ and $R''_h$ are in the ortho position of the pyridinium group and $R'_h$ and $R'''_h$ represent a hydrogen atom.

Another aspect of the invention relates to the dyes of formula (XVa) or (XV'a) having $R_g$ and $R''_g$ groups in the 3' position and $R'_g/R'''_g$ groups which represent a hydrogen atom.

Advantageously, the dyes of formula (XVa) and (XV'a) have their ethenylene group in the para position of the phenyl carrying the amino group $R'(CH_2)_p$—N—$(CH_2)_q$—R and/or $R''(CH_2)_{p'}$—N—$(CH_2)_{q'}$—R''', i.e. in the 4' position, and preferably have an ethenylene or styryl group connecting the pyridinium part to the phenyl in the ortho position of the pyridinium, i.e. as 2,4'-.

According to another specific form of the invention, the dyes of the invention belong to the formula (XVI) or (XVI'):

in which formula (XVI) or (XVI'):
$R_1$ represents a $C_1$-$C_6$ alkyl group substituted by one or more hydroxyl or —C(O)OR' groups with R' representing a hydrogen atom or a $C_1$-$C_4$ alkyl group or else a —C(O)—O$^-$ group and, in the latter case, an anionic counterion An$^-$ is absent; in particular $R_1$ represents a $C_1$-$C_6$ alkyl group substituted by one or more hydroxyl groups and more specifically by just one hydroxyl group;
$R_2$ represents a $C_1$-$C_6$ alkyl group optionally substituted by one or more hydroxyl groups;
or else the groups $R_1$ and $R_2$ form, together with the nitrogen atom which carries them, a saturated heterocyclic radical substituted at least with one hydroxyl, (poly)hydroxy($C_1$-$C_4$)alkyl and/or —C(O)OR', with R' representing a hydrogen atom or a $C_1$-$C_4$ alkyl group, or else a —C(O)—O$^-$ group and, in this case, an anionic counterion An$^-$ is absent, such as pyrrolidinyl and piperidyl;
$R_3$ represents a hydrogen atom or a —C(O)OR" group, with R" representing a hydrogen atom, an alkali metal or a $C_1$-$C_6$ alkyl group, or else $R_3$ represents a —C(O)—O$^-$ group and, in this case, an anionic counterion An$^-$ is absent;

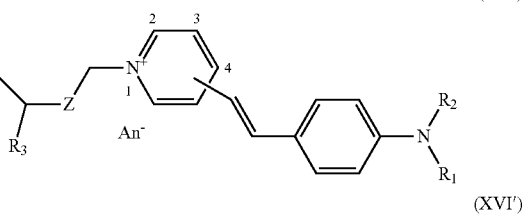

(XVI)

(XVI')

Z represents a divalent amido group —C(O)—N(R)— or —N(R)—C(O)—, or a divalent $C_1$-$C_{10}$ alkylene group interrupted by an amido group —C(O)—N(R)— and —N(R)—C(O)—, such as —$(CH_2)_{n'}$—C(O)—N(R)—$(CH_2)_p$— and —$(CH_2)_{n''}$—N(R)—C(O)—$(CH_2)_p$—, with n' representing an integer between 0 and 3 inclusive; preferably, n' has a value 0, 2, 3; p representing an integer between 0 and 4 inclusive, n" representing an integer between 0 and 3 inclusive and in particular n'=n"=p=0, and R representing a hydrogen atom or a $C_1$-$C_6$ alkyl group;

An⁻ represents an anionic counterion;

Y is as defined above;

it being understood that, when the compound of formula (XVI) or (XVI') comprises other cationic parts, it is combined with one or more anionic counterions which make it possible to achieve the electrical neutrality of the formula (XVI) or (XVI').

According to a specific form of the invention, the dyes of the invention belong to the formula (XVIa) or (XVI'a):

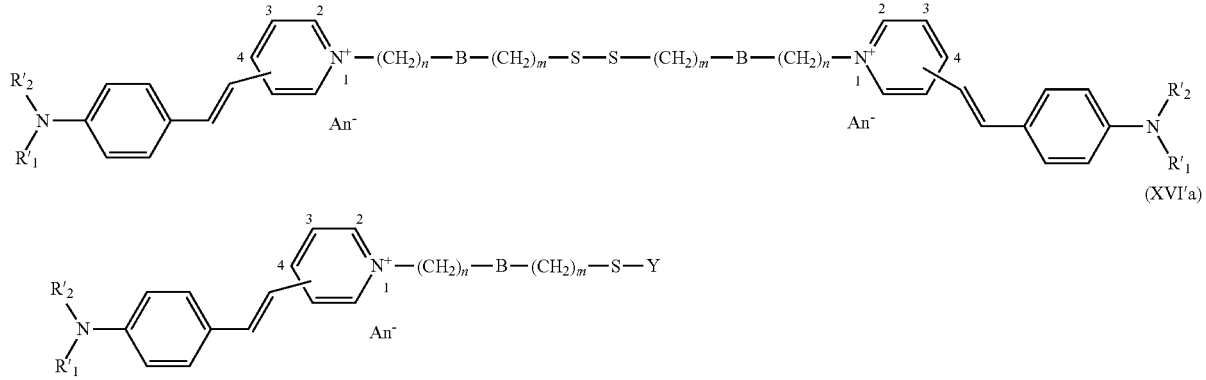

(XVIa)

(XVI'a)

in which formulae (XVIa) and (XVI'a):

$R'_1$ represents a $C_1$-$C_4$ alkyl group substituted by one or more hydroxyl groups, particularly by just one hydroxyl group, or —C(O)OR' groups, with R' representing a hydrogen atom or a $C_1$-$C_4$ alkyl group, or else a —C(O)—O⁻ group and, in the latter case, an anionic counterion An⁻ is absent; preferably, $R'_1$ represents a $C_1$-$C_4$ alkyl group substituted by a hydroxyl group;

$R'_2$ represents a $C_1$-$C_4$ alkyl group optionally substituted by one or more hydroxyl groups, in particular by just one hydroxyl group; more particularly, $R'_1$ and $R'_2$ are identical;

An⁻ represents an anionic counterion as defined above;

B represents a divalent amido group —C(O)—N(R)— or —N(R)—C(O)—, with R representing a hydrogen atom or a ($C_1$-$C_6$)alkyl group; preferably, R=H;

n and m, which are identical or different, represent an integer between 1 and 4 inclusive; preferably, n has a value 3 and m has a value 2;

Y is as defined above;

it being understood that the bond between the pyridinium ring and the double bond of the ethenylene or styryl group is positioned in the 2 or 4 position of the pyridinium, preferably in the 4 position.

Mention may be made, as examples of disulphide, thiol and protected thiol direct dyes of formula (I) of the invention, of those with the following chemical structures:

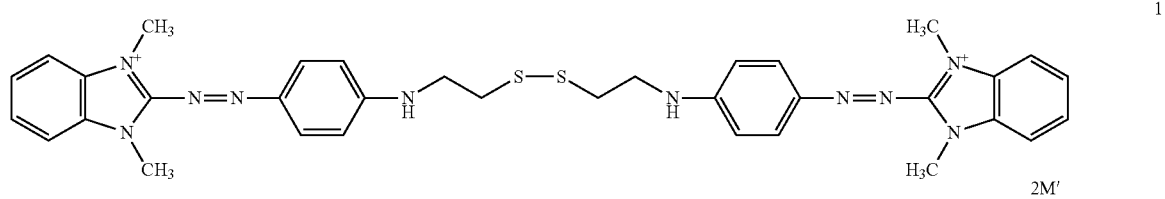

1

2M'

-continued
| | |
|---|---|
| 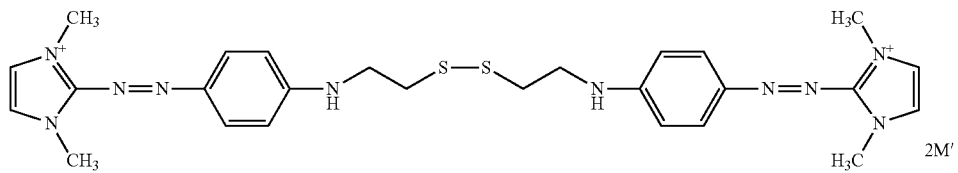 2M' | 2 |
| 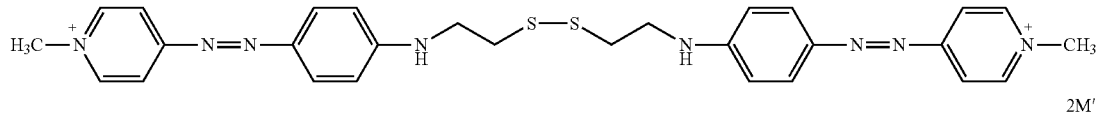 2M' | 3 |
| 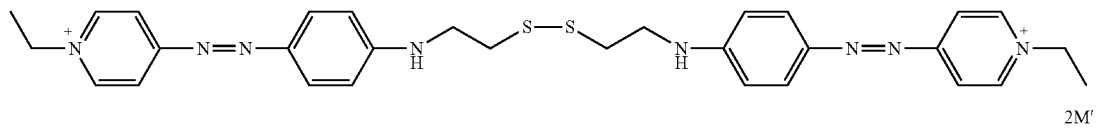 2M' | 4 |
| 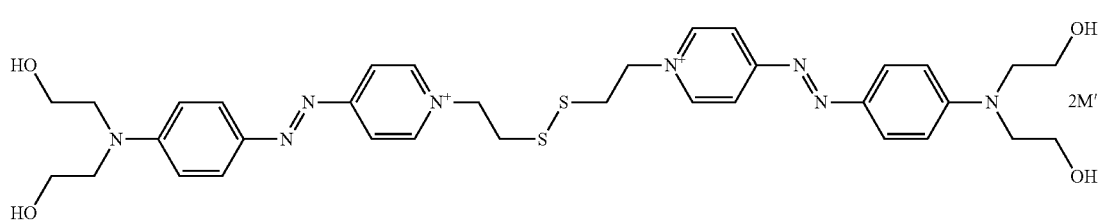 2M' | 5 |
| 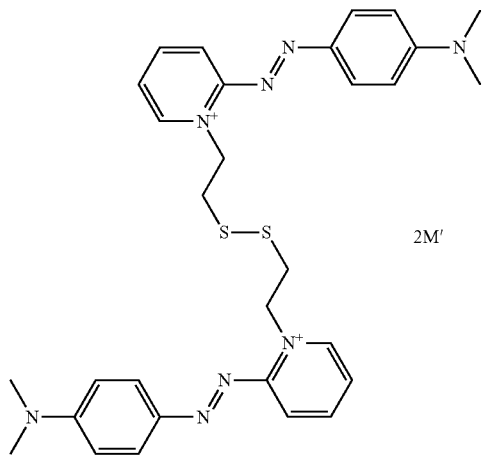 2M' | 6 |
| 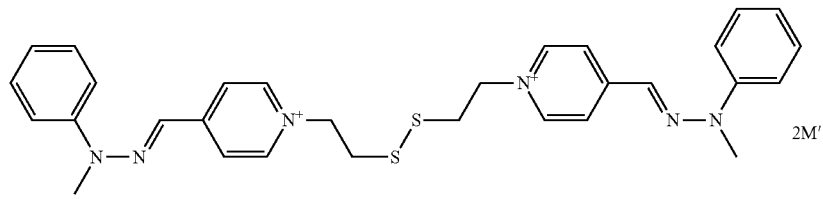 2M' | 7 |
| 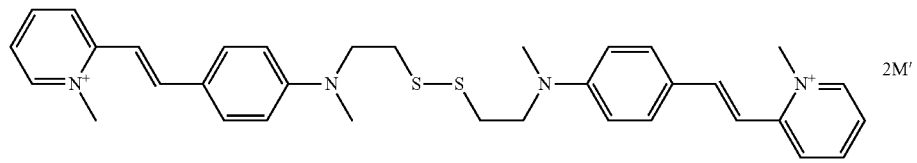 2M' | 8 |

-continued
9
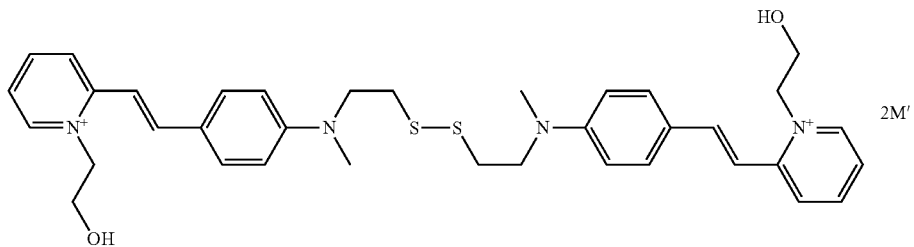
2M'
10
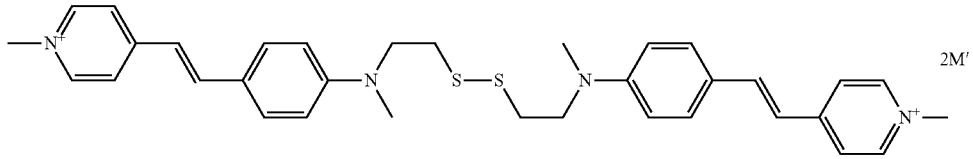
2M'
11
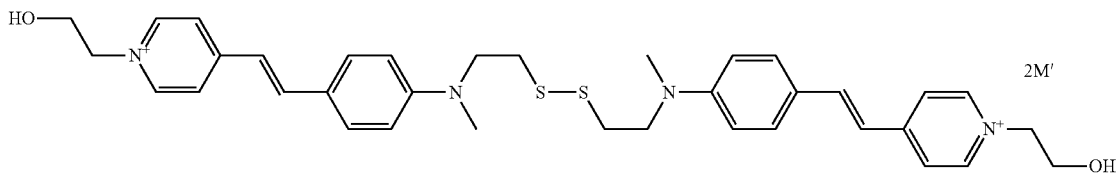
2M'
12
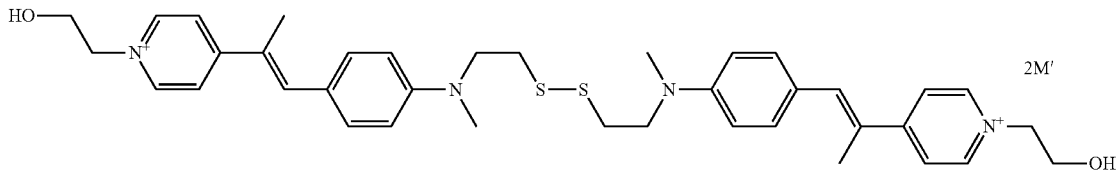
2M'
13
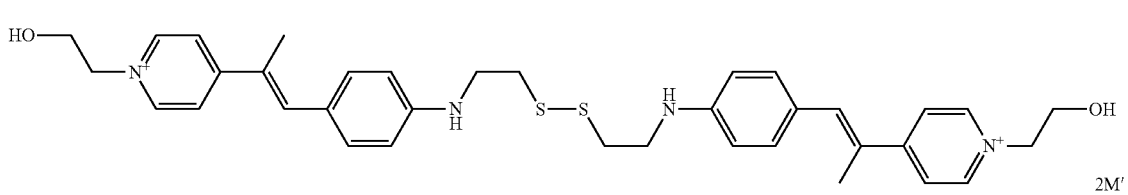
2M'
14
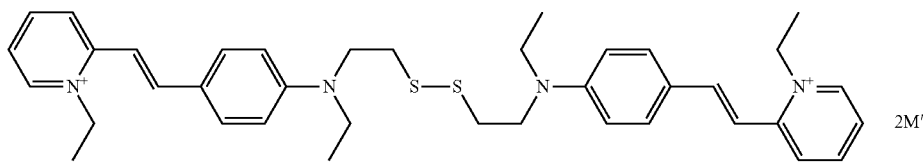
2M'
15
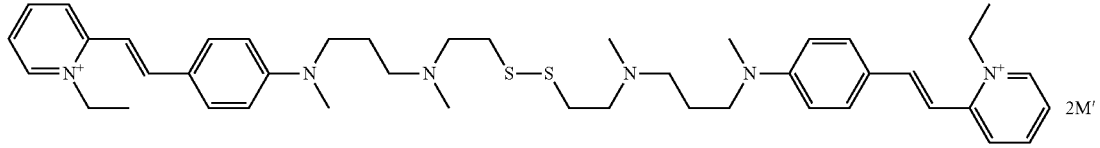
2M'
16
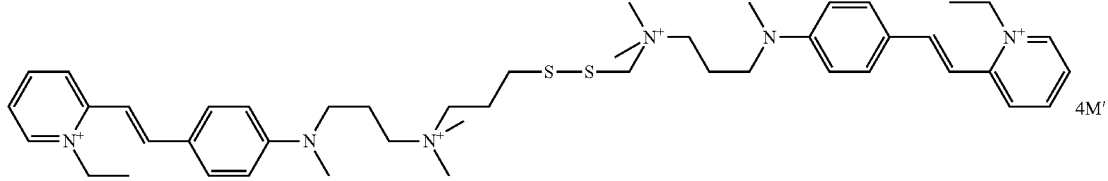
4M'

-continued
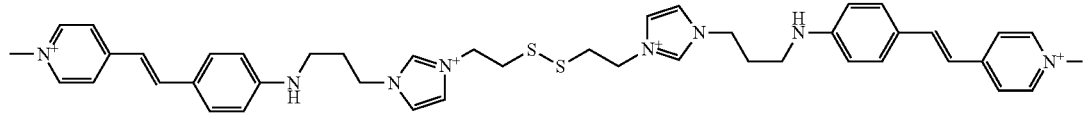
17
4M'
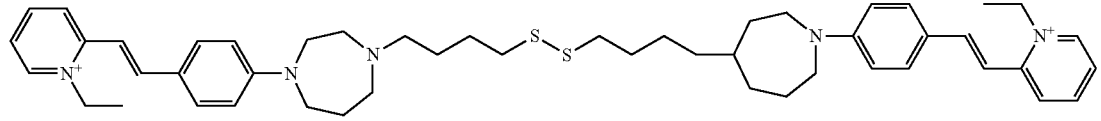
18
2M'
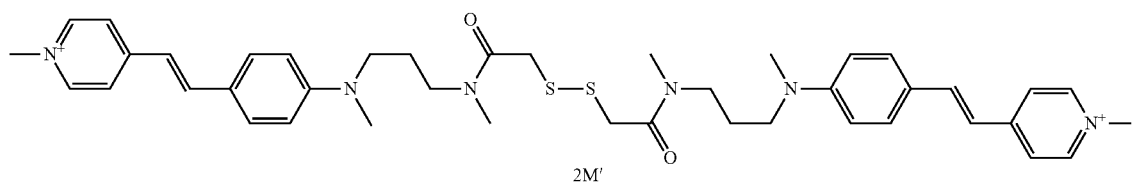
19
2M'
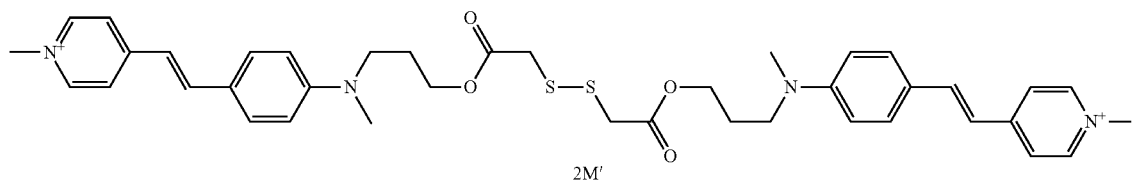
20
2M'
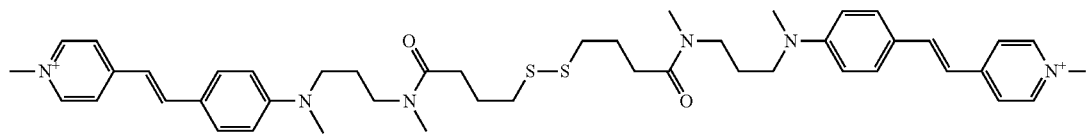
21
2M'
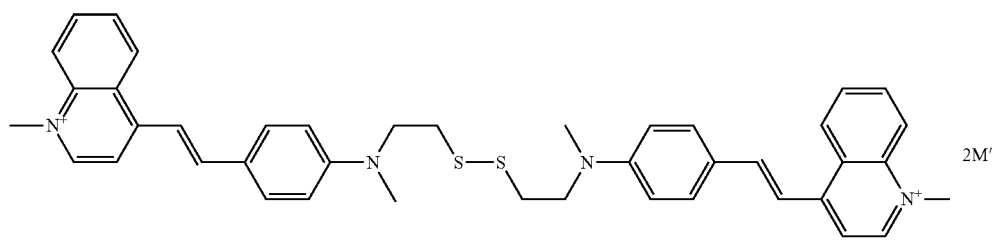
22
2M'
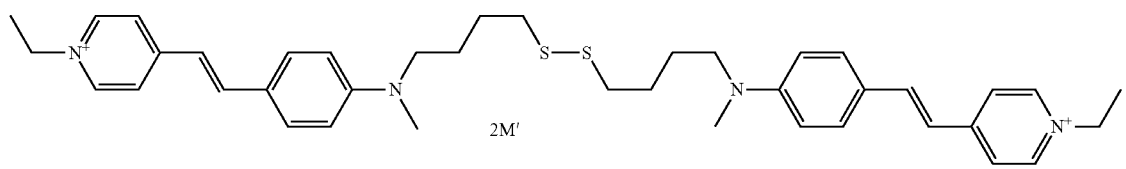
23
2M'
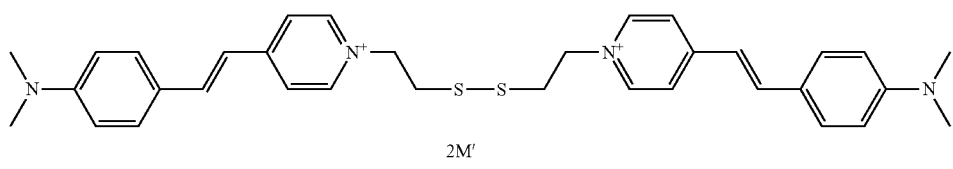
24
2M'

-continued
| | |
|---|---|
| 25 | 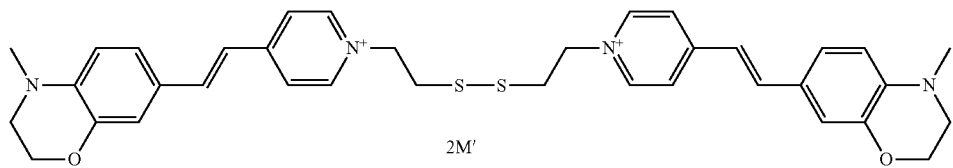 2M′ |
| 26 | 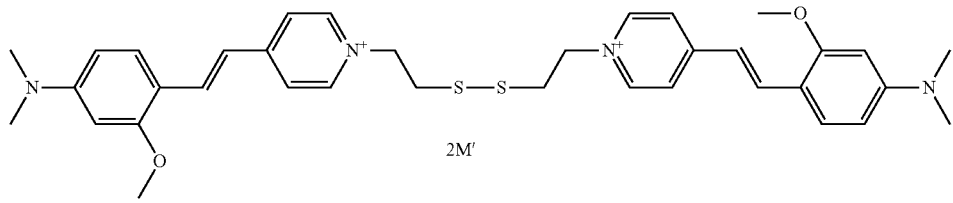 2M′ |
| 27 | 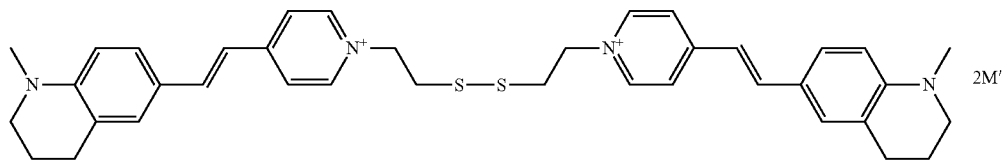 2M′ |
| 28 | 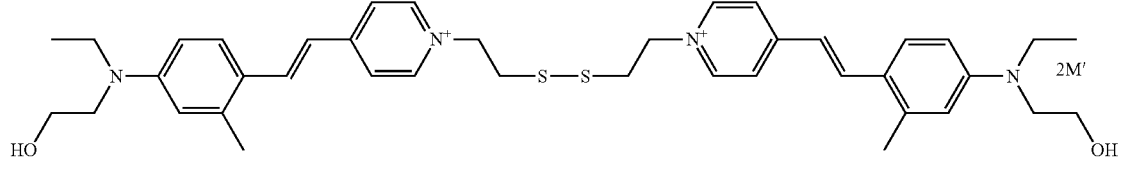 2M′ |
| 29 | 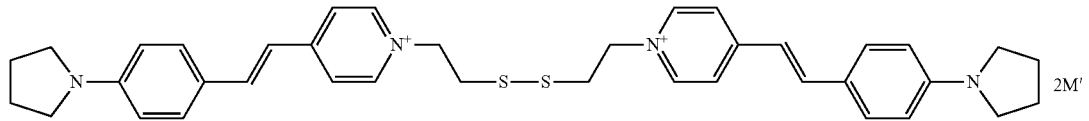 2M′ |
| 30 | 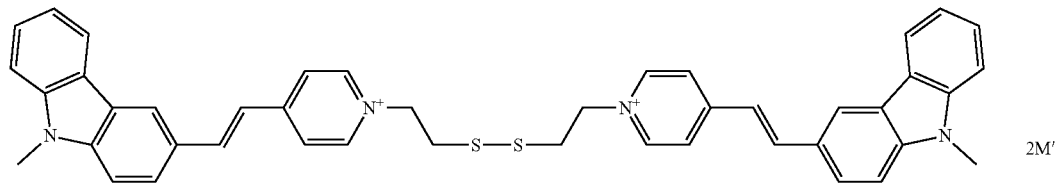 2M′ |
| 31 | 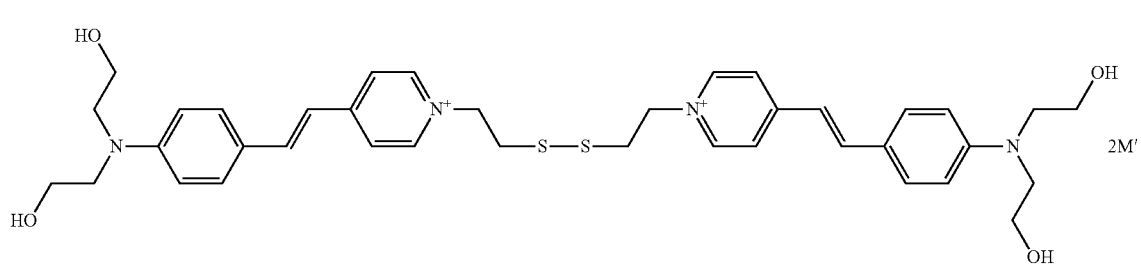 2M′ |
| 32 | 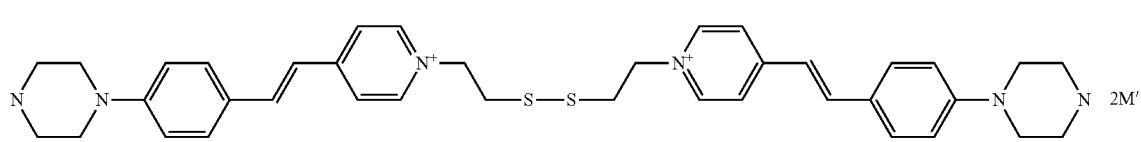 2M′ |
| 33 | 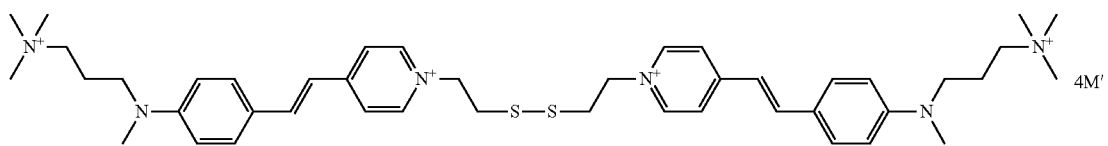 4M′ |

-continued
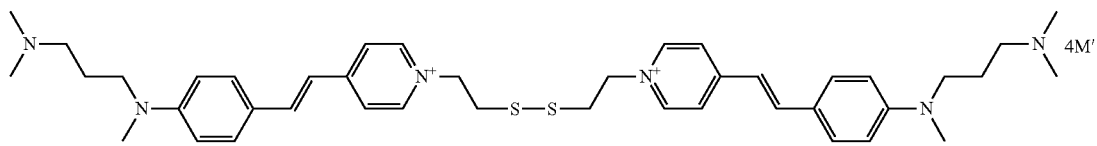
34
4M'
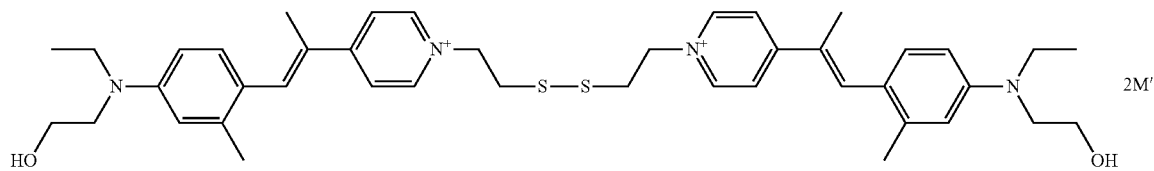
35
2M'
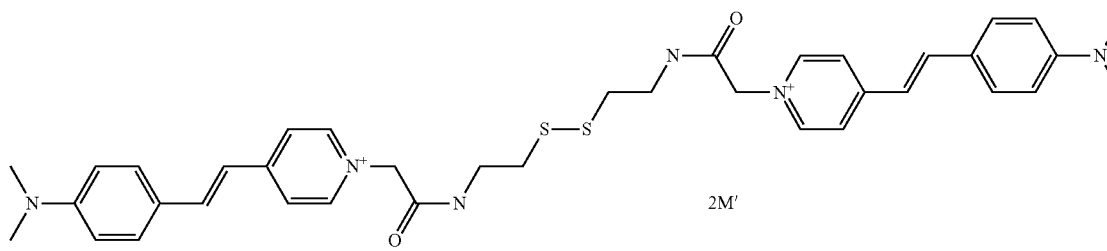
36
2M'
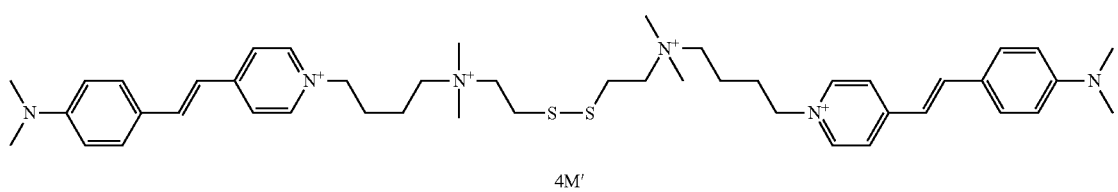
37
4M'
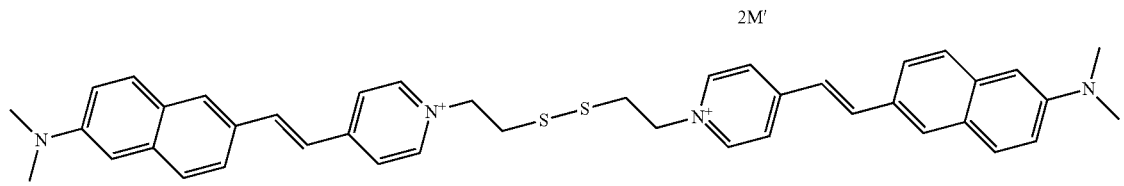
38
2M'
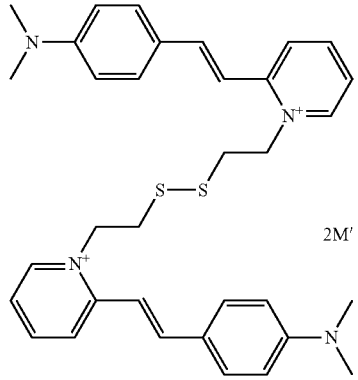
39
2M'
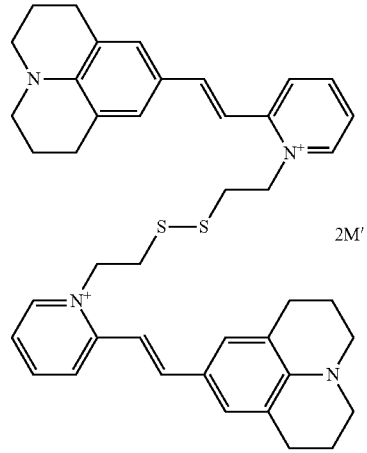
40
2M'

-continued
41
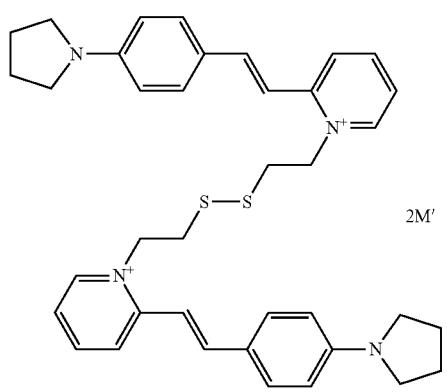
2M'
42
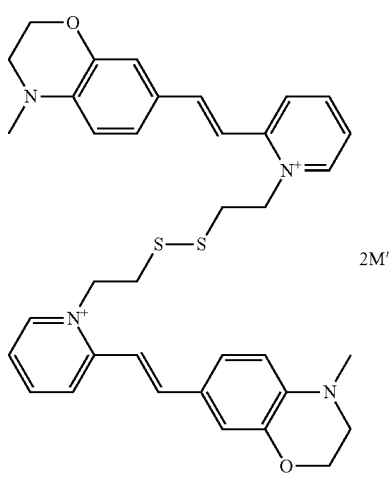
2M'
43
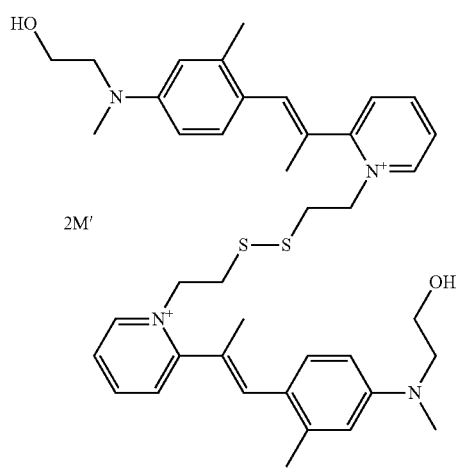
2M'
44
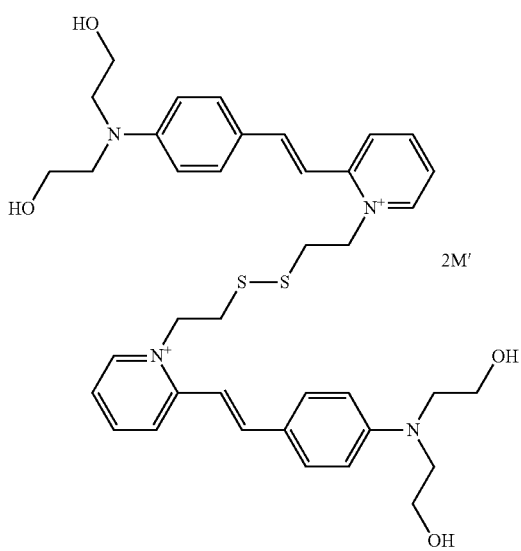
2M'
45
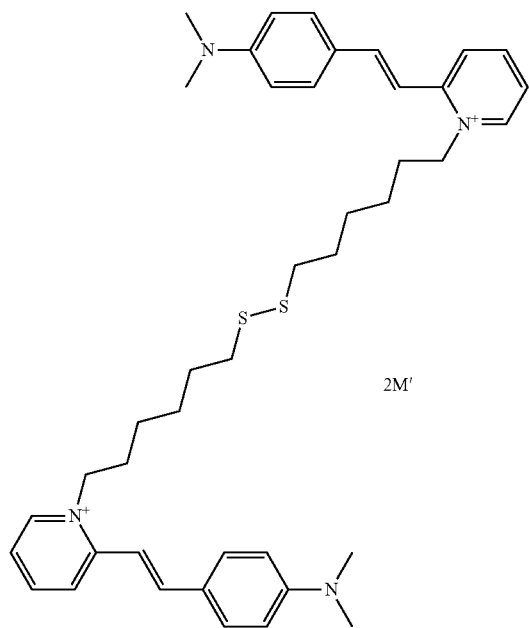
2M'

-continued
46
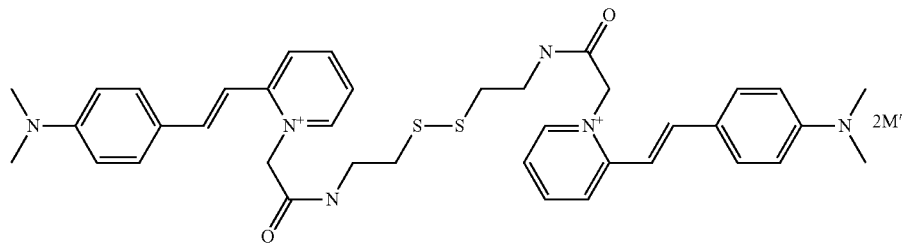
2M'
47
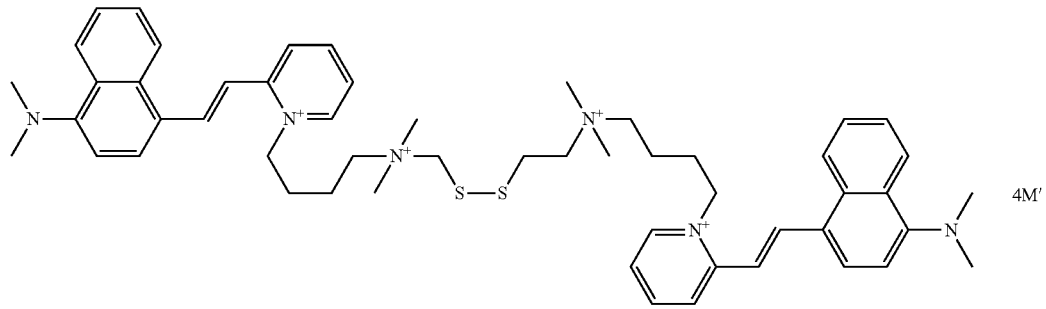
4M'
48
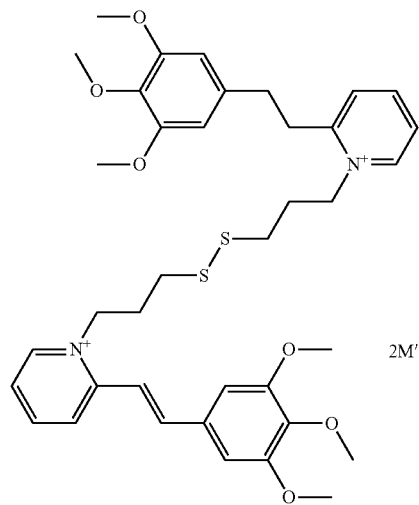
2M'
49
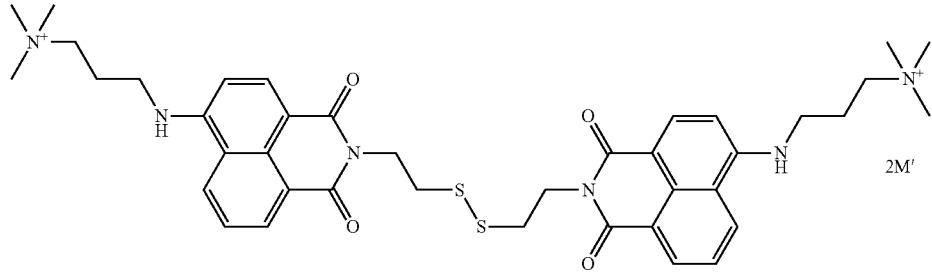
2M'
49a
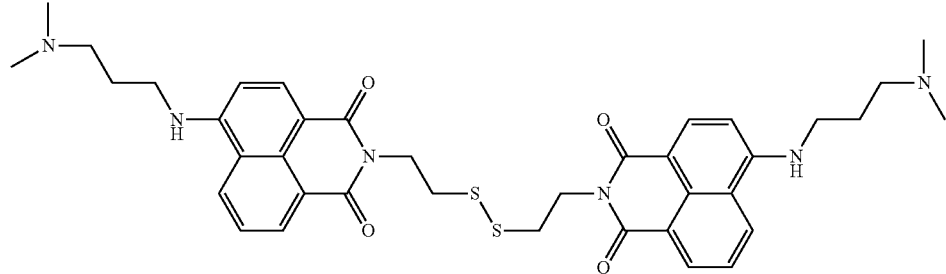

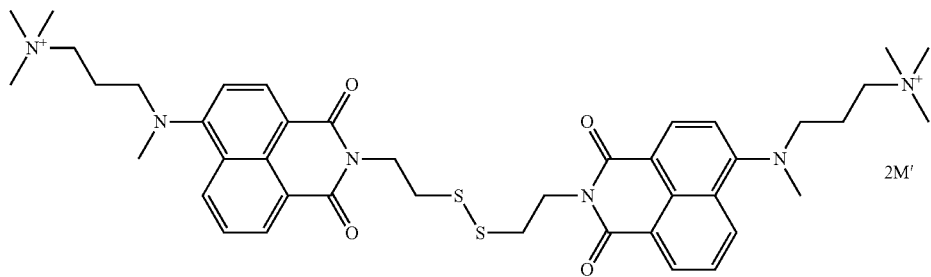
50
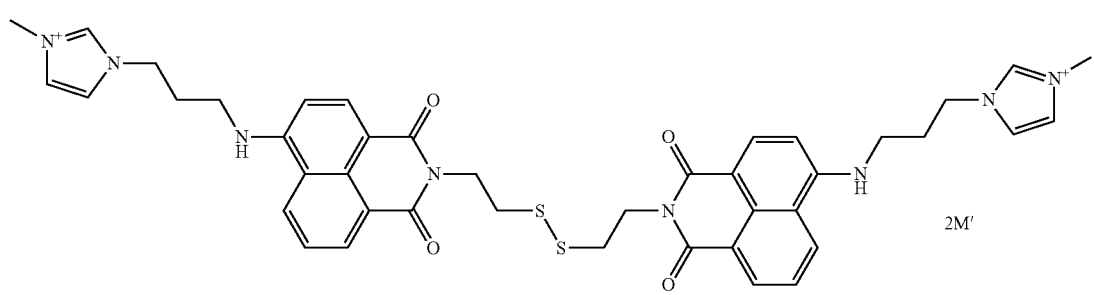
51
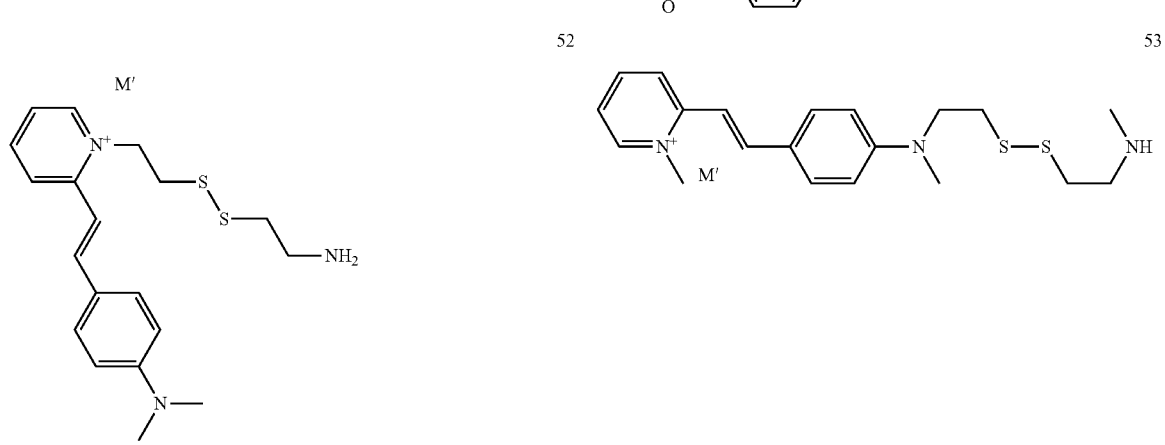
52
53
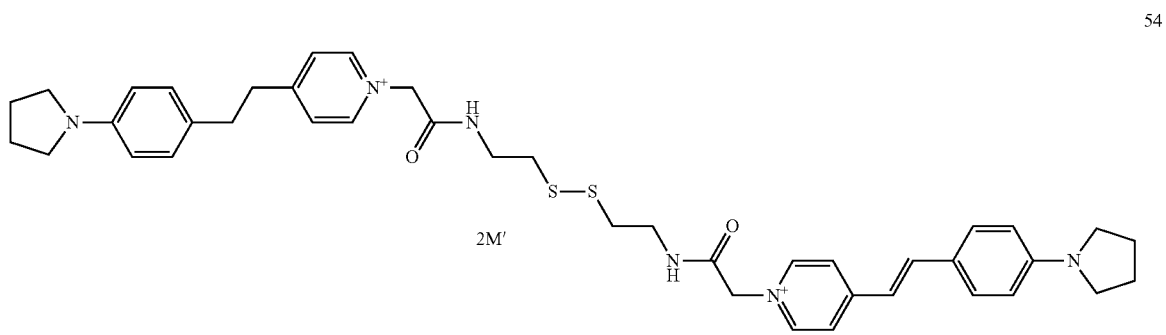
54
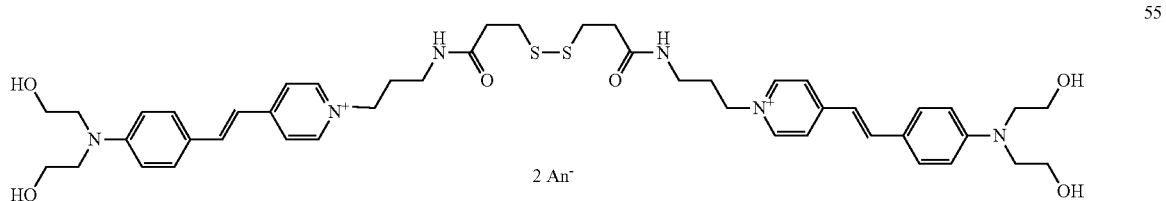
55

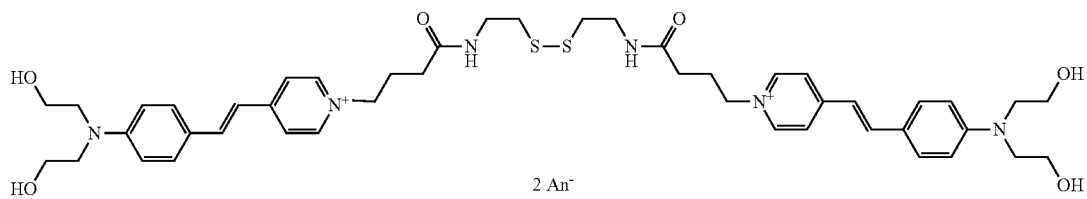
56
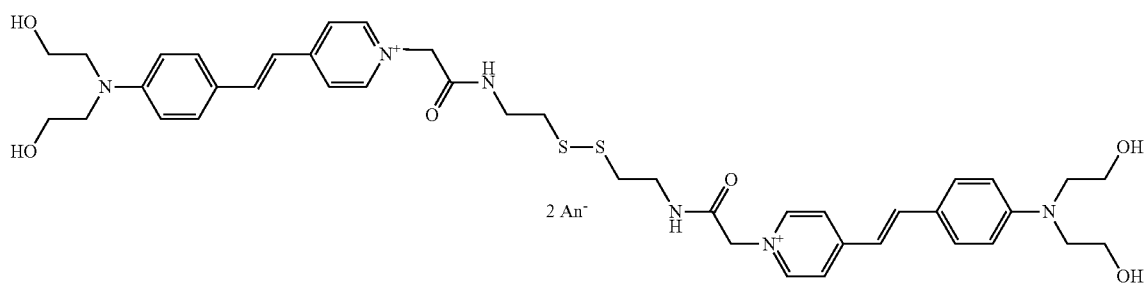
57
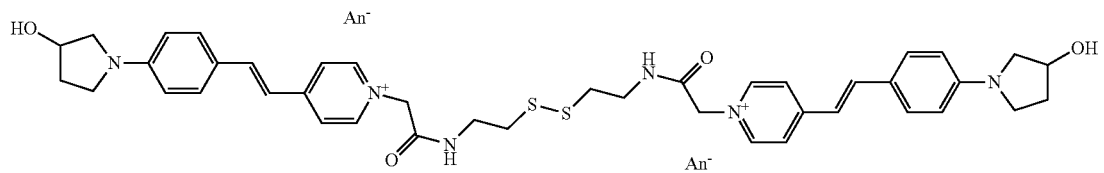
58
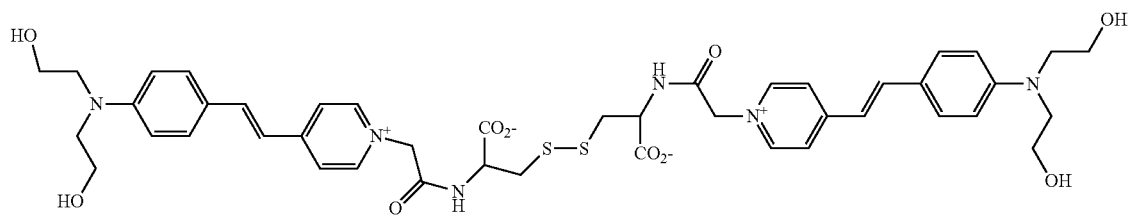
59
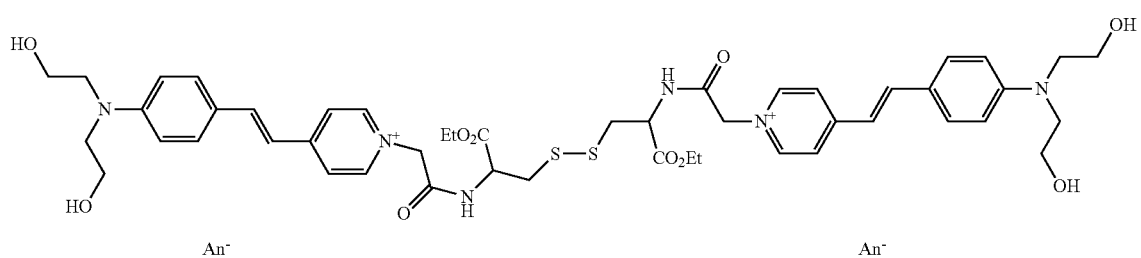
60
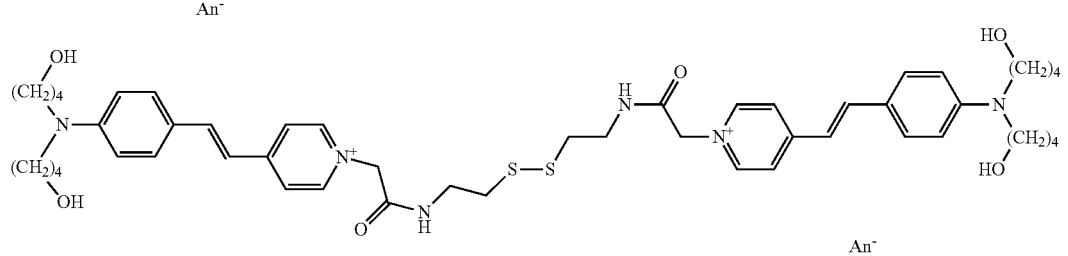
61

-continued
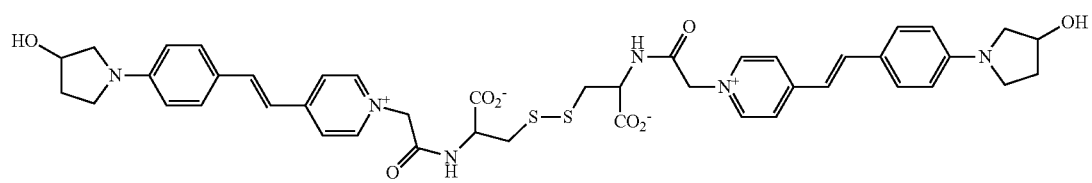
62
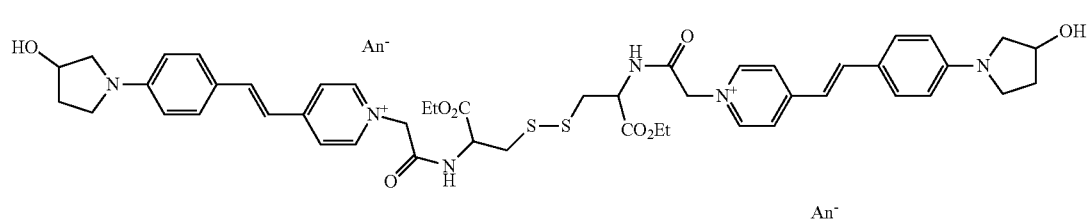
63
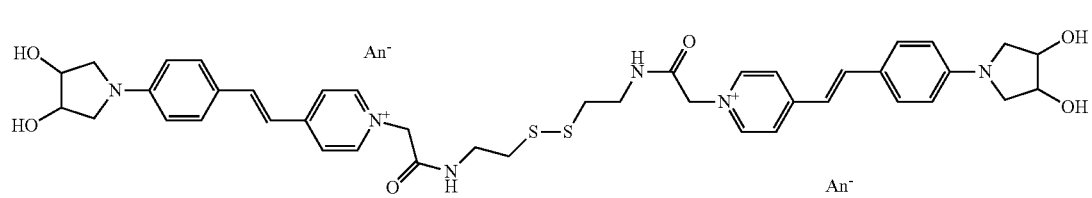
64
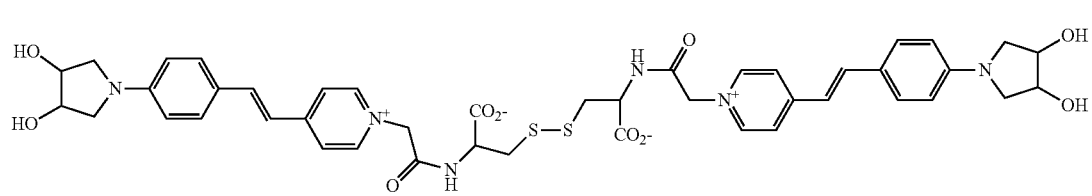
65
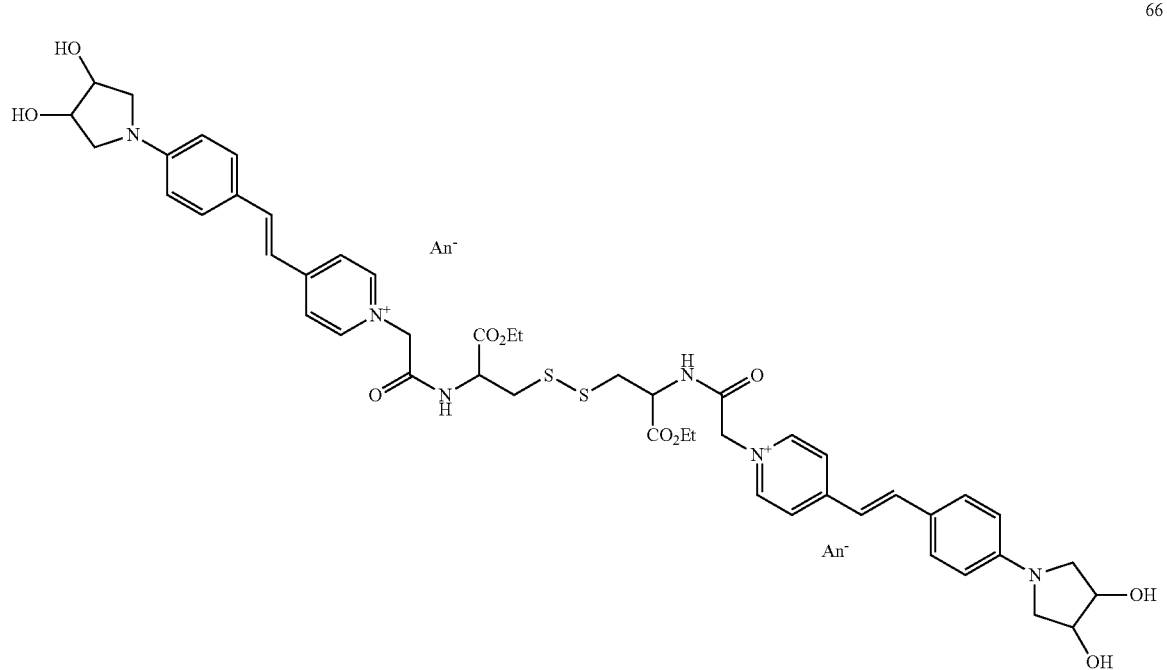
66

-continued
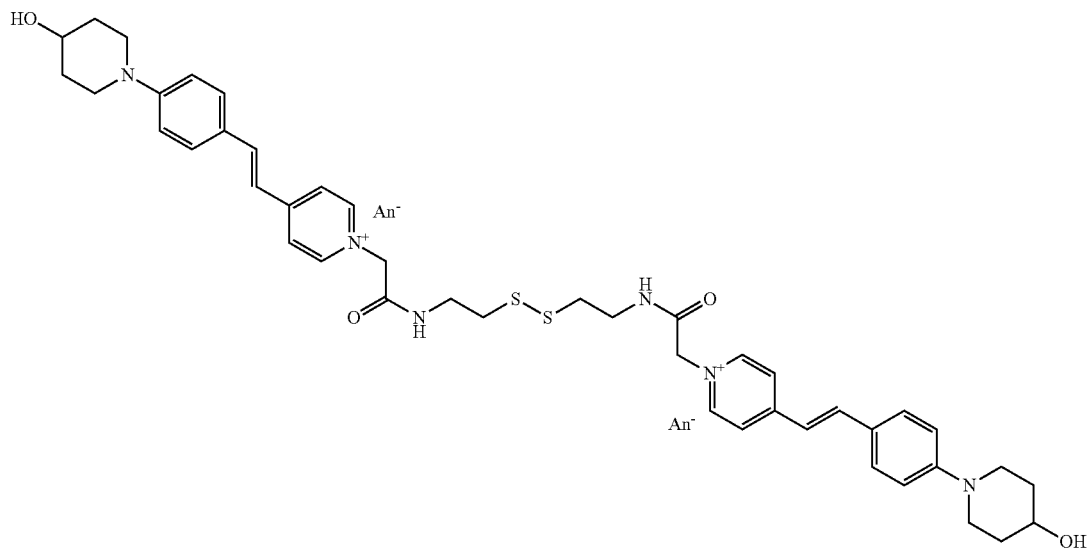
67
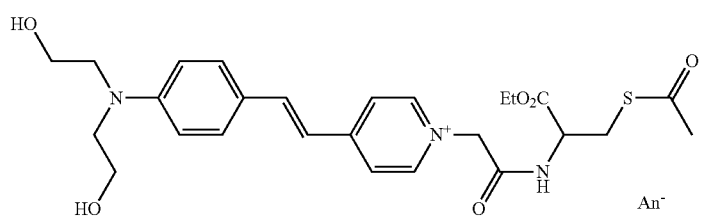
68
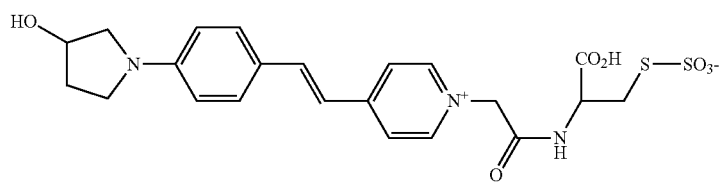
69
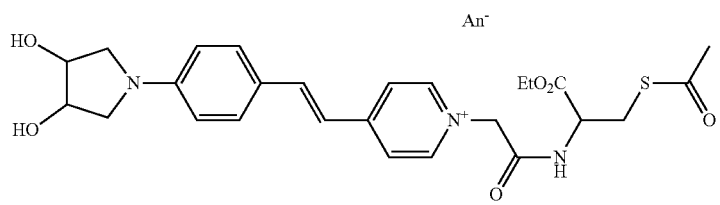
70

-continued
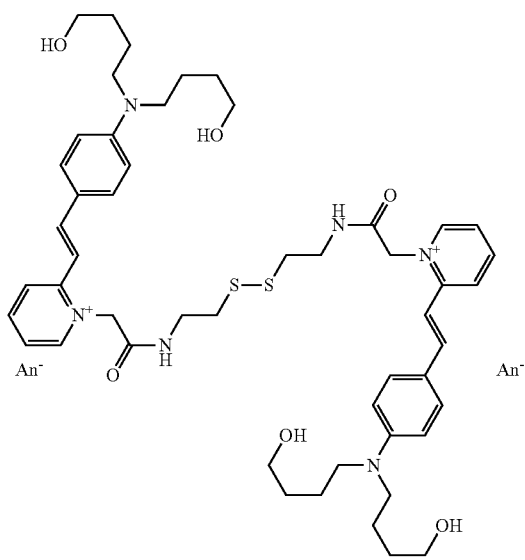
71
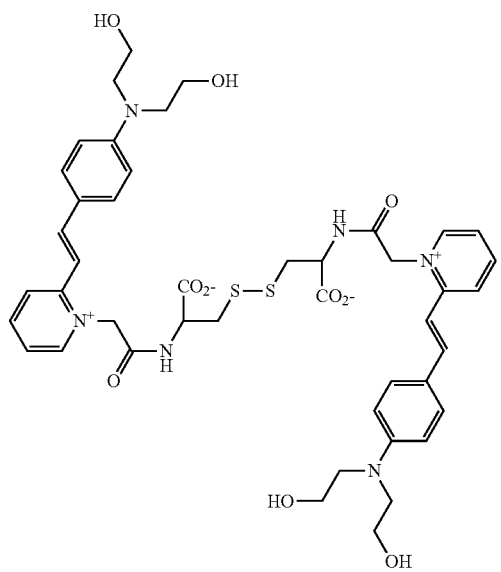
72
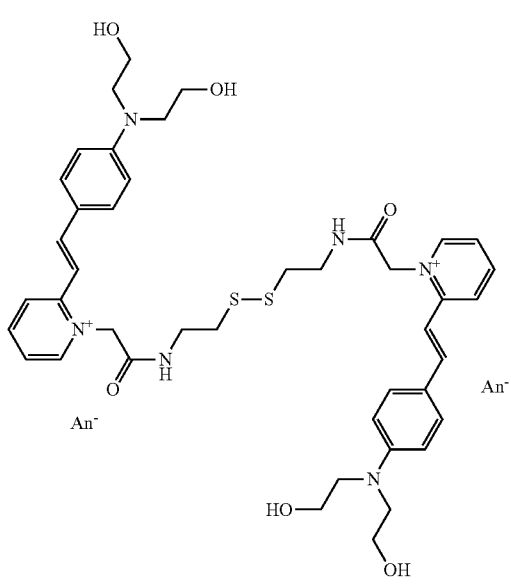
73
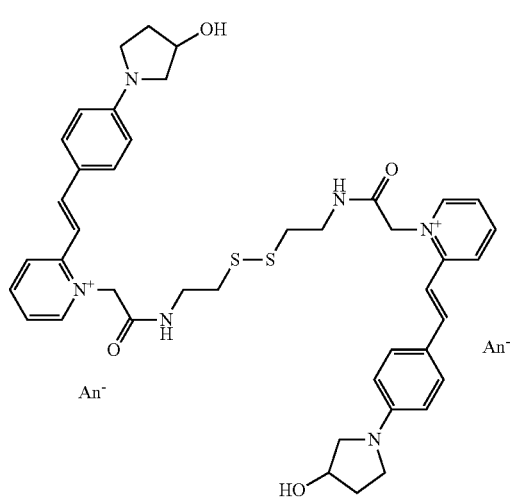
74

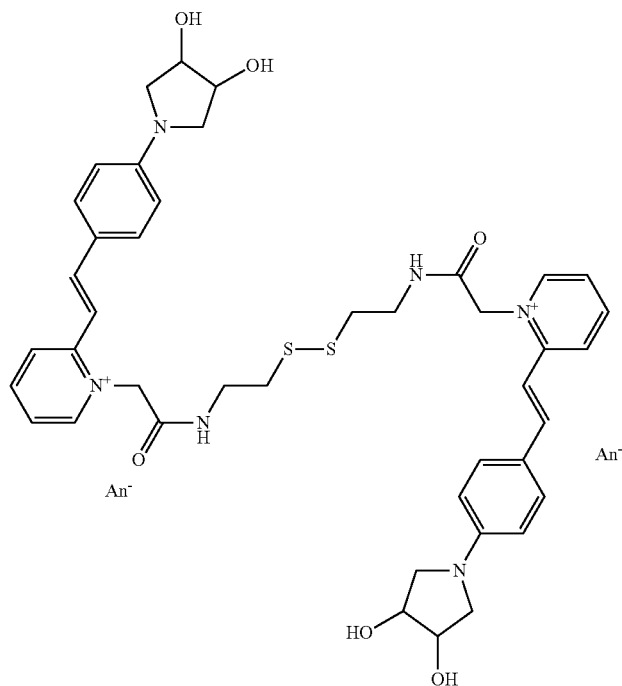
75
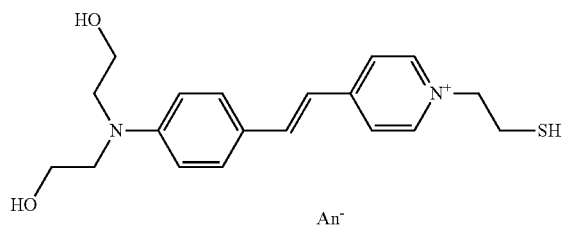
76
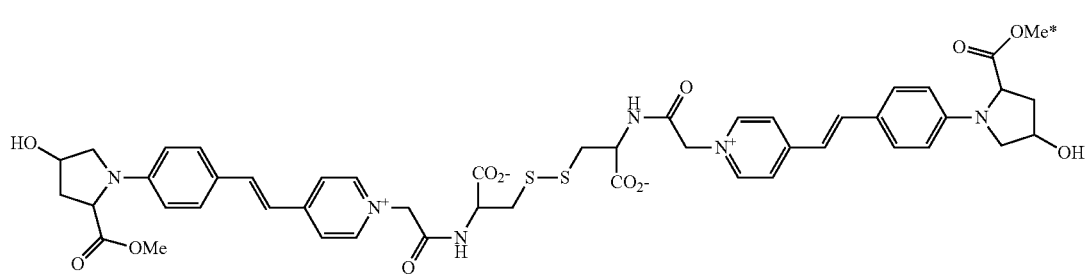
77
Me* represents an alkali metal or ½ alkaline earth metal; or a methyl
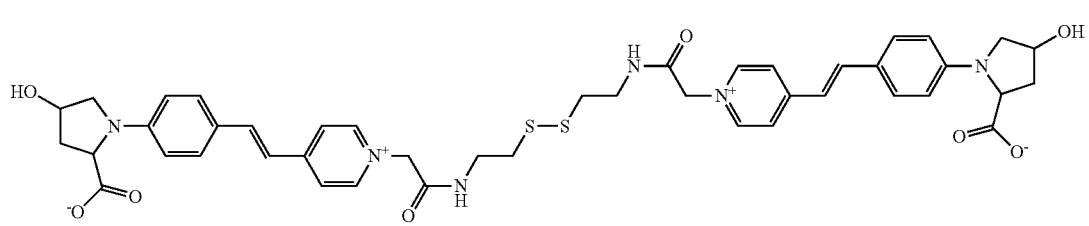
78

79
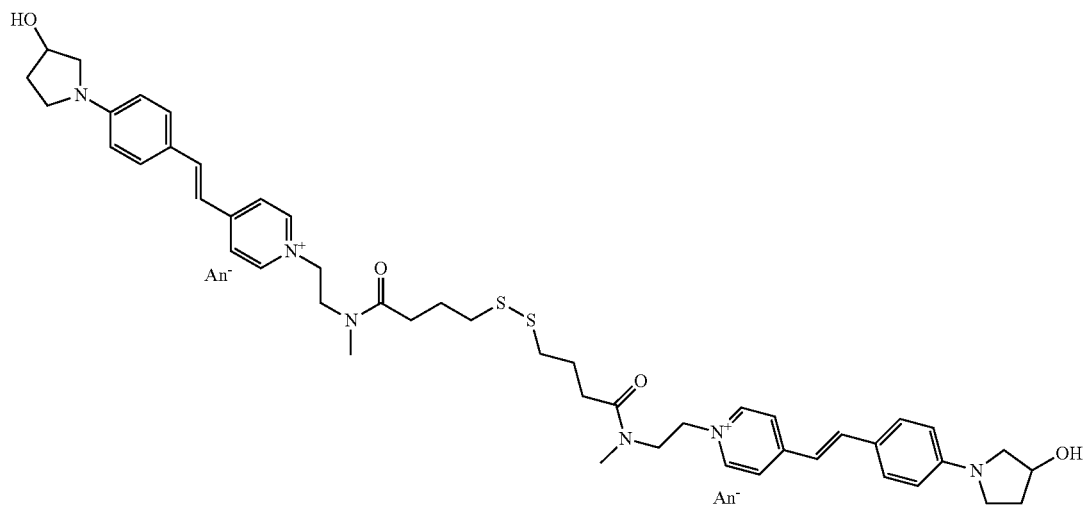
80
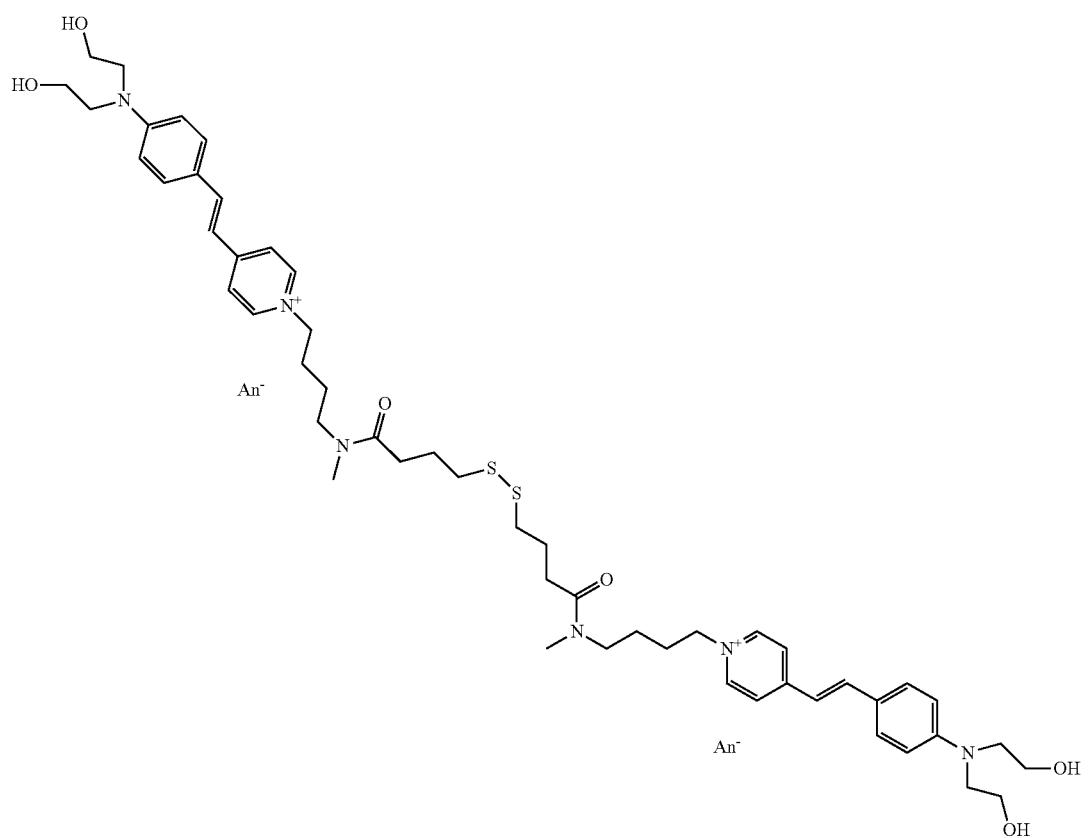

81
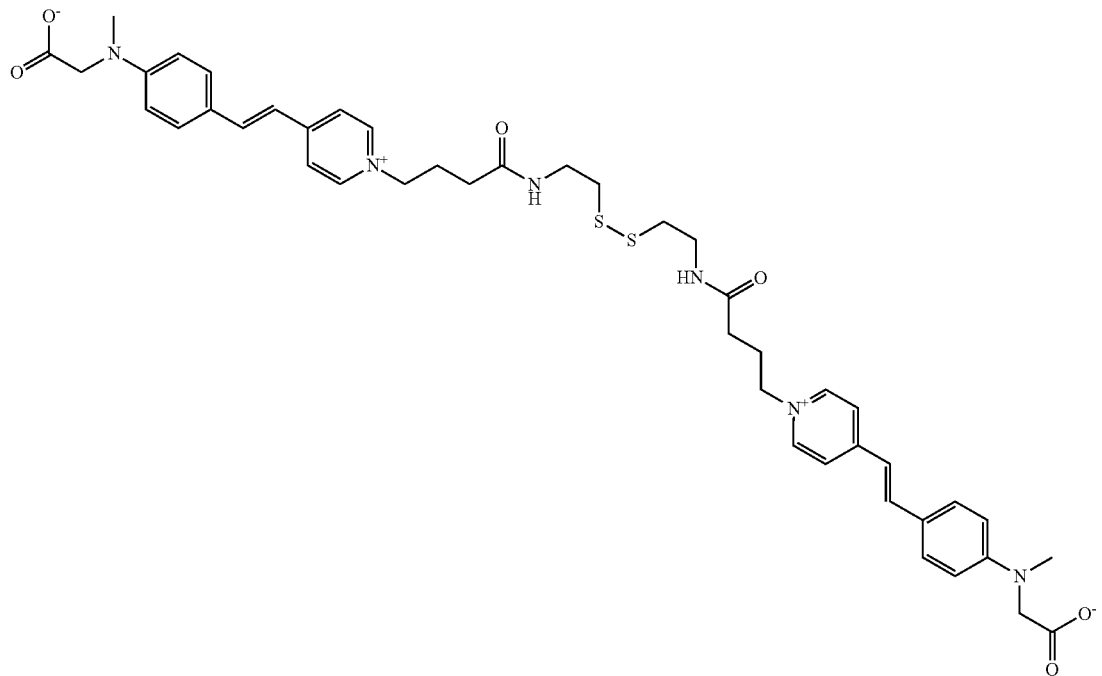
82
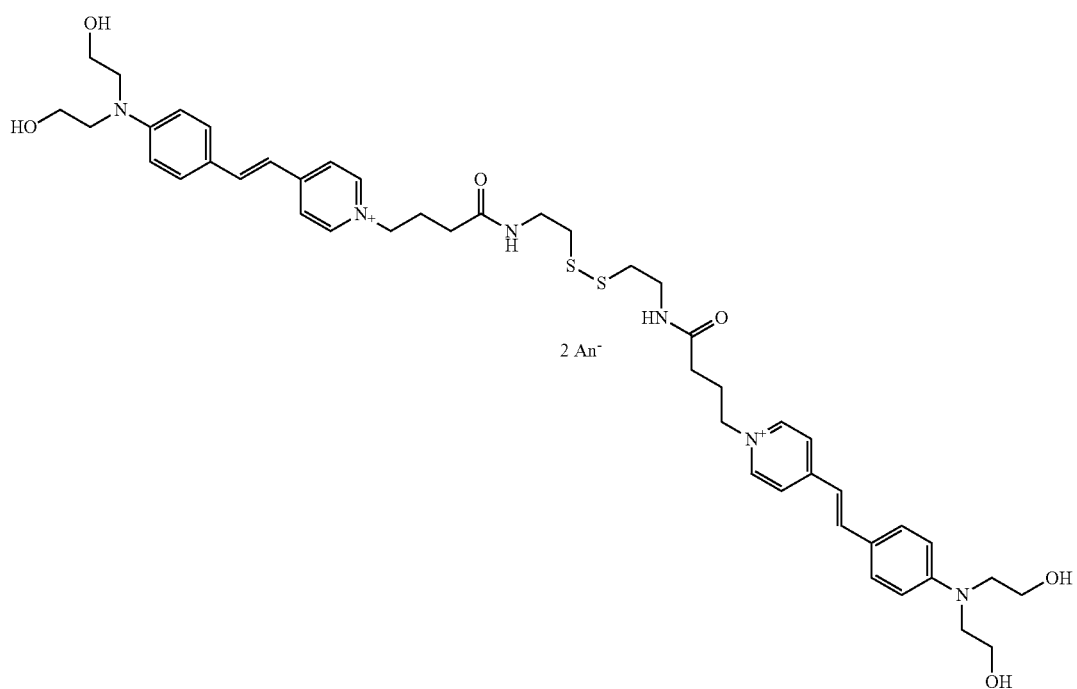

-continued
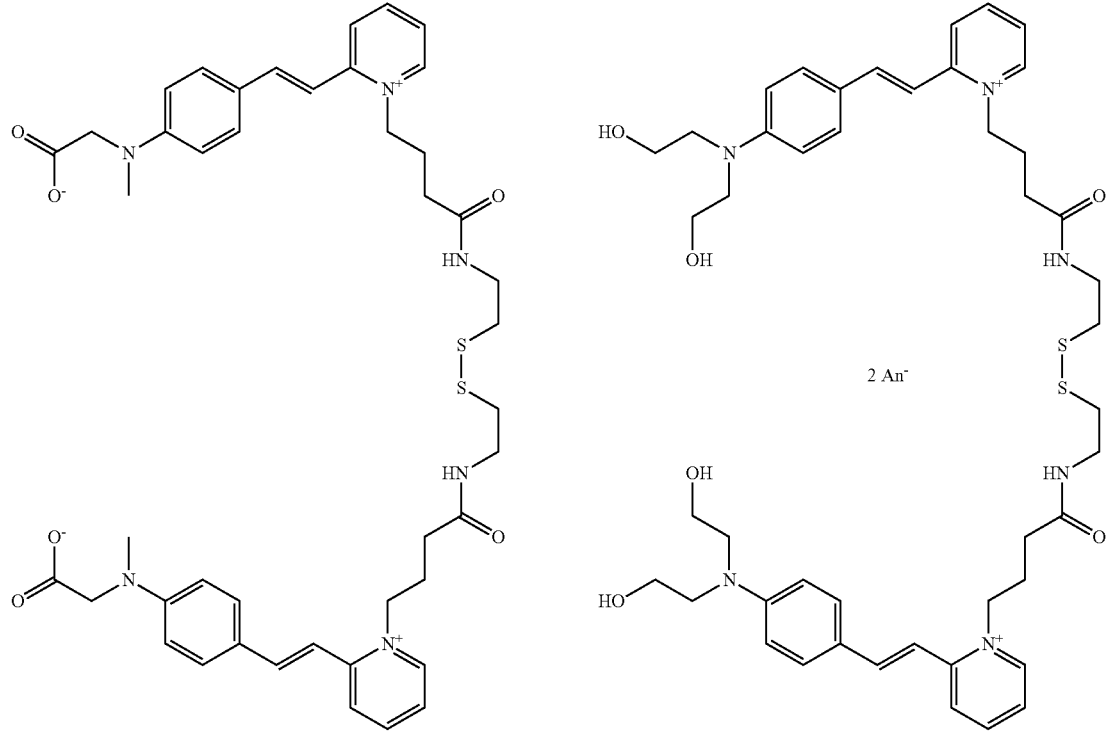
83
84
2 An⁻
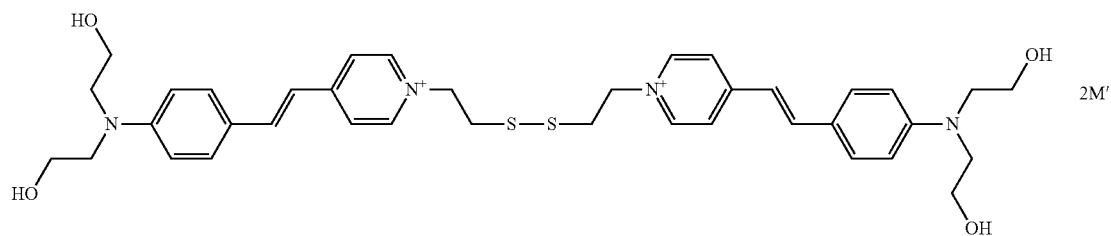
85
2M′
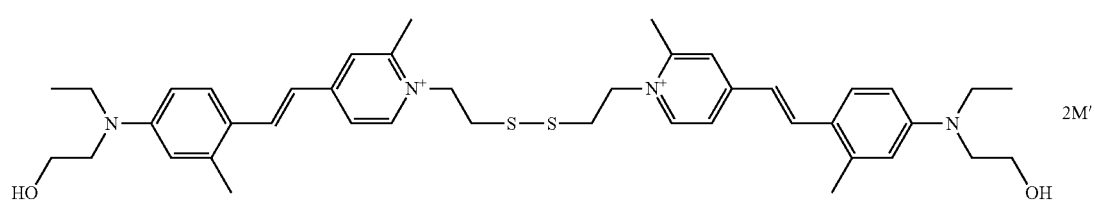
86
2M′
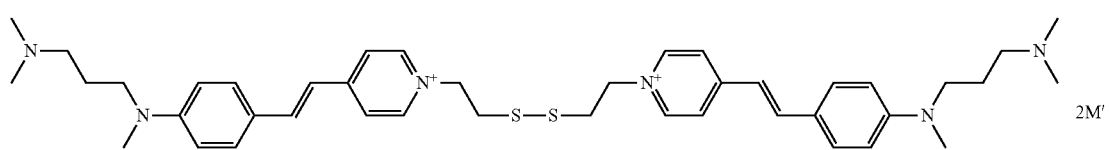
87
2M′

-continued
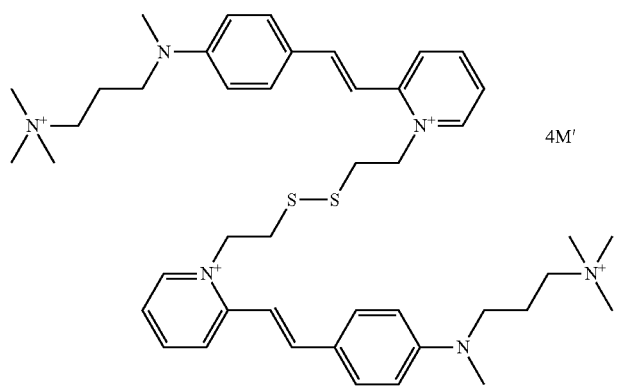
88
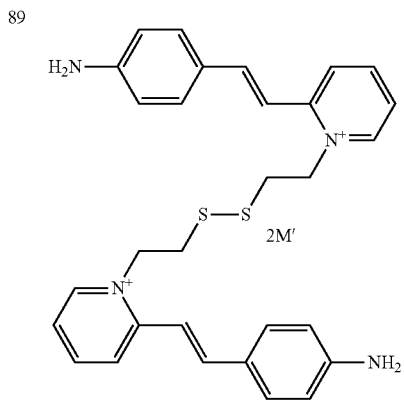
89
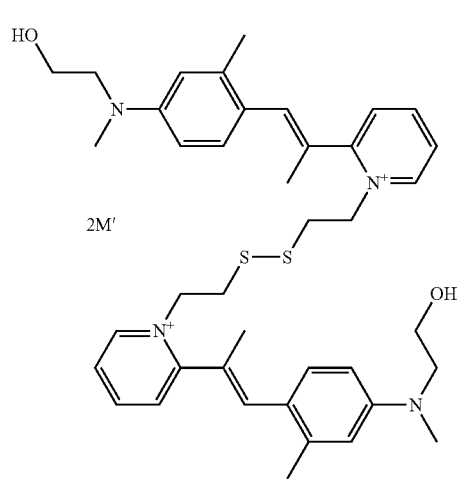
90
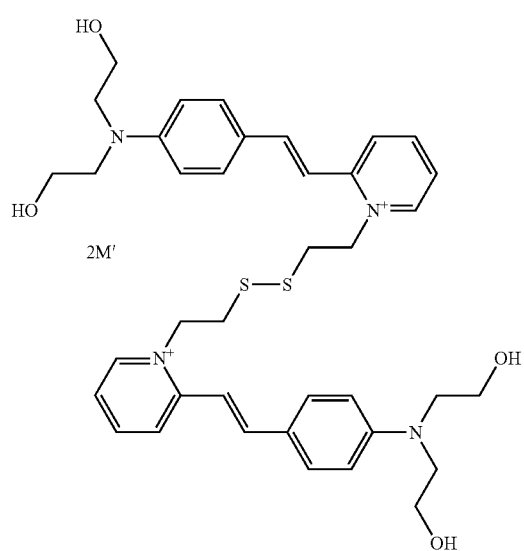
91

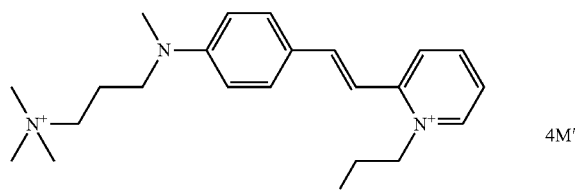
4M'
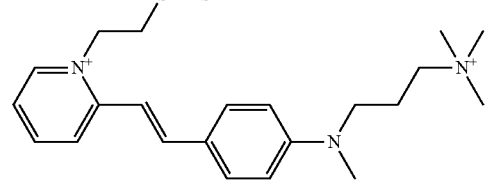
2M'
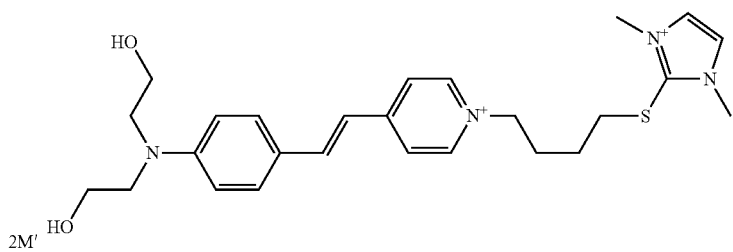
2M'
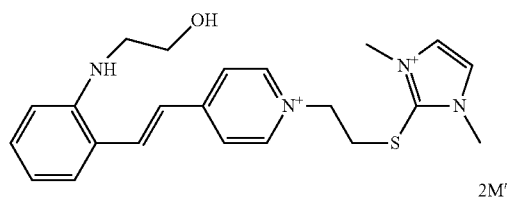
2M'
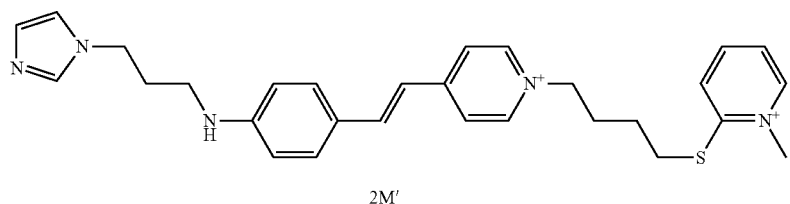
2M'
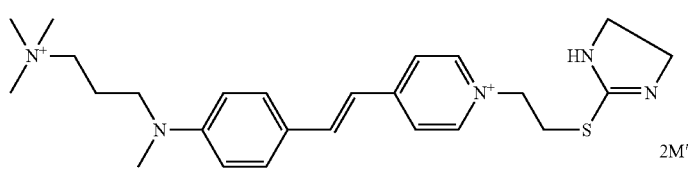
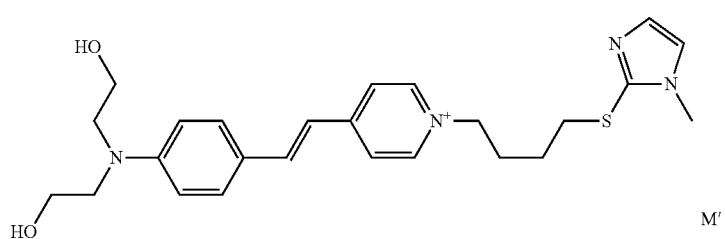
M'

-continued
98
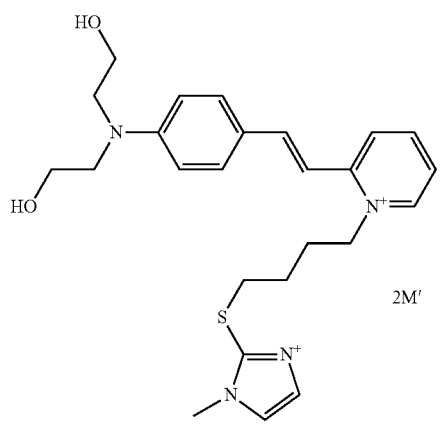
99
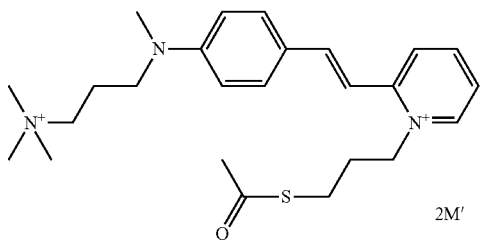
100
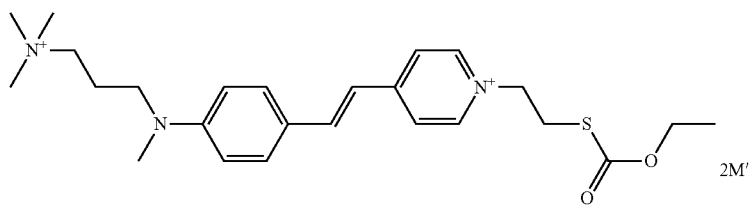
101
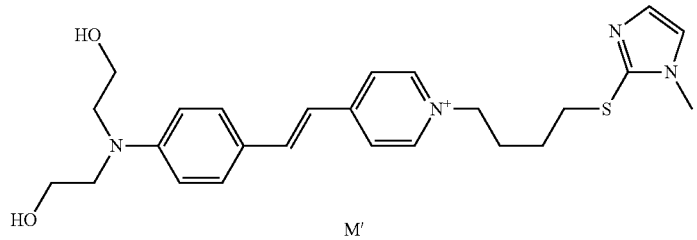
102
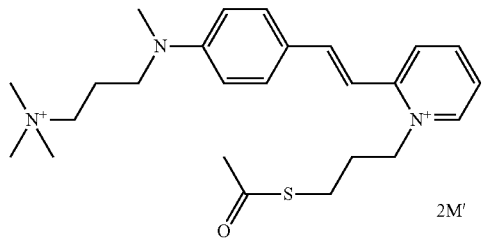
102
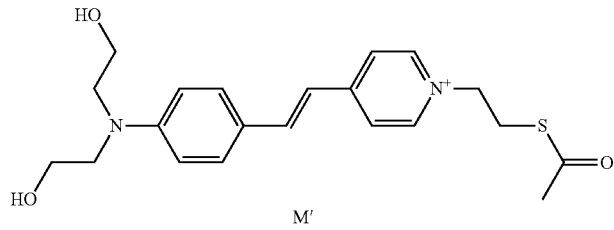
103
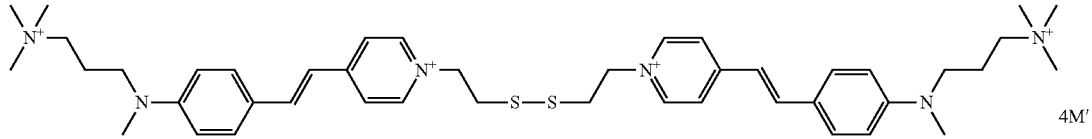

-continued
| | |
|---|---|
| 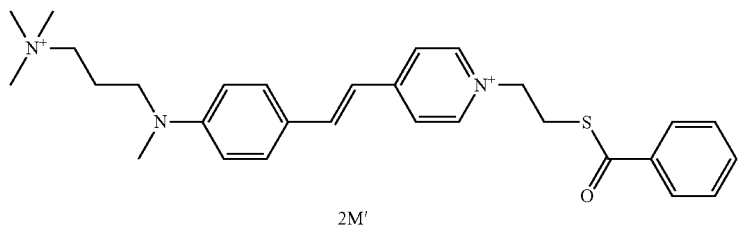 2M' | 104 |
| 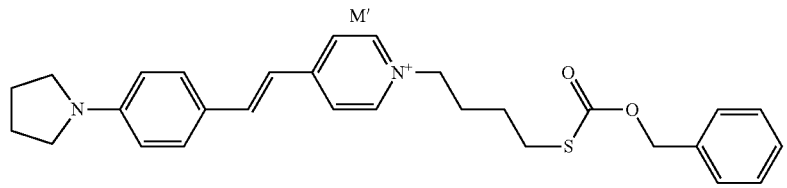 M' | 105 |
| 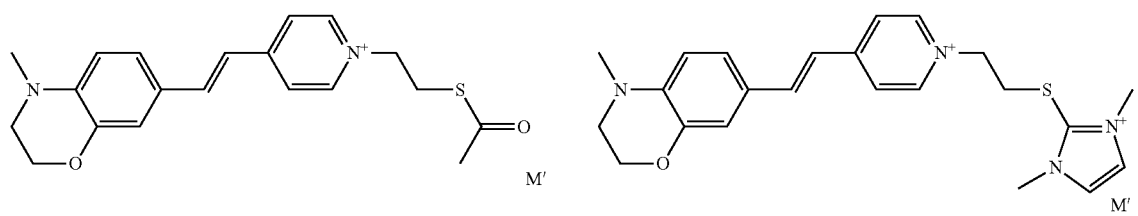 M' | 106 107 |
| 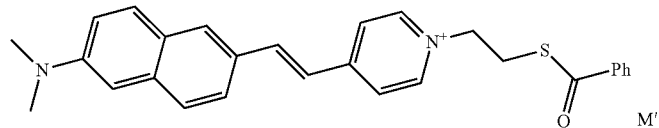 M' | 108 |
| 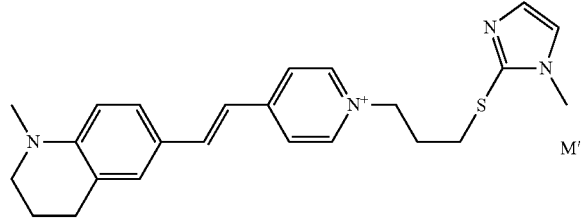 M' | 109 |
| 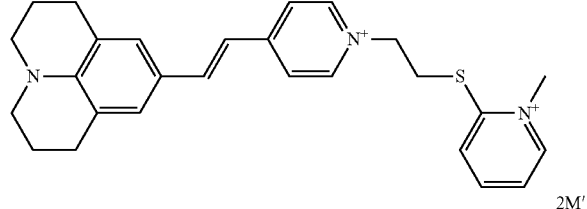 2M' | 110 |
| 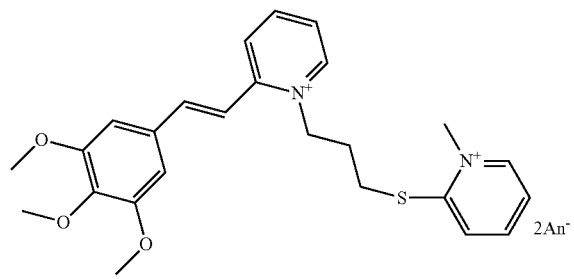 2An⁻ | 111 |

-continued
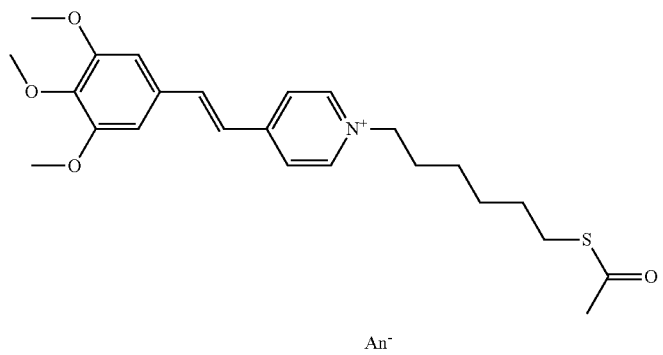
112
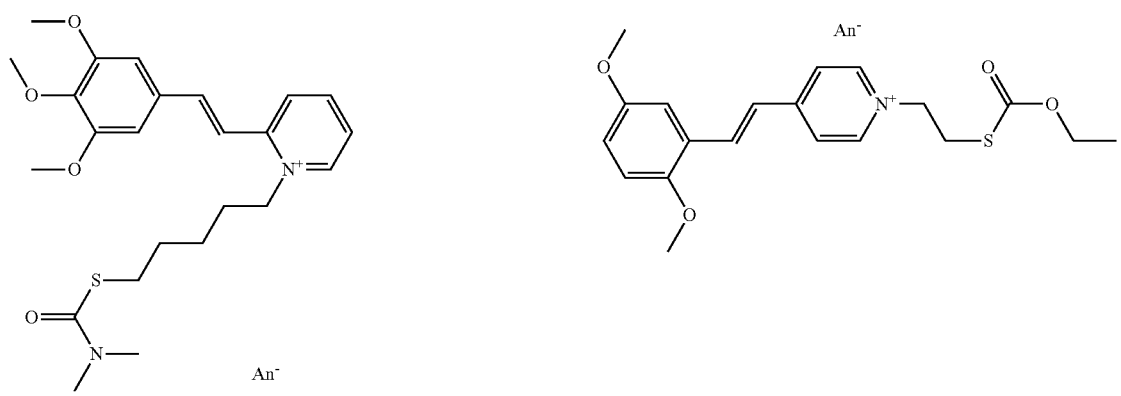
113
114
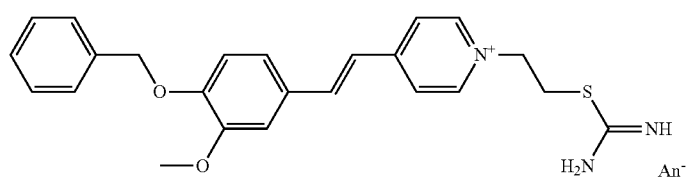
115
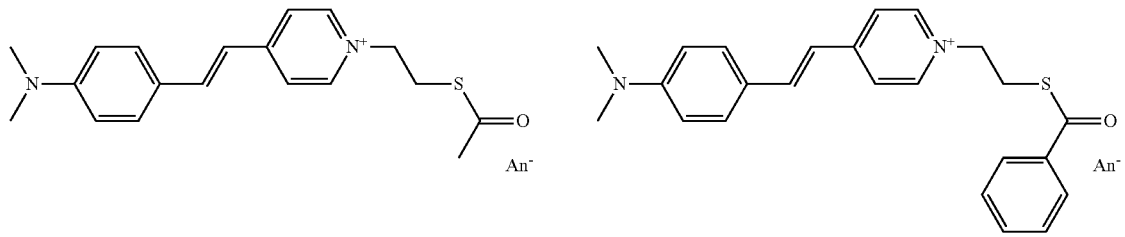
116
117
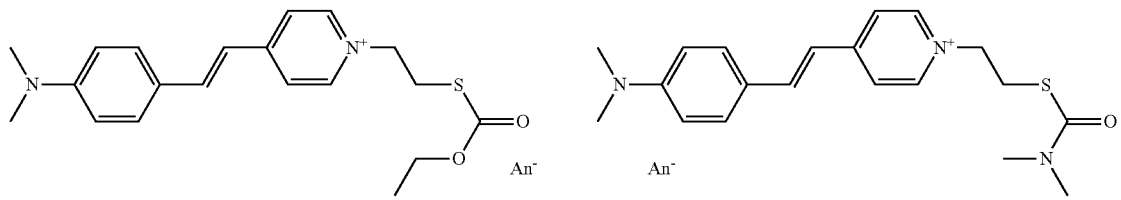
118
119

-continued

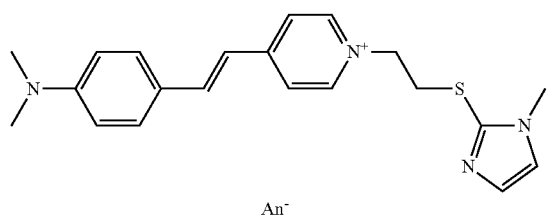

120

An⁻

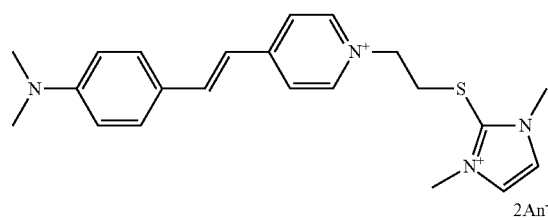

121

2An⁻

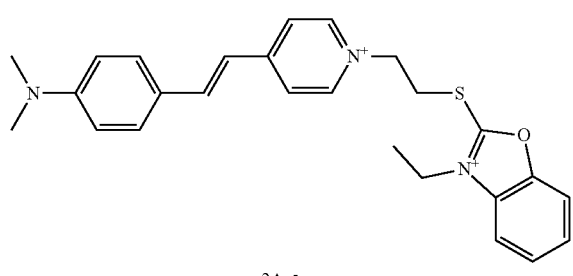

122

2An⁻

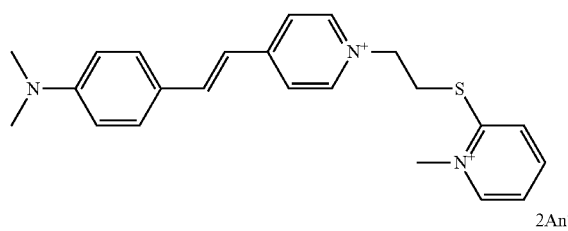

123

2An⁻ with An⁻ and M', which are identical or different, preferably identical, representing anionic counterions. More particularly, the anionic counterion is chosen from halides, such as chloride, alkyl sulphate, such as methyl sulphate, mesylate and $½(O═)_2SO^{2-}$ or $½SO_4^{2-}$.

More preferably, the dyes 0 as defined above are chosen from compounds 44, 49, 49a and 55, in particular 44, 49 and 55.

According to a particularly advantageous embodiment of the invention, the dye 0 is a dye comprising a "permanent" cationic charge, that is to say having, in its structure, at least one quaternized nitrogen (ammonium) atom or quaternized phosphorus (phosphonium) atom, preferably quaternized nitrogen atom.

The composition according to the invention comprises, in a cosmetic medium, an amount of dyes having a disulphide, thiol or protected thiol functional group as defined above, in particular of formula (I) as defined above, generally of between 0.001 and 30% inclusive, with respect to the total weight of the composition.

Preferably, the amount of dyes having a disulphide, thiol or protected thiol functional group as defined above, in particular of formula (I) is between 0.01 and 5% by weight inclusive, with respect to the total weight of the composition. By way of example, the dye or dyes occur(s) in an amount of between 0.01 and 2% inclusive.

i). 5). The Organic or Inorganic Acid Salt and Counterion of the Dyes of the Invention which is Cosmetically Acceptable.

They are chosen from the "organic or inorganic acid salt" and "anionic counterion" as defined above.

Furthermore, the addition salts which can be used in the context of the invention can be chosen from addition salts with a cosmetically acceptable base, such as the basifying agents as defined below, for example alkali metal hydroxides, such as sodium hydroxide or potassium hydroxide, aqueous ammonia, amines or alkanolamines.

ii) At Least One Thickening Organic Polymer:

The composition according to the invention comprises ii) one or more thickening organic polymers.

The thickening organic polymers according to the invention can be of natural or synthetic origin.

The thickening polymers can be anionic, cationic, amphoteric or nonionic polymers which may or may not be associative.

They can be aqueous- or oily-phase thickeners.

Mention may be made, as aqueous-phase thickening polymers, of nonassociative thickening polymers having sugar units.

Sugar unit is understood to mean, within the meaning of the present invention, a unit resulting from a carbohydrate of formula $C_n(H_2O)_{n-1}$ or $(CH_2O)_n$ which can optionally be modified by substitution and/or by oxidation and/or by dehydration.

The sugar units which can participate in the composition of the thickening polymers of the invention preferably result from the following sugars:
glucose;
galactose;
arabinose;
rhamnose;
mannose;
xylose;
fucose;
anhydrogalactose;
galacturonic acid;

glucuronic acid;
mannuronic acid;
galactose sulphate;
anhydrogalactose sulphate and
fructose.

Mention may in particular be made, as thickening polymers of the invention, of native gums, such as:

a) tree or shrub exudates, including:
   gum arabic (branched polymer of galactose, arabinose, rhamnose and glucuronic acid);
   ghatti gum (polymer resulting from arabinose, galactose, mannose, xylose and glucuronic acid);
   karaya gum (polymer resulting from galacturonic acid, galactose, rhamnose and glucuronic acid);
   gum tragacanth (polymer of galacturonic acid, galactose, fucose, xylose and arabinose);

b) gums resulting from algae, including:
   agar (polymer resulting from galactose and anhydrogalactose);
   alginates (polymers of mannuronic acid and glucuronic acid);
   carrageenans and furcellarans (polymers of galactose sulphate and anhydrogalactose sulphate);

c) gums resulting from seeds or tubers, including:
   guar gum (polymer of mannose and galactose);
   locust bean gum (polymer of mannose and galactose);
   fenugreek gum (polymer of mannose and galactose);
   tamarind gum (polymer of galactose, xylose and glucose);
   konjac gum (polymer of glucose and mannose);

d) microbial gums, including:
   xanthan gum (polymer of glucose, mannose acetate, mannose/pyruvic acid and glucuronic acid);
   gellan gum (polymer of partially acylated glucose, rhamnose and glucuronic acid);
   scleroglucan gum (polymer of glucose);

e) plant extracts, including:
   cellulose (polymer of glucose);
   starch (polymer of glucose) and
   inulin.

These polymers may be physically or chemically modified. A physical treatment that may especially be mentioned is the temperature.

Mention may be made, as chemical treatments, of esterification, etherification, amidation or oxidation reactions. These treatments can lead to polymers that may especially be nonionic, anionic or amphoteric.

Preferably, these chemical or physical treatments are applied to guar gums, locust bean gums, starches and celluloses.

The nonionic guar gums which can be used according to the invention can be modified by (poly)hydroxy($C_1$-$C_6$)alkyl groups.

Mention may be made, among (poly)hydroxy($C_1$-$C_6$) alkyl groups, by way of example, of the hydroxymethyl, hydroxyethyl, hydroxypropyl and hydroxybutyl groups.

These guar gums are well known in the prior art and can be prepared, for example, by reacting the corresponding alkene oxides, such as, for example, propylene oxides, with the guar gum so as to obtain a guar gum modified with hydroxypropyl groups.

The degree of hydroxyalkylation preferably ranges from 0.4 to 1.2, and corresponds to the number of alkylene oxide molecules consumed by the number of free hydroxyl functional groups present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The botanical origin of the starch molecules used in the present invention may be cereals or tubers. Thus, the starches are chosen, for example, from maize starch, rice starch, cassava starch, barley starch, potato starch, wheat starch, sorghum starch and pea starch.

The starches can be modified chemically or physically, in particular by one or more of the following reactions: pregelatinization, oxidation, crosslinking, esterification, etherification, amidation or heat treatments.

Distarch phosphates or compounds rich in distarch phosphate will preferentially be used, for instance the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized maize distarch phosphate).

According to the invention, amphoteric starches may also be used, these amphoteric starches comprising one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulphate type, preferably carboxylic type. The cationic groups may be of primary, secondary, tertiary or quaternary amine type.

The starch molecules may be derived from any plant source of starch, especially such as maize, potato, oat, rice, tapioca, sorghum, barley or wheat. It is also possible to use the hydrolysates of the starches mentioned above. The starch is preferably derived from potato.

The nonassociative thickening polymers of the invention can be cellulose polymers not comprising a $C_{10}$-$C_{30}$ fatty chain in their structure.

"Cellulose" polymer is understood to mean, according to the invention, any polysaccharide compound having, in its structure, sequences of glucose residues joined up via β-1,4 bonds; in addition to unsubstituted celluloses, the cellulose derivatives can be anionic, cationic, amphoteric or nonionic.

Thus, the cellulose polymers of the invention can be chosen from unsubstituted celluloses, including under a microcrystalline form, and cellulose ethers.

Among these cellulose polymers, cellulose ethers, cellulose esters and cellulose ester ethers are distinguished.

Cellulose esters include inorganic esters of cellulose (cellulose nitrates, sulphates or phosphates, and the like), organic esters of cellulose (cellulose monoacetates, triacetates, amidopropionates, acetate butyrates, acetate propionates or acetate trimellitates, and the like) and mixed organic/inorganic esters of cellulose, such as cellulose acetate butyrate sulphates and acetate propionate sulphates. Among the cellulose ester ethers, mention may be made of hydroxypropylmethylcellulose phthalates and ethylcellulose sulphates.

Mention may be made, among nonionic cellulose ethers without a $C_{10}$-$C_{30}$ fatty chain, i.e. "nonassociative" cellulose ethers, of ($C_1$-$C_4$)alkylcelluloses, such as methylcelluloses and ethylcelluloses (for example, Ethocel Standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); or (poly)hydroxy($C_r$ $C_4$)alkyl-($C_1$-$C_4$)

alkylcellulose mixed celluloses, such as hydroxypropylmethylcelluloses (for example, Methocel E4M from Dow Chemical), hydroxyethyl-methylcelluloses, hydroxyethylethylcelluloses (for example, Bermocoll E 481 FQ from Akzo Nobel) and hydroxybutyl-methylcelluloses.

Mention may be made, among anionic cellulose ethers without a fatty chain, of (poly)carboxy($C_1$-$C_4$)alkylcelluloses and their salts. Examples that may be mentioned include carboxymethylcelluloses, carboxymethylmethylcelluloses (for example, Blanose 7M from the company Aqualon) and carboxymethylhydroxyethylcelluloses, and the sodium salts thereof.

Mention may be made, among cationic cellulose ethers without a fatty chain, of cationic cellulose derivatives, such as cellulose copolymers or cellulose derivatives grafted with a water-soluble quaternary ammonium monomer and described in particular in U.S. Pat. No. 4,131,576, such as (poly)hydroxy($C_1$-$C_4$)alkylcelluloses, for example hydroxymethyl-, hydroxyethyl- or hydroxypropylcelluloses, grafted in particular with a methacryloylethyltrimethylammonium, methacrylamidopropyltrimethylammonium, dimethyl-diallylammonium salt. The commercial products corresponding to this definition are more particularly the products sold under the names "Celquat® L 200" and "Celquat® H 100" by National Starch.

Among the nonassociative thickening polymers not bearing sugar units that may be used, mention may be made of crosslinked acrylic or methacrylic acid homopolymers or copolymers, crosslinked 2-acrylamido-2-methylpropanesulphonic acid homopolymers and crosslinked acrylamide copolymers thereof, ammonium acrylate homopolymers, or copolymers of ammonium acrylate and of acrylamide, alone or as mixtures.

A first family of nonassociative thickening polymers that is suitable is represented by crosslinked acrylic acid homopolymers.

Among the homopolymers of this type, mention may be made of those crosslinked with an allyl ether of an alcohol of the sugar series, such as, for example, the products sold under the names Carbopol 980, 981, 954, 2984 and 5984 by the company Noveon or the products sold under the names Synthalen M and Synthalen K by the company 3 VSA.

The nonassociative thickening polymers may also be crosslinked (meth)acrylic acid copolymers, such as the polymer sold under the name Aqua SF1 by the company Noveon.

The nonassociative thickening polymers may be chosen from crosslinked 2-acrylamido-2-methylpropanesulphonic acid homopolymers and the crosslinked acrylamide copolymers thereof.

Among the partially or totally neutralized crosslinked copolymers of 2-acrylamido-2-methylpropanesulphonic acid and of acrylamide, mention may be made in particular of the product described in Example 1 of the document EP 503 853, and reference may be made to said document as regards these polymers.

The composition may similarly comprise, as nonassociative thickening polymers, ammonium acrylate homopolymers or copolymers of ammonium acrylate and of acrylamide.

Among the ammonium acrylate homopolymers that may be mentioned by way of examples is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made especially to the documents FR 2 416 723, U.S. Pat. No. 2,798,053 and U.S. Pat. No. 2,923,692 as regards the description and preparation of such compounds.

Mention may also be made, among aqueous-phase thickening polymers, of non cellulose associative polymers well known to a person skilled in the art and in particular of nonionic, anionic, cationic or amphoteric nature.

It should be remembered that "associative polymers" are polymers capable, in an aqueous medium, of being reversibly combined with one another or with other molecules.

Their chemical structure more particularly comprises at least one hydrophilic region and at least one hydrophobic region.

"Hydrophobic group" is understood to mean a radical or polymer having a saturated or unsaturated and linear or branched hydrocarbon chain comprising at least 10 carbon atoms, preferably from 10 to 30 carbon atoms, in particular from 12 to 30 carbon atoms and more preferably from 18 to 30 carbon atoms.

Preferentially, the hydrocarbon group is derived from a monofunctional compound. By way of example, the hydrophobic group may be derived from a fatty alcohol, such as stearyl alcohol, dodecyl alcohol or decyl alcohol. It may also denote a hydrocarbon polymer, for instance polybutadiene.

Among the associative polymers of anionic type that may be mentioned are:
(a) those comprising at least one hydrophilic unit and at least one allyl ether unit having a fatty chain, more particularly those for which the hydrophilic unit is composed of an unsaturated ethylenic anionic monomer, or particularly still of a vinylcarboxylic acid and very particularly of an acrylic acid or a methacrylic acid or the mixtures of these.

Preference is particularly given among these anionic associative polymers, according to the invention, to the polymers formed from 20 to 60% by weight of acrylic and/or methacrylic acid, from 5 to 60% by weight of lower alkyl (meth)acrylates, from 2 to 50% by weight of allyl ether having a fatty chain, and from 0 to 1% by weight of a crosslinking agent which is a well known copolymerizable unsaturated polyethylenic monomer, such as diallyl phthalate, allyl (meth)acrylate, divinylbenzene, (poly)ethylene glycol dimethacrylate and methylenebisacrylamide.

Among the latter, preference is very particularly given to crosslinked terpolymers of methacrylic acid, ethyl acrylate and alkyl ether of polyethylene glycol (10 EO) ether of stearyl alcohol (Steareth 10), in particular those sold by Ciba under the names Salcare SC800 and Salcare SC900, which are 30% aqueous emulsions of a crosslinked terpolymer of methacrylic acid, ethyl acrylate and steareth-10 allyl ether (40/50/10).

(b) those comprising i) at least one hydrophilic unit of unsaturated olefinic carboxylic acid type and ii) at least one hydrophobic unit of ($C_{10}$-$C_{30}$)alkyl ester of unsaturated carboxylic acid type.

($C_{10}$-$C_{30}$)Alkyl esters of unsaturated carboxylic acids of use in the invention comprise, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. No. 3,915,921 and U.S. Pat. No. 4,509,949.

Use will more particularly be made, among anionic associative polymers of this type, of those composed of from 95 to 60% by weight of acrylic acid (hydrophilic unit), from 4 to 40% by weight of $C_{10}$-$C_{30}$ alkyl acrylate (hydrophobic unit) and from 0 to 6% by weight of crosslinking polymerizable monomer or else those composed of from 98 to 96% by weight of acrylic acid (hydrophilic unit), from 1 to 4% by weight of $C_{10}$-$C_{30}$ alkyl acrylate (hydrophobic unit) and from 0.1 to 0.6% by weight of crosslinking polymerizable monomer, such as those described above.

Preference is very particularly given, among the above said polymers, according to the present invention, to the products sold by Goodrich under the trade names Pemulen TR1®, Pemulen TR20 and Carbopol 1382®, more preferably still Pemulen TR1®, and the product sold by Seppic under the name Coatex SX®. Mention may also be made of the acrylic acid/lauryl methacrylate/vinylpyrrolidone terpolymer sold under the name Acrylidone LM by ISP.

(c) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by Newphase Technologies.

(d) acrylic terpolymers comprising:
  i) approximately 20% to 70% by weight of a carboxylic acid having an α,β-monoethylenic unsaturation [A],
  ii) approximately 20 to 80% by weight of a non-surface-active monomer having an α,β-monoethylenic unsaturation other than [A],
  iii) approximately 0.5 to 60% by weight of a nonionic monourethane which is the reaction product of a monohydric surfactant with a monoisocyanate having a monoethylenic unsaturation, such as those described in Patent Application EP-A-0 173 109 and more particularly the terpolymer described in Example 3, namely a methacrylic acid/methyl acrylate/ethoxylated (40 EO) behenyl alcohol dimethyl(meta-isopropenyl)benzyl isocyanate terpolymer, as a 25% aqueous dispersion.

(e) copolymers comprising, among their monomers, an α,β-monoethylenically unsaturated carboxylic acid and an ester of an α,β-monoethylenically unsaturated carboxylic acid and of an oxyalkylnated fatty alcohol.

Preferentially, these compounds also comprise, as monomer, an ester of an α,β-monoethylenically unsaturated carboxylic acid and of a $C_1$-$C_4$ alcohol.

Mention may be made, as example of this type of compound, of Aculyn 22®, sold by Rohm & Haas, which is a methacrylic acid/ethyl acrylate/oxyalkylnated stearyl methacrylate terpolymer.

(f) amphiphilic polymers comprising at least one ethylenically unsaturated monomer having a sulphonic group, in the free or partially or completely neutralized form, and comprising at least one hydrophobic part. These polymers may be crosslinked or noncrosslinked. They are preferably crosslinked.

The ethylenically unsaturated monomers having a sulphonic group are chosen in particular from vinylsulphonic acid, styrenesulphonic acid, (meth)acrylamido($C_1$-$C_{22}$) alkylsulphonic acids, N—($C_1$-$C_{22}$)alkyl(meth)acrylamido ($C_1$-$C_{22}$)alkylsulphonic acids, such as undecylacrylamidomethanesulphonic acid, and their partially or completely neutralized forms.

Use will more preferably be made of (meth)acrylamido ($C_1$-$C_{22}$)alkylsulphonic acids, such as, for example, acrylamidomethanesulphonic acid, acrylamidoethanesulphonic acid, acrylamidopropanesulphonic acid, 2-acrylamido-2-methylpropanesulphonic acid, 2-methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid, 2-acrylamido-2,6-dimethyl-3-heptanesulphonic acid and their partially or completely neutralized forms.

2-Acrylamido-2-methylpropanesulphonic acid (AMPS), and also partially or totally neutralized forms thereof, will more particularly be used.

The polymers of this family can be chosen in particular from random amphiphilic AMPS polymers modified by reaction with a mono(n-alkyl)amine or a di(n-alkyl)amine in which the alkyl group is a $C_6$-$C_{22}$ alkyl group, such as those described in Patent Application WO 00/31154. These polymers can also comprise other hydrophilic ethylenically unsaturated monomers chosen, for example, from (meth) acrylic acids, their β-substituted alkyl derivatives or their esters obtained with monoalcohols or mono- or polyalkylene glycols, (meth)acrylamides, vinylpyrrolidone, maleic anhydride, itaconic acid or maleic acid or the mixtures of these compounds.

The preferred polymers of this family are chosen from amphiphilic copolymers of AMPS and of at least one hydrophobic ethylenically unsaturated monomer.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or the mixtures of these compounds.

These copolymers are described in particular in Patent Application EP-A-750899, U.S. Pat. No. 5,089,578 and the following publications by Yotaro Morishima:

« Self-assembling amphiphilic polyelectrolytes and their nanostructures—*Chinese Journal of Polymer Science*, Vol. 18, No. 40 (2000), 323-336»;

« Micelle formation of random copolymers of sodium 2-(acrylamido)-2-methylpropanesulfonate and a nonionic surfactant macromonomer in water as studied by fluorescence and dynamic light scattering—*Macromolecules*, Vol. 33, No. 10 (2000), 3694-3704»;

« Solution properties of micelle networks formed by non-ionic moieties covalently bound to an polyelectrolyte: salt effects on rheological behavior—*Langmuir*, Vol. 16, No. 12 (2000), 5324-5332»;

« Stimuli responsive amphiphilic copolymers of sodium 2-(acrylamido)-2-methylpropanesulfonate and associative macromonomers—*Polym. Preprint, Div. Polym. Chem.*, 40(2) (1999), 220-221».

Mention may be made, among these polymers, of:

neutralized or normeutralized and crosslinked or non-crosslinked copolymers comprising from 15 to 60% by weight of AMPS units and from 40 to 85% by weight of ($C_8$-$C_{16}$)alkyl(meth)acrylamide units or of ($C_8$-$C_{16}$) alkyl (meth)acrylate units, with respect to the polymer, such as described in Application EP-A 750 899;

terpolymers comprising from 10 to 90 mol % of acrylamide units, from 0.1 to 10 mol % of AMPS units and from 5 to 80 mol % of n-($C_6$-$C_{18}$)alkylacrylamide units, such as those described in U.S. Pat. No. 5,089,578.

Mention may also be made of copolymers of completely neutralized AMPS and of dodecyl methacrylate and non-crosslinked and crosslinked copolymers of AMPS and of n-dodecylmethacrylamide, such as those described in the abovementioned papers by Morishima.

Mention may be made, among cationic associative polymers, of:
- (I) cationic associative polyurethanes;
- (II) the compound sold by Noveon under the name Aqua CC and which corresponds to the INCI name Polyacrylate-1 Crosspolymer.

Polyacrylate-1 Crosspolymer is the product of the polymerization of a mixture of monomers comprising:
- a di($C_1$-$C_4$ alkyl)amino($C_1$-$C_6$ alkyl) methacrylate,
- one or more $C_1$-$C_{30}$ alkyl esters of (meth)acrylic acid,
- a polyethoxylated (20-25 mol of ethylene oxide units) $C_{10}$-$C_{30}$ alkyl methacrylate,
- a 30/5 polyethylene glycol/polypropylene glycol allyl ether,
- a hydroxy($C_2$-$C_6$ alkyl) methacrylate, and
- an ethylene glycol dimethacrylate.

(III) quaternized (poly)hydroxyethylcelluloses modified by groups comprising at least one fatty chain, such as alkyl, arylalkyl or alkylaryl groups comprising at least 8 carbon atoms, or mixtures of these. The alkyl radicals carried by the quaternized celluloses or hydroxyethylcelluloses above preferably comprise from 8 to 30 carbon atoms. The aryl radicals preferably denote phenyl, benzyl, naphthyl or anthryl groups. There may be indicated, as examples of quaternized alkylhydroxyethylcelluloses having $C_8$-$C_{30}$ fatty chains, the products Quatrisoft LM 200®, Quatrisoft LM-X 529-18-A®, Quatrisoft LM-X 529-18-B® ($C_{12}$ alkyl) and Quatrisoft LM-X 529-8® ($C_{18}$ alkyl), sold by Aqualon, the products Crodacel QM®, Crodacel QL® ($C_{12}$ alkyl) and Crodacel QS® ($C_{18}$ alkyl), sold by Croda and the product Softcat SL 100@ sold by Aqualon.

(IV) cationic polyvinyllactam polymers.

Such polymers are described, for example, in Patent Application WO00/68282.

Use is made in particular, as cationic poly(vinyllactam) polymers according to the invention, of vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamido-propylammonium tosylate terpolymers or vinylpyrrolidone/dimethyl-aminopropylmethacrylamide/lauryldimethylmethacrylamidopropylammonium tosylate or chloride terpolymers.

The amphoteric associative polymers are preferably chosen from those comprising at least one noncyclic cationic unit. More particularly still, preference is given to those prepared from or comprising from 1 to 20 mol % of monomer comprising a fatty chain, preferably from 1.5 to 15 mol % and more particularly still from 1.5 to 6 mol %, with respect to the total number of moles of monomers.

Amphoteric associative polymers according to the invention are, for example, described and prepared in Patent Application WO 98/44012.

Preference is given, among the amphoteric associative polymers according to the invention, to acrylic acid/(meth)acrylamidopropyltrimethylammonium chloride/stearyl methacrylate terpolymers.

The associative polymers of nonionic type that may be used according to the invention are preferably chosen from:
- (a) copolymers of vinylpyrrolidone and of hydrophobic monomers having a fatty chain, of which examples that may be mentioned include:
  - the products Antaron V216® and Ganex V216® (vinylpyrrolidone/hexadecene copolymer) sold by the company ISP,
  - the products Antaron V220® or Ganex V220® (vinylpyrrolidone/eicosene copolymer) sold by ISP,
- (b) copolymers of $C_1$-$C_6$ alkyl methacrylates or acrylates and of amphiphilic monomers comprising at least one fatty chain, such as, for example, the methyl acrylate/oxyethylenated stearyl acrylate copolymer sold by Goldschmidt under the name Antil 208®,
- (c) copolymers of hydrophilic methacrylates or acrylates and of hydrophobic monomers comprising at least one fatty chain, for instance the polyethylene glycol methacrylate/lauryl methacrylate copolymer,
- (d) polyurethane polyethers comprising in their chain both hydrophilic blocks usually of polyoxyethylenated nature and hydrophobic blocks, which may be aliphatic sequences alone and/or cycloaliphatic and/or aromatic sequences,
- (e) polymers having an aminoplast ether backbone possessing at least one fatty chain, such as the Pure Thix® compounds provided by Sud-Chemie,
- (f) celluloses or their derivatives, modified by groups comprising at least one fatty chain, such as alkyl, arylalkyl or alkylaryl groups or their mixtures, where the alkyl groups are $C_8$-$C_{30}$ alkyl groups and in particular:
  - nonionic alkylhydroxyethylcelluloses, such as the products Natrosol Plus Grade 330 CS and Polysurf 67 ($C_{16}$ alkyl) sold by Aqualon;
  - nonionic nonoxynyl hydroxyethylcelluloses, such as the product Amercell HM-1500 sold by Amerchol;
  - nonionic alkylcelluloses, such as the product Bermocoll EHM 100 sold by Berol Nobel;
- (g) associative guar derivatives, such as hydroxypropyl guars modified by a fatty chain, such as the product Esaflor HM 22 (modified by a $C_{22}$ alkyl chain) sold by Lamberti; the product Miracare XC 95-3 (modified by a $C_{14}$ alkyl chain) and the product RE 205-146 (modified by a $C_{20}$ alkyl chain), which are sold by Rhodia Chimie.

Preferably, the polyurethane polyethers comprise at least two lipophilic hydrocarbon chains, having from 6 to 30 carbon atoms, separated by a hydrophilic block, it being possible for the hydrocarbon chains to be pendant chains or chains at the end of the hydrophilic block. In particular, it is possible for one or more pendant chains to be provided. In addition, the polymer may comprise a hydrocarbon chain at one end or at both ends of a hydrophilic block.

The polyurethane polyethers may be multiblock, in particular in triblock form. The hydrophobic blocks can be at each end of the chain (for example: triblock copolymer comprising a central hydrophilic block) or distributed both at the ends and in the chain (multiblock copolymer, for example). These same polymers may also be graft polymers or star polymers.

The nonionic polyurethane polyethers having a fatty chain may be triblock copolymers in which the hydrophilic block is a polyoxyethylenated chain comprising from 50 to 1000 oxyethylene groups. The nonionic polyurethane polyethers comprise a urethane bond between the hydrophilic blocks, hence the origin of the name.

By extension, also included among the nonionic polyurethane polyethers having a fatty chain are those in which the hydrophilic blocks are bonded to the lipophilic blocks via other chemical bonds.

As examples of nonionic polyurethane polyethers having a fatty chain that may be used in the invention, it is also possible to use Rheolate 205® containing a urea functional group, sold by the company Rheox, or Rheolate® 208, 204 or 212, and also Acrysol RM 184®.

Mention may also be made of the product Elfacos T210® having a $C_{12-14}$ alkyl chain and the product Elfacos T212® having a $C_{18}$ alkyl chain from Akzo.

The product DW 1206B® from Rohm & Haas having a $C_{20}$ alkyl chain and having a urethane bond, provided at a solids content of 20% in water, can also be used.

It is also possible to use solutions or dispersions of these polymers, especially in water or in aqueous-alcoholic medium. Examples of such polymers that may be mentioned are Rheolate® 255, Rheolate® 278 and Rheolate® 244, sold by the company Rheox. The products DW 1206F and DW 1206J, sold by the company Rohm & Haas, may also be used.

The polyurethane polyethers that may be used according to the invention are in particular those described in the paper by G. Formum, J. Bakke and Fk. Hansen—*Colloid Polym. Sci.*, 271, 380-389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold in particular by Rohm & Haas under the names Aculyn 46® and Aculyn 44® [Aculyn 46® is a polycondensate of polyethylene glycol comprising 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol comprising 150 or 180 mol of ethylene oxide, of decyl alcohol and of methylenebis(4-cyclohexyl isocyanate) (SMDI), at 35% by weight in a mixture of propylene glycol (39%) and water (26%)].

Use may also be made of fatty-phase thickening polymers.

Preferably, the polymers which structure the oily phase via physical interactions are chosen from polyamides, silicone polyamides, saccharide or polysaccharide mono- or polyalkyl esters, N-acylated amino acid amide derivatives, or copolymers comprising an alkylene or styrene block, it being possible for these copolymers to be diblock, triblock, multiblock or radial-block polymers, the radial-block polymers also being known as star copolymers, or also comb polymers.

1) Polymers Carrying, in the Backbone, at Least One Crystallizable Block

These are also polymers that are soluble or dispersible in the oil or fatty phase by heating above their melting point m.p. These polymers are especially block copolymers consisting of at least two blocks of different chemical nature, one of which is crystallizable.

Mention may be made, as polymers carrying, in the backbone, at least one crystallizable block suitable for the implementation of the invention, of:

i) the polymers defined in the document U.S. Pat. No. 5,156,911;

ii) the block copolymers of olefin or of cycloolefin having a crystallizable chain, such as those resulting from the block polymerization of:

cyclobutene, cyclohexene, cyclooctene, norbornene (that is to say, bicyclo[2.2.1]hept-2-ene), 5-methylnorbornene, 5-ethylnorbornene, 5,6-dimethyl-norbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene and their mixtures;

with ethylene, propylene, 1-butene, 3-methyl-1-butene, 1-hexene, 4-methyl-1-pentene, 1-octene, 1-decene or 1-eicosene, or mixtures thereof. These block copolymers may be in particular (ethylene/norbornene) block copolymers and (ethylene/propylene/ethylidenenorbornene) block terpolymers.

Use may also be made of those resulting from the block copolymerization of at least 2 $C_2$-$C_{16}$ and better still $C_2$-$C_{12}$ α-olefins, such as those mentioned above, in particular the block biopolymers of ethylene and 1-octene.

The copolymers exhibit at least one crystallizable block, the rest of the copolymer being amorphous (at room temperature). These copolymers may also exhibit two crystallizable blocks of different chemical nature. The preferred copolymers are those that simultaneously contain at room temperature a crystallizable block and an amorphous block that is both hydrophobic and lipophilic, distributed blockwise; mention may be made, for example, of polymers containing one of the crystallizable blocks and one of the amorphous blocks below:

Block that is crystallizable by nature: a) of polyester type, for instance poly(alkylene terephthalate), b) of polyolefin type, for instance polyethylenes or polypropylenes.

Amorphous and lipophilic block, for instance amorphous polyolefins or copoly(olefin)s, such as poly(isobutylene), hydrogenated polybutadiene or hydrogenated poly(isoprene).

As examples of such copolymers containing a crystallizable block and an amorphous block, mention may be made of:

a) Poly(δ-caprolactone)-b-poly(butadiene) block copolymers, used preferably hydrogenated, such as those described in the paper "Melting behavior of poly(δ-caprolactone)-block-polybutadiene copolymers" by S, Nojima, *Macromolecules*, 32, 3727-3734 (1999).

b) Block or multiblock hydrogenated poly(butylene terephthalate)-b-poly(isoprene) block copolymers, cited in the paper "Study of morphological and mechanical properties of PP/PBT" by B. Boutevin et al., *Polymer Bulletin*, 34, 117-123 (1995).

c) Poly(ethylene)-b-copoly(ethylene/propylene) block copolymers, cited in the papers "Morphology of semicrystalline block copolymers of ethylene-(ethylene-alt-propylene)" by P. Rangarajan et al., *Macromolecules*, 26, 4640-4645 (1993), and "Polymer aggregates with crystalline cores: the system poly(ethylene)-poly(ethylene-propylene)", P. Richter et al., *Macromolecules*, 30, 1053-1068, 25 (1997).

d) Poly(ethylene)-b-poly(ethylethylene) block copolymers, cited in the general article "Crystallization in block copolymers" by I. W. Hamley, *Advances in Polymer Science*, vol. 148, 113-137 (1999).

The semi-crystalline polymers that may be used in the context of the invention may be non-crosslinked or partially crosslinked, provided that the degree of crosslinking does not impede their dissolution or dispersion in the liquid oily phase by heating above their melting point. It may then be a case of chemical crosslinking, by reaction with a polyfunctional monomer during the polymerization. It may also be a case of physical crosslinking, which may then be due either to the establishment of bonds of hydrogen or dipolar type between groups carried by the polymer, for instance dipolar interactions between carboxylate ionomers, these interactions being in small amount and carried by the polymer backbone; or due to a phase separation between the crystallizable blocks and the amorphous blocks carried by the polymer.

Preferably, the semi-crystalline polymers that are suitable for the invention are noncrosslinked.

Mention may be made, as a specific example of semicrystalline polymer which can be used in the composition according to the invention, of the Intelimer® products from Landec described in the "Intelimer® Polymers" brochure. These polymers are in solid form at room temperature (25° C.). They carry crystallizable side chains and exhibit the monomer. Mention may in particular be made of "Landec IP22®", having a melting point m.p. of 56° C., which is a product which is viscous at ambient temperature, impermeable and nontacky.

Use may also be made of the semicrystalline polymers described in Examples 3, 4, 5, 7 and 9 of the document U.S. Pat. No. 5,156,911, resulting from the copolymerization of acrylic acid and $C_5$ to $C_{16}$ alkyl (meth)acrylate, such as those resulting from the copolymerization:
of acrylic acid, of hexadecyl acrylate and of isodecyl acrylate in a 1/16/3 ratio,
of acrylic acid and of pentadecyl acrylate in a 1/19 ratio,
of acrylic acid, of hexadecyl acrylate and of ethyl acrylate in a 2.5/76.5/20 ratio,
of acrylic acid, of hexadecyl acrylate and of methyl acrylate in a 5/85/10 ratio,
of acrylic acid and octadecyl methacrylate in a 2.5/97.5 ratio.

Use may also be made of the polymer "Structure O" sold by National Starch, such as that described in the document U.S. Pat. No. 5,736,125, with an m.p. of 44° C., and also semicrystalline polymers having crystallizable pendant chains comprising fluorinated groups, such as described in Examples 1, 4, 6, 7 and 8 of the document WO-A-01/19333.

Use may also be made of semicrystalline polymers obtained by copolymerization of stearyl acrylate and of acrylic acid or of NVP or by copolymerization of behenyl acrylate and of acrylic acid or of NVP, such as described in the document U.S. Pat. No. 5,519,063 or EP-A-0 550 745.

According to a specific alternative embodiment, the semi-crystalline polymers suitable for the implementation of the present invention are in particular alkyl acrylates, among which the following Landec copolymers may be mentioned:
Doresco IPA 13-1®: poly(stearyl acrylate), m.p. of 49° C. and Mw of 145 000;
Doresco IPA 13-3®: poly(acrylate/methacrylic acid), m.p. of 65° C. and Mw of 114 000;
Doresco IPA 13-4®: poly(acrylate/vinylpyrrolidone) m.p. of 44° C. and Mw of 387 000;
Doresco IPA 13-5®: poly(acrylate/hydroxyethyl methacrylate), m.p. of 47° C. and Mw of 397 600;
Doresco IPA 13-6®: poly(behenyl acrylate), m.p. of 66° C.

2) Non-Silicone Polyamides

The specific polyamides used in the composition according to the present invention are preferably those described in the document U.S. Pat. No. 5,783,657 from Union Camp.

Each of these polyamides satisfies in particular the following formula (XVII):

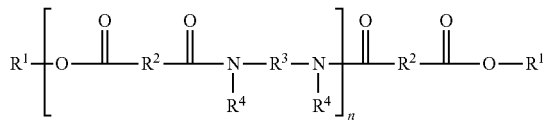
(XVII)

in which formula (XVII):
n denotes a whole number of amide units, such that the number of ester groups represents from 10 to 50% of the total number of the ester and amide groups;
$R^1$ is independently, in each case, an alkyl or alkenyl group having at least 4 carbon atoms and in particular from 4 to 24 carbon atoms;
$R^2$ independently represents, in each case, a $C_4$ to $C_{55}$ hydrocarbon group, provided that at least 50% of the $R_2$ groups represent a $C_{30}$ to $C_{55}$ hydrocarbon group;
$R^3$ independently represents, in each case, an organic group provided with at least 2 carbon atoms, with hydrogen atoms and optionally with one or more oxygen or nitrogen atoms; and
$R^4$ independently represents, in each case, a hydrogen atom, a $C_1$ to $C_{10}$ alkyl group or a direct bond to $R_3$ or to another $R_4$, so that the nitrogen atom to which both $R_3$ and $R_4$ are bonded forms part of a heterocyclic structure defined by $R_4$—N—$R_3$, with at least 50% of the $R_4$ groups representing a hydrogen atom.

In particular, the ester groups of this polyamide represent from 15 to 40% and at best from 20 to 35% of the total number of ester and amide groups. Furthermore, n advantageously represents an integer ranging from 1 to 10 and better still from 1 to 5, limits inclusive.

Preferably, $R^1$ is a $C_{12}$ to $C_{22}$ and preferably $C_{16}$ to $C_{22}$ alkyl group. Advantageously, $R^2$ can be a $C_{10}$ to $C_{42}$ hydrocarbon (alkylene) group. Preferably, at least 50% and better still at least 75% of the $R^2$ groups are groups having from 30 to 42 carbon atoms. The other $R^2$ groups are hydrogenated $C_4$ to $C_{19}$ and preferably $C_4$ to $C_{12}$ groups. Preferably, $R^3$ represents a $C_2$ to $C_{36}$ hydrocarbon group or a polyoxyalkylene group and $R^4$ represents a hydrogen atom. Preferably, $R^3$ represents a $C_2$ to $C_{12}$ hydrocarbon group. The hydrocarbon groups may be linear, cyclic or branched and saturated or unsaturated groups. Moreover, the alkyl and alkylene groups may be linear or branched and saturated or unsaturated groups.

The thickening of the liquid fatty phase may be obtained by means of one or more polyamides defined above. In general, these polyamides are provided in the form of blends, it being possible for these blends additionally to comprise a synthetic product corresponding to a polyamide as defined above with n having the value 0, that is to say a diester.

Mention may also be made, as structuring polyamide which can be used in the invention, of polyamide resins resulting from the condensation of an aliphatic dicarboxylic acid and of a diamine (including compounds having more than two carbonyl groups and two amine groups), the carbonyl and amine groups of adjacent individual units being condensed via an amide bond. These polyamide resins are especially the products sold under the trade name Versamid® by the companies General Mills Inc. and Henkel Corp., under the trade name Onamid®, especially Onamid S or C. These resins have a weight-average molecular weight ranging from 6000 to 9000. For more information with regard to these polyamides, reference may be made to the documents U.S. Pat. Nos. 3,645,705 and 3,148,125. Use is made more especially of Versamid® 30 or 744.

It is also possible to use the polyamides sold or manufactured by the company Arizona under the references Uni-Rez (2658, 2931, 2970, 2621, 2613, 2624, 2665, 1554, 2623, 2662) and the product sold under the reference Macromelt 6212 by the company Henkel. For further information regarding these polyamides, reference may be made to the document U.S. Pat. No. 5,500,209.

As examples of structuring polyamides that may be used in the composition according to the invention, mention may also be made of the commercial products sold or manufactured by the company Arizona Chemical under the names Uniclear 80 and Uniclear 100. They are sold, respectively, in the form of an 80% (active material) gel and a 100% (active material) gel in a mineral oil. They have a softening point of 88 to 105° C. These commercial products are a blend of copolymers of a $C_{36}$ diacid condensed with ethylenediamine, with an average molecular weight of approximately 6000. The terminal ester groups result from the esterification of the remaining acid end groups with cetyl alcohol, stearyl alcohol or mixtures thereof (also known as cetylstearyl alcohol).

2) Saccharide or Polysaccharide Mono- or Polyalkyl Esters

Among the saccharide or polysaccharide mono- or polyalkyl esters that are suitable for use in the invention, mention may be made of dextrin or inulin alkyl or polyalkyl esters.

The product concerned may in particular be a mono- or polyester of dextrin and of at least one fatty acid, in particular corresponding to the following formula (XVIII):

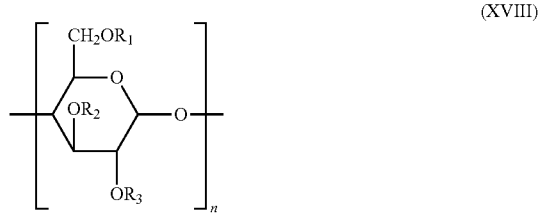

(XVIII)

in which formula (XVIII):
  n is an integer ranging from 3 to 200, in particular ranging from 20 to 150 and especially ranging from 25 to 50,
  $R_1$, $R_2$ and $R_3$, which are identical or different, are chosen from hydrogen or an acyl (R—C(O)—) group in which the R radical is a saturated or unsaturated and linear or branched hydrocarbon group having from 7 to 29, in particular from 7 to 21, especially from 11 to 19, more particularly from 13 to 17, indeed even 15, carbon atoms, with the proviso that at least one of the said $R_1$, $R_2$ or $R_3$ radicals is other than hydrogen.

In particular, $R_1$, $R_2$ and $R_3$ can represent hydrogen or an acyl (R—C(O)—) group in which R is a hydrocarbon radical as defined above, with the proviso that at least two of the said radicals $R_1$, $R_2$ or $R_3$ are identical and different from hydrogen.

All the $R_1$, $R_2$ and $R_3$ radicals can represent an identical or different and in particular identical acyl (R—C(O)) group.

In particular, n set out above advantageously varies from 25 to 50 and in particular is equal to 38 in the general formula of the saccharide ester which can be used in the present invention.

In particular when the $R_1$, $R_2$ and/or $R_3$ radicals, which are identical or different, represent an acyl (R—C(O)) group, these can be chosen from caprylic, capric, lauric, myristic, palmitic, stearic, arachidic, behenic, isobutyric, isovaleric, 2-ethylbutyric, ethyl methyl acetic, isoheptanoic, 2-ethyl hexanoic, isononanoic, isodecanoic, isotridecanoic, isomyristic, isopalmitic, isostearic, isoarachidic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and their mixtures.

Preferably, at least one dextrin palmitate is used as ester of dextrin and of fatty acid(s). This ester may be used alone or as a mixture with other esters.

Advantageously, the fatty acid ester of dextrin has a degree of substitution of less than or equal to 2.5, especially ranging from 1.5 to 2.5 and preferably from 2 to 2.5, on the basis of one glucose unit. The weight-average molecular weight of the dextrin ester can in particular be from 10 000 to 150 000, especially from 12 000 to 100 000 and indeed even from 15 000 to 80 000.

Dextrin esters, in particular dextrin palmitates, are commercially available under the name Rheopearl TL or Rheopearl KL from the company Chiba Flour.

3) N-Acylated Amino Acid Amide Derivatives

The N-acylated, amino acid amides that may be used are, for example, diamides from the combination of an N-acylamino acid with amines comprising from 1 to 22 carbon atoms, such as those described in the document FR 2 281 162. These are, for example, the amide derivatives of alkylglutamic acid, such as laurylglutamic acid dibutylamide, sold by Ajinomoto under the name "Gelling agent GP-1", or 2-ethylhexanoylglutamic acid dibutylamide, sold by Ajinomoto under the name "Gelling agent GA-01".

4) Copolymers Comprising an Alkylene or Styrene Block

The copolymers can have a comb structure or block structure of diblock, triblock, multiblock and/or radical or star type and can comprise at least two segments which are incompatible thermodynamically.

The structuring agent can comprise, for example, a styrene segment block, as described in Applications EP 0 497 144, WO98/42298, U.S. Pat. Nos. 6,225,690, 6,174,968 and 6,225,390, an ethylene/butylene segment, an ethylene/propylene segment, as described in Applications U.S. Pat. Nos. 6,225,690, 6,174,968 and 6,225,390, a butadiene segment, an isoprene segment, a polyvinyl segment, such as, for example, a poly(alkyl(meth)acrylate) or poly(vinyl alcohol) or poly(vinyl acetate) segment, a silicone segment, such as described in Applications U.S. Pat. No. 5,468,477 and U.S. Pat. No. 5,725,882, or a combination of these segments.

A diblock copolymer is usually defined as being of A-B type in which a hard segment (A) is followed by a soft segment (B).

A triblock copolymer is usually defined as being of A-B-A type or as a ratio of a hard segment, a soft segment and a hard segment.

A multiblock, radial or star copolymer may comprise any type of combination of hard segments and soft segments, with the proviso that the characteristics of the hard segments and of the soft segments are retained.

An example of hard segments of block copolymers that may be mentioned is styrene, and examples of soft segments of block copolymers that may be mentioned include ethylene, propylene and butylene, and a combination thereof.

The triblock copolymers, in particular those of polystyrene/polyisoprene or polystyrene/polybutadiene type, suitable for the implementation of the invention can be those sold under the reference Luvitol HSB by BASF. Mention may also be made of the triblock copolymers of polystyrene/copoly(ethylene-propylene) or polystyrene/co-poly(ethylene-butylene) type, such as those sold under the reference Kraton by Shell Chemical Co. or under the reference Gelled Permethyl 99 A by Penreco. Such triblock copolymers are particularly preferred according to the invention.

As a further example of block copolymers that may be suitable for use in the present invention, mention may also be made of the block copolymers sold under the reference Versagel by the company Penreco, those sold under the reference Kraton by the company Shell and those sold under the reference Gel Base by the company Brooks Industries.

Preference is given, among the fatty-phase thickening polymers, to the polymers carrying, in the backbone, at least one crystallizable block.

The aqueous-phase or fatty-phase thickening polymers may be used alone or as mixtures in all proportions.

Preferably, the thickeners are aqueous-phase thickeners.

Preferably, the polymers of the cosmetic compositions in accordance with the present invention advantageously exhibit, as a 1% solution or dispersion of active material in water, a viscosity, measured using the Rheomat RM 180 rheometer, at 25° C., of greater than 0.1 cp and more advantageously still of greater than 0.2 cP, at a shear rate of 200 $s^{-1}$.

According to a specific form of the invention, the organic thickening polymer or polymers is or are chosen from cellulose polymers.

The organic thickening polymer or polymers is or are present in the composition according to the invention in a content ranging from 0.01 to 10% by weight and preferably from 0.1 to 5% by weight, with respect to the total weight of the composition.

iii) At Least One (Poly)Ethoxylated Fatty Alcohol and/or at Least One Nonionic Surfactant:

According to a specific embodiment of the invention, the composition of the invention comprises iii) one or more (poly)ethoxylated fatty alcohols.

The (poly)ethoxylated fatty alcohols suitable for the implementation of the invention are chosen more particularly from the alcohols comprising from 8 to 40 carbon atoms, preferably from 8 to 30 carbon atoms and more particularly from 12 to 22 carbon atoms.

The poly(ethoxylated) fatty alcohols more particularly exhibit one or more saturated or unsaturated and linear or branched hydrocarbon groups comprising from 8 to 40 carbon atoms which are optionally substituted, in particular by one or more (in particular from 1 to 4) hydroxyl groups. If they are unsaturated, these compounds can comprise from one to three conjugated or nonconjugated carbon-carbon double bonds.

The (poly)ethoxylated fatty alcohol or alcohols are preferably of following formula:

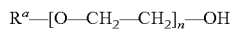

with

—$R^a$ representing a linear or branched $C_8$-$C_{40}$, preferably $C_8$-$C_{30}$, alkyl group or a linear or branched $C_8$-$C_{40}$, preferably $C_8$-$C_{30}$, alkenyl group which is optionally substituted by one or more hydroxyl groups, and n represents an integer between 1 and 200 inclusive, preferably between 2 and 50 and more particularly between 8 and 30 inclusive, such as 20.

The (poly)ethoxylated fatty alcohols are more particularly fatty alcohols comprising from 8 to 22 carbon atoms and oxyethylenated by from 1 to 30 mol of ethylene oxide (1 to 30 EO). Mention may more particularly be made, among them, of lauryl alcohol 2 EO, lauryl alcohol 3 EO, decyl alcohol 3 EO, decyl alcohol 5 EO and oleyl alcohol 20 EO.

Use may also be made of mixtures of these (poly) oxyethylenated fatty alcohols.

According to the present invention, the (poly)ethoxylated fatty alcohol(s) are preferably present in the composition in an amount ranging from 0.01 to 40% by weight, preferably from 0.05 to 20% by weight and better still from 0.1 to 3% by weight, with respect to the total weight of the composition.

According to another specific embodiment of the invention, the composition of the invention comprises iii) one or more nonionic surfactants preferably different from the (poly)ethoxylated fatty alcohol or alcohols.

Mention may be made, among nonionic surfactants, alone or mixtures, of fatty alcohols, α-diols or alkylphenols, these 3 compound types being polyethoxylated, polypropoxylated and/or polyglycolated and having a fatty chain comprising, for example, from 8 to 40 carbon atoms, it being possible for the number of ethylene oxide or propylene oxide groups to range in particular from 2 to 50 and it being possible for the number of glycerol groups to range in particular from 2 to 30. Mention may also be made of copolymers of ethylene oxide and of propylene oxide, condensates of ethylene oxide and propylene oxide with fatty alcohols, polyethoxylated fatty amides preferably having from 2 to 30 mol of ethylene oxide, polyglycerolated fatty amides comprising on average from 1 to 5 glycerol groups and in particular from 1.5 to 4, oxyethylenated sorbitan fatty acid esters having from 2 to 30 mol of ethylene oxide, sucrose fatty acid esters, polyethylene glycol fatty acid esters, alkyl polyglycosides (or APG), N-alkylglucamine derivatives or amine oxides, such as ($C_{10}$-$C_{14}$)alkylamine oxides or N-acylaminopropylmorpholine oxides.

Preferably, the nonionic surfactant is chosen from glycerolated fatty alcohols and alkyl polyglycosides, more preferably alkylpolyglycosides or APGs.

The term fatty chain is understood to mean a saturated or unsaturated and linear or branched hydrocarbon chain comprising from 8 to 40 carbon atoms and preferably from 8 to 30 carbon atoms.

As regards the alkyl polyglycosides or APGs, these compounds are well known to a person skilled in the art (see, for example, Kirk-Othmer's Encyclopedia: http://onlinelibrary.wiley.com/doi/10.1002/0471238961.1921180612251414.a01.pub2/pdf or Ullmann's Encyclopedia of Industrial Chemistry http://onlinelibrary.wiley.com/doi/10.1002/14356007.a25_747/pdf). These compounds are represented more particularly by the following general formula:

in which formula (XIX):

$R_1$ represents a linear or branched alkyl and/or alkenyl radical comprising approximately from 8 to 24 carbon atoms or an alkylphenyl radical, the linear or branched alkyl radical of which comprises from 8 to 24 carbon atoms;

$R_2$ represents an alkylene radical comprising approximately from 2 to 4 carbon atoms;

G represents a sugar unit comprising from 5 to 6 carbon atoms;

t denotes a value ranging from 0 to 10 and preferably from 0 to 4, and v denotes a value ranging from 1 to 15.

Preferred alkyl polyglycosides according to the present invention are compounds of formula (XIX) in which $R_1$ more particularly denotes a saturated or unsaturated and linear or branched alkyl radical comprising from 8 to 18 carbon atoms, t denotes a value ranging from 0 to 3 and more particularly still equal to 0, and G can denote glucose, fructose or galactose, preferably glucose.

The degree of polymerization, i.e. the value of v in the formula (XIX), can range from 1 to 15 and preferably from 1 to 4. The average degree of polymerization is more particularly between 1 and 2 and even more preferentially from 1.1 to 1.5.

The glycoside bonds between the sugar units are of 1-6 or 1-4 type and preferably of 1-4 type.

Compounds of formula (XIX) are represented in particular by the products sold by Cognis under the names Plantaren® (600 CS/U, 1200 and 2000) or Plantacare® (818, 1200 and 2000). Use may also be made of the products sold by Seppic under the names Triton CG 110 (or Oramix CG 110) and Triton CG 312 (or Oramix® NS 10), the products sold by BASF under the name Lutensol GD 70 or the products sold by Chem Y under the name AG10 LK.

Use may also be made, for example, of $C_8$-$C_{16}$ alkyl 1,4-polyglucoside as a 53% aqueous solution, sold by Cognis under the reference Plantacare® 818 UP.

As regards the mono- or polyglycerolated surfactants, they preferably comprise on average from 1 to 30 glycerol groups, more particularly from 1 to 10 glycerol groups and in particular from 1.5 to 5.

The monoglycerolated or polyglycerolated surfactants are preferably chosen from the following compounds:

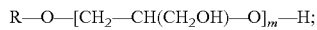

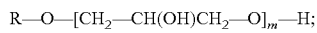

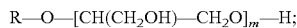

in which formulae:
   R represents a saturated or unsaturated and linear or branched hydrocarbon radical comprising from 8 to 40 carbon atoms and preferably from 10 to 30 carbon atoms; R can optionally comprise heteroatoms, such as oxygen and nitrogen; in particular, R can optionally comprise one or more hydroxyl and/or ether and/or amide groups;
   m is a number between 1 and 30 inclusive, preferably between 1 and 10 and more particularly from 1.5 to 6.
   R preferably denotes optionally mono- or polyhydroxylated $C_{10}$-$C_{20}$ alkyl and/or alkenyl radicals.

Use may be made, for example, of polyglycerolated (3.5 mol) hydroxylauryl ether, sold under the name Chimexane® NF by Chimex.

The amount of nonionic surfactants is preferably between 0.5% and 25% by weight inclusive, in particular between 1% and 20% by weight inclusive and more particularly between 2% and 10% by weight inclusive, with respect to the total weight of the composition of the invention.

Use is preferably made, among nonionic surfactants, of $C_6$-$C_{24}$ alkyl polyglucosides and more particularly $C_8$-$C_{16}$ alkyl polyglucosides.

According to the present invention, the nonionic surfactant or surfactants are preferably present in the composition in an amount ranging from 0.01 to 40% by weight, preferably from 0.05 to 20% by weight and better still from 0.1 to 3% by weight, with respect to the total weight of the composition.

According to another specific embodiment of the invention, the composition of the invention comprises iii) one or more (poly)ethoxylated fatty alcohols and one or more nonionic surfactants different from the (poly)ethoxylated fatty alcohol or alcohols.

According to the present invention, the (poly)ethoxylated fatty alcohol(s) and the nonionic surfactant or surfactants are preferably present in the composition in a total amount ranging from 0.01 to 40% by weight, preferably from 0.05 20% by weight and better still from 0.1 to 3% by weight, with respect to the total weight of the composition.

iv) At Least One Alkaline Agent:

The composition of the invention comprises one or more alkaline agents. This agent may be chosen from inorganic or organic or hybrid alkaline agents, or mixtures thereof. This agent is preferably chosen from alkaline agents comprising at least one amino group, it being possible for this amino group to be substituted or unsubstituted.

According to a particularly advantageous embodiment of the invention, the composition or the method of the invention does not employ sodium hydroxide NaOH.

The inorganic alkaline agent(s) are preferably chosen from aqueous ammonia, alkali metal carbonates or bicarbonates, such as sodium or potassium carbonates and sodium or potassium bicarbonates, sodium hydroxide or potassium hydroxide, or mixtures thereof.

According to an advantageous embodiment of the invention, the alkaline agent or agents are organic amines, i.e. they comprise at least one substituted or unsubstituted amino group.

The organic alkaline agent or agents are more preferably chosen from organic amines whose $pK_b$ at 25° C. is less than 12, preferably less than 10 and more advantageously still less than 6. It should be noted that it is the $pK_b$ corresponding to the functional group of highest basicity.

Mention may be made, as hybrid compounds, of the salts of the abovementioned amines with acids, such as carbonic acid or hydrochloric acid.

The organic alkaline agent or agents are chosen, for example, from alkanolamines, oxyethylenated and/or oxypropylenated ethylenediamines, amino acids and compounds of following formula (XX):

in which formula (XX):
   W is a divalent $C_1$-$C_6$ alkylene radical optionally substituted by a hydroxyl group or a $C_1$-$C_6$ alkyl radical and/or optionally interrupted by one or more heteroatoms, such as oxygen or NRu;
   $R^x$, $R^y$, $R^z$, $R^t$ and $R^u$, which are identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

Alkanolamine is understood to mean an organic amine comprising a primary, secondary or tertiary amino functional group and one or more linear or branched $C_1$-$C_8$ alkyl groups carrying one or more hydroxyl radicals.

Suitable in particular for the implementation of the invention are alkanolamines, such as mono-, di- or trialkanolamines, comprising from one to three identical or different $C_1$-$C_4$ hydroxyalkyl radicals.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid functional group chosen more particularly from carboxylic acid, sulphonic acid, phosphonic acid or phosphoric acid functional groups. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine functional group optionally included in a ring or in a ureido functional group.

Such basic amino acids are preferably chosen from those corresponding to the following formula (XXI):

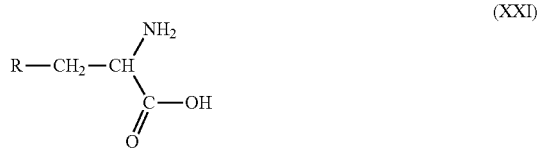

in which formula (XXI):
R denotes a group chosen from:

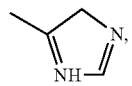

aminopropyl: —(CH$_2$)$_3$—NH$_2$, aminoethyl —(CH$_2$)$_2$—NH$_2$, —(CH$_2$)$_2$—NH—C(O)—NH$_2$ and

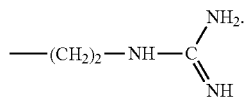

The corresponding compounds of the formula (XXI) are histidine, lysine, arginine, ornithine and citrulline.

The organic amine may also be chosen from organic amines of heterocyclic type. Besides histidine, that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine is chosen from compounds comprising a guanidine functional group. Mention may in particular be made, as amines of this type which can be used in the present invention, in addition to arginine already mentioned as amino acid, of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulphonic acid.

Mention may be made in particular of the use of guanidine carbonate or monoethanolamine hydrochloride as hybrid compounds.

The composition of the invention preferably contains one or more alkanolamines and/or one or more basic amino acids, more advantageously one or more alkanolamines. More preferentially still, the organic amine is monoethanolamine.

According to a specific embodiment, the composition of the invention comprises, as alkaline agent, one or more alkanolamines.

Preferably, the alkanolamine is ethanolamine (or monoethanolamine).

In one alternative form of the invention, the composition comprises, as alkaline agent, one or more alkanolamines (preferably ethanolamine) and aqueous ammonia. In this alternative form, the alkanolamine or alkanolamines are present in a predominant amount with respect to the aqueous ammonia.

Advantageously, the composition according to the invention exhibits a content of alkaline agent(s) ranging from 0.01 to 30% by weight, preferably from 0.1 to 20% by weight and better still from 1 to 10% by weight, with respect to the weight of the said composition.

v) At Least One Reducing Agent:

The composition of the invention comprises one or more reducing agents.

Preferably, the reducing agent or agents are chosen from thiols, such as thioglycolic acid, thiolactic acid, 3-mercaptopropionic acid, thiomalic acid, 2,3-dimercaptosuccinic acid, cysteine, N-glycyl-L-cysteine, L-cysteinylglycine and their esters and salts, thioglycerol, cysteamine and its $C_1$-$C_4$ acylated derivatives, N-mesylcysteamine, N-acetylcysteine, N-mercaptoalkylamides of sugars, such as N-(2-mercaptoethyl)gluconamide, pantetheine, N-(mercaptoalkyl)-ω-hydroxyalkylamides, for example those described in Patent Application EP-A-354 835, N-mono- or N,N-dialkyl-4-mercaptobutyramides, for example those described in Patent Application EP-A-368 763, aminomercaptoalkylamides, for example those described in Patent Application EP-A-432 000, derivatives of N-(mercapto-alkyl)succinamic acids and of N-(mercaptoalkyl)succinimides, for example those described in Patent Application EP-A-465 342, (alkylamino)mercaptoalkylamides, for example those described in Patent Application EP-A-514 282, the azeotropic mixture of 2-hydroxypropyl thioglycolate and 2-hydroxy-1-methylethyl thioglycolate, such as described in Patent Application FR-A-2 679 448, mercaptoalkylaminoamides, for example those described in Patent Application FR-A-2 692 481, or N-mercaptoalkylalkanediamides, for example those described in Patent Application EP-A-653 202.

The reducing agent can alternatively be chosen from hydrides, such as sodium borohydride or potassium borohydride, sulphites or bisulphites of an alkali metal or alkaline earth metal, or phosphorus derivatives, such as phosphines or phosphites.

The reducing agent or agents are preferably chosen from thiols.

The preferred reducing agents are thioglycolic acid and cysteine or their salts. The reducing agent is preferably used in aqueous solution.

Generally, the concentration of reducing agent(s) is between 0.01 and 30% by weight inclusive, preferably between 0.1 and 25% by weight inclusive and more particularly between 0.5 and 10% by weight inclusive, with respect to the total weight of the composition applied to the keratinous fibres.

vi) Optionally at Least One Oxidizing Agent:

The composition according to the invention can also comprise one or more chemical oxidizing agent(s). "Chemical oxidizing agent" is understood to mean oxidizing agents other than atmospheric oxygen.

The chemical oxidizing agents are chosen, for example, from hydrogen peroxide, urea hydrogen peroxide, alkali metal bromates or ferricyanides or peroxygenated salts, such as, for example, persulphates, perborates, peracids and their precursors and percarbonates of alkali metals or alkaline earth metals. Advantageously, the oxidizing agent is hydrogen peroxide.

The content of oxidizing agent(s) more particularly represents from 0.1 to 20% by weight and preferably from 0.5 to 10% by weight, with respect to the weight of the composition comprising it or them.

vii) The adjuvants:

The composition comprising the ingredient or ingredients 0 to v) as defined above can also include various adjuvants conventionally used in compositions for dyeing the hair, such as anionic, cationic, nonionic, other than the (poly) ethoxylated fatty alcohols iii), amphoteric or zwitterionic surface-active agents or their mixtures, anionic, cationic, nonionic, amphoteric or zwitterionic polymers or their mixtures, inorganic thickening agents, penetrating agents, sequestering agents, fragrances, buffers, dispersing agents, conditioning agents, such as, for example, volatile or non-volatile and modified or unmodified silicones, film-forming agents, ceramides, preservatives or opacifying agents.

The above adjuvants are generally present in an amount, for each of them, of between 0.01 and 20% by weight inclusive, with respect to the weight of the composition.

Of course, a person skilled in the art will take care to choose this or these optional additional compounds so that the advantageous properties intrinsically attached to the dyeing composition in accordance with the invention are not, or not substantially, detrimentally affected by the envisaged addition or additions.

viii) The Additional Dyes:

The composition comprising the dye or dyes having a disulphide, thiol or protected thiol functional group in particular of formula (I) as defined above of the process of the invention can additionally comprise one or more additional direct dyes other than the disulphide, thiol or protected thiol direct dyes of formula (I) according to the invention. These direct dyes are, for example, chosen from those conventionally used in direct dyeing, among which may be mentioned all the aromatic and/or nonaromatic dyes commonly used, such as neutral, acid or cationic nitrobenzene direct dyes, neutral, acid or cationic azo direct dyes, natural direct dyes, neutral, acid or cationic quinone and in particular anthraquinone direct dyes, azine, triarylmethane or indoamine direct dyes, methines, styryls, porphyrins, metalloporphyrins, phthalocyanines, methinecyanines and fluorescent dyes other than the dyes of formula (I).

The composition comprising the dye(s) having a disulphide, thiol or protected thiol functional group especially of formula (I) as defined previously of the process of the invention may also contain one or more oxidation bases and/or one or more couplers conventionally used for the dyeing of keratinous fibres.

Among the oxidation bases, mention may be made of para-phenylenediamines, bisphenylalkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene couplers and heterocyclic couplers, and the addition salts thereof.

The coupler or couplers are each generally present in an amount of between 0.001 and 10% by weight inclusive of the total weight of the dyeing composition, preferably between 0.005 and 6% by weight inclusive.

The oxidation base or bases present in the dyeing composition are generally each present in an amount of between 0.001 and 10% by weight inclusive of the total weight of the dyeing composition, preferably between 0.005 and 6% by weight inclusive.

In general, the addition salts of the oxidation bases and couplers which can be used in the context of the invention are especially chosen from the addition salts with an acid, such as the hydrochlorides, hydrobromides, sulphates, citrates, succinates, tartrates, lactates, tosylates, benzenesulphonates, phosphates and acetates, and the addition salts with a base, such as alkali metal hydroxides, for instance sodium hydroxide, potassium hydroxide, aqueous ammonia, amines or alkanolamines.

According to one particular embodiment, the composition of the process of the invention contains at least one oxidation base and optionally at least one coupler as defined above.

This embodiment can be employed in the presence of one or more chemical oxidizing agents. Chemical oxidizing agent is understood to mean chemical oxidizing agents other than atmospheric oxygen, such as those described above. The use of hydrogen peroxide is particularly preferred.

The content of oxidizing agent(s) is generally between 1 and 40% by weight inclusive, with respect to the weight of the composition, preferably between 1 and 20% by weight inclusive, with respect to the weight of the composition comprising it or them.

The pH:

The pH of the composition according to the invention is generally between, inclusive, 2 and 12 approximately and preferably between, inclusive, 3 and 11 approximately. It can be adjusted to the desired value using acidifying or basifying agents normally used in the dyeing of keratinous fibres or else using conventional buffer systems.

The pH of the composition is preferably between 6 and 9 inclusive, particularly between 7 and 9 inclusive and more particularly between 7.5 and 9 inclusive.

Mention may be made, among the acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among the basifying agents, by way of example, of aqueous ammonia, alkaline carbonates, alkanolamines, such as mono-, di- and triethanolamines, and other alkaline agents iv) as defined above.

Forms of the Composition:

The dyeing composition comprising i) the dye or dyes having a disulphide, thiol or protected thiol functional group, in particular of formula (I), such as are defined above, and the ingredients ii), iii), iv) and v) as defined above can be provided in various formulation forms, such as in the form of liquids, lotions, creams or gels or in any other form appropriate for carrying out dyeing of keratinous fibres. It can also be packaged under pressure in an aerosol container in the presence of a propellant or in a non-aerosol container and can form a foam.

2). Dyeing Methods of the Invention

The method for dyeing keratinous fibres, in particular dark keratinous fibres, according to the invention comprises the stage of application, to the keratinous fibres, of:
  i) at least one direct dye having a disulphide, thiol or protected thiol functional group as defined above;
  ii) at least one thickening organic polymer as defined above;

iii) at least one (poly)ethoxylated fatty alcohol as defined above;
iv) at least one alkaline agent as defined above; and
v) at least one reducing agent as defined above;
it being possible for the ingredients i) to v) to be applied either together to the said fibres or separately.

When it is desired to lighten dark keratinous fibres without the use of a chemical oxidizing agent, use is made, in the composition or the dyeing method, of an ingredient i) which is fluorescent. Preferably, the fluorescent dyes of formula (I) are chosen from the dyes of formulae (XIII), (XIII'), (XIV), (XIV'), (XVa), (XV'a), (XV) to (XV'), (XVI), (XVI'), (XVIa) and (XVI'a) as defined above. More particularly, the fluorescent dyes i) as defined above used for the lightening of keratinous fibres are chosen from the compounds 44, 49, 49a and 55.

The dyeing method according to the invention can be carried out in one stage, by application to the keratinous fibres of the composition according to the invention comprising ingredients i) to v) as defined above, or in several stages.

According to a specific embodiment of the method of the invention, the reducing agent v) as defined above can be applied in pretreatment before the application of the dyeing composition comprising the ingredients i) to iv).

According to another advantageous alternative form, the reducing composition comprising the reducing agent v) and the ingredients iv) and iii) as defined above is applied to the keratinous fibres in pretreatment before the application of the dyeing composition comprising the ingredients i) and ii) as defined above.

According to another alternative form of the invention, the reducing composition comprising the reducing agent v) and the ingredient iv) as defined above is applied to the keratinous fibres in pretreatment before the application of the dyeing composition comprising the ingredients i), ii) and iii) as defined above.

According to yet another alternative form of the invention, the reducing composition comprising the reducing agent v) and the ingredient iii) as defined above is applied to the keratinous fibres in pretreatment before the application of the dyeing composition comprising the ingredients i), ii) and iv) as defined above.

According to another alternative form of the invention, the reducing composition comprising the reducing agent v) and the ingredient ii) as defined above is applied to the keratinous fibres in pretreatment before the application of the dyeing composition comprising the ingredients i), iii) and iv) as defined above.

The reducing pretreatment can be of short duration, in particular from 1 second to 30 minutes, preferably from 1 minute to 15 minutes, with one or more reducing agents as mentioned above.

The keratinous fibres are preferably rinsed with water between the reducing pretreatment stage and the stage of dyeing using the composition comprising the ingredient i) as defined above.

The leave-in time of the dyeing composition, i.e. comprising ingredient i) as defined above, is between 5 minutes and 1 hour inclusive, preferably between 10 minutes and 40 minutes inclusive.

The dyeing composition, i.e. the composition comprising the ingredient i), is generally applied at ambient temperature. However, it can be applied at temperatures varying from 20 to 180° C.

According to another alternative form, instead of using the reducing agent in pretreatment, it is used in post-treatment, after the application of the dyeing composition.

According to another specific dyeing method of the invention, the dyeing method does not comprise a stage of reducing pretreatment or post-treatment. The dyeing method then comprises the stage of application of the composition according to the invention which comprises the ingredients i) to v) as defined above.

When the ingredient i) is a protected thiol dye, i.e. the thiol dye of formula (I) as defined above in which U=Y with Y a protective group, the method of the invention can be preceded by a deprotection stage targeted at the in situ restoration of the SH functional group.

By way of example, it is possible to deprotect the S—Y functional group of the dyes of the invention with Y a protective group by adjusting the pH as follows:

| Y: Protective group | Deprotection |
| --- | --- |
| alkylcarbonyl | pH > 9 |
| arylcarbonyl | pH > 9 |
| alkoxycarbonyl | pH > 9 |
| aryloxycarbonyl | pH > 9 |
| arylalkoxycarbonyl | pH > 9 |
| (di)(alkyl)aminocarbonyl | pH > 9 |
| (alkyl)arylaminocarbonyl | pH > 9 |
| optionally substituted aryl, such as phenyl | pH > 9 |
| 5-, 6- or 7-membered monocyclic heteroaryl, such as oxazolium | pH > 9 |
| 8- to 11-membered bicyclic heteroaryl, such as benzimidazolium or benzoxazolium | pH > 9 |

The deprotection stage may also be performed during a stage of pretreatment of the hair, for instance the hair-reducing pretreatment.

A treatment with one or more chemical oxidizing agents can optionally be carried out after the application of the ingredients i) to v) to the keratinous fibres. In order to do this, use may be made of a fixing composition comprising at least one cosmetic chemical oxidizing agent, such as the ingredient vi) defined above, and optionally at least the ingredient ii) as defined above. It can be chosen in particular from hydrogen peroxide, urea hydrogen peroxide, alkali metal bromates, persalts, such as perborates and persulphates, and enzymes, among which may be mentioned peroxidases, 2-electron oxidoreductases, such as uricases, and 4-electron oxygenases, such as laccases. The use of hydrogen peroxide is particularly preferred.

The leave-in time of the oxidizing (fixing) composition is preferably between 1 second and 40 minutes inclusive and preferably between 15 seconds and 15 minutes inclusive.

Preferably, the oxidizing composition is applied after the application of the dyeing composition, i.e. the composition comprising the ingredient i) as defined above and optionally the ingredient ii) as defined above.

The keratinous fibres are preferably rinsed with water between the stage of dyeing using the composition comprising the ingredient i) as defined above and optionally the ingredient ii) as defined above and the fixing stage.

When the ingredients i) and v) are not found in the same composition, the pH of the composition which comprises i) is preferably between 4 and 10 inclusive and in particular between 5 and 7 inclusive and the pH of the composition which comprises v) is preferably between 4 and 10 inclusive and in particular between 7 and 10 inclusive.

The dyeing and/or lightening method according to the invention can be followed by shampooing with a conventional shampoo and/or drying the keratinous fibres.

According to particularly advantageous embodiments, the method is carried out in three different alternative forms starting from the compositions A, A', A", B, B', B" and C, in which:

the dyeing composition A comprises:
i) at least one fluorescent disulphide dye in a concentration of between 0.01 g % and 5 g % inclusive and preferably between 0.05 g % and 2 g % inclusive;
ii) at least one organic thickening agent, preferably a cellulose thickening agent, in a concentration of between 0.05 g % and 10 g % inclusive and more particularly of between 0.5 g % and 5 g % inclusive;
the pH of composition A preferably being between 4 and 10 inclusive and more particularly between 5 and 7 inclusive;
the reducing composition B comprises:
v) at least one thiol-comprising reducing agent with a concentration preferably of between 0.5 g % and 50 g % inclusive and more particularly of between 10 g % and 30 g % inclusive;
iv) at least one alkaline agent preferably comprising an amino group with a concentration in particular of between 0.1 g % and 30 g % inclusive and more particularly of between 0.5 g % and 5 g % inclusive;
iii) at least one ethoxylated fatty alcohol with a concentration of between 0.5 g % and 30 g % inclusive and preferably between 1 g % and 10 g % inclusive;
and optionally at least one fragrance with a concentration preferably of between 0.01 g % and 10 g % inclusive and preferably between 0.2 g % and 2 g % inclusive;
the pH of composition B preferably being between 5 and 12 inclusive and more particularly between 7 and 10 inclusive;
or else
the dyeing composition A' comprises:
i) at least one fluorescent disulphide dye in a concentration preferably of between 0.01 g % and 5 g % inclusive and more particularly between 0.05 g % and 2 g % inclusive;
ii) at least one cellulose organic thickening agent in a concentration preferably of between 0.05 g % and 10 g % inclusive and more particularly of between 0.5 g % and 5 g % inclusive;
iii) at least one nonionic surfactant of APG type with a concentration preferably of between 0.5 g % and 30 g % inclusive and more particularly of between 5 g % and 20 g % inclusive;
the pH of composition A' preferably being between 4 and 10 inclusive and more particularly between 5 and 7 inclusive;
the reducing composition B' comprises:
v) at least one thiol-comprising reducing agent with a concentration preferably of between 0.5 g % and 50 g % inclusive and more particularly between 10 g % and 30 g % inclusive;
iv) at least one alkaline agent comprising an amino group with a concentration preferably of between 0.1 g % and 30 g % inclusive and more particularly between 0.5 g % and 5 g % inclusive;
and optionally at least one fragrance with a concentration preferably of between 0.01 g % and 10 g % inclusive and more particularly between 0.2 g % and 2 g % inclusive;
the pH of composition B preferably being between 5 and 12 inclusive and more particularly between 7 and 10 inclusive;
or else
the dyeing composition A" comprises:
i) at least one fluorescent disulphide dye in a concentration preferably of between 0.01 g % and 5 g % inclusive and more particularly between 0.05 and 2 g % inclusive;
ii) at least one cellulose organic thickening agent in a concentration preferably of between 0.05 g % and 10 g % inclusive and more particularly of between 0.5 g % and 5 g % inclusive;
iii) at least one nonionic surfactant other than ethoxylated fatty alcohols, such as APG, with a concentration preferably of between 0.5 g % and 30 g % inclusive and more particularly between 5 g % and 20 g % inclusive;
the pH of composition A preferably being between 4 and 10 inclusive and more particularly between 5 and 7 inclusive;
the reducing composition B" comprises:
v) at least one thiol-comprising reducing agent with a concentration preferably of between 0.5 g % and 50 g % inclusive and more particularly of between 10 g % and 30 g % inclusive;
iv) at least one alkaline agent preferably comprising an amino group with a concentration in particular of between 0.1 g % and 30 g % inclusive and more particularly of between 0.5 g % and 5 g % inclusive;
iii) at least one ethoxylated fatty alcohol with a concentration of between 0.5 g % and 30 g % inclusive and preferably between 1 g % and 10 g % inclusive;
and optionally at least one fragrance with a concentration preferably of between 0.01 g % and 10 g % inclusive and preferably between 0.2 g % and 2 g % inclusive;
the pH of composition B preferably being between 5 and 12 inclusive and more particularly between 7 and 10 inclusive;
the fixing composition C comprises:
vi) at least one oxidizing agent with a concentration preferably of between 0.01 g % and 30 g % inclusive and in particular between 0.5 g % and 5 g % inclusive;
the pH of composition C preferably being between 1.5 and 7 inclusive and more particularly between 2 and 5 inclusive;
it being understood that the fixing composition can also comprise a thickening organic polymer ii) as defined above, just like compositions A, A', A" and/or B, B', B".

Alternative Form 1:
The dyeing composition A is mixed with the reducing composition B, or composition A' is mixed with composition B', or composition A" is mixed with composition B", in the following proportions: mixing 9 volumes of composition A, A' or A" with 1 volume of composition B, B' or B" in a basin. The mixture is applied to hair with a leave-in time preferably of between 5 minutes and 1 hour inclusive and preferably between 10 minutes and 40 minutes inclusive. The hair is rinsed, then shampooing is optionally carried out, preferably shampooing is carried out, and then the hair is dried.

Alternative Form 2:
The dyeing formulation A is mixed with the reducing composition B, or composition A' is mixed with composition B', or composition A" is mixed with composition B", in the following proportions: mixing 9 volumes of composition A, A' or A" with 1 volume of composition B, B' or B" in a basin. The mixture is applied to hair with a leave-in time preferably of between 5 minutes and 1 hour inclusive and more particularly of between 10 minutes and 40 minutes inclusive.

The hair is optionally rinsed; preferably, rinsing is carried out. Subsequently, the fixing composition C is applied to the hair with a leave-in time preferably of between 1 minute and 30 minutes and more particularly of between 3 minutes and 10 minutes inclusive.

The hair is rinsed, then shampooing is or is not carried out (preferably, shampooing is carried out) and then the hair is dried.

Alternative Form 3:

The reducing formulation is applied to hair with a leave-in time preferably of between 5 minutes and 1 hour inclusive and more particularly of between 10 minutes and 40 minutes inclusive. The hair is optionally rinsed; preferably, rinsing is carried out. The dyeing formulation is applied to the hair with a leave-in time preferably of between 5 minutes and 1 hour inclusive and more particularly of between 10 minutes and 40 minutes inclusive. The hair is optionally rinsed; preferably, rinsing is carried out. The fixing composition C is subsequently applied to the hair with a leave-in time preferably of between 1 minute and 30 minutes inclusive and more particularly of between 3 minutes and 10 minutes inclusive.

The hair is rinsed, then shampooing is optionally carried out, preferably shampooing is carried out, and then the hair is dried.

3). Dyeing Kit of the Invention

Another subject-matter of the invention is a multicompartment device or kit for dyeing comprising a first compartment including a dyeing composition comprising the composition comprising the ingredient i); a second compartment which includes a reducing agent v) as defined above, the ingredients ii) to iv) as defined above being distributed in the first two compartments, and optionally a third compartment comprising at least one oxidizing agent as defined above.

According to an alternative form, the device comprises a first compartment which includes a dyeing composition comprising the composition comprising the ingredients i) to iv), a second compartment which includes at least one reducing agent v) as defined above and optionally a third compartment comprising at least one oxidizing agent vi) as defined above.

Alternatively, the dyeing device comprises a first compartment including a dyeing composition which comprises at least i) a protected thiol dye and the ingredients ii) to iv), a second compartment including an agent capable of deprotecting the protected thiol in order to release the thiol, a third compartment which includes at least one reducing agent v) as defined above and optionally a fourth compartment comprising an oxidizing agent vi) as defined above.

According to other alternative forms:
the first compartment comprises i) and ii) as defined above and the second compartment comprises the ingredients v), iv) and HO as defined above;
or else the first compartment comprises the ingredients i), ii) and iii) as defined above and the second compartment comprises the ingredients v) and iv);
or else the first compartment comprises the ingredients i), iii) and iv) as defined above and the second compartment comprises the ingredients v) and ii).

For these alternative forms, a third compartment may be present which comprises an oxidizing agent vi) as defined above, and optionally the ingredient ii) as defined above and optionally a fourth compartment may be present including an agent capable of deprotecting the protected thiol in order to release the thiol, if the ingredient i) of the first compartment is a protected thiol.

Each of the devices mentioned above may be equipped with a means which makes it possible to deliver the desired mixture to the hair, for example such as the devices described in Patent FR 2 586 913.

The examples which follow serve to illustrate the invention without, however, exhibiting a limiting nature.

The thiol, protected thiol or disulphide direct dyes of formula (I) of use in the present invention are known compounds and can be prepared according to methods known to a person skilled in the art, in particular from the methods described in Applications EP 1 647 580, EP 2 004 759, WO 2007/110541, WO 2007/110540, WO 2007/110539, WO 2007/110538, WO 2007/110537, WO 2007/110536, WO 2007/110535, WO 2007/110534, WO 2007/110533, WO 2007/110532, WO 2007/110531, EP 2 070 988 and WO 2009/040354.

DYEING EXAMPLE

Concentration of the starting materials in this form.

Composition A:

| Ingredient | Trade name | Supplier | Amount |
|---|---|---|---|
| Disulphide dye of formula 44 with disulphate $SO_4^{2-}$ as counterion (ingredient i)) | | | 0.5 g % |
| Hydroxyethyl cellulose (Mw: 720 000) ingredient ii) | Natrosol 250 MR | Aqualon | 2 g % |
| Mixture of methyl, butyl, ethyl, propyl and isobutyl p-hydroxybenzoates (7/57/22/14) | Sharomix 431 | Clariant | 0.12 g % |
| Alkyl ($C_8/C_{10}$ 50/50) polyglucoside (2) as a 60% aqueous solution ingredient iii) | Oramix CG 110 | Seppic | 10 g % |
| Propylene glycol | Propylene Glycol USP/EP | Univar | 4 g % |
| Polyethylene glycol (8 EO) | Polyethylene Glycol 400 DUB PEG 8 | Stearinerie Dubois | 6 g % |
| Water | | | q.s. for 100 g % |

Composition B

| Ingredient | Trade name | Supplier | Amount |
|---|---|---|---|
| Ammonium thioglycolate as a 71% aqueous solution (pH 6) | Ammonium thioglycolate 71% | Bruno Bock | 20 g % |
| Diethylenetriaminepentaacetic acid, pentasodium salt, as a 40% aqueous solution | Versenex 80 | Univar | 0.4 g % |
| Fresh mint | Fragrance | Mane | 0.8 g % |
| Pure monoethanolamine, ingredient iv) | Monoethanolamine care | Univar | 1.21 g % |
| Oxyethylenated (20 EO) oleyl alcohol ingredient iii) | Brij O20-SO-(MV) | Croda | 6 g % |
| Water | | | q.s. for 100 g |

Composition C

| Ingredient | Trade name | Supplier | Amount |
|---|---|---|---|
| Hydrogen peroxide as a 50% solution (200 vol. aqueous hydrogen peroxide solution) | H$_2$O$_2$ Interox ST-50 | Brenntag | 0.48 g % |
| Etidronic acid, tetrasodium salt, as a 30% aqueous solution | Turpinal 4 NL | Brenntag | 0.02 g % |
| Sodium salicylate | Sodium salicylate | Merck | 0.0035 g % |
| Tetrasodium pyrophosphate | Tetrasodium pyrophosphate 10 H$_2$O PRS | Penreac | 0.004 g % |
| Polydimethyldiallyl-ammonium chloride at 40% in water | Merquat 100 | Nalco | 0.125 g % |
| Phosphoric acid | Prayphos P5 85 | Prayon | 0.012 g % |
| Crosslinked methacryloyloxyethyl-trimethylammonium chloride homopolymer as an inverse emulsion in mineral oil | Salcare SC 95 | Ciba | 1.3 g % |
| Water | | | q.s. for 100 g |

9 parts of composition A are mixed with 1 part of composition B in a basin.

The mixture is applied to brown hair (dark hair having a tone height of 4 (TH4)) with a leave-in time of 20 minutes.

The hair is rinsed.

The fixing formulation C is applied to the hair with a leave-in time of 5 minutes.

The hair is rinsed, then shampooing is carried out and then the hair is dried.

Colorimetric Evaluation Results in the L*a*b* System for Evaluating the Coloring of the Locks:

The color of the locks was evaluated in the L*a*b* system by means of a MINOLTA® CM 3600D spectrocolorimeter (Illuminant D65).

In this L*a*b* system, L* represents the lightness, a* indicates the green/red color axis and b* the blue/yellow color axis. The higher the value of L, the lighter or weaker the color. Conversely, the lower the value of L, the darker or much stronger the color. The higher the value of a*, the redder the shade, and the higher the value of b*, the more yellow the shade.

The variation in coloring between the TH4 dyed and treated locks of hair is measured by (ΔE) according to the following equation:

$$\Delta E = \sqrt{(L^* - L_o^*)^2 + (a^* - a_o^*)^2 + (b^* - b_o^*)^2}$$

In this equation, L*, a* and b* represent the values after treatment, and L$_o$*, a$_o$* and b$_o$* represent the values measured before treatment.

The greater the value of ΔE, the greater the difference in color between the TH4 locks and the uncolored locks.

| | L* | a* | b* | ΔE* |
|---|---|---|---|---|
| TH4 reference | 24.27 | 3.96 | 4.72 | — |
| After treatment A + B + C | 25.21 | 8.43 | 8.9 | 6.19 |

It is noted that the ΔE value is significantly high after treatment with compositions A+B+C. A mahogany colouration is obtained which is intense and persistent (even after several washing operations).

On the other hand the colour changed very little after the shampooing operations, given the number of successive shampooing operations (even after more than 10 shampooing operations. It is also observed that the coloration is particularly resistant vs. perspiration.

The invention claimed is:

1. A cosmetic composition comprising:
   i) at least one direct dye chosen from dyes of formula (I), comprising at least one functional group chosen from disulphide, thiol and protected thiol functional groups:

$$A\text{-}(X)_p\text{---}C_{sat}\text{---}S\text{---}U \qquad (I)$$

the salts thereof with an organic or inorganic acid, the optical or geometric isomers thereof, the tautomers thereof, and the solvates thereof,
   wherein:
   U is a radical chosen from:
      a) —S—C'$_{sat}$—(X')$_p$-A'; and
      b) —Y;
   A and A', which may be identical or different, are chosen polymethine radicals of formula (VI'), below:

$$Ar\text{---}[C(R^d)\text{=}C(R^c)]_{m'}\text{---}W'^+\text{---}(*)Q^- \qquad (VI')$$

wherein:
   W$^+$ is chosen from cationic heterocyclic and heteroaryl groups;
   Ar is an optionally substituted aryl group;
   m' is an integer ranging from 1 to 4 inclusive;
   R$^c$ and R$^d$, which may be identical or different, are chosen from hydrogen and optionally substituted (C$_1$-C$_8$) alkyl groups or alternative R$^c$ contiguous with W'$^+$ and/or R$^d$ contiguous with Ar form, with the atoms that bear them, a (hetero)cycloalkvl;
   Q$^-$ is an anionic counterion;
   (*) is the part of the chromophore linked to the rest of the molecule of formula (I);
   Y is chosen from i) hydrogen and ii) protective groups for the thiol functional group;
   X and X', which may be identical or different, are chosen from saturated or unsaturated and linear or branched divalent C$_1$-C$_{30}$ hydrocarbon chains optionally interrupted and/or optionally terminated at one or both ends by at least one divalent group chosen from:
      —N(R)—, —N$^+$(R)(R)—, —O—, —S—, —CO—, and —SO$_2$—, wherein R, which may be identical or different, is chosen from hydrogen, C$_1$-C$_4$ alkyl radicals, hydroxyalkyl radicals and aminoalkyl radicals;
      fused or nonfused, saturated or unsaturated and aromatic or nonaromatic (hetero)cyclic radicals optionally comprising at least one identical or different optionally substituted heteroatom;
   p and p', which may be identical or different, are equal to 0 or 1;

$C_{sat}$ and $C'_{sat}$, which may be identical or different, are chosen from linear or branched $C_1$-$C_{18}$ alkylene chains which may be optionally substituted and optionally cyclic;

ii) at least one thickening organic polymer;

iii) at least one (poly)ethoxylated fatty alcohol and/or at least one nonionic surfactant;

iv) at least one alkaline agent; and v) at least one reducing agent chosen from thioglycolic acid, thiolactic acid, 3-mercaptopropionic acid, thiomalic acid, 2,3-dimercaptosuccinic acid, cysteine, N-glycyl-L-cysteine, L-cysteinylglycine, and esters and salts thereof; thioglycerol; cysteamine and $C_1$-$C_4$ acyl derivatives thereof; N-mesylcysteamine; N-acetylcysteine; N-(mercapto-2-ethyl) gluconamide; pantetheine, N-(mercaptoalkyl)-(ω-hydroxyalkylamides; N-mono- or N,N-dialkylmercapto-4-butyramides; aminomercaptoalkyl amides; N-(mercaptoalkyl)succinamic acids and N-(mercaptoalkyl)succinimides; alkylamino mercaptoalkyl amides; the azeotropic mixture of 2-hydroxypropyl thioglycolate and of (2-hydroxy-1-methyl)ethyl thioglycolate; ammonium thioglycolate; mercaptoalkylamino amides; and N-mercaptoalkylalkanediamides.

2. The composition according to claim 1, wherein the radicals A and/or A' of the at least one direct dye of formula (I), which may be identical or different, are chosen from radicals comprising at least one quaternized cationic chromophore.

3. The composition according to claim 1 wherein which the at least one direct dye of formula (I) is a disulphide dye, wherein U is a radical chosen from a) —S—$C'_{sat}$—$(X')_{p'}$-A'.

4. The composition according to claim 3, wherein the at least one direct dye of formula (I) is a symmetrical disulphide dye of following formula (Ia):

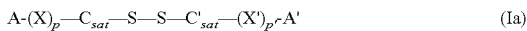

wherein A=A', X=X', p=p', and $C_{sat}$=$C'_{sat}$.

5. The composition according to claim 1, wherein the at least one direct dye of formula (I) is a dye comprising a thiol or protected thiol functional group, wherein U is the radical b) Y, chosen from hydrogen and the following radicals:

($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthio-thiocarbonyl;
(di)($C_1$-$C_4$)(alkyl)aminocarbonyl;
(di)($C_1$-$C_4$)(alkyl)aminothiocarbonyl;
arylcarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
carboxyl;
$SO_3^-M^+$, wherein $M^+$ is chosen from alkali metal ions, or else a counterion of the cationic chromophore A and $M^+$ are absent;
optionally substituted aryl;
optionally substituted heteroaryl;
optionally substituted heterocycloalkyl which is optionally cationic;
—C(NR'$^c$R'$^d$)=N$^+$R'$^e$R'$^f$An''''$^-$, wherein R'$^c$, R'$^d$, R'$^e$ and R'$^f$, which may be identical or different, are chosen from hydrogen and ($C_1$-$C_4$)alkyl groups and An''''$^-$ is a counterion;

—C(NR'$^c$R'$^d$)=NR'$^e$, wherein R'$^c$, R'$^d$ and R'$^e$ are defined above;
optionally substituted (di)aryl($C_1$-$C_4$)alkyl;
optionally substituted (di)heteroaryl($C_1$-$C_4$)alkyl;
—CR$^1$R$^2$R$^3$, wherein R$^1$, R$^2$ and R$^3$, which may be identical or different, are chosen from halogen atoms and the following groups:
($C_1$-$C_4$)alkyl;
($C_1$-$C_4$)alkoxy;
optionally substituted aryl;
optionally substituted heteroaryl; and
P(Z$^1$)R'$^1$R'$^2$R'$^3$, wherein R'$^1$ and R'$^2$, which may be identical or different, are chosen from hydroxyl, ($C_1$-$C_4$)alkoxy and alkyl groups, R'$^3$ is chosen from hydroxyl and ($C_1$-$C_4$)alkoxy groups and Z$^1$ is chosen from oxygen and sulphur;
sterically hindered rings; and
optionally substituted alkoxyalkyl.

6. The composition according to claim 1, wherein, in formula (I), $C_{sat}$ and $C'_{sat}$, which may be identical or different, are chosen from —(CH$_2$)$_k$—chains, wherein k is an integer ranging from 1 to 8 inclusive.

7. The composition according to claim 1, wherein, in formula (I), when p and p' are equal to 1, X and X', which may be identical or different, are chosen from the following sequence:

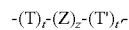

wherein the sequence is symmetrically connected in the formula (I) as follows:

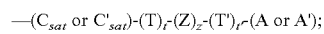

wherein:

T and T', which may be identical or different, are chosen from at least one of:
—O—; —S—; —N(R)—; —N$^+$(R)(R.)—; —S(O)—; —S(O)$_2$—; and —C(O)—; wherein R and R., which may be identical or different, are chosen from hydrogen; $C_1$-$C_4$ alkyl radicals; $C_1$-$C_4$ hydroxyalkyl radicals; aryl($C_1$-$C_4$)alkyl radicals; and cationic or noncationic, heterocycloalkyl or heteroaryl radicals, optionally monocyclic and optionally comprising two heteroatoms;

t and t', which may be identical or different, are equal to 0 or 1;

Z is chosen from:
—(CH$_2$)$_m$—, wherein m is an integer ranging from 1 to 8 inclusive;
—(CH$_2$CH$_2$O)$_q$— and —(OCH$_2$CH$_2$)$_q$—, wherein q is an integer ranging from 1 to 5 inclusive;
aryl, alkylaryl and arylalkyl radicals, wherein the alkyl radical is chosen from $C_1$-$C_4$ alkyl radicals, optionally substituted by at least one SO$_3$M group, wherein M is chosen from hydrogen, alkali metals, and ammonium groups substituted by at least one radical, which may be identical or different, chosen from linear or branched $C_1$-$C_{18}$ alkyl radicals optionally carrying at least one hydroxyl group; and z is 0 or 1.

8. The composition according to claim 1, wherein the at least one dye of formula (I) is chosen from disulfide dyes of formulae XII and thiol or protected-thiol dyes of formulae XII' below:

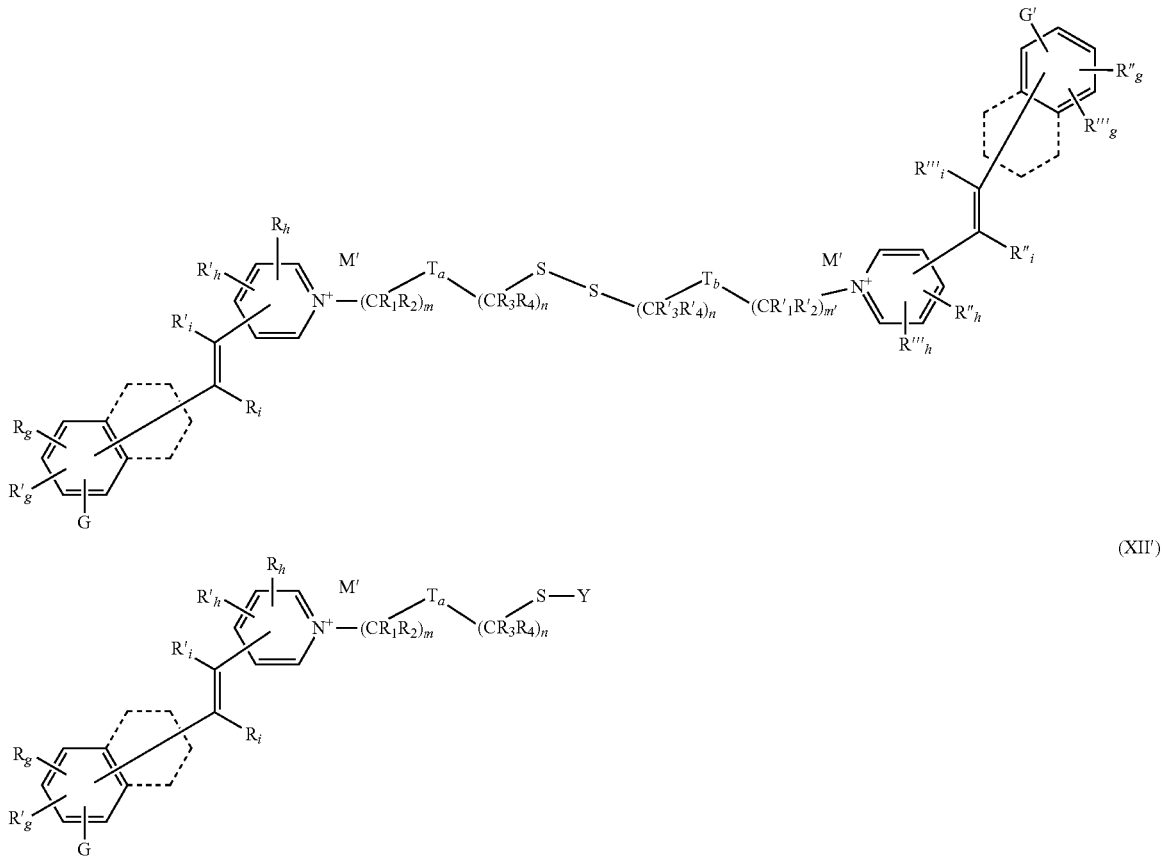

wherein:
G and G', which may be identical or different, are chosen from —NR$_c$R$_d$, —NR'$_c$R'$_d$, and C$_1$-C$_6$ alkoxy groups which are optionally substituted;

R$_c$, R'$_c$, R$_d$ and R'$_d$, which may be identical or different, are chosen from hydrogen, aryl(C$_1$-C$_4$)alkyl and C$_1$-C$_6$ alkoxy groups and C$_1$-C$_6$ alkyl groups which are optionally substituted;

or alternatively two adjacent radicals R$_c$ and R$_d$, R'$_c$, and R'$_d$ borne by the same nitrogen atom, together form a heterocyclic or heteroaryl group;

R$_g$, R'$_g$, R''$_g$, R'''$_g$, R$_h$, R'$_h$, R''$_h$ and R'''$_h$, which may be identical or different, are chosen from hydrogen, halogen atoms, amino, C$_1$-C$_4$ alkylamino, C$_1$-C$_4$ dialkylamino, cyano, carboxyl, hydroxyl and trifluoromethyl group, acylamino, C$_1$-C$_4$ alkoxy, (poly)hydroxy(C$_2$-C$_4$) alkoxy, alkylcarbonyloxy, alkoxycarbonyl and alkylcarbonylamino radicals, acylamino, carbamoyl and alkylsulfonylamino radicals, aminosulfonyl radicals, and C$_1$-C$_{16}$ alkyl radicals optionally substituted with a group chosen from C$_1$-C$_{12}$ alkoxy, hydroxyl, cyano, carboxyl, amino, C$_1$-C$_4$ alkylamino and C$_1$-C$_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups R$_g$ and R'$_g$; R''$_g$ and R'''$_g$; R$_h$ and R'$_h$; R''$_h$ and R'''$_h$ borne by two adjacent carbon atoms together form a benzo or indeno ring, a fused heterocycloalkyl or fused heteroaryl group; wherein the benzo, indeno, heterocycloalkyl and heteroaryl rings are optionally substituted with an entity chosen from halogen atoms, amino, C$_1$-C$_4$ alkylamino, C$_1$-C$_4$ dialkylamino, nitro, cyano, carboxyl, hydroxyl and trifluoromethyl groups, acylamino, C$_1$-C$_4$ alkoxy, (poly)hydroxy(C$_2$-C$_4$)alkoxy, alkylcarbonyloxy, alkoxycarbonyl and alkylcarbonylamino radicals, acylamino, carbamoyl and alkylsulfonylamino radicals, aminosulfonyl radicals, and C$_1$-C$_{16}$ alkyl radicals optionally substituted with a group chosen from C$_1$-C$_{12}$ alkoxy, hydroxyl, cyano, carboxyl, amino, C$_1$-C$_4$ alkylamino, and C$_1$-C$_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups R$_i$ and R$_g$; R'''$_i$ and R'''$_g$; R'$_i$; and R'$_h$and/or R''$_i$; and R''$_h$ together form a fused (hetero)cycloalkyl;

or alternatively when G represents —NR$_c$R$_d$ and G' represents —NR'$_c$R'$_d$, two groups R$_c$ and R'$_g$; R'$_c$and R''$_g$;R$_d$ and R$_g$; R'$_d$ and R'''$_g$ together form a saturated heteroaryl or heterocycle, optionally substituted with at least one (C$_1$-C$_6$)alkyl group, and optionally comprising at least one heteroatom chosen from nitrogen and oxygen;

R$_i$, R'$_i$, R''$_i$, and R'''$_i$, which may be identical or different, are chosen from hydrogen and C$_1$-C$_4$ alkyl groups;

$R_1$, $R_2$, $R_3$, $R_4$, $R'_1$, $R'_2$, $R'_3$ and $R'_4$, which may be identical or different, are chosen from hydrogen and $C_1$-$C_4$ alkyl, $C_1$-$C_{12}$ alkoxy, hydroxyl, cyano, carboxyl, amino, $C_1$-$C_4$ alkylamino and $C_1$-$C_4$ dialkyl amino group, the alkyl radicals possibly forming, with the nitrogen atom that bears them, a 5- to 7-membered heterocycle optionally comprising another nitrogen or non-nitrogen heteroatom;

$T_a$ and $T_b$, which may be identical or different, are chosen from i) a covalent a bond, ii) at least one radical chosen from —$SO_2$—, —O—, —S—, —N(R)—, —$N^+$(R)(R.)—, and —CO—, wherein R, R., which may be identical or different, are chosen from hydrogen, $C_1$-$C_4$ alkyl and $C_1$-$C_4$ hydroxyalkyl radicals; and aryl($C_1$-$C_4$) alkyl radicals, or iii) cationic or non-cationic, heterocycloalkyl or heteroaryl radicals;

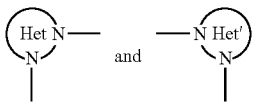

which may be identical or different, are chosen from optionally substituted heterocyclic groups;

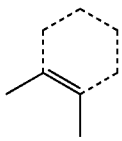

is chosen from aryl and heteroaryl groups fused to the imidazolium or phenyl ring; or alternatively is absent from the imidazolium or phenyl ring;

m, m', n and n', which may be identical or different, are integers ranging from 0 to 6 inclusive, wherein the sums m+n and m'+n'are equal to integers ranging from 1 to 10 inclusive;

Y is chosen from hydrogen and the following protecting groups:
($C_1$-$C_4$)alkylcarbonyl;

arylcarbonyl;

($C_1$-$C_4$)alkoxycarbonyl;

aryloxycarbonyl;

aryl($C_1$-$C_4$)alkoxycarbonyl;

(di)($C_1$-$C_4$)(alkyl)aminocarbonyl;

($C_1$-$C_4$)(alkyl)arylaminocarbonyl;

optionally substituted aryl;

5- or 6-membered monocyclic heteroaryl;

5- or 6-membered cationic monocyclic heteroaryl;

8- to 11-membered cationic bicyclic heteroaryl;

cationic heterocycles having the following formula:

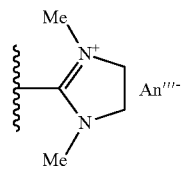 [SMILES: *C1=[N+](C)CCN1C]

—$C(NH_2)=N^+H_2$; $An'''^-$; wherein $An'''^-$ is an anionic counterion;

—$C(NH_2)=NH$;

$SO_3^-M^+$, wherein $M^+$ is a metal ion; and

M' is an anionic counterion.

9. The composition according to claim 1, wherein the at least one direct dye of formula (I) is chosen from:

dyes of the following formulae (XV) and (XV'):

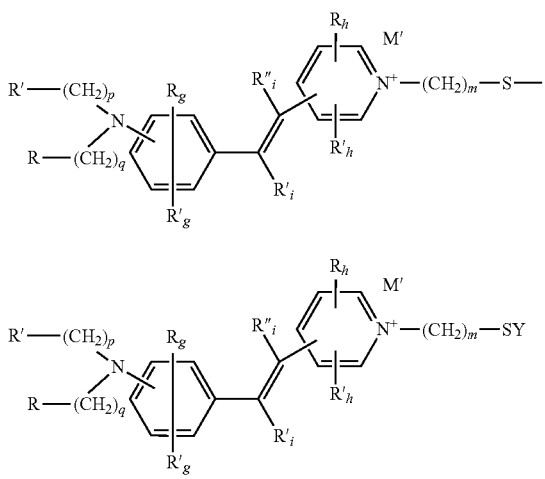

(XV)

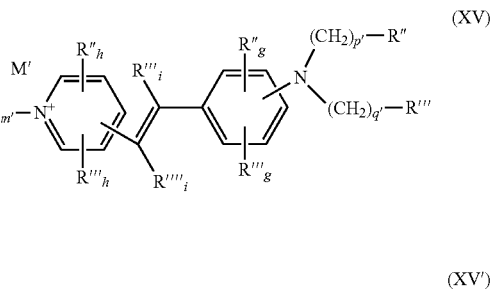

(XV')

wherein in formulae (XV) and (XV'):
R and R''', which may be identical or different, are chosen from hydroxyl, amino ($NR_aR_b$) and ammonium ($N^+R_aR_bR_c$) $An^-$ groups, wherein $R_a$, $R_b$ and $R_c$, which may be identical or different, are chosen from hydrogen and ($C_1$-$C_4$)alkyl groups; or else two alkyl groups $R_a$ and $R_b$ of the amino or ammonium group form a 5- to 7-membered heterocycle optionally comprising another heteroatom identical to or different from the nitrogen atom;

R' and R", which may be identical or different, are chosen from hydrogen and hydroxyl, amino ($NR_aR_b$) and ammonium ($N^+R_aR_bR_c$) $An^-$ groups;

$R_g$, $R'_g$, $R''_g$, $R'''_g$, $R_h$, $R'_h$, $R''_h$ and $R'''_h$, which may be identical or different, are chosen from hydrogen; halogen atoms; amino, (di)($C_1$-$C_4$)alkylamino, cyano, carboxyl, hydroxyl, trifluoromethyl, acylamino, $C_1$-$C_4$ alkoxy, (poly)hydroxy($C_2$-$C_4$)alkoxy, ($C_1$-$C_4$)alkylcarbonyloxy, ($C_1$-$C_4$)alkoxycarbonyl, ($C_1$-$C_4$)alkylcarbonylamino, acylamino, carbamoyl and ($C_1$-$C_4$)alkylsulphonylamino groups; aminosulphonyl radicals and ($C_1$-$C_{16}$)alkyl radicals optionally substituted by a group chosen from ($C_1$-$C_{12}$)alkoxy, hydroxyl, cyano, carboxyl, amino and (di)($C_1$-$C_4$)alkylamino groups, or else the two alkyl radicals carried by the nitrogen atom of the amino group form a 5- to 7-membered heterocycle optionally comprising another heteroatom which is identical to or different from the nitrogen atom;

$R'_i$, $R''_i$, $R'''_i$ and $R''''_i$, which may be identical or different, are chosen from hydrogen and ($C_1$-$C_4$)alkyl groups;

m and m', which may be identical or different, are integers ranging from 1 to 10 inclusive;

p, p', q and q', which may be identical or different, are integers ranging from 1 to 6 inclusive;

M' is an anionic counterion; and

Y is chosen from hydrogen and the following protective groups:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
5- or 6-membered cationic monocyclic heteroaryl;
8- to 11-membered cationic bicyclic heteroaryl;
cationic heterocycles of following formula:

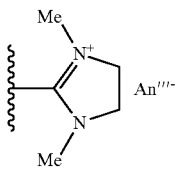

—$C(NH_2)=N^+H_2$ $An''''^-$; wherein $An''''^-$ is an anionic counterion;
—$C(NH_2)=NH$; and
$SO_3^-M^+$, wherein $M^+$ is a metal ion;

it being understood that, when the compound of formula (XV) or (XV') comprises other cationic parts, it is combined with one or more anionic counterions which make it possible to achieve the electrical neutrality of the formula (XV) or (XV'); and the dyes of the following formulae (XVI) and (XVI'):

(XVI)

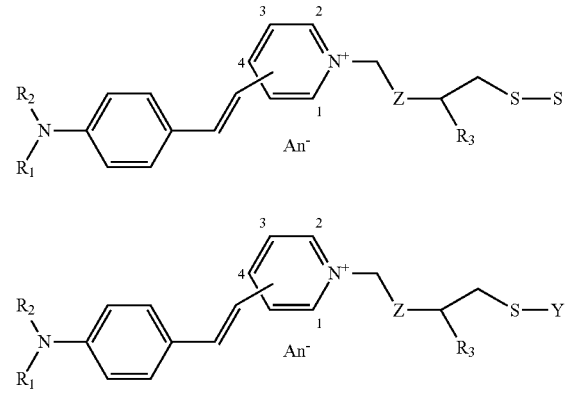

(XVI')

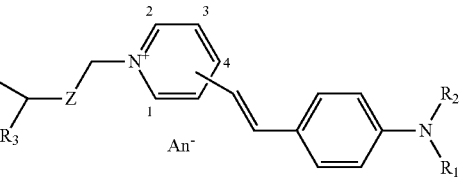

wherein in formulae (XVI) and (XVI'):

$R_1$ is chosen from $C_1$-$C_6$ alkyl groups substituted by at least one group chosen from hydroxyl and —C(O)OR' groups wherein R' is chosen from hydrogen and $C_1$-$C_4$ alkyl groups or else a —C(O)—$O^-$ group and, in the latter case, the anionic counterion $An^-$ is absent;

$R_2$ is chosen from $C_1$-$C_6$ alkyl groups optionally substituted by at least one hydroxyl group;

or else the groups $R_1$ and $R_2$ form, together with the nitrogen atom which carries them, a saturated heterocyclic radical substituted with at least one group chosen from hydroxyl, (poly)hydroxy($C_1$-$C_4$)alkyl and/or —C(O)OR' groups, wherein R' is chosen from hydrogen and $C_1$-$C_4$ alkyl groups, or else a —C(O)—$O^-$ group and, in this case, the anionic counterion $An^-$ is absent;

$R_3$ is chosen from hydrogen and —C(O)OR" groups, wherein R" is chosen from hydrogen, alkali metals and $C_1$-$C_6$ alkyl groups, or else $R_3$ is a —C(O)—$O^-$ group and, in this case, the anionic counterion $An^-$ is absent;

Z is chosen from divalent amido groups —C(O)—N(R)— and —N(R)—C(O)—, and divalent $C_1$-$C_{10}$alkylene groups interrupted by an amido group chosen from —$(CH_2)_{n'}$—C(O)—N(R)—$(CH_2)_p$— and —$(CH_2)_{n''}$—N(R)—C(O)—$(CH_2)_p$—, wherein n' is an integer ranging from 0 to 3 inclusive; p is an integer ranging from 0 to 4 inclusive, n" is an integer ranging from 0 to 3 inclusive, and R is chosen from hydrogen and $C_1$-$C_6$ alkyl groups;

$An^-$ is an anionic counterion;

Y is chosen from hydrogen and the following protective groups:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;

5- or 6-membered monocyclic heteroaryl;
5- or 6-membered cationic monocyclic heteroaryl;
8- to 11-membered cationic bicyclic heteroaryl;
cationic heterocycles of following formula:

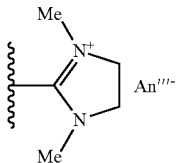

—C(NH$_2$)=N$^+$H$_2$ An''''$^-$; wherein An''''$^-$ is an anionic counterion;

—C(NH$_2$)=NH; and

—SO$_3^-$M$^+$, wherein M$^+$ is a metal ion;

it being understood that, when the compound of formula (XVI) or (XVI') comprises other cationic parts, it is combined with one or more anionic counterions which make it possible to achieve the electrical neutrality of the formula (XVI) or (XVI').

10. The composition according to claim 1, wherein the at least one direct dye of formula (I) is chosen from dyes of the following chemical structures:

25

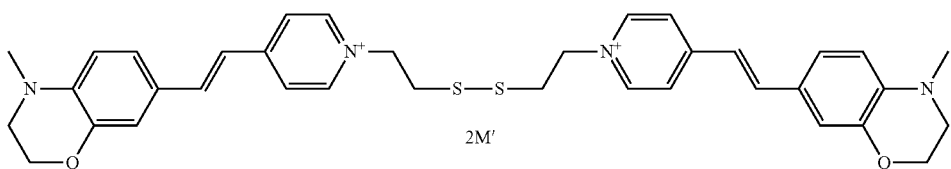

26

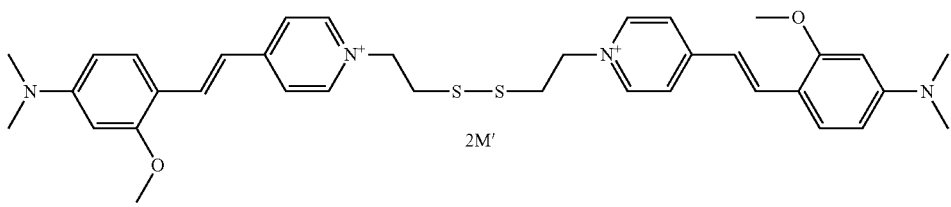

27

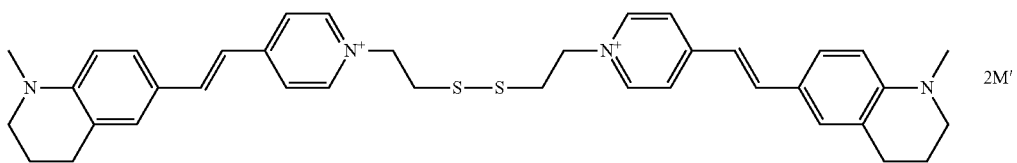

28

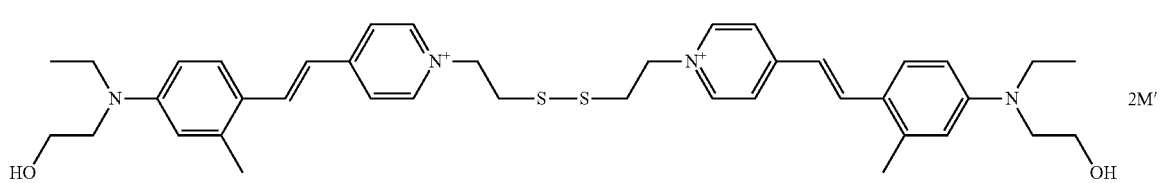

29

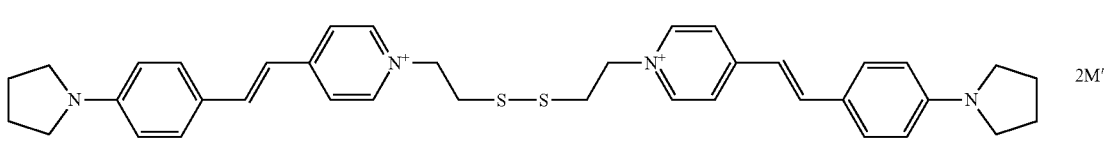

30

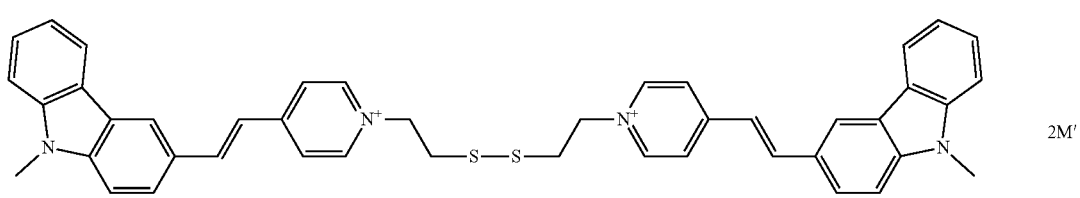

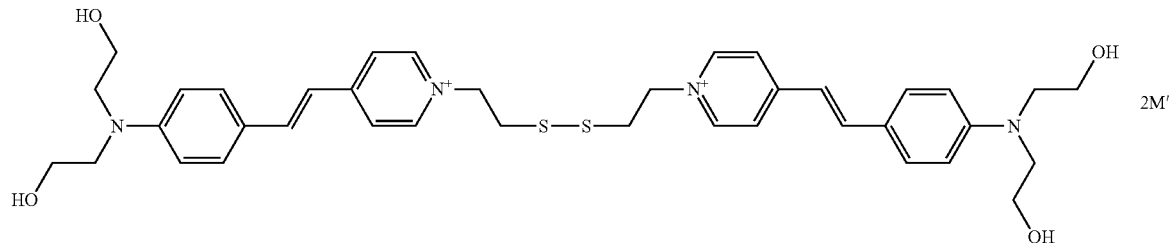
31
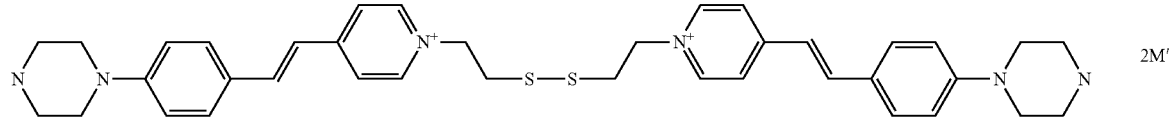
32
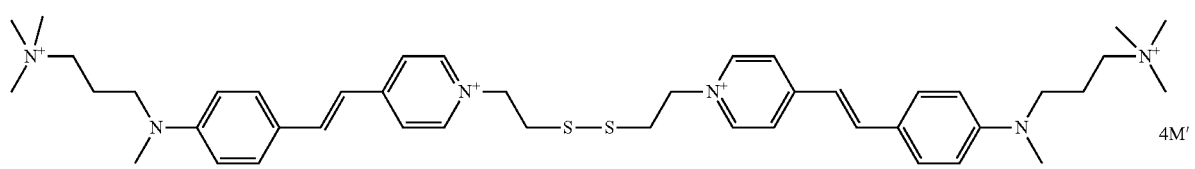
33
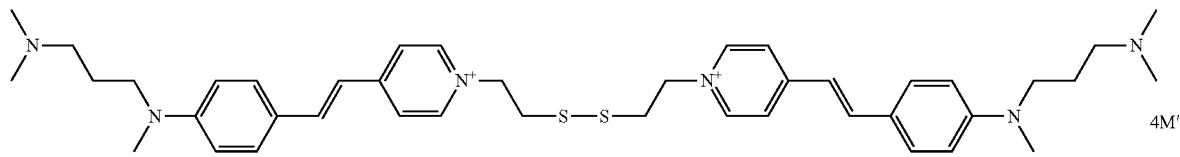
34
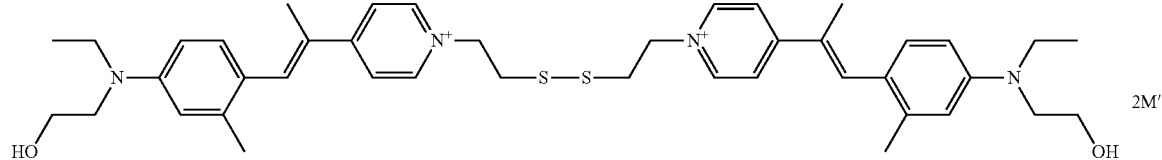
35
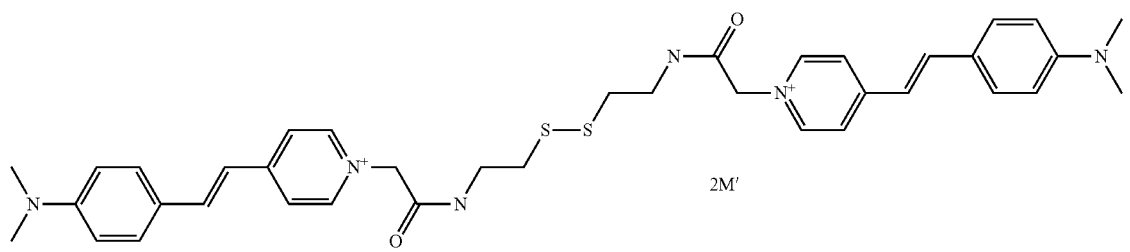
36
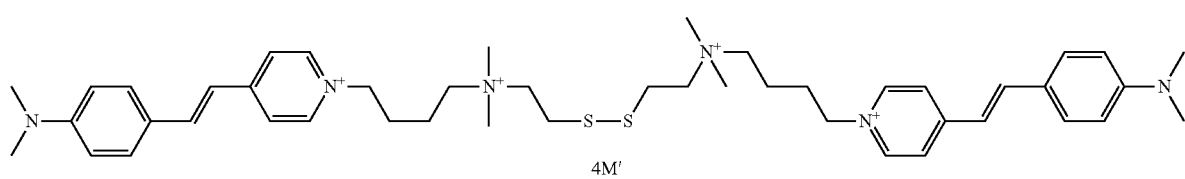
37
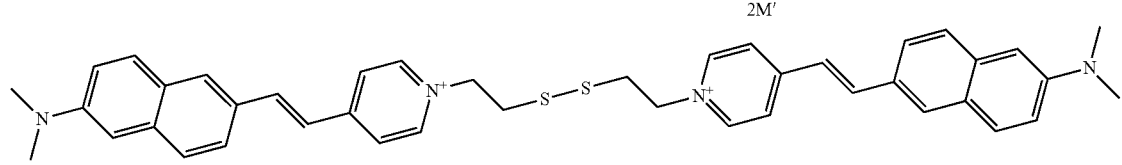
38

123  124
-continued
39
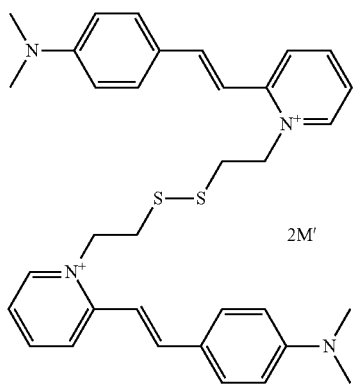
2M′
40
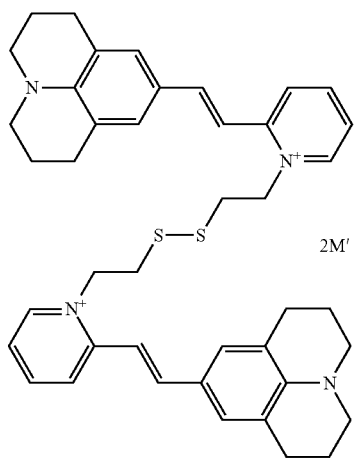
2M′
41
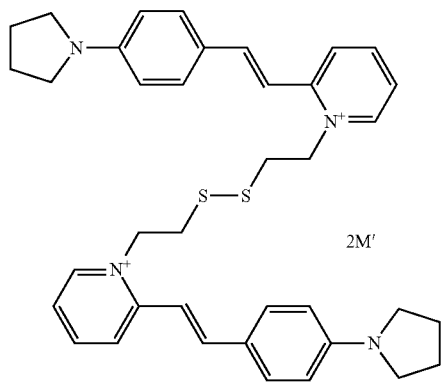
2M′
42
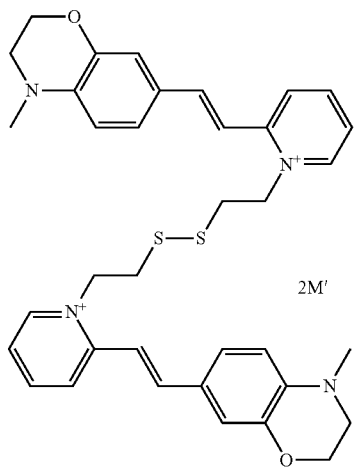
2M′
43
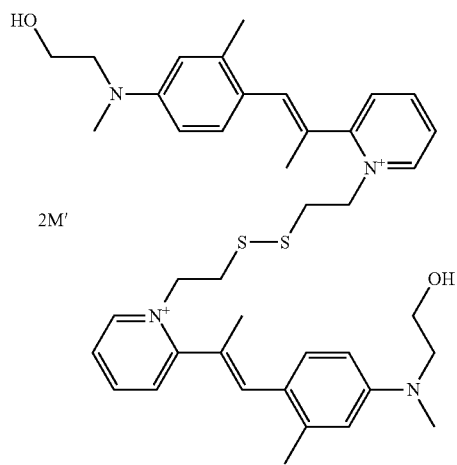
2M′
44
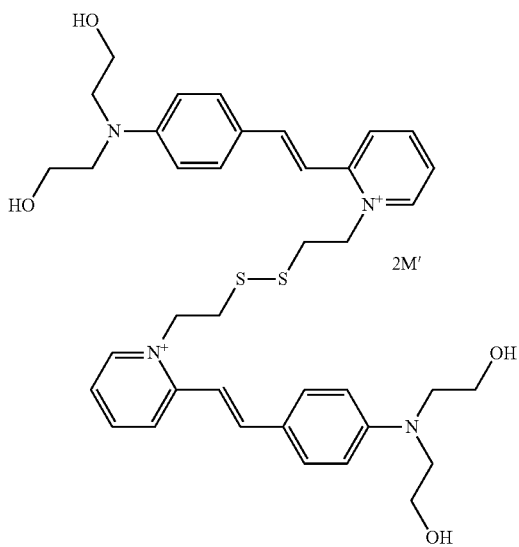
2M′

45
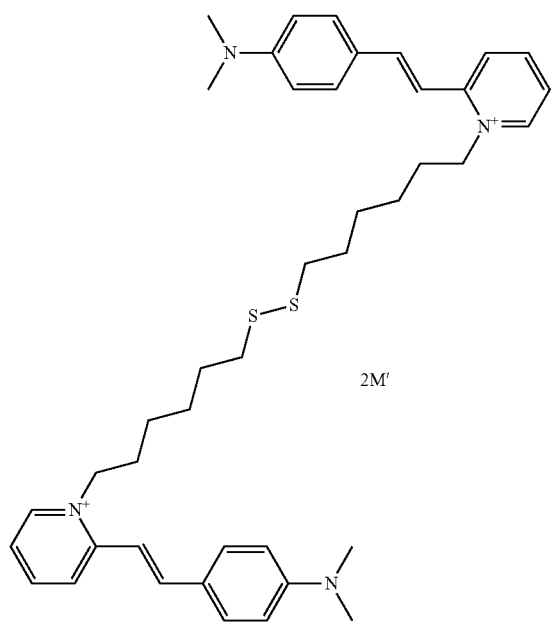
2M'
46
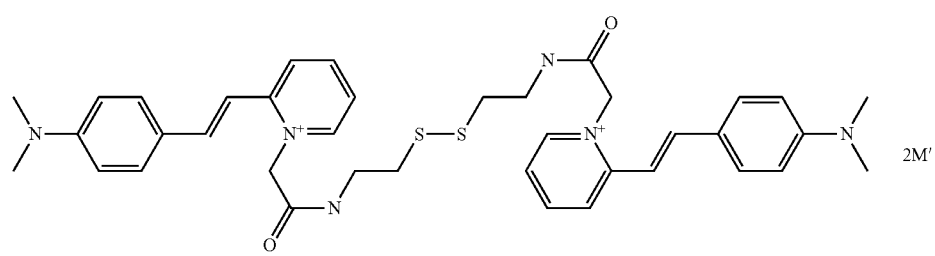
2M'
47
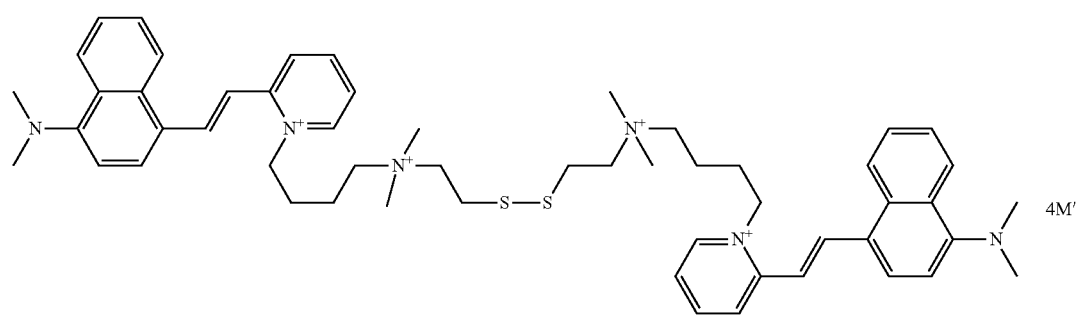
4M'

48
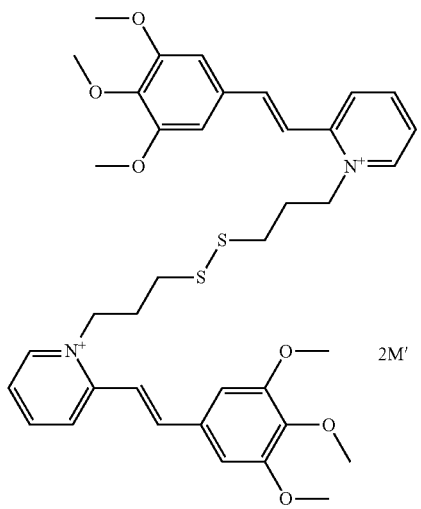
2M'
52
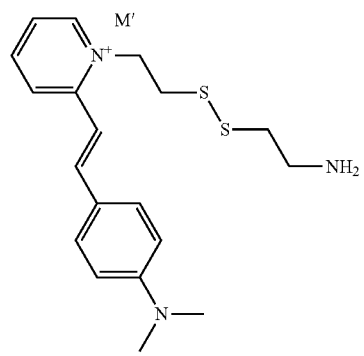
M'
54
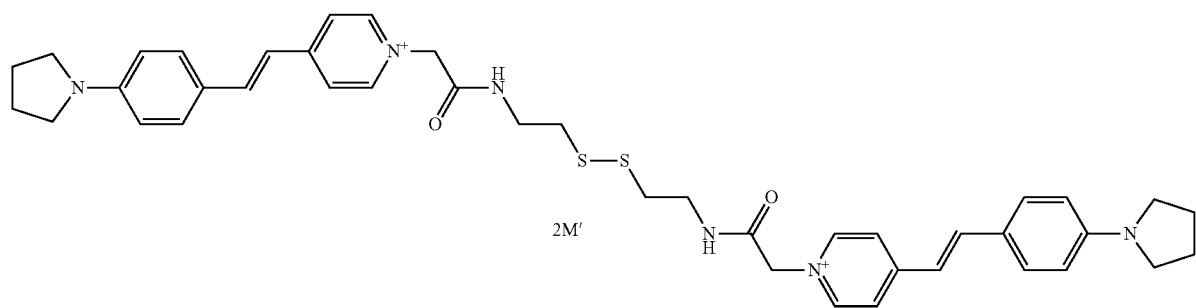
2M'
55
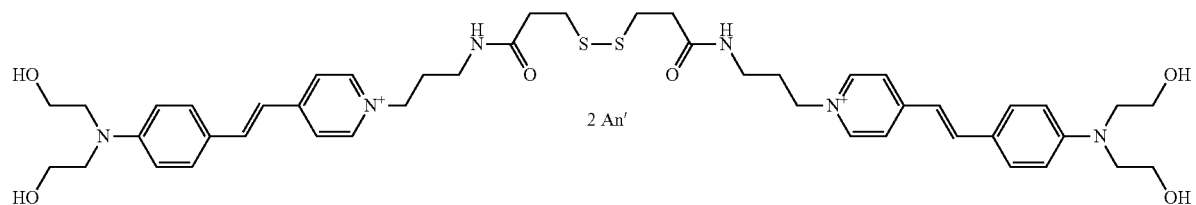
2 An'

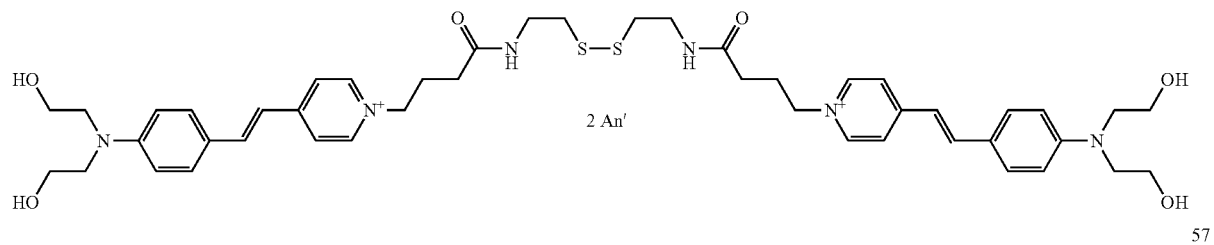
56
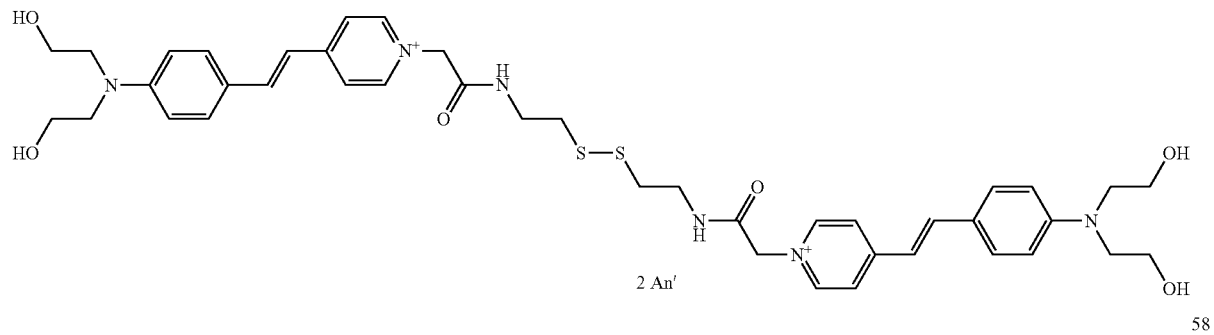
57
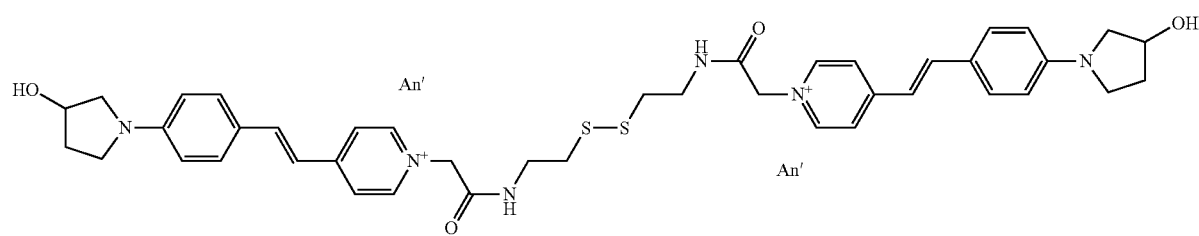
58
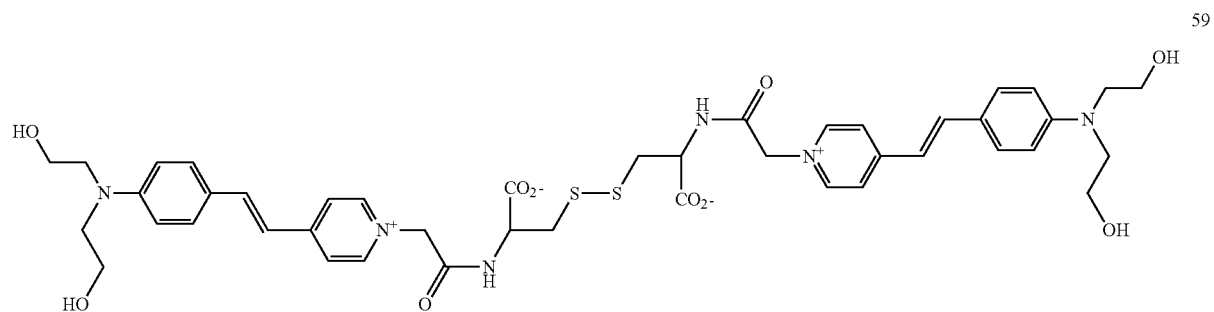
59
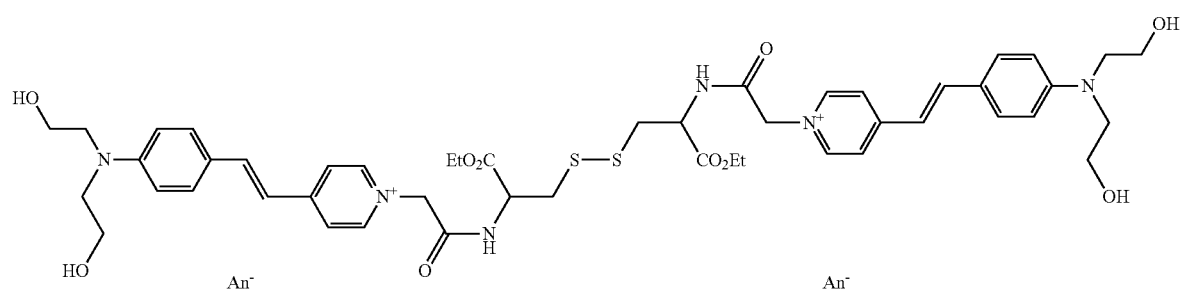
60

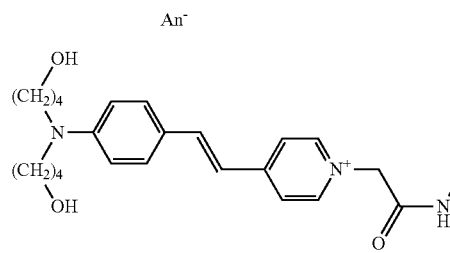
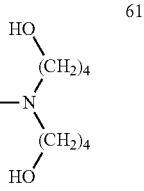
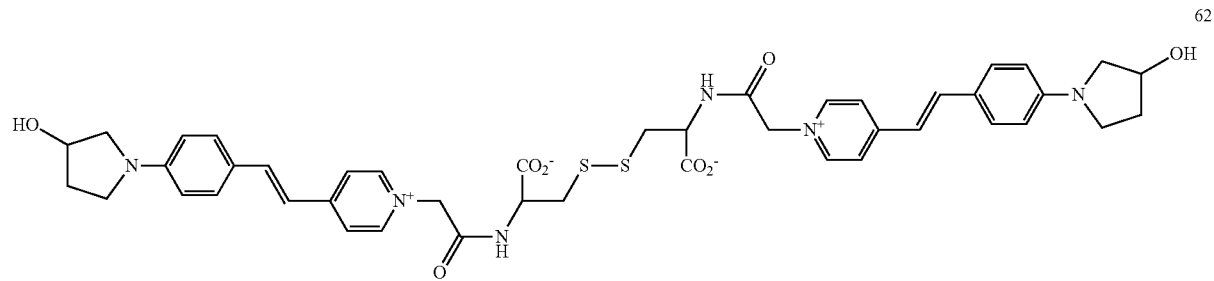
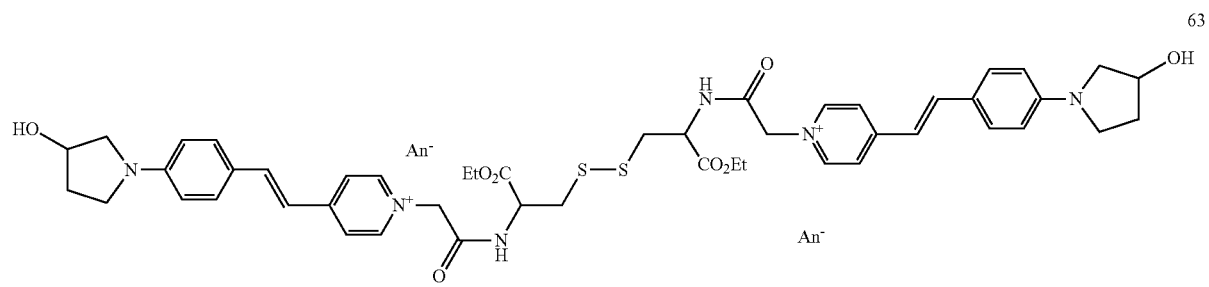
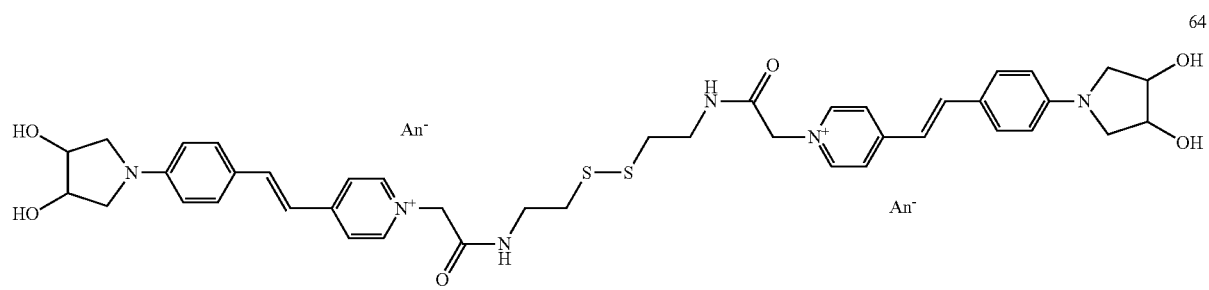
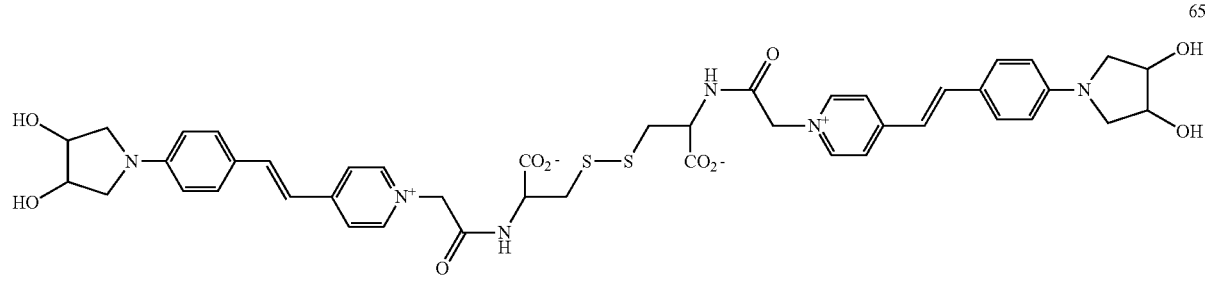

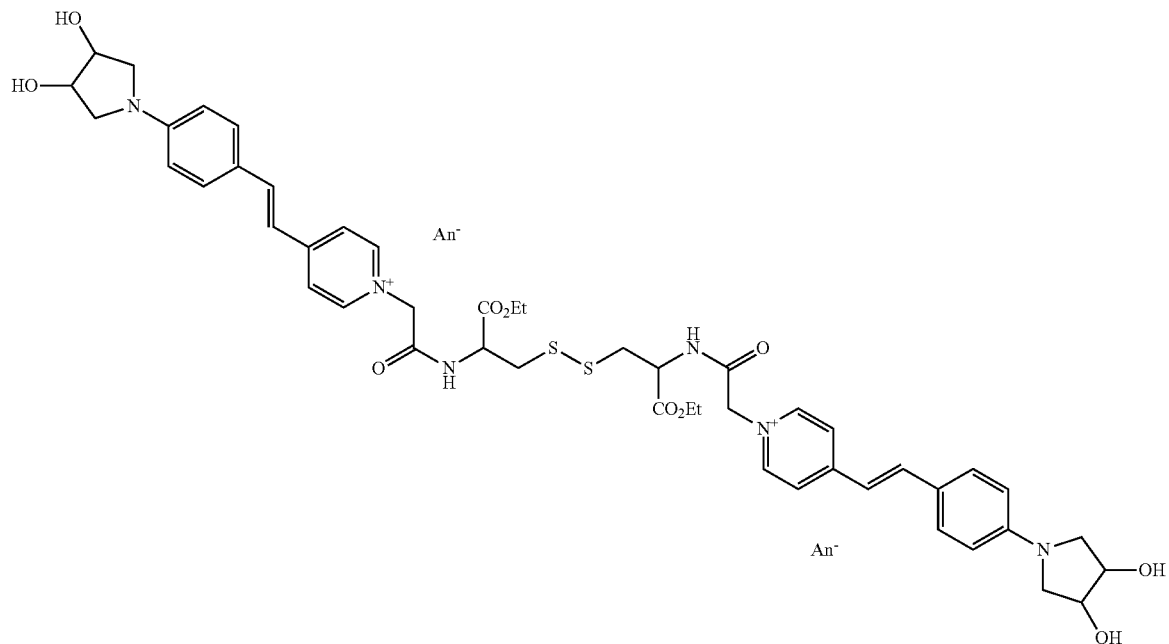
66
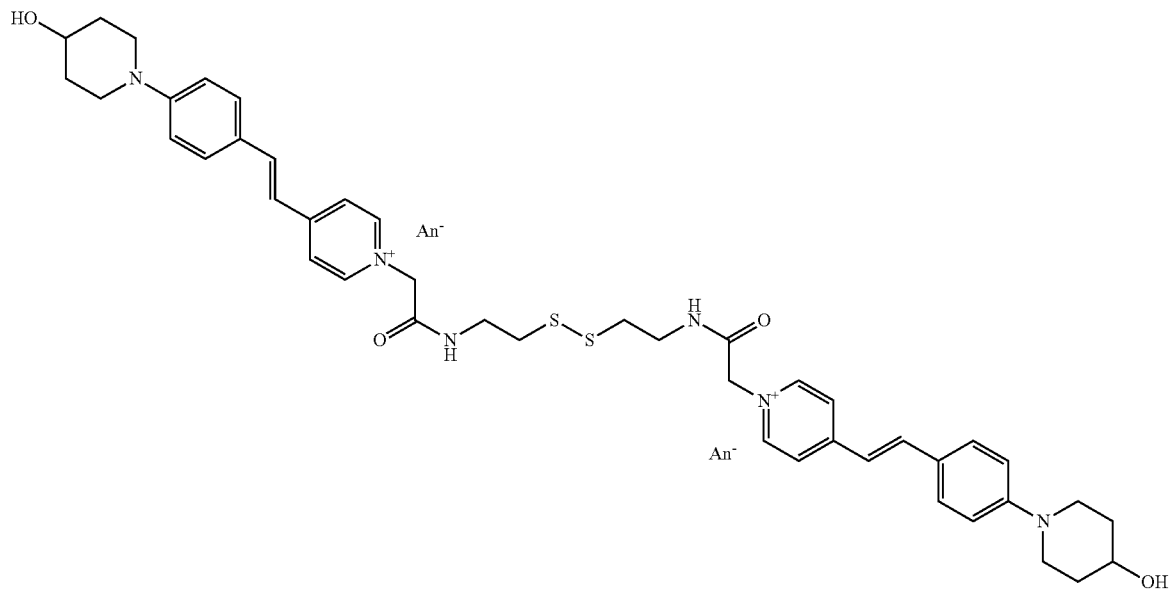
67
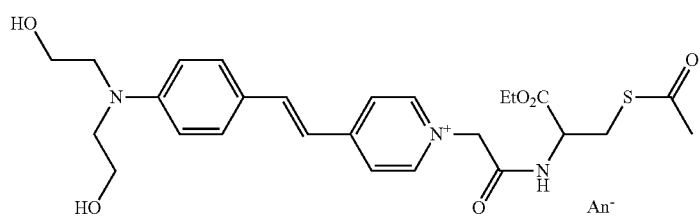
68
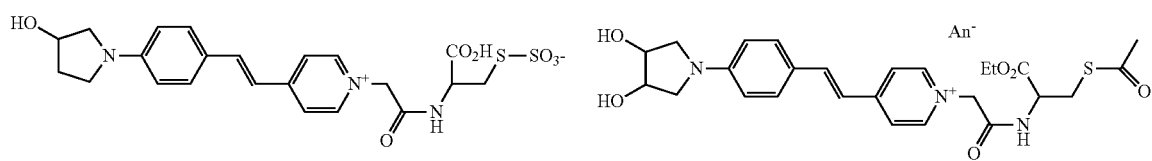

-continued
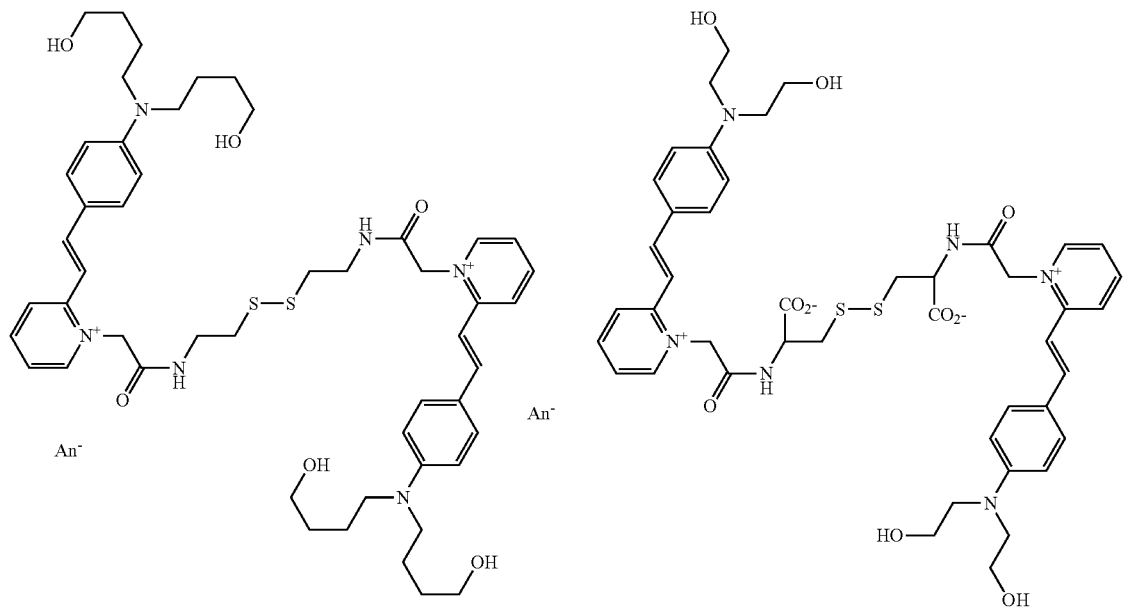
71
72
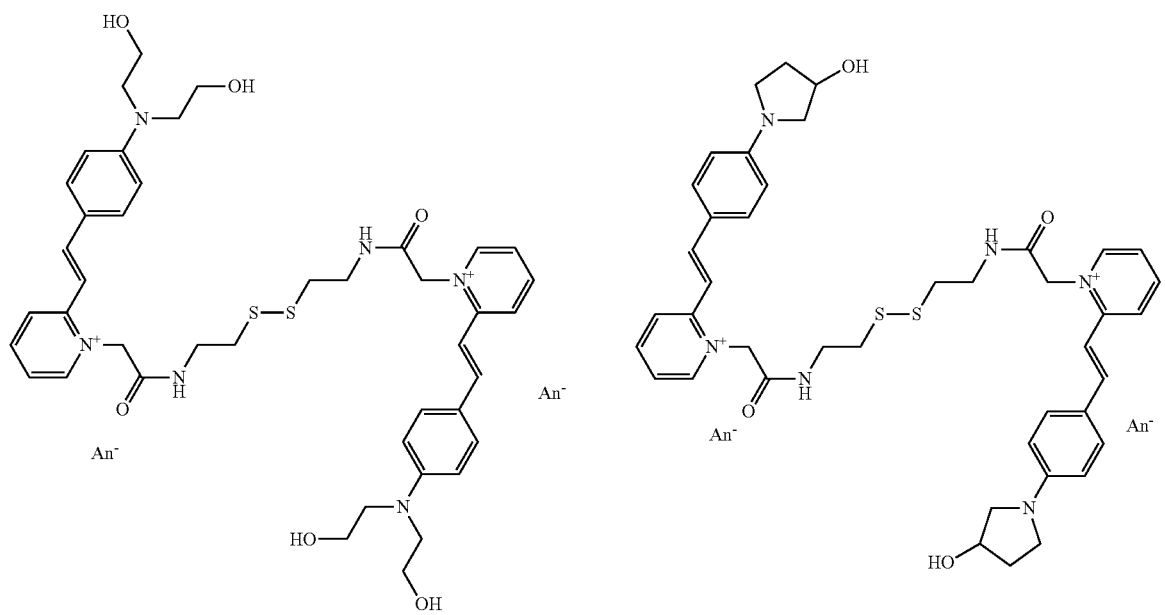
73
74

75 76
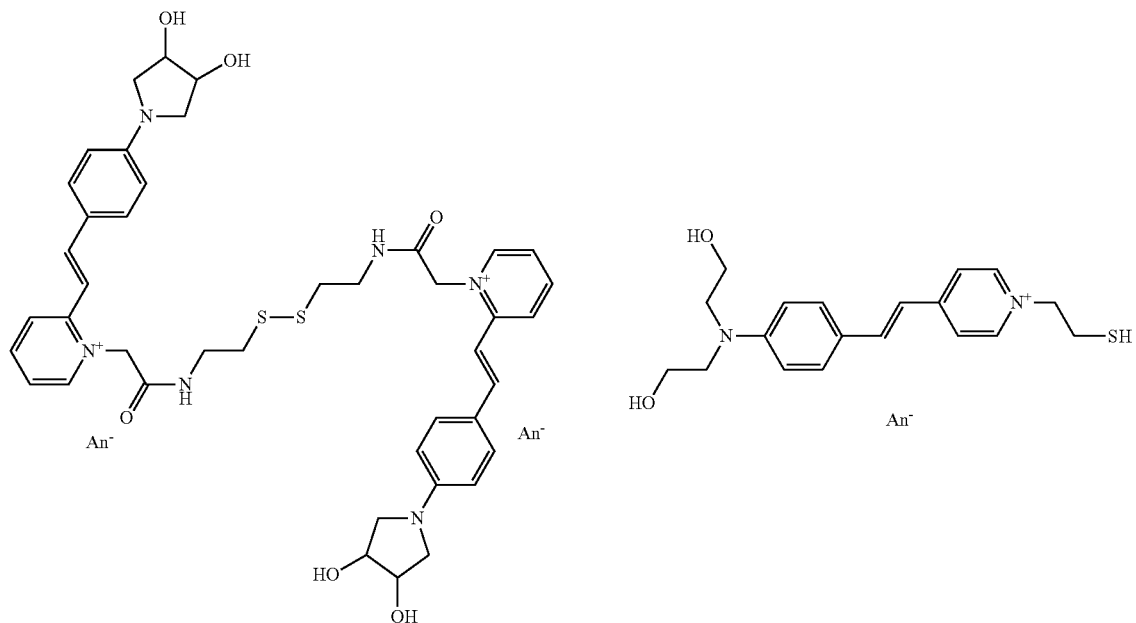
77
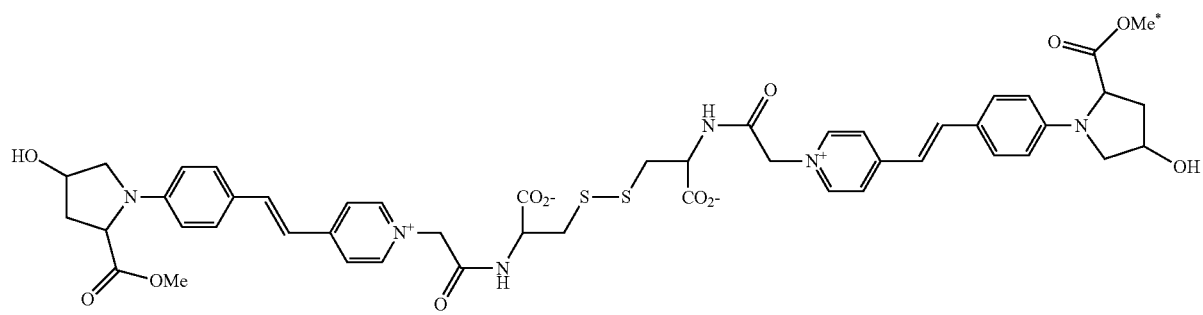
Me* represents an alkali metal or ½ alkaline earth metal; or a methyl
78
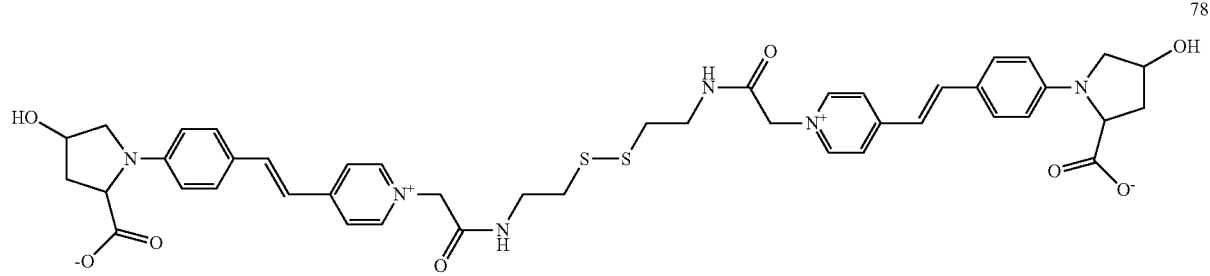

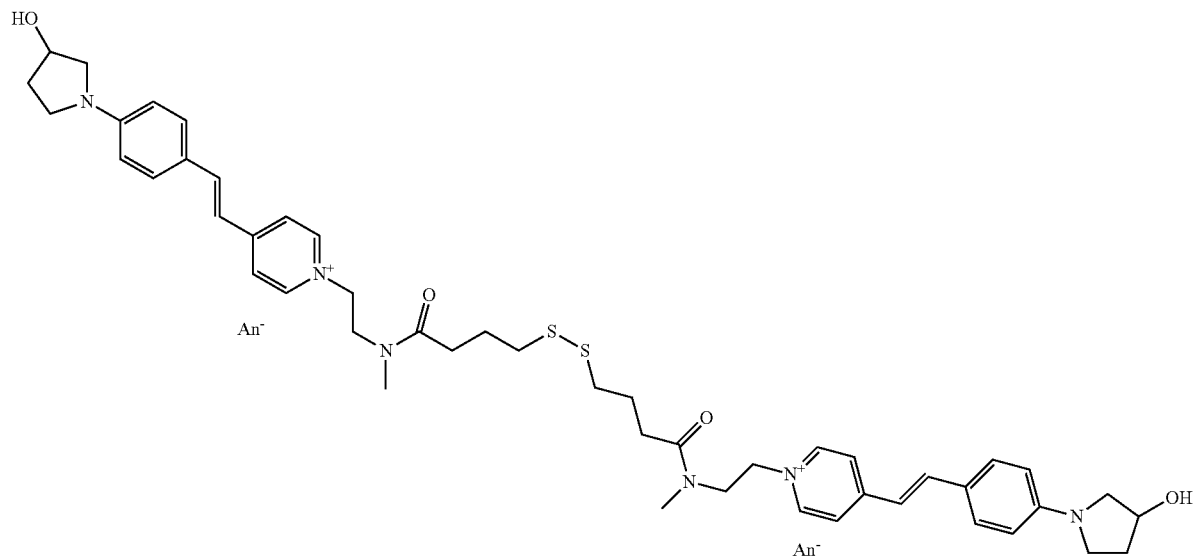
79
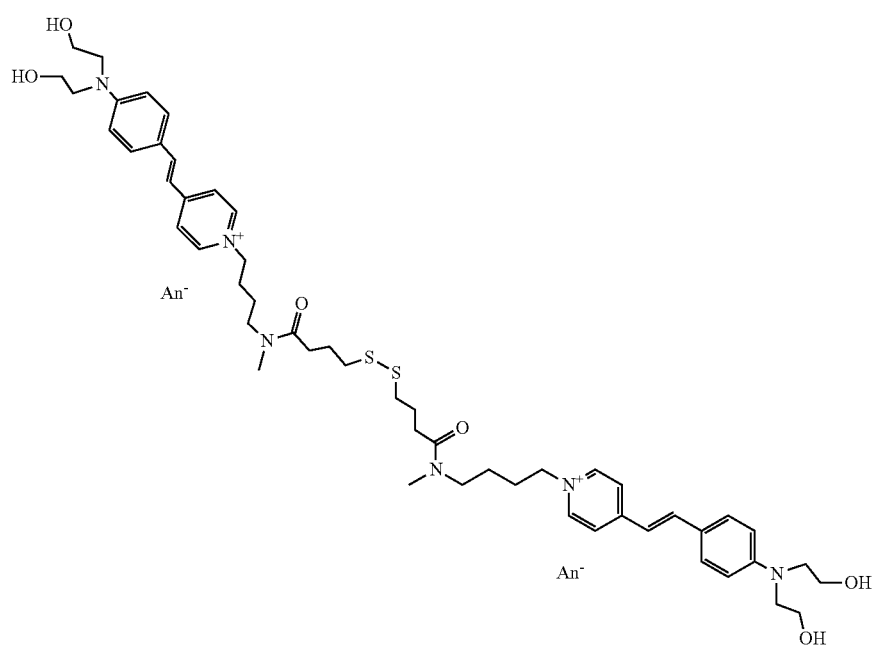
80

-continued
81
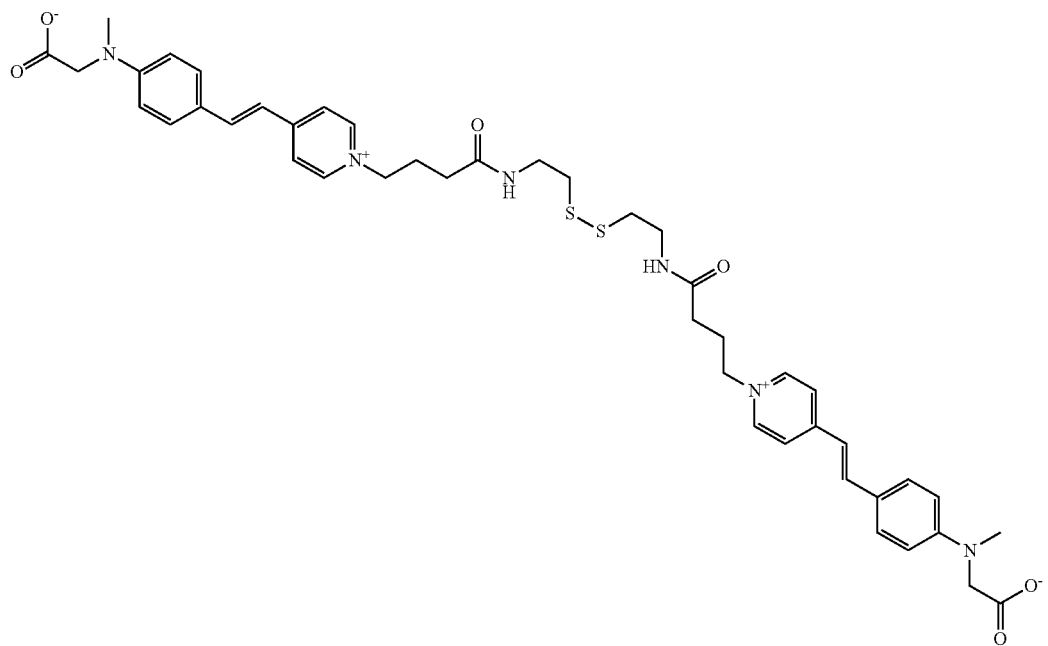
82
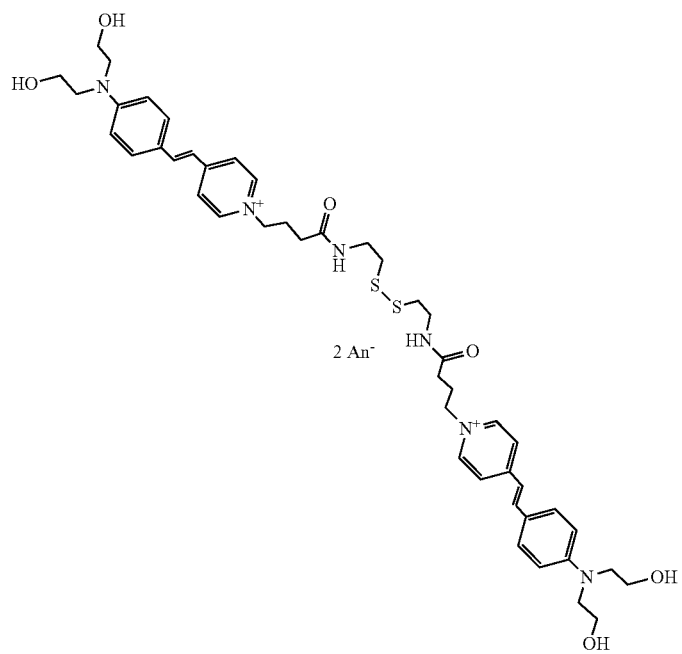

143 144
-continued
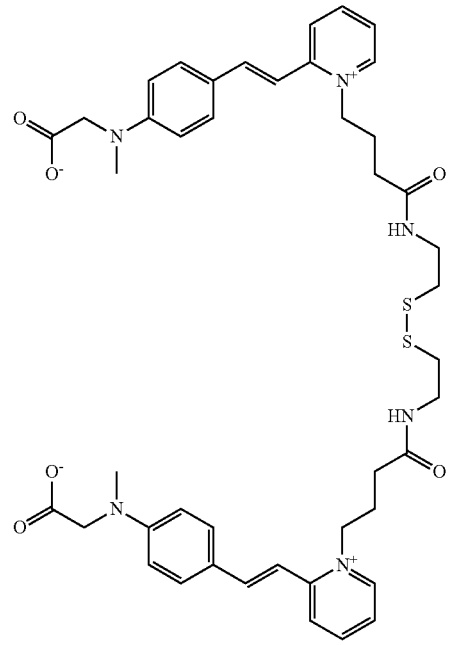
83
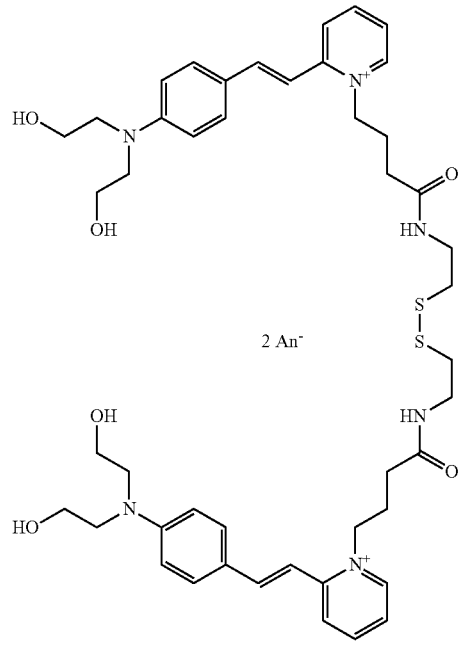
84
2 An⁻
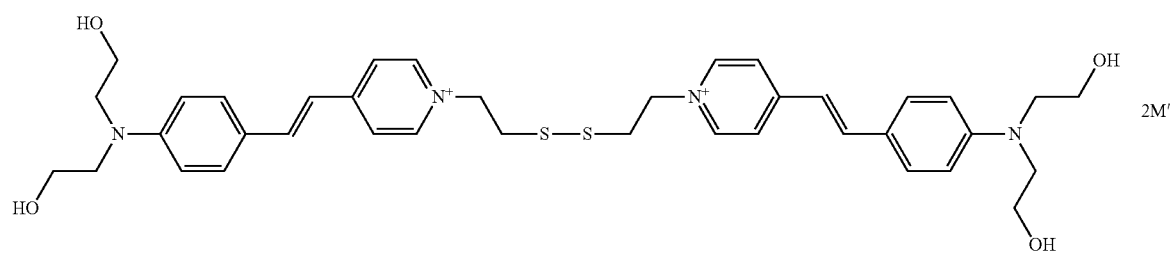
85
2M'
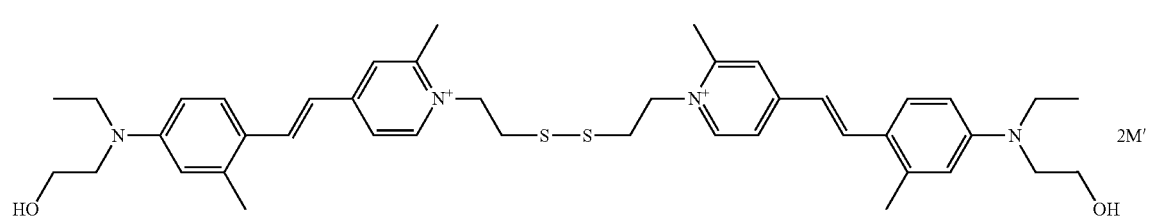
86
2M'
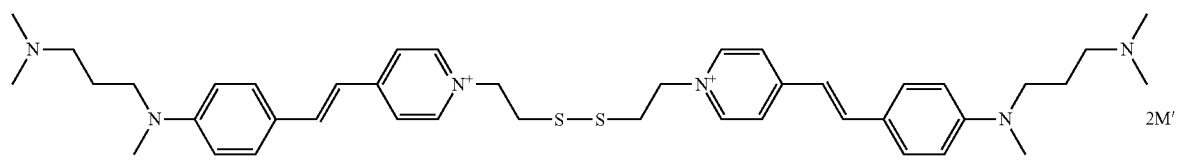
87
2M'

-continued
88
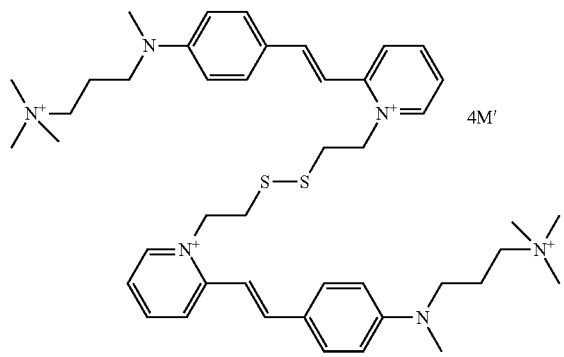
89
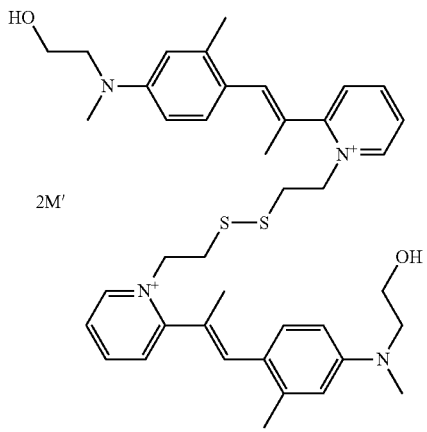
90
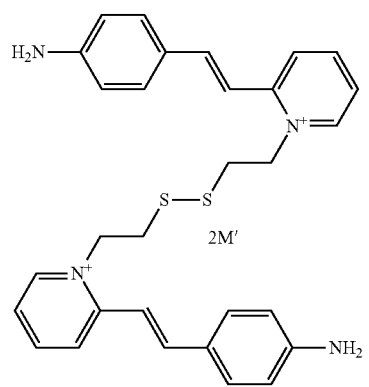
91
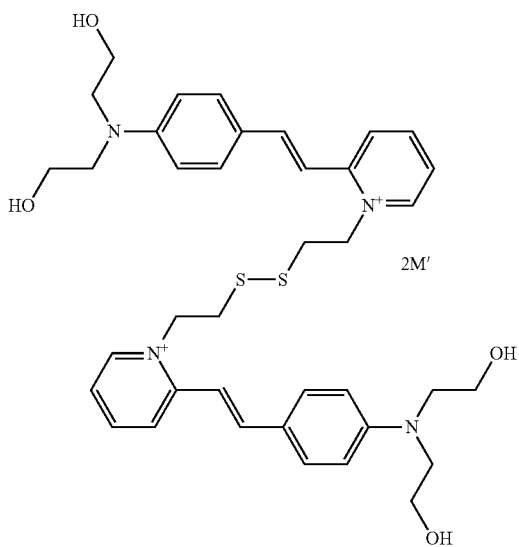
92
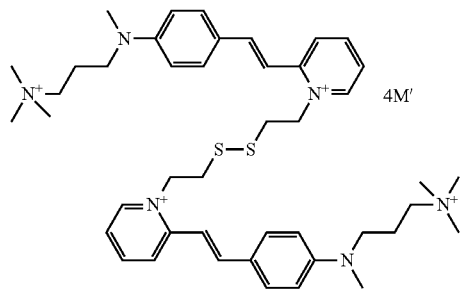
93
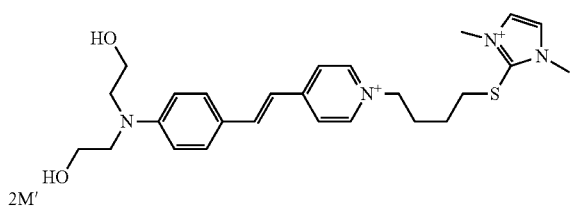
94
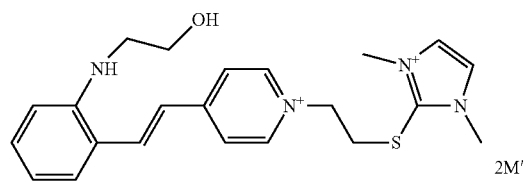

95
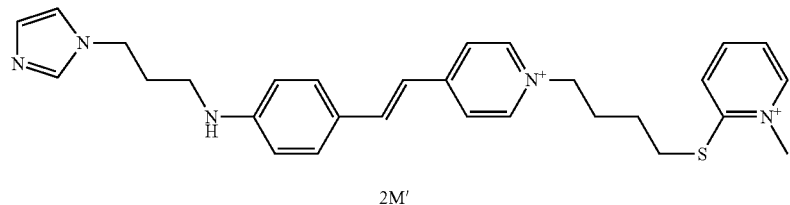
2M′
96
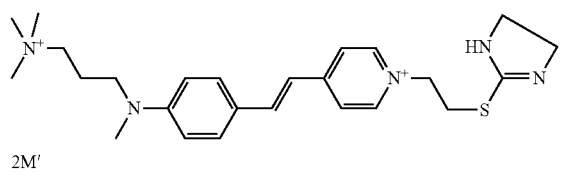
2M′
97
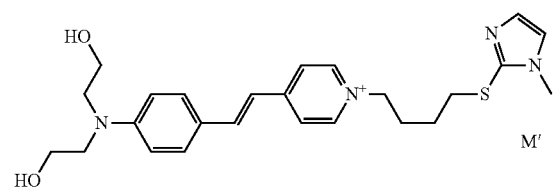
M′
98
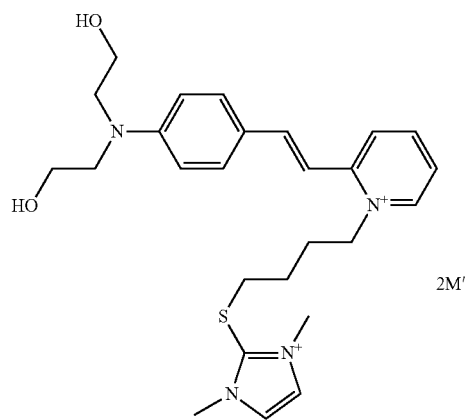
2M′
99
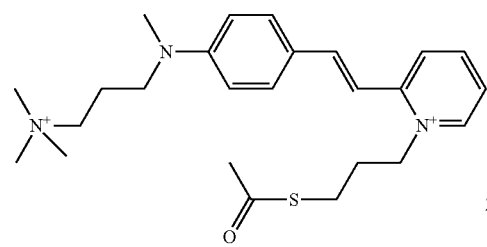
2M′
100
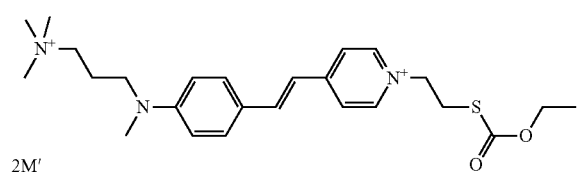
2M′
101
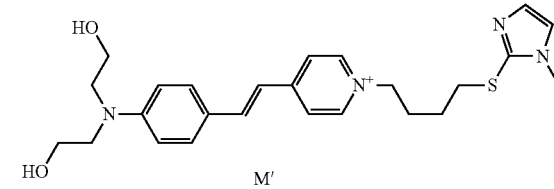
M′
102
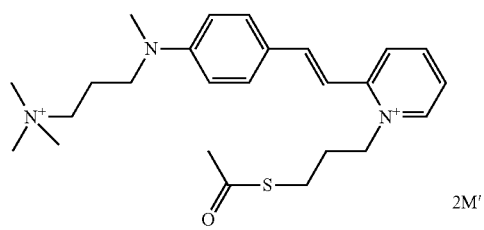
2M′
102
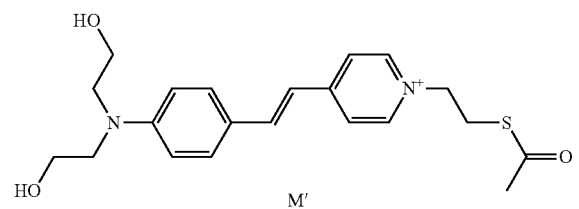
M′
103
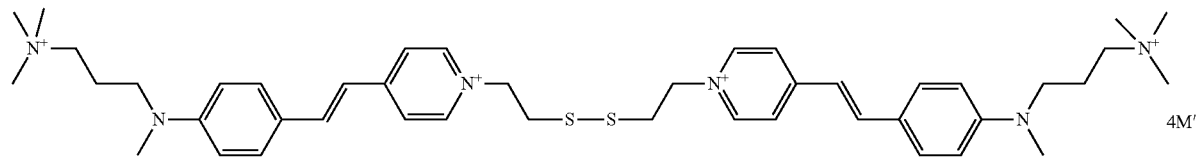
4M′

-continued
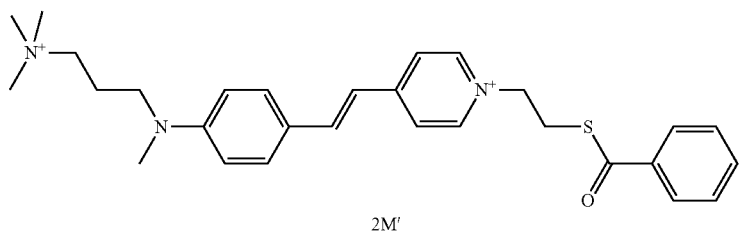
104
2M'
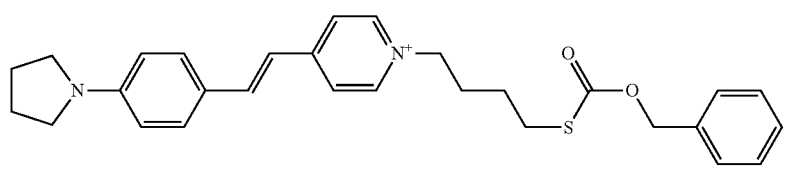
105
M'
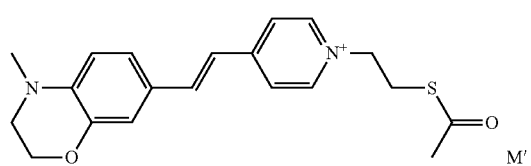
106
M'
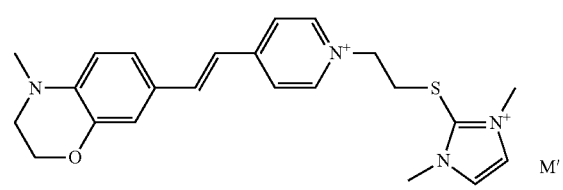
107
M'
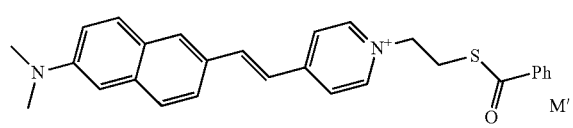
108
M'
109
M'
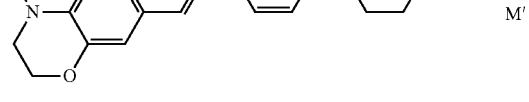
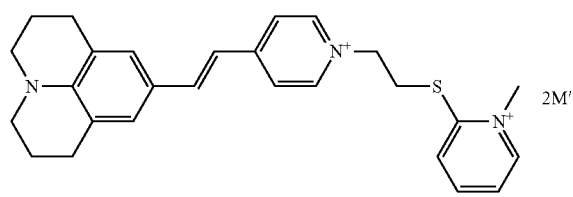
110
2M'
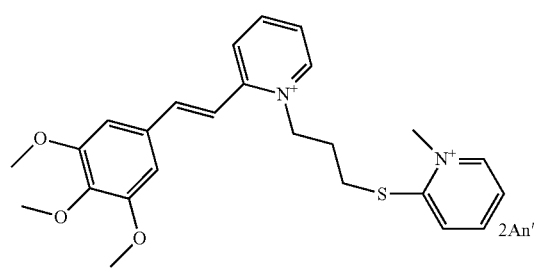
111
2An'
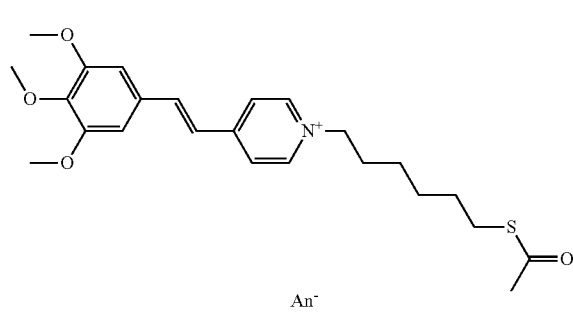
112
An⁻
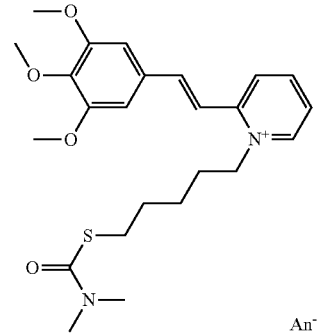
113
An⁻

-continued
114
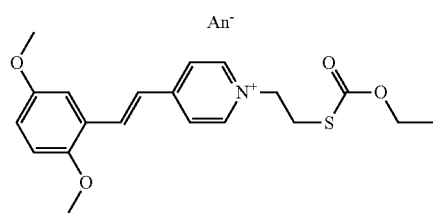
115
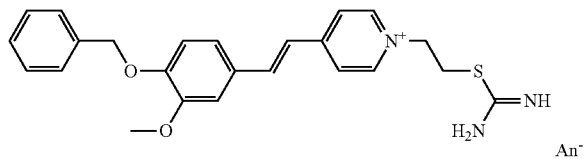
116
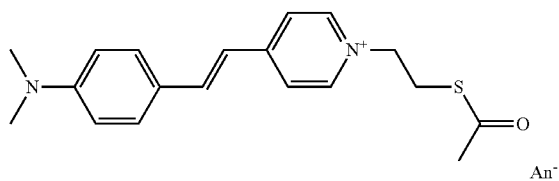
117
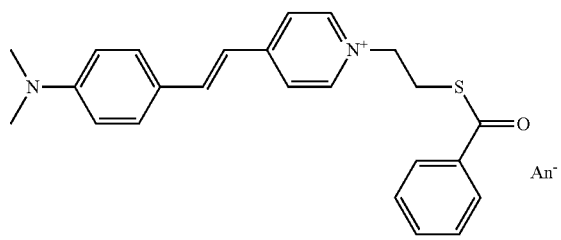
118
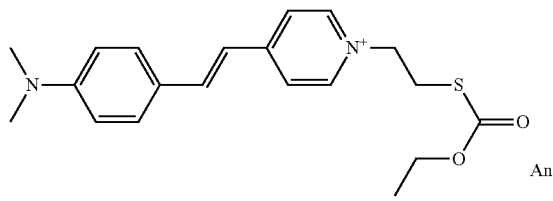
119
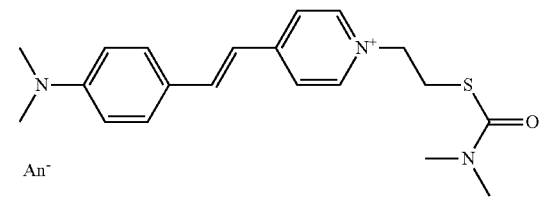
120
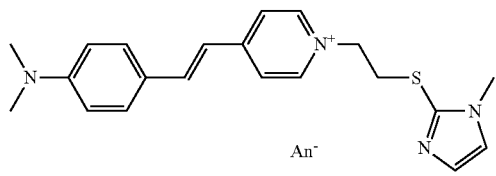
121
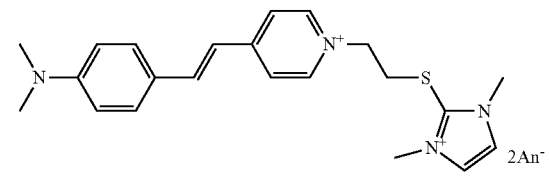
122
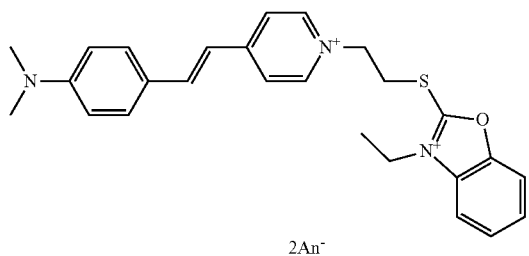
123
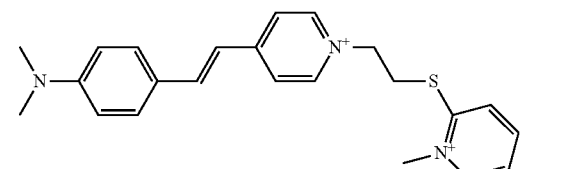

wherein An⁻ and M', which may be identical or different are anionic counterions.

11. The composition according to claim 10, wherein An⁻ and M' are identical and/or are chosen from halides and alkyl sulphates.

12. The composition according to claim 10, wherein the at least one direct dye of formula (I) is chosen from dyes of formulae 44 and 55.

13. The composition according to claim 1, wherein the at least one thickening organic polymer is chosen from anionic, cationic, amphoteric and non-ionic, nonassociative and associative polymers.

14. The composition according to claim 13, wherein the at least one thickening organic polymer ii) is chosen from thickening organic polymers comprising sugar units.

15. The composition according to claim 14, wherein the at least one thickening organic polymer ii) is chosen from cellulose polymers.

16. The composition according to claim 1, wherein the at least one thickening organic polymer ii) is chosen from associative and non-associative aqueous-phase thickening polymers.

17. The composition according to claim 1, wherein the at least one (poly)ethoxylated fatty alcohol iii) is chosen from (poly)ethoxylated fatty alcohols of the following formula:

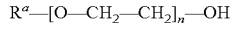

wherein:
R$^a$ is chosen from linear or branched $C_8$-$C_{40}$ alkyl groups and linear or branched $C_8$-$C_{40}$ alkenyl groups optionally substituted by at least one hydroxyl group, and
n is an integer ranging from 1 to 200 inclusive.

18. The composition according to claim 1, wherein the at least one non-ionic surfactant iii) is chosen from glycerolated fatty alcohols and alkyl polyglycosides of formula (XIX):

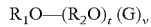

wherein:
$R_1$ is chosen from linear or branched alkyl and/or alkenyl radicals comprising from 8 to 24 carbon atoms and alkylphenyl radicals, the linear or branched alkyl radical of which comprises from 8 to 24 carbon atoms;
$R_2$ is chosen from alkylene radicals comprising from 2 to 4 carbon atoms;
G is a sugar unit comprising from 5 to 6 carbon atoms;
t is a value ranging from 0 to 10, and v is a value ranging from 1 to 15.

19. The composition according to claim 1, wherein the at least one alkaline agent iv) is chosen from aqueous ammonia, alkali metal carbonates and bicarbonates, sodium hydroxide, potassium hydroxide, and mixtures thereof, alkanolamines, oxyethylenated and/or oxypropylenated ethylenediamines, amino acids and compounds of the following formula (XX):

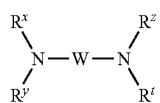

wherein:
W is chosen from divalent $C_1$-$C_6$ alkylene radicals optionally substituted by at least one group chosen from hydroxyl and $C_1$-$C_6$ alkyl radicals and/or optionally interrupted by at least one heteroatom chosen from oxygen and NR$^u$;
R$^x$, R$^y$, R$^z$, R$^t$ and R$^u$, which may be identical or different, are chosen from hydrogen and $C_1$-$C_6$ alkyl, $C_1$-$C_6$ hydroxyalkyl and $C_1$-$C_6$ aminoalkyl radicals.

20. The composition according to claim 1, wherein the at least one reducing agent v) is chosen from thioglycolic acid, cysteine, and their esters and salts.

21. A method for dyeing and/or lightening keratinous fibers comprising applying to the keratinous fibers:
i) at least one direct dye of formula (I) according to claim 1;
ii) at least one thickening organic polymer;
iii) at least one (poly)ethoxylated fatty alcohol and/or at least one nonionic surfactant;
iv) at least one alkaline agent;
v) at least one reducing agent chosen from thioglycolic acid, thiolactic acid, 3-mercaptopropionic acid, thiomalic acid, 2,3-dimercaptosuccinic acid, cysteine, N-glycyl-L-cysteine, L-cysteinylglycine, and esters and salts thereof; thioglycerol;
cysteamine and $C_1$-$C_4$ acyl derivatives thereof; N-mesylcysteamine; N-acetylcysteine;
N-(mercapto-2-ethyl) gluconamide; pantetheine, N-(mercaptoalkyl)-ω-hydroxyalkylamides; N-mono- or N,N-dialkylmercapto-4-butyramides;
aminomercaptoalkyl amides; N-(mercaptoalkyl)succinamic acids and N-(mercaptoalkyl)succinimides; alkylamino mercaptoalkyl amides; the azeotropic mixture of 2-hydroxypropyl thioglycolate and of (2-hydroxy-1-methyl)ethyl thioglycolate; ammonium thioglycolate; mercaptoalkylamino amides; and N-mercaptoalkylalkanediamides; and
vi) optionally at least one chemical oxidizing agent;
wherein the ingredients i) to vi) are applied to the keratinous fibers either together or separately.

22. The method according to claim 21 comprising:
applying to the keratinous fibers a reducing composition comprising iii) at least one (poly)ethoxylated fatty alcohol and/or at least one non-ionic surfactant, iv) at least one alkaline agent and v) at least one reducing agent, followed by the application of a dyeing composition comprising i) at least one direct dye of formula (I) and ii) at least one thickening organic polymer;
applying to the keratinous fibers a reducing composition comprising iv) at least one alkaline agent and v) at least one reducing agent, followed by the application of a dyeing composition comprising i) at least one direct dye of formula (I), ii) at least one thickening organic polymer and iii) at least one (poly)ethoxylated fatty alcohol and/or at least one non-ionic surfactant; or
applying to the keratinous fibers a reducing composition comprising v) at least one reducing agent, followed by the application of a dyeing composition comprising i) at least one direct dye of formula (I), ii) at least one thickening organic polymer, iii) at least one (poly)ethoxylated fatty alcohol and/or at least one non-ionic surfactant and iv) at least one alkaline agent.

23. The method according to claim 21, wherein the keratinous fibers are dark keratinous fibers having a tone depth of less than or equal to 6, and wherein the at least one direct dye of formula (I) is chosen from:

dyes of formulae (XII) and (XII')

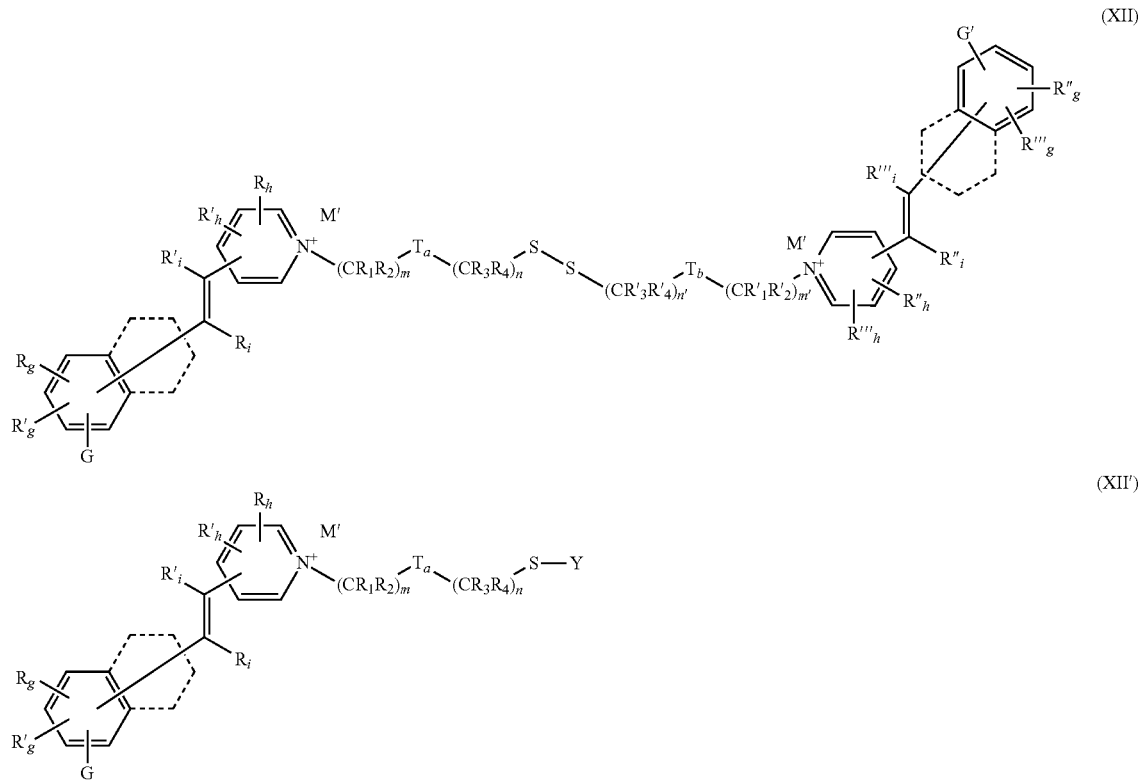

wherein:
G and G', which may be identical or different, are chosen from —NR$_c$R$_d$, —NR'$_c$R'$_d$, and C$_1$-C$_6$ alkoxy groups which are optionally substituted;

R$_g$, R'$_g$, R''$_g$, R'''$_g$, R$_h$, R'$_h$, R''$_h$ and R'''$_h$, which may be identical or different, are chosen from hydrogen, halogen atoms, amino, C$_1$-C$_4$ alkylamino, C$_1$-C$_4$ dialkylamino, cyano, carboxyl, hydroxyl and trifluoromethyl group, acylamino, C$_1$-C$_4$ alkoxy, (poly)hydroxy(C$_2$-C$_4$) alkoxy, alkylcarbonyloxy, alkoxycarbonyl and alkylcarbonylamino radicals, acylamino, carbamoyl and alkylsulfonylamino radicals, aminosulfonyl radicals, and C$_1$-C$_{16}$ alkyl radicals optionally substituted with a group chosen from C$_1$-C$_{12}$ alkoxy, hydroxyl, cyano, carboxyl, amino, C$_1$-C$_4$ alkylamino and C$_1$-C$_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups R$_g$ and R'$_g$; R''$_g$ and R'''$_g$; R$_h$ and R'$_h$; R''$_h$ and R'''$_h$ borne by two adjacent carbon atoms together form a benzo or indeno ring, a fused heterocycloalkyl or fused heteroaryl group; wherein the benzo, indeno, heterocycloalkyl and heteroaryl rings are optionally substituted with an entity chosen from halogen atoms, amino, C$_1$-C$_4$ alkylamino, C$_1$-C$_4$ dialkylamino, nitro, cyano, carboxyl, hydroxyl and trifluoromethyl groups, acylamino, C$_1$-C$_4$ alkoxy, (poly)hydroxy(C$_2$-C$_4$)alkoxy, alkylcarbonyloxy, alkoxycarbonyl and alkylcarbonylamino radicals, acylamino, carbamoyl and alkylsulfonylamino radicals, aminosulfonyl radicals, and C$_1$-C$_{16}$ alkyl radicals optionally substituted with a group chosen from C$_1$-C$_{12}$ alkoxy, hydroxyl, cyano, carboxyl, amino, C$_1$-C$_4$ alkylamino, and C$_1$-C$_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups R$_i$ and R$_g$; R'''$_i$; and R'''$_g$; R'$_i$ and R'$_h$; and/or R''$_i$; and R''$_h$ together form a fused (hetero)cycloalkyl;

or alternatively when G represents —NR$_c$R$_d$ and G' represents —NR'$_c$R'$_d$, two groups R$_c$ and R'$_g$; R'$_c$ and R''$_g$; R$_d$ and R$_g$; R'$_d$ and R'''$_g$ together form a saturated heteroaryl or heterocycle, optionally substituted with at least one (C$_1$-C$_6$)alkyl group, and optionally comprising at least one heteroatom chosen from nitrogen and oxygen;

R$_i$,R'$_i$, R''$_i$, and R'''$_i$, which may be identical or different, are chosen from hydrogen and C$_1$-C$_4$ alkyl groups;

R$_1$, R$_2$, R$_3$, R$_4$, R'$_1$, R'$_2$, R'$_3$ and R'$_4$, which may be identical or different, are chosen from hydrogen and C$_1$-C$_4$ alkyl, C$_1$-C$_{12}$ alkoxy, hydroxyl, cyano, carboxyl, amino, C$_1$-C$_4$ alkylamino and C$_1$-C$_4$ dialkyl amino group, the alkyl radicals possibly forming, with the nitrogen atom that bears them, a 5- to 7-membered heterocycle optionally comprising another nitrogen or non-nitrogen heteroatom;

T$_a$ and T$_b$, which may be identical or different, are chosen from i) a covalent a bond, ii) at least one radical chosen from —SO$_2$—,—O—, —S—, —N(R)—,)—N$^+$(R)(R○)—, and —CO—, wherein R, R○, which may be identical or different, are chosen from hydrogen, C$_1$-C$_4$ alkyl and $C_1$-$C_4$ hydroxyalkyl radicals; and aryl($C_1$-$C_4$) alkyl radicals, or iii) cationic or non-cationic, heterocycloalkyl or heteroaryl radicals;

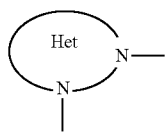

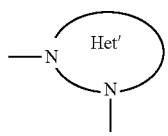

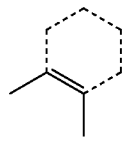

is chosen from aryl and heteroaryl groups fused to the imidazolium or phenyl ring; or alternatively is absent from the imidazolium or phenyl ring;

m, m', n and n', which may be identical or different, are integers ranging from 0 to 6 inclusive, wherein the sums m+n and m'+n'are equal to integers ranging from 1 to 10 inclusive;

Y is chosen from hydrogen and the following protecting groups:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
5- or 6-membered cationic monocyclic heteroaryl;
8- to 11-membered cationic bicyclic heteroaryl;
cationic heterocycles having the following formula:

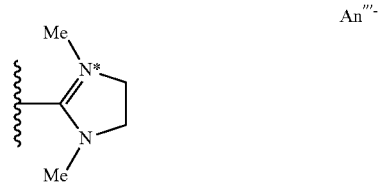

—C(NH$_2$)=N$^+$H$_2$; An''''$^-$; wherein An''''$^-$ is an anionic counterion;
—C(NH$_2$)=NH;
SO$_3^-$M$^+$, wherein M$^+$ is a metal ion; and
M' is an anionic counterion.

24. The method according to claim 23, wherein the at least one direct dye of formula (I) is chosen from dyes of the following chemical structures:

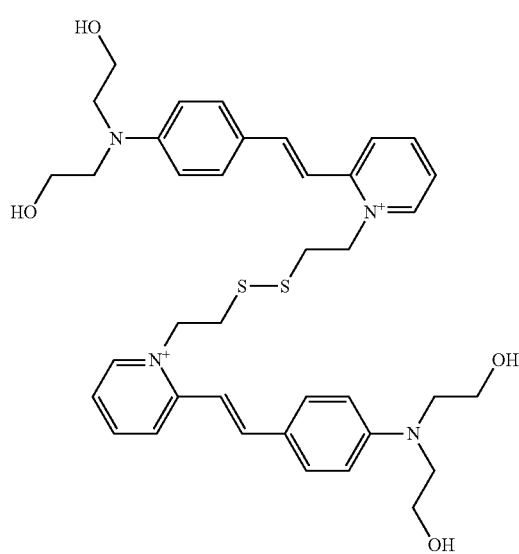

-continued

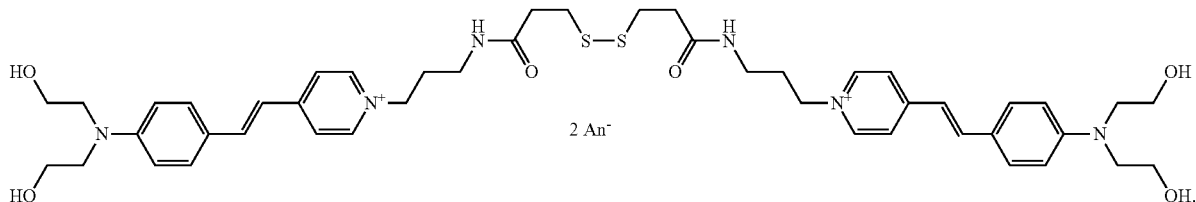

2 An⁻

25. A multi-compartment device or kit for dyeing keratinous fibers comprising:
   a first compartment comprising a dyeing composition comprising i) at least one direct Dye of formula (I) according to claim 1;
   a second compartment comprising v) at least one reducing agent chosen from thioglycolic acid, thiolactic acid, 3-mercaptopropionic acid, thiomalic acid, 2,3-dimercaptosuccinic acid, cysteine, N-glycyl-L-cysteine, L-cysteinylglycine, and esters and salts thereof; thioglycerol; cysteamine and $C_1$-$C_4$ acyl derivatives thereof; N-mesylcysteamine; N-acetylcysteine; N-(mercapto-2-ethyl) gluconamide; pantetheine, N-(mercaptoalkyl)-(ω-hydroxyalkylamides; N-mono- or N,N-dialkylmercapto-4-butyramides;
   aminomercaptoalkyl amides; N-(mercaptoalkyl)succinamic acids and N-(mercaptoalkyl)succinimides; alkylamino mercaptoalkyl amides; the azeotropic mixture of 2-hydroxypropyl thioglycolate and of (2-hydroxy-1-methyl)ethyl thioglycolate; ammonium thioglycolate; mercaptoalkylamino amides; and N-mercaptoalkylalkanediamides; and
   optionally, a third compartment comprising vi) at least one chemical oxidizing agent;
wherein the first and/or second compartment further comprises ii) at least one thickening organic polymer, iii) at least one (poly)ethoxylated fatty alcohol and/or at least one nonionic surfactant, and/or iv) at least one alkaline agent.

26. The method according to claim 21, wherein the keratin fibers have a tone height of less than or equal to 6, wherein the at least one direct dye of formula (I) is chosen from dyes of formulae (XV), (XV'):

wherein in formulae (XV) and (XV'):
   R and R''', which may be identical or different, are chosen from hydroxyl, amino ($NR_aR_b$) and ammonium ($N^+R_aR_bR_c$)An⁻ groups; wherein $R_a$, $R_b$ and $R_c$, which may be identical or different, are chosen from hydrogen atom and ($C_1$-$C_4$)alkyl groups, and An⁻ is an anionic counterion;
   or alternatively two alkyl groups $R_a$ and $R_b$ of the amino or ammonium group form a 5- to 7-membered heterocycle optionally comprising another nitrogen or non-nitrogen heteroatom;
   R' and R'', which may be identical or different, are chosen from hydrogen and hydroxyl, amino ($NR_aR_b$) and ammonium ($N^+R_aR_bR_c$) An⁻ groups;
   $R_g$, $R'_g$, $R''_g$, $R'''_g$, $R_h$, $R'_h$, $R''_h$ and $R'''_h$, which may be identical or different, are chosen from hydrogen, halogen atoms, amino, (di)($C_1$-$C_4$)alkylamino, cyano, carboxyl, hydroxyl, trifluoromethyl, acylamino, $C_1$-$C_4$ alkoxy, (poly)hydroxy($C_2$-$C_4$)alkoxy, ($C_1$-$C_4$)alkylcarbonyloxy, ($C_1$-$C_4$)alkoxycarbonyl, ($C_1$-$C_4$)alkylcarbonylamino, acylamino, carbamoyl and ($C_1$-$C_4$)alkylsulfonylamino groups, aminosulfonyl radicals and ($C_1$-$C_{16}$)alkyl radicals optionally substituted with a group chosen from ($C_1$-$C_{12}$)alkoxy, hydroxyl, cyano, carboxyl, amino and (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom;
   $R'_i$, $R''_i$, $R'''_i$ and $R''''_i$, which may be identical or different, are chosen from hydrogen and ($C_1$-$C_4$)alkyl groups;

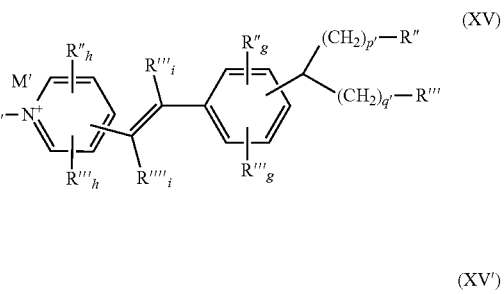

(XV)

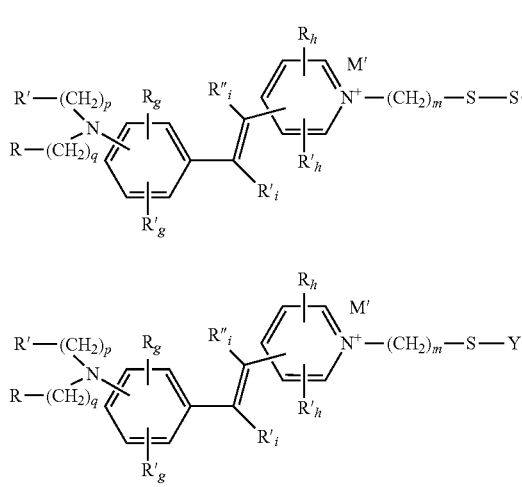

(XV')

m and m', which may be identical or different, are integers ranging from 1 to 10 inclusive;

p, p', q and q', which may be identical or different, are integers ranging from 1 to 6 inclusive;

M' is an anionic counterion; and

Y is chosen from hydrogen and the following protective groups:
- $(C_1-C_4)$alkylcarbonyl;
- arylcarbonyl;
- $(C_1-C_4)$alkoxycarbonyl;
- aryloxycarbonyl;
- aryl$(C_1-C_4)$alkoxycarbonyl;
- (di)$(C_1-C_4)$(alkyl)aminocarbonyl;
- $(C_1-C_4)$(alkyl)arylaminocarbonyl;
- optionally substituted aryl;
- 5- or 6-membered monocyclic heteroaryl;
- 5- or 6-membered cationic monocyclic heteroaryl;
- 8- to 11-membered cationic bicyclic heteroaryl;
- cationic heterocycles of following formula:

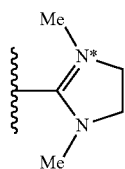

—C(NH$_2$)=N$^+$H$_2$ An'''$^-$; wherein An'''$^-$ is an anionic counterion;

—C(NH$_2$)=NH; and

SO$_3^-$M$^+$, wherein M$^+$ is a metal ion;

it being understood that when the compound of formula (XV) or (XV') contains other cationic parts, it is combined with one or more anionic counterions that afford formula (XV) or (XV') electrical neutrality.

27. The method according to claim 21, wherein the keratin fibers have a tone height of less than or equal to 6, wherein the at least one direct dye of formula (I) is chosen from dyes of formulae (XVI), (XVI'):

wherein in formula (XVI) and (XVI'):

$R_1$ is chosen from $C_1$-$C_6$ alkyl groups substituted with at least one group chosen from hydroxyl groups and —C(O)OR' groups, wherein R' is chosen from hydrogen and $C_1$-$C_4$ alkyl groups or alternatively a group —C(O)—O$^-$ and, in the latter case, the anionic counterion An$^-$ is absent;

$R_2$ is chosen from $C_1$-$C_6$ alkyl groups optionally substituted with at least one hydroxyl group;

or alternatively the groups $R_1$ and $R_2$ form, together with the nitrogen atom that bears them, a saturated heterocyclic radical substituted with at least one hydroxyl, (poly)hydroxy$(C_1-C_4)$alkyl and/or —C(O)OR' group wherein R' is chosen from hydrogen and $C_1$-$C_4$ alkyl groups or a group —C(O)—O$^-$ and, in the latter case, the anionic counterion An$^-$ is absent;

$R_3$ is chosen from hydrogen and —C(O)OR" groups wherein R" is chosen from hydrogen, alkali metals and $C_1$-$C_6$ alkyl groups, or alternatively $R_3$ is a group —C(O)—O$^-$ and, in the latter case, the anionic counterion An$^-$ is absent;

Z is chosen from divalent amido groups —C(O)—N(R)—, —N(R)—C(O)—, and divalent $C_1$-$C_{10}$ alkylene groups interrupted with an amido group chosen from —(CH$_2$)$_{n'}$—C(O)—N(R)—(CH$_2$)$_p$—, —(CH$_2$)$_{n''}$—N(R)—C(O)—(CH$_2$)$_p$—, wherein n' is an integer ranging from 0 to 3 inclusive; p is an integer ranging from 0 to 4 inclusive, n" is an integer ranging from 0 to 3 inclusive and R is chosen from hydrogen and $C_1$-$C_6$ alkyl groups;

An$^-$ is an anionic counterion;

Y is chosen from hydrogen and the following protective groups:
- $(C_1-C_4)$alkylcarbonyl;
- arylcarbonyl;
- $(C_1-C_4)$alkoxycarbonyl;
- aryloxycarbonyl;
- aryl$(C_1-C_4)$alkoxycarbonyl;
- (di)$(C_1-C_4)$(alkyl)aminocarbonyl;
- $(C_1-C_4)$(alkyl)arylaminocarbonyl;
- optionally substituted aryl;
- 5- or 6-membered monocyclic heteroaryl;

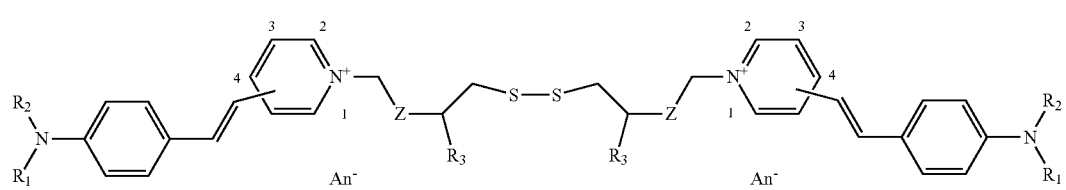

(XVI)

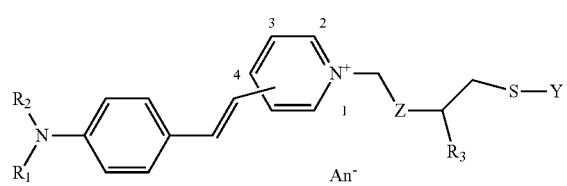

(XVI')

5- or 6-membered cationic monocyclic heteroaryl;
8- to 11-membered cationic bicyclic heteroaryl;
cationic heterocycles of following formula:

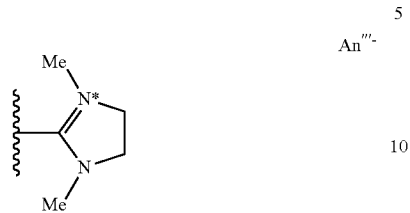

—C(NH$_2$)=N$^+$H$_2$ An''''$^-$; wherein An''''$^-$ is an anionic counterion;
—C(NH$_2$)=NH; and
SO$_3^-$M$^+$, wherein M$^+$ is a metal ion;
it being understood that when the compound of formula (XVI) or (XVI') contains other cationic parts, it is combined with one or more anionic counterions that afford formula (XVI) or (XVI') electrical neutrality.

* * * * *

UNITED STATES PATENT AND TRADEMARK OFFICE
CERTIFICATE OF CORRECTION

PATENT NO. : 9,522,106 B2
APPLICATION NO. : 14/001321
DATED : December 20, 2016
INVENTOR(S) : Frédéric Guerin et al.

It is certified that error appears in the above-identified patent and that said Letters Patent is hereby corrected as shown below:

In the Claims

Claim 1, Column 110, Line 45, change "(hetero)cycloalkvl" to -- (hetero)cycloalkyl --;

Claim 7, Column 112, Line 39, please change "-N+(R)(R.)-" to -- -N+(R)(R°)- --;

Claim 7, Column 112, Line 40, please change "R." to -- R° --;

Claim 8, Column 114, Line 44, please change "al kylcarbonyloxy," to -- alkylcarbonyloxy, --;

Claim 8, Column 114, Line 57, please change "and R';and/or" to -- and R'h and/or --;

Claim 8, Column 115, Line 10, please change "covalent a bond" to -- covalent sigma bond --;

Claim 8, Column 115, Lines 11-12, please change "-N+(R)(R.)-" to -- -N+(R)(R°)- --; and change "R, R.," to -- R, R°, --;

Claim 10, Columns 121-122, chemical structure 34, please change "4M'" to -- 2M' --;

Claim 10, Columns 127-128, chemical structure 55, please change "2 An'" to -- 2 An- --;

Claim 10, Columns 129-130, chemical structure 56, please change "2 An'" to -- 2 An- --;

Claim 10, Columns 129-130, chemical structure 57, please change "2 An'" to -- 2 An- --;

Claim 10, Columns 129-130, chemical structure 58, please change "An'" to -- An- -- (both occurrences);

Signed and Sealed this
Thirteenth Day of August, 2019

Andrei Iancu
*Director of the United States Patent and Trademark Office*

CERTIFICATE OF CORRECTION (continued)
U.S. Pat. No. 9,522,106 B2

Claim 10, Columns 137-138, please delete chemical structure 77 and insert chemical structure 77 as shown below:

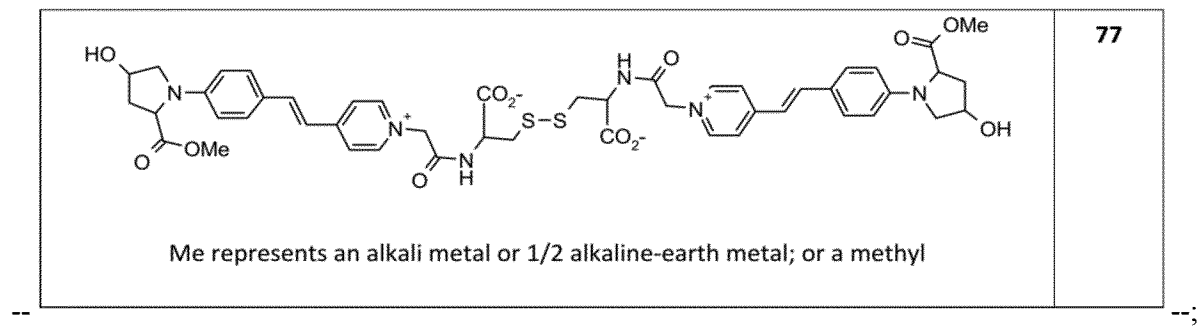

Claim 10, Columns 149-150, chemical structure 111, please change "2An'" to -- 2An- --;

Claim 23, Column 155, Line 64, please change "al kylcarbonyloxy," to -- alkylcarbonyloxy, --;

Claim 23, Column 156, Line 43, please remove the ";" after "R'''," and "R'''g";

Claim 23, Column 156, Line 44, please remove the ";" after "R",";

Claim 23, Column 156, Line 64, please change "covalent a bond" to -- covalent sigma bond --;

Claim 23, Column 156, Lines 65-66, please change "-N+(R)(Ro)-," to -- -N+(R)(R°)-, --; and please change "Ro," to -- R°, --;

Claim 24, Column 157, please delete chemical structure 44 and insert the following chemical structure 44:

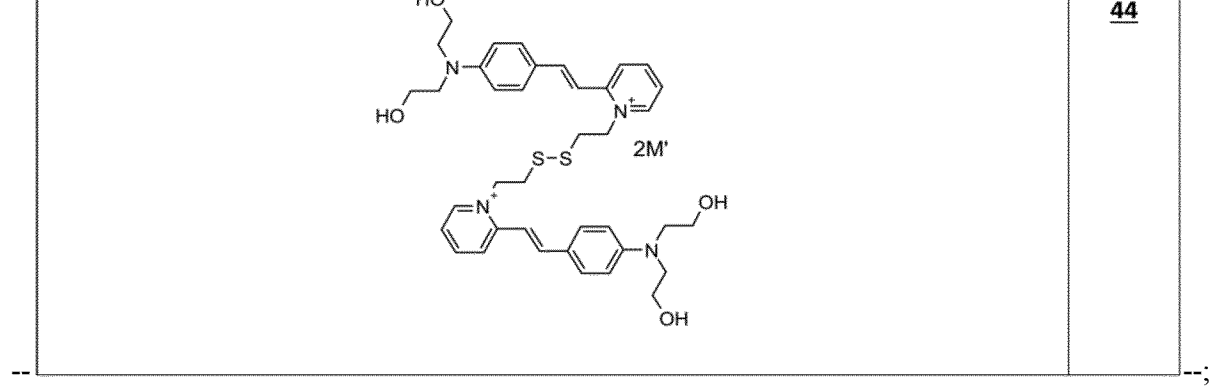

CERTIFICATE OF CORRECTION (continued)
U.S. Pat. No. 9,522,106 B2

Claim 26, Columns 159-160, please delete chemical formula (XV) and insert the following chemical formula (XV):

-- 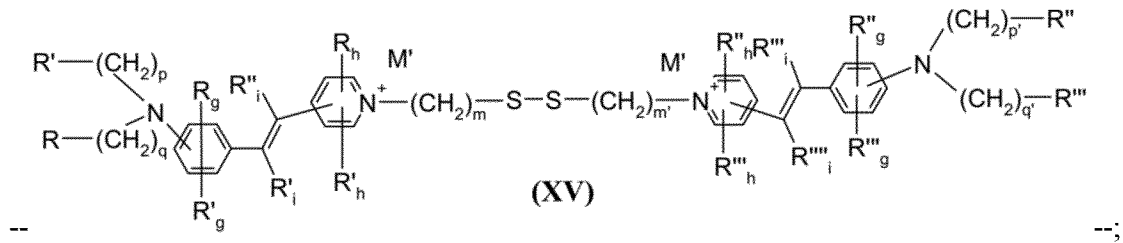 --;

Claim 26, Column 161, Lines 20-30, please delete the chemical formula and insert the following chemical formula:

-- 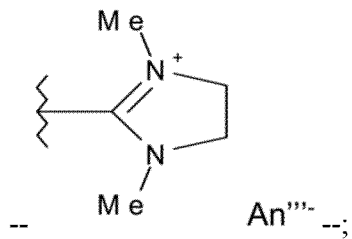 --;

Claim 27, Column 162, Lines 26 and 27, please change "(CH2p,(CH2)n -N(R)-C(O)-(CH2)p" to --(CH2)p-, -(CH2)n"-N(R)-C(O)-(CH2)p- --; and Claim 27, Column 163, Lines 5-14, please delete the chemical formula and insert the following chemical formula:

-- 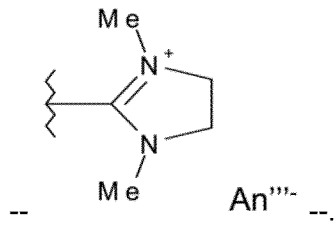 --.